United States Patent
Takashima et al.

(10) Patent No.: US 7,838,130 B2
(45) Date of Patent: Nov. 23, 2010

(54) AMINODIBENZOFLUORENE DERIVATIVE AND ORGANIC ELECTROLUMINESCENCE DEVICE USING THE SAME

(75) Inventors: Yoriyuki Takashima, Chiba (JP); Masakazu Funahashi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 374 days.

(21) Appl. No.: 11/928,276

(22) Filed: Oct. 30, 2007

(65) Prior Publication Data

US 2009/0267491 A1 Oct. 29, 2009

(30) Foreign Application Priority Data

Nov. 1, 2006 (JP) ............... 2006-298127

(51) Int. Cl.
*H01L 51/50* (2006.01)
*C07C 211/54* (2006.01)

(52) U.S. Cl. ............... 428/690; 313/504; 564/426

(58) Field of Classification Search ............... None
See application file for complete search history.

(56) References Cited

U.S. PATENT DOCUMENTS

| | | | | |
|---|---|---|---|---|
| 5,972,247 | A * | 10/1999 | Shi et al. ............ | 252/583 |
| 2003/0143422 | A1 * | 7/2003 | Chen ............ | 428/690 |

FOREIGN PATENT DOCUMENTS

| | | |
|---|---|---|
| JP | 03-200889 | 9/1991 |
| JP | 07-138561 | 5/1995 |
| JP | 08-012600 | 1/1996 |
| JP | 08-239655 | 9/1996 |
| JP | 3008897 | 2/2000 |
| JP | 2001-118682 | 4/2001 |
| JP | 2002-063988 | 2/2002 |
| JP | 2004-075567 | 3/2004 |
| JP | 2004-083481 | 3/2004 |
| WO | WO 03/051092 A1 | 6/2003 |
| WO | WO 2004/061047 A3 | 7/2004 |

OTHER PUBLICATIONS

U.S. Appl. No. 11/932,100, filed Oct. 31, 2007, Takashima, et al.

* cited by examiner

*Primary Examiner*—D. Lawrence Tarazano
*Assistant Examiner*—Gregory Clark
(74) *Attorney, Agent, or Firm*—Oblon, Spivak, McClelland, Maier & Neustadt, L.L.P.

(57) ABSTRACT

A novel compound which is useful as a constitutional component for an organic EL device is provided by an aminodibenzofluorene derivative comprising (A) at least one dibenzofluorene structure and (B) at least one amino group in a molecule, a material for an organic electroluminescence (EL) device comprising the same, a light emitting material for an organic EL device, a light emitting organic solution, an organic EL device in which an organic compound layer comprising a single layer or plural layers including at least a light emitting layer is interposed between a pair of electrodes, wherein at leas one layer in the organic compound layer described above contains at least one kind of the aminodibenzofluorene derivative described above and an equipment comprising the same. A practical organic EL device which has a low operating voltage, a long lifetime and a high current efficiency and which provides blue light emission having an excellent color purity is materialized by using the above compound.

16 Claims, 3 Drawing Sheets

AMINODIBENZOFLUORENE DERIVATIVE AND ORGANIC ELECTROLUMINESCENCE DEVICE USING THE SAME

BACKGROUND OF THE INVENTION

1. Field of the Invention

The present invention relates to an aminodibenzofluorene derivative, a material for an organic electroluminescence (EL) device obtained by using the same, a light emitting material for an organic EL device, an organic EL device, an equipment comprising the same and a light emitting organic solution, specifically to an organic EL device which has a long lifetime and a high current efficiency and which provides blue light emission, an aminodibenzofluorene derivative materializing the same, a material for an organic EL device obtained by using the same, a light emitting material for an organic EL device, an organic EL device, an equipment comprising the same and a light emitting organic solution.

2. Related Art

An organic electroluminescence device (hereinafter "electroluminescence" shall be abbreviated as EL) is a spontaneous luminescent device making use of the principle that a fluorescent substance emits light by recombination energy of holes injected from an anode and electrons injected from a cathode by applying an electric field. Since an organic EL device of a laminate type driven at a low voltage was reported by C. W. Tang et al. of Eastman Kodak Company (C. W. Tang and S. A. Vanslyke, Applied Physics Letters, Vol. 51, p. 913, 1987 and the like), researches on organic EL devices comprising organic materials as structural materials have actively been carried out. Tang et al. use tris(8-quinolinolate)aluminum for the light emitting layer and a triphenyldiamine derivative for the hole transporting layer. The advantages of the laminate structure include an elevation in an efficiency of injecting holes into a light emitting layer, a rise in a production efficiency of excitons produced by blocking electrons injected from a cathode to recombine them and shutting up of excitons produced in a light emitting layer. As shown in the above example, a two-layer type comprising a hole transporting (injecting) layer and an electron transporting and light emitting layer and a three-layer type comprising a hole transporting (injecting) layer, a light emitting layer and an electron transporting (injecting) layer are well known as the device structures of an organic EL device. In the above laminate type structural devices, device structures and forming methods are studied in order to enhance a recombination efficiency of holes and electrons injected.

Known as light emitting materials are light emitting materials such as chelate complexes such as a tris(8-quinolinolate) aluminum complex, coumarin derivatives, tetraphenylbutadiene derivatives, bisstyrylarylene derivatives, oxadiazole derivatives and the like. It is reported that light emission of a blue color to a red color in a visible region is obtained from them, and it is expected that a color display device is materialized (for example, a patent document 1, a patent document 2, a patent document 3 and the like).

Devices prepared by using bisanthracene derivatives as a light emitting material are disclosed in a patent document 4 and a patent document 5. Bisanthracene is used as a blue light emitting material, but an efficiency and a lifetime thereof do not reach practicable levels and are unsatisfactory.

Also, devices prepared by using symmetric pyrene derivatives as a light emitting material are disclosed in a patent document 6, a patent document 7, a patent document 8 and a patent document 9. The above symmetric pyrene derivatives are used as a blue light emitting material, but a lifetime of the devices has been required to be improved.

Further, a device using a dibenzofluorene derivative as a light emitting material is disclosed in a patent document 10, but the specific physical property values are not described. Also, a high molecular organic EL device prepared by using a benzofluorene derivative is disclosed in a patent document 11. The above (di)benzofluorene derivatives are used as a blue light emitting material, but a color purity and a lifetime of the devices have been required to be improved.

Patent document 1: Japanese Patent Application Laid-Open No. 239655/1996

Patent document 2: Japanese Patent Application Laid-Open No. 138561/1995

Patent document 3: Japanese Patent Application Laid-Open No. 200289/1991

Patent document 4: Japanese Patent No. 3008897

Patent document 5: Japanese Patent Application Laid-Open No. 12600/1996

Patent document 6: Japanese Patent Application Laid-Open No. 118682/2001

Patent document 7: Japanese Patent Application Laid-Open No. 63988/2002

Patent document 8: Japanese Patent Application Laid-Open No. 75567/2004

Patent document 9: Japanese Patent Application Laid-Open No. 83481/2004

Patent document 10: International Publication No. 03/051092

Patent document 11: International Publication No. 04/061047

SUMMARY OF THE INVENTION

The present invention has been made in order to solve the problems described above, and an object of the present invention is to provide a novel compound which is useful as a constitutional component of an organic EL device and materialize a practical organic EL device which has a low operating voltage, a long lifetime and a high current efficiency and which provides blue light emission having an excellent color purity by using the above compound.

Intensive researches repeated by the present inventors in order to achieve the object described above have resulted in finding that an aminodibenzofluorene derivative in which at least one amino group is bonded directly to a dibenzofluorene structure in a molecule exhibits blue light emission having a narrow half value width. Further, the present inventors have found that blue light emission having a high current efficiency, an excellent color purity and a long lifetime is obtained by using an organic EL device prepared by using the above compound, and thus they have come to complete the present invention.

That is, the present invention provides an aminodibenzofluorene derivative comprising (A) at least one dibenzofluorene structure and (B) at least one amino group in a molecule, a material for an organic EL device comprising the above derivative, a light emitting material for an organic EL device and a light emitting organic solution.

Further, the present invention provides an organic EL device in which an organic compound layer comprising a single layer or plural layers including at least a light emitting layer is interposed between a pair of electrodes, wherein at least one layer in the organic compound layer described above contains at least one kind of the aminodibenzofluorene derivative described above and an equipment comprising the same.

A practical organic EL device which has a low operating voltage, a long lifetime and a high current efficiency and which provides blue light emission having an excellent color purity is obtained by using the aminodibenzofluorene derivatives of the present invention as a material for the organic EL device.

EXPLANATIONS OF THE CODES

Figure 1:
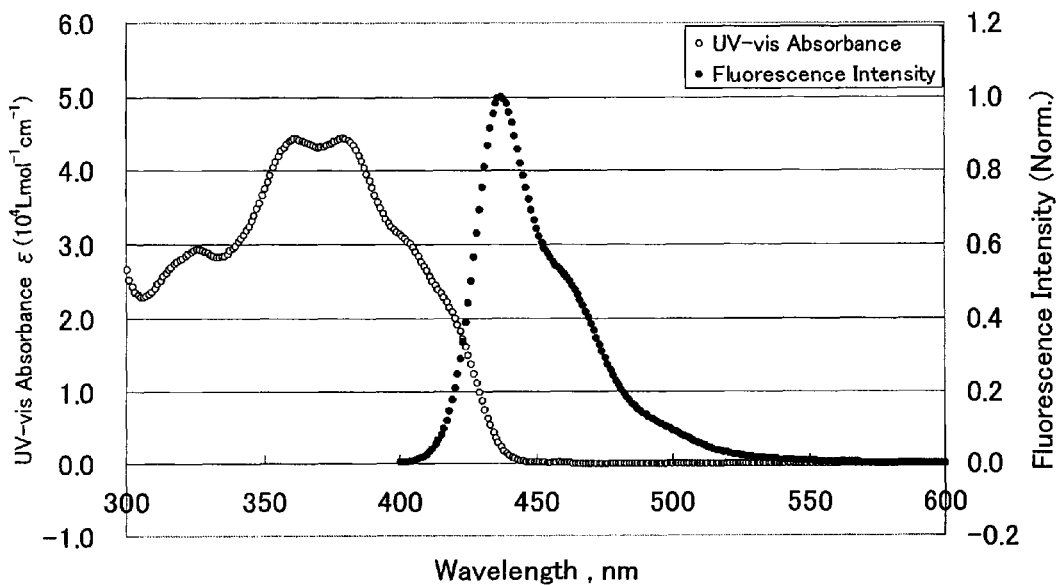
FIG. 1 is a diagram showing results obtained by measuring a UV ray absorbance and a fluorescence intensity of a compound (1a-29) produced in Synthetic Example 1.

10 Anode
20 Organic compound layer
21 Hole injecting layer
22 Hole transporting layer
23 Light emitting layer
24 Electron transporting layer
25 Electron injecting layer
30 Cathode

BEST MODE FOR CARRYING OUT THE INVENTION

The aminodibenzofluorene derivative of the present invention comprises (A) at least one dibenzofluorene structure and (B) at least one or more amino group in a molecule.

To be specific, the aminodibenzofluorene derivative of the present invention is represented preferably by any of the following Formulas (1-a) to (1-f):

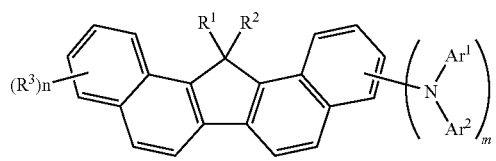

1-a

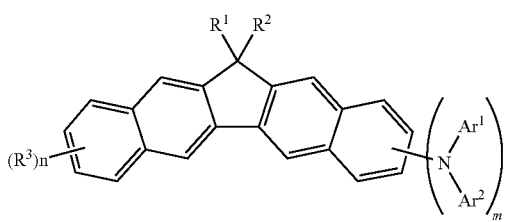

1-b

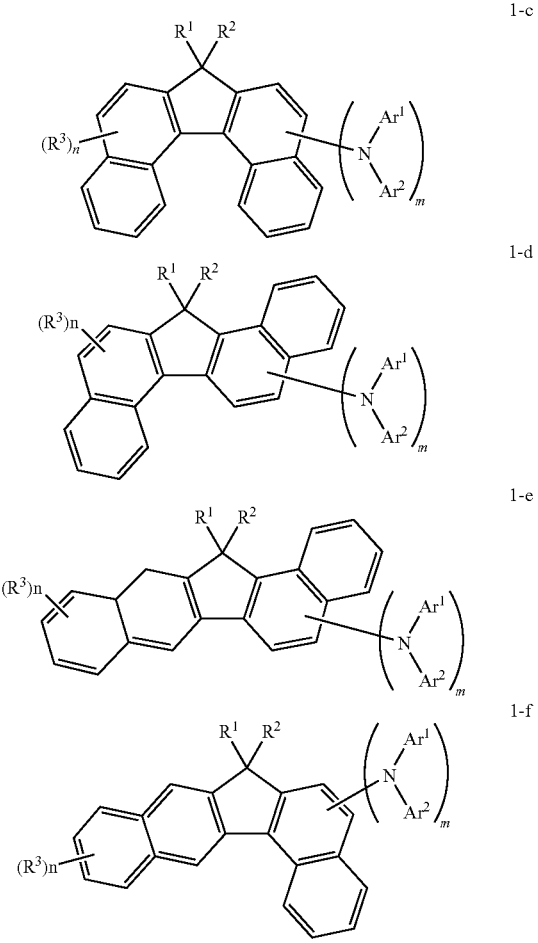

In Formulas (1-a) to (1-f), $R^1$ to $R^2$ each represent independently a hydrogen atom, a substituted or non-substituted alkyl group having 1 to 50 carbon atoms, a substituted or non-substituted aralkyl group having 1 to 50 carbon atoms, a substituted or non-substituted cycloalkyl group having 5 to 50 carbon atoms, a substituted or non-substituted aryl group having 5 to 50 carbon atoms forming the aromatic ring or a substituted or non-substituted heteroaryl group having 5 to 50 atoms forming a ring;

$R^3$ represents a substituted or non-substituted alkyl group having 1 to 50 carbon atoms, a substituted or non-substituted aralkyl group having 1 to 50 carbon atoms, a substituted or non-substituted cycloalkyl group having 5 to 50 carbon atoms, a substituted or non-substituted alkoxyl group having 1 to 50 carbon atoms, a substituted or non-substituted alkoxycarbonyl group having 1 to 50 carbon atoms, a substituted or non-substituted aryl group having 5 to 50 carbon atoms forming the aromatic ring, a substituted or non-substituted aryloxy group having 5 to 50 atoms forming a ring, a substituted or non-substituted arylthio group having 5 to 50 atoms forming a ring, a substituted or non-substituted heteroaryl group having 5 to 50 atoms forming a ring, a substituted or non-substituted silyl group having 1 to 20 carbon atoms, a halogen atom, a cyano group or a nitro group;

$Ar^1$ to $Ar^2$ each represent independently a substituted or non-substituted aryl group having 5 to 50 carbon atoms forming the aromatic ring or a substituted or non-substituted heteroaryl group having 5 to 50 atoms forming a ring;

m is an integer of 1 to 4, and n is an integer of 0 to 8;

when $R^1$, $R^2$, $R^3$, $Ar^1$ and $Ar^2$ are not a hydrogen atom, a halogen atom, a cyano group and a nitro group, the groups which are adjacent to each other may be combined with each other to form saturated or unsaturated cyclic structures, and these cyclic structures may be substituted.

The specific examples of the respective groups represented by $R^1$, $R^2$, $R^3$, $Ar^1$ and $Ar^2$ in Formulas (1-a) to (1-f) shall be explained below.

The substituted or non-substituted aryl group having 5 to 50 carbon atoms forming the aromatic ring represented by $R^1$, $R^2$, $R^3$, $Ar^1$ and $Ar^2$ includes phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4''-t-butyl-p-terphenyl-4-yl and the like. It is preferably a substituted or non-substituted aryl group having 6 to 20 carbon atoms forming the aromatic ring.

The substituted or non-substituted heteroaryl group having 5 to 50 atoms forming a ring represented by $R^1$, $R^2$, $R^3$, $Ar^1$ and $Ar^2$ includes 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like. It is preferably a substituted or non-substituted heteroaryl group having 5 to 20 atoms forming a ring.

The substituted or non-substituted alkyl group having 1 to 50 carbon atoms represented by $R^1$, $R^2$ and $R^3$ includes methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl and the like. It is preferably a substituted or non-substituted alkyl group having 1 to 20 carbon atoms.

The substituted or non-substituted cycloalkyl group having 1 to 50 carbon atoms represented by $R^1$, $R^2$ and $R^3$ includes cyclopentyl, cyclohexyl, 4-methylcyclohexyl, 1-adamantyl, 2-adamantyl, 1-norbornyl, 2-norbornyl and the like. It is preferably a substituted or non-substituted cycloalkyl group having 5 to 10 carbon atoms.

The substituted or non-substituted alkoxyl group having 1 to 50 carbon atoms represented by $R^3$ is a group represented by —OY, and Y includes the same examples as given in the substituted or non-substituted alkyl group having 1 to 50 carbon atoms represented by $R^1$, $R^2$ and $R^3$ described above. It is preferably a substituted or non-substituted alkoxyl group having 1 to 20 carbon atoms.

The substituted or non-substituted aralkyl group having 6 to 50 carbon atoms represented by $R^1$, $R^2$ and $R^3$ includes benzyl, 1-phenylethyl, 2-phenylethyl, 1-phenylisopropyl, 2-phenylisopropyl, phenyl t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, 1-chloro-2-phenylisopropyl and the like. It is preferably a substituted or non-substituted aralkyl group having 7 to 20 carbon atoms.

The substituted or non-substituted aryloxy group having 5 to 50 atoms forming a ring and the substituted or non-substituted arylthio group having 5 to 50 atoms forming a ring each represented by $R^3$ are groups represented respectively by —OY' and SY", and Y' and Y" include the same examples as given in the substituted or non-substituted aryl group having 5 to 50 carbon atoms forming the aromatic ring represented by $R^1$, $R^2$, $R^3$, $Ar^1$ and $Ar^2$ described above. It is preferably a substituted or non-substituted aryloxy group having 5 to 20 atoms forming a ring.

The substituted or non-substituted alkoxycarbonyl group having 2 to 50 carbon atoms represented by $R^3$ is a group represented by —COOZ, and Z includes the same examples as given in the substituted or non-substituted alkyl group having 1 to 50 carbon atoms represented by $R^1$, $R^2$, $R^3$, $Ar^1$ and $Ar^2$ described above. It is preferably a substituted or non-substituted alkoxycarbonyl group having 1 to 20 carbon atoms.

The halogen atom represented by $R^3$ includes a fluorine atom, a chlorine atom, a bromine atom and an iodine atom.

Substituents in the groups represented by $R^1$, $R^2$, $R^3$, $Ar^1$ and $Ar^2$ include a halogen atom, a hydroxyl group, a nitro group, a cyano group, a silyl group, an alkyl group, an aryl group, a cycloalkyl group, an alkoxyl group, an aromatic heteroaryl group, an aralkyl group, an aryloxy group, an arylthio group, an alkoxycarbonyl group or a carboxyl group.

In $R^1$, $R^2$, $R^3$, $Ar^1$ and $Ar^2$, saturated or unsaturated cyclic structures formed by allowing the groups which are adjacent to each other to be combined with each other are preferably five-membered or six-membered rings, and these cyclic structures may be substituted.

The above cyclic structures include cycloalkanes having 4 to 12 carbon atoms such as cyclobutane, cyclopentane, cyclohexane, adamantane, norbornane and the like, cycloalkenes having 4 to 12 carbon atoms such as cyclobutene, cyclopentene, cyclohexene, cycloheptene, cyclooctene and the like, cycloalkadienes having 6 to 12 carbon atoms such as cyclohexadiene, cycloheptadiene, cyclooctadiene and the like and aromatic rings having 6 to 50 carbon atoms such as benzene, naphthalene, phenanthrene, anthracene, pyrene chrysene, acenaphthylene and the like. Substituents therefor include the same groups as the examples described above.

The specific examples of the aminodibenzofluorene derivative of the present invention are shown below but shall not be restricted to these compounds given as the examples.

1-a

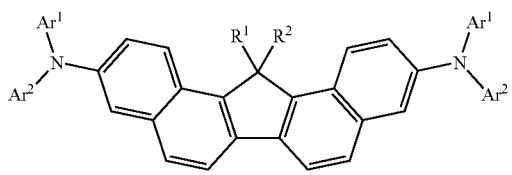

| Compound for example | $R^1$ | $R^2$ | $Ar^1$ | $Ar^2$ |
| --- | --- | --- | --- | --- |
| 1a-1 | Me | Me | Ph | Ph |
| 1a-2 | Me | Me | Ph | —C₆H₄—Me (p) |
| 1a-3 | Me | Me | Ph | —C₆H₄—Me (m) |
| 1a-4 | Me | Me | Ph | —C₆H₄—Me (o) |
| 1a-5 | Me | Me | Ph | —C₆H₄—CH(CH₃)₂ (p) |
| 1a-6 | Me | Me | Ph | —C₆H₄—C(CH₃)₃ (p) |

-continued 1-a

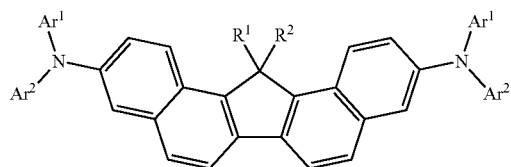

| Compound for example | R¹ | R² | Ar¹ | Ar² |
|---|---|---|---|---|
| 1a-7 | Me | Me | Ph | 2,4-dimethylphenyl |
| 1a-8 | Me | Me | Ph | 2,3,5-trimethylphenyl |
| 1a-9 | Me | Me | 4-methylphenyl | 4-methylphenyl |
| 1a-10 | Me | Me | 3-methylphenyl | 3-methylphenyl |
| 1a-11 | Me | Me | 2-methylphenyl | 2-methylphenyl |
| 1a-12 | Me | Me | 2,4-dimethylphenyl | 2,4-dimethylphenyl |
| 1a-13 | Me | Me | 2,3,4,5-tetramethylphenyl | 2,3,4-trimethylphenyl |
| 1a-14 | Me | Me | 4-isopropylphenyl | 4-isopropylphenyl |
| 1a-15 | Me | Me | 4-methylphenyl | 4-isopropylphenyl |
| 1a-16 | Me | Me | Ph | 4-biphenyl |

-continued
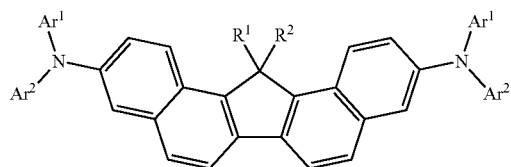
1-a
| Compound for example | R¹ | R² | Ar¹ | Ar² |
|---|---|---|---|---|
| 1a-17 | Me | Me | Ph | 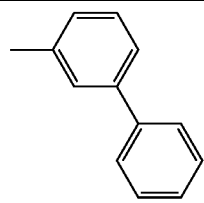 |
| 1a-18 | Me | Me | Ph | 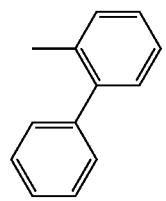 |
| 1a-19 | Me | Me | Ph | 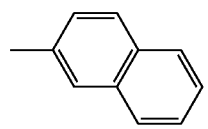 |
| 1a-20 | Me | Me | Ph | 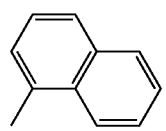 |
| 1a-21 | Me | Me | 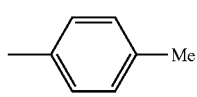 | 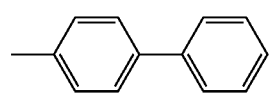 |
| 1a-22 | Me | Me | 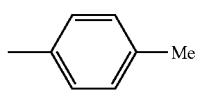 | 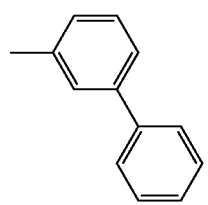 |
| 1a-23 | Me | Me | 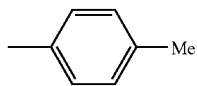 | 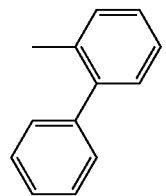 |
| 1a-24 | Me | Me | 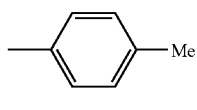 | 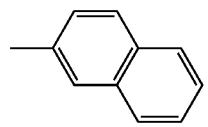 |

-continued
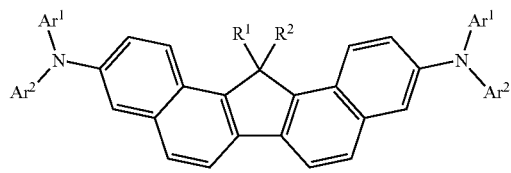
1-a
| Compound for example | R¹ | R² | Ar¹ | Ar² |
|---|---|---|---|---|
| 1a-25 | Me | Me | 4-methylphenyl | 1-naphthyl |
| 1a-26 | Me | Me | 4-biphenyl | 4-biphenyl |
| 1a-27 | Me | Me | 3-biphenyl | 3-biphenyl |
| 1a-28 | Me | Me | 2-biphenyl | 2-biphenyl |
| 1a-29 | Me | Me | 2-naphthyl | 2-naphthyl |
| 1a-30 | Me | Me | 4-methyl-1-naphthyl | 4-methyl-1-naphthyl |
| 1a-31 | Me | Me | Ph | 9,9-dimethyl-2-fluorenyl |
| 1a-32 | Me | Me | Ph | 9-methyl-10-phenanthryl |

-continued
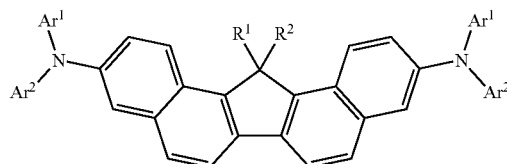
1-a
| Compound for example | R¹ | R² | Ar¹ | Ar² |
|---|---|---|---|---|
| 1a-33 | Me | Me | 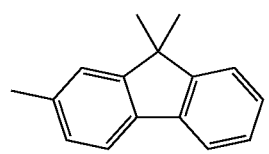 | 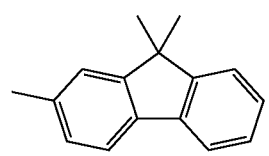 |
| 1a-34 | Me | Me | 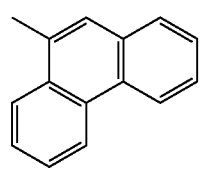 | 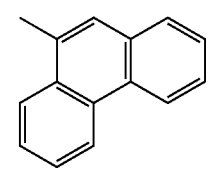 |
| 1a-35 | Me | Me | Ph | 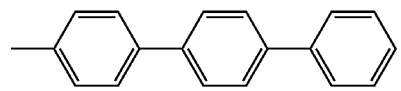 |
| 1a-36 | Me | Me | Ph | 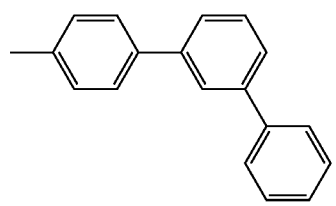 |
| 1a-37 | Me | Me | Ph | 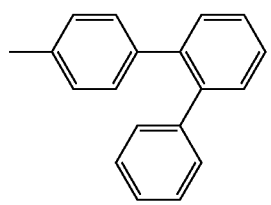 |
| 1a-38 | Me | Me | Ph | 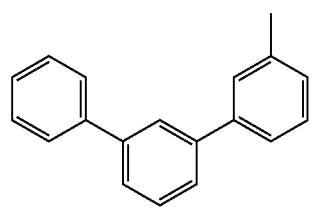 |
| 1a-39 | Me | Me | Ph | 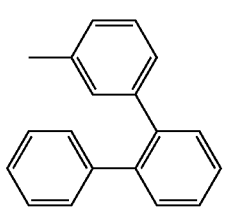 |

-continued
1-a
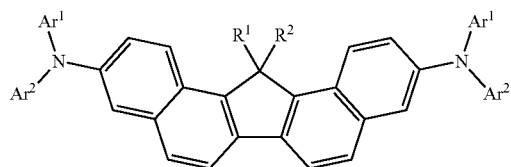
| Compound for example | R¹ | R² | Ar¹ | Ar² |
|---|---|---|---|---|
| 1a-40 | Me | Me | Ph | *o,p-terphenyl group* |
| 1a-41 | Me | Me | Ph | *m,o-terphenyl group* |
| 1a-42 | Me | Me | Ph | *o-biphenyl-phenyl group* |
| 1a-43 | Me | Me | Ph | *phenanthrenyl group* |
| 1a-44 | Me | Me | Ph | *pyrenyl group* |
| 1a-45 | Me | Me | Ph | *4-(1-naphthyl)phenyl group* |
| 1a-46 | Me | Me | Ph | *4-(2-naphthyl)phenyl group* |
| 1a-47 | Me | Me | Ph | *4-phenyl-1-naphthyl group* |

-continued

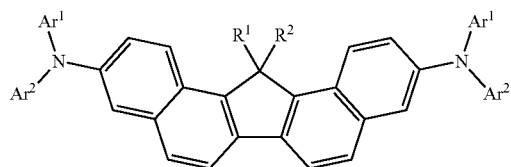

1-a

| Compound for example | R¹ | R² | Ar¹ | Ar² |
|---|---|---|---|---|
| 1a-48 | Me | Me | Ph | 6-phenyl-2-naphthyl |
| 1a-49 | Me | Me | 4-(1-naphthyl)phenyl | 4-(1-naphthyl)phenyl |
| 1a-50 | Me | Me | 4-(2-naphthyl)phenyl | 4-(2-naphthyl)phenyl |
| 1a-51 | n-Hexyl | n-Hexyl | Ph | Ph |
| 1a-52 | n-Hexyl | n-Hexyl | 4-methylphenyl | 4-methylphenyl |
| 1a-53 | n-Hexyl | n-Hexyl | 4-isopropylphenyl | 4-isopropylphenyl |
| 1a-54 | n-Hexyl | n-Hexyl | 4-tert-butylphenyl | 4-tert-butylphenyl |
| 1a-55 | n-Hexyl | n-Hexyl | 3,4,5-trimethylphenyl | 3,4,5-trimethylphenyl |
| 1a-56 | n-Hexyl | n-Hexyl | 2-naphthyl | 2-naphthyl |
| 1a-57 | n-Hexyl | n-Hexyl | 1-naphthyl | 1-naphthyl |
| 1a-58 | n-Hexyl | n-Hexyl | 4-biphenyl | 4-biphenyl |

-continued

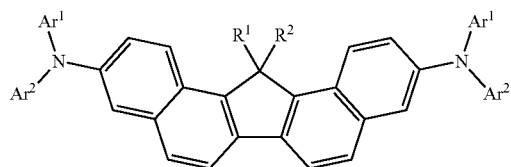

1-a

| Compound for example | R¹ | R² | Ar¹ | Ar² |
|---|---|---|---|---|
| 1a-59 | n-Octyl | n-Octyl | Ph | Ph |
| 1a-60 | n-Octyl | n-Octyl | —C₆H₄-Me (p) | —C₆H₄-Me (p) |
| 1a-61 | n-Octyl | n-Octyl | —C₆H₄-iPr (p) | —C₆H₄-iPr (p) |
| 1a-62 | n-Octyl | n-Octyl | —C₆H₄-C(CH₃)₃ (p) | —C₆H₄-C(CH₃)₃ (p) |
| 1a-63 | n-Octyl | n-Octyl | 2,3,4-trimethylphenyl | 2,3,4-trimethylphenyl |
| 1a-64 | n-Octyl | n-Octyl | 2-naphthyl | 2-naphthyl |
| 1a-65 | n-Octyl | n-Octyl | 1-naphthyl | 1-naphthyl |
| 1a-66 | 2-ethylhexyl | 2-ethylhexyl | 4-biphenyl | 4-biphenyl |
| 1a-67 | 2-ethylhexyl | 2-ethylhexyl | Ph | Ph |
| 1a-68 | 2-ethylhexyl | 2-ethylhexyl | —C₆H₄-Me (p) | —C₆H₄-Me (p) |
| 1a-69 | 2-ethylhexyl | 2-ethylhexyl | —C₆H₄-iPr (p) | —C₆H₄-iPr (p) |
| 1a-70 | 2-ethylhexyl | 2-ethylhexyl | —C₆H₄-C(CH₃)₃ (p) | —C₆H₄-C(CH₃)₃ (p) |
| 1a-71 | 2-ethylhexyl | 2-ethylhexyl | 2-naphthyl | 2-naphthyl |

-continued
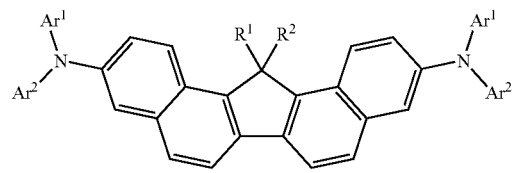
1-a
| Compound for example | R¹ | R² | Ar¹ | Ar² |
|---|---|---|---|---|
| 1a-72 | 2-ethylhexyl | 2-ethylhexyl | 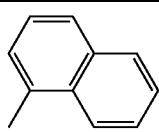 | 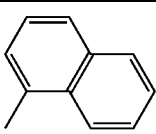 |
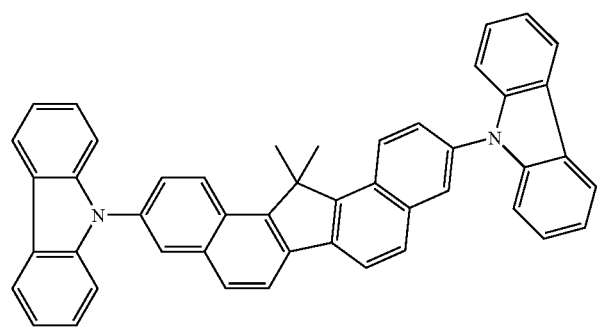
1a-73
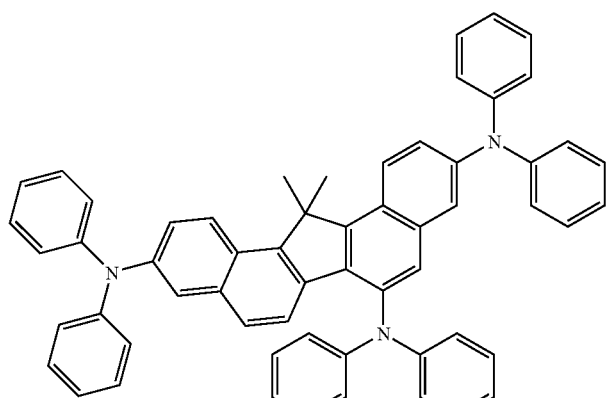
1a-74
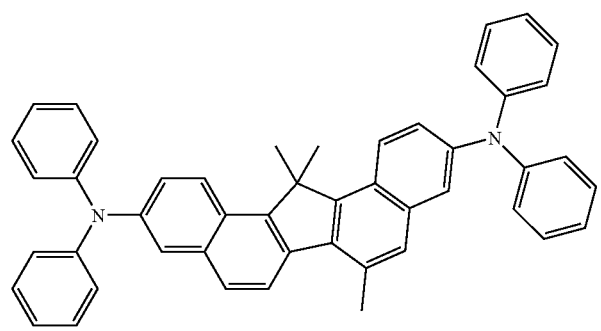
1a-75

-continued
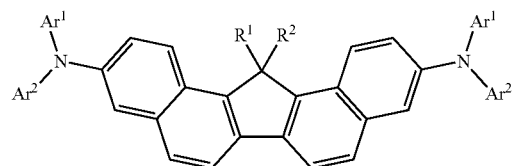
1-a
| Compound for example | R¹ | R² | Ar¹ | Ar² |
|---|---|---|---|---|
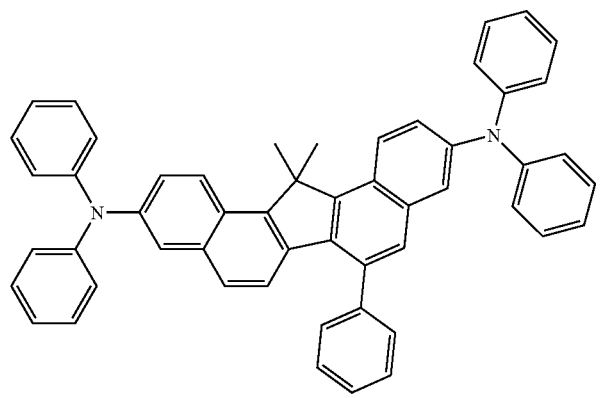
1a-76
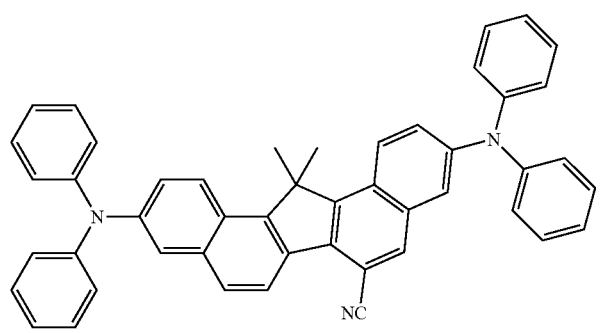
1a-77
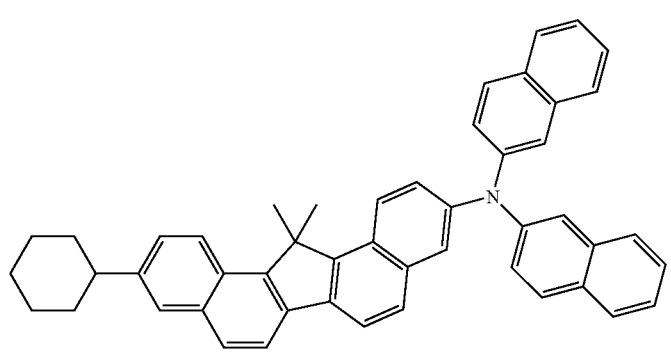
1a-78

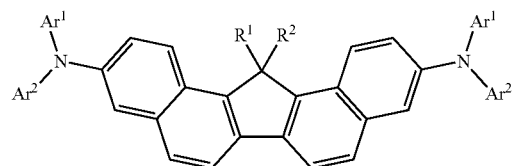
1-a
| Compound for example | R¹ | R² | Ar¹ | Ar² |
|---|---|---|---|---|
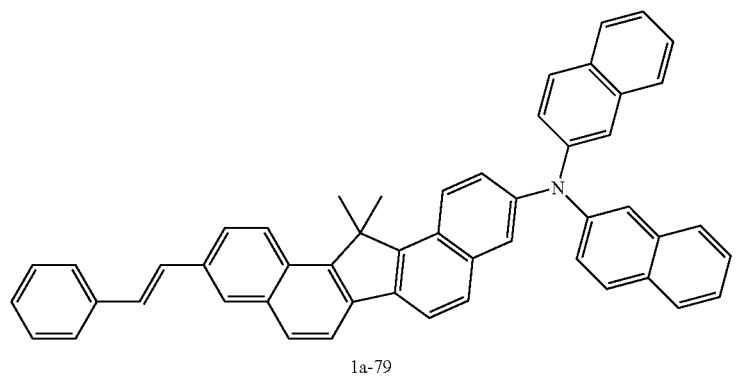
1a-79
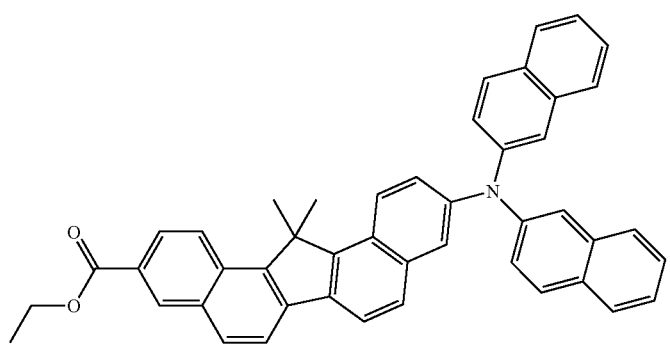
1a-80
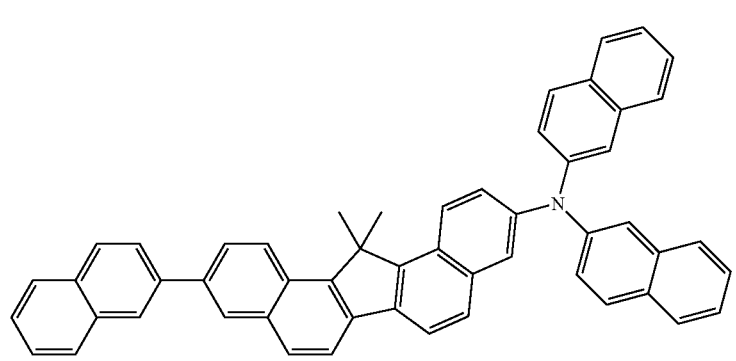
1a-81

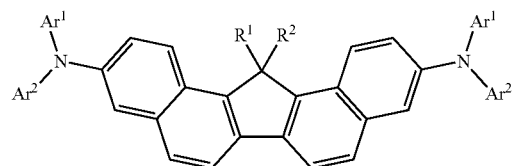
1-a
| Compound for example | R¹ | R² | Ar¹ | Ar² |
|---|---|---|---|---|
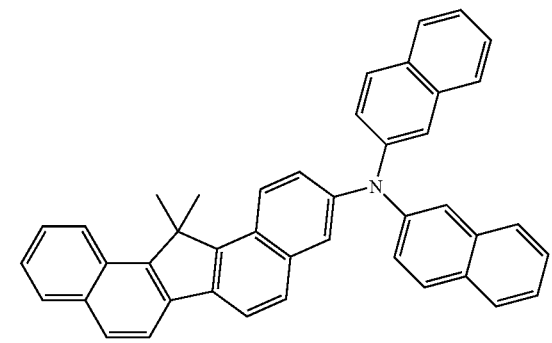
1a-82
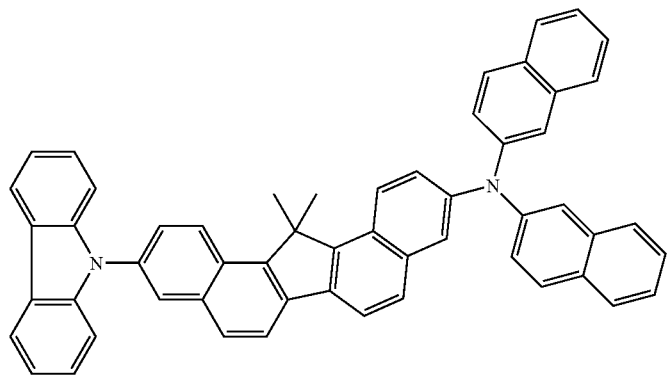
1a-83
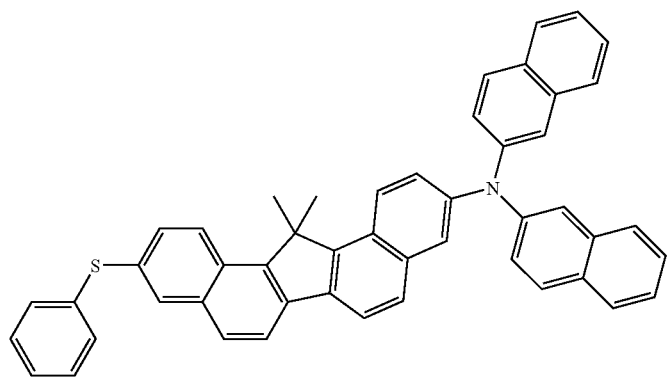
1a-84

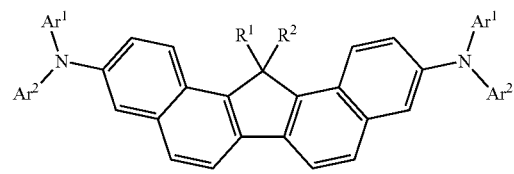
1-a
| Compound for example | R¹ | R² | Ar¹ | Ar² |
|---|---|---|---|---|
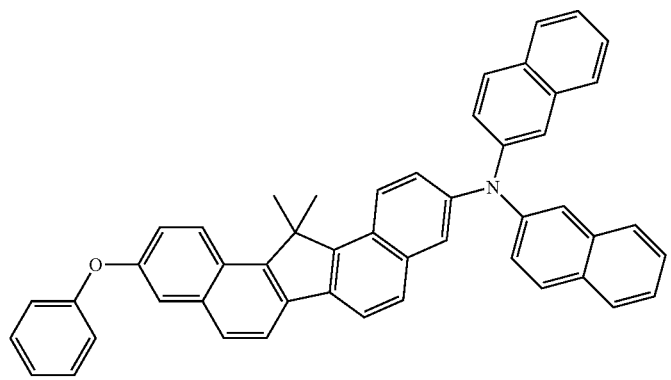
1a-85
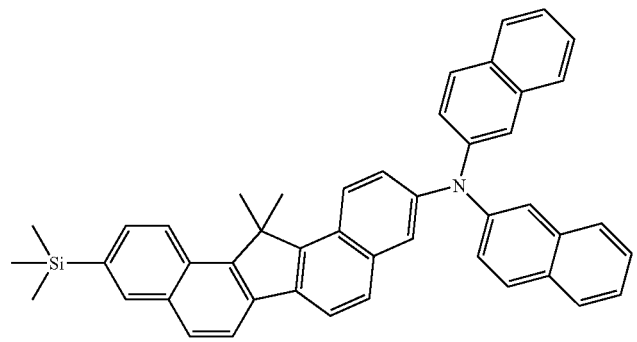
1a-86
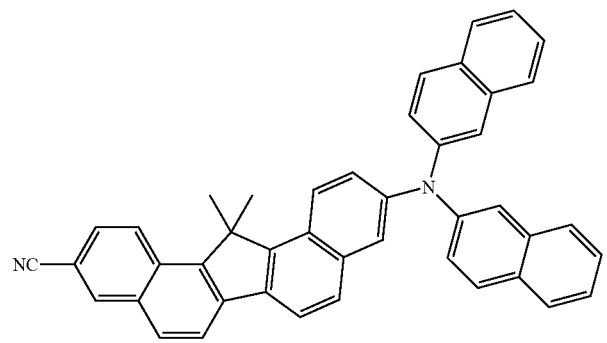
1a-87

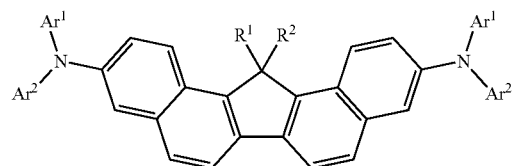
| Compound for example | R¹ | R² | Ar¹ | Ar² |
|---|---|---|---|---|
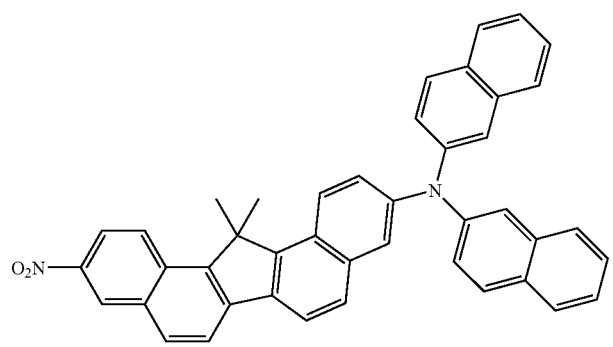
1a-88
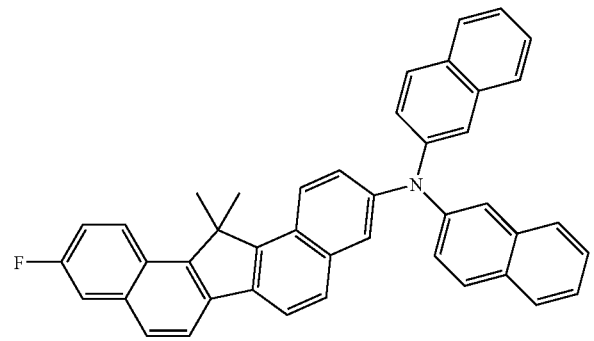
1a-89
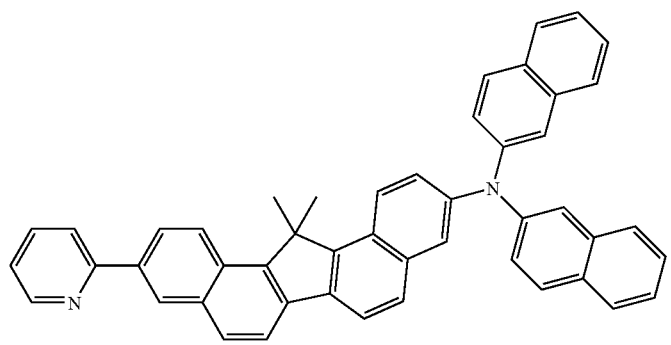
1a-90

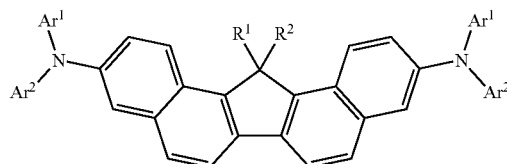
1-a
| Compound for example | R¹ | R² | Ar¹ | Ar² |
|---|---|---|---|---|
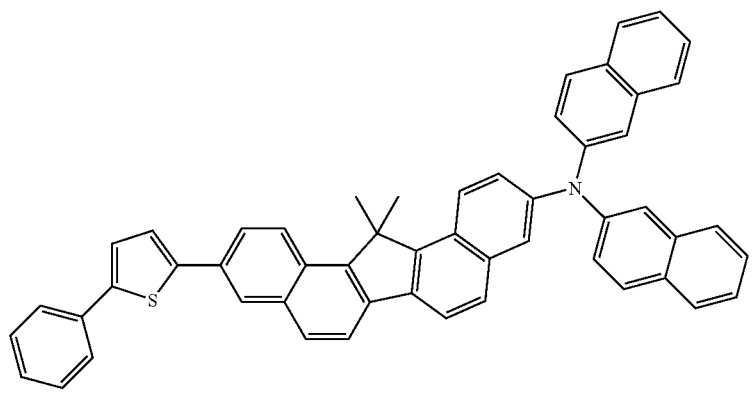
1a-91
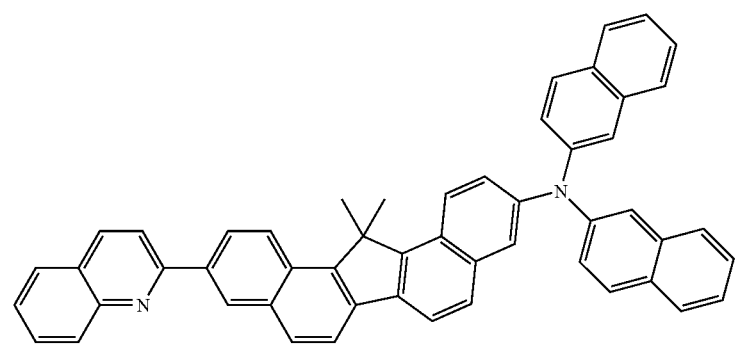
1a-92
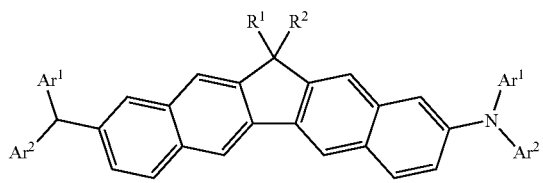
1-b
| Compound for example | R¹ | R² | Ar¹ | Ar² |
|---|---|---|---|---|
| 1b-1 | Me | Me | Ph | Ph |
| 1b-2 | Me | Me | Ph | 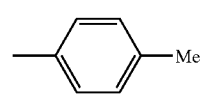 |

-continued
1-b
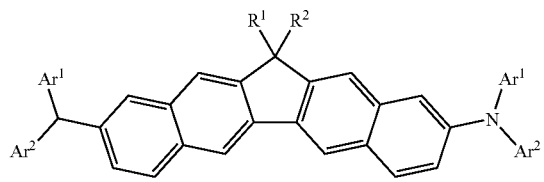
| Compound for example | R¹ | R² | Ar¹ | Ar² |
|---|---|---|---|---|
| 1b-3 | Me | Me | Ph | 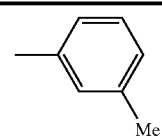 |
| 1b-4 | Me | Me | Ph | 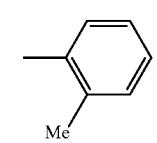 |
| 1b-5 | Me | Me | Ph | 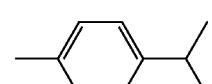 |
| 1b-6 | Me | Me | Ph | 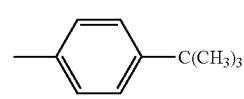 |
| 1b-7 | Me | Me | Ph | 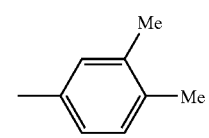 |
| 1b-8 | Me | Me | Ph | 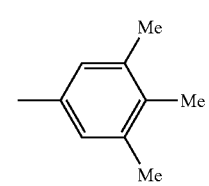 |
| 1b-9 | Me | Me |  |  |
| 1b-10 | Me | Me | 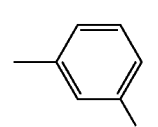 | 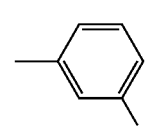 |
| 1b-11 | Me | Me | 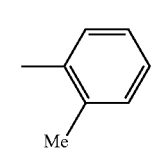 | 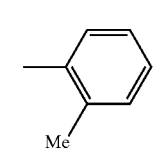 |
| 1b-12 | Me | Me | 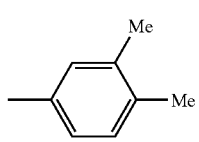 | 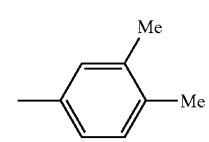 |

-continued
1-b
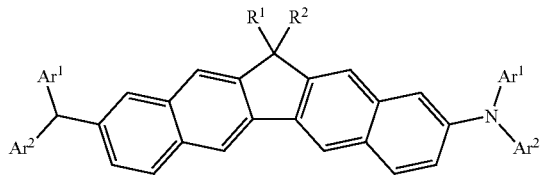
| Compound for example | R¹ | R² | Ar¹ | Ar² |
|---|---|---|---|---|
| 1b-13 | Me | Me | 2,3,5-trimethylphenyl | 2,3,5-trimethylphenyl |
| 1b-14 | Me | Me | 4-isopropylphenyl | 4-isopropylphenyl |
| 1b-15 | Me | Me | 4-methylphenyl | 4-isopropylphenyl |
| 1b-16 | Me | Me | Ph | 4-biphenylyl |
| 1b-17 | Me | Me | Ph | 3-biphenylyl |
| 1b-18 | Me | Me | Ph | 2-biphenylyl |
| 1b-19 | Me | Me | Ph | 2-naphthyl |
| 1b-20 | Me | Me | Ph | 1-naphthyl |
| 1b-21 | Me | Me | 4-methylphenyl | 4-biphenylyl |

-continued
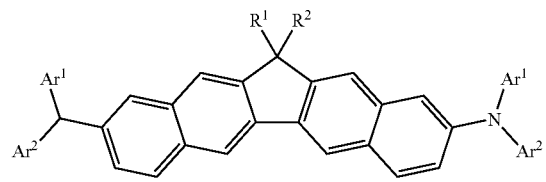
1-b
| Compound for example | R¹ | R² | Ar¹ | Ar² |
|---|---|---|---|---|
| 1b-22 | Me | Me | 4-MeC6H4 | 3-biphenyl |
| 1b-23 | Me | Me | 4-MeC6H4 | 2-biphenyl |
| 1b-24 | Me | Me | 4-MeC6H4 | 2-naphthyl |
| 1b-25 | Me | Me | 4-MeC6H4 | 1-naphthyl |
| 1b-26 | Me | Me | 4-biphenyl | 4-biphenyl |
| 1b-27 | Me | Me | 3-biphenyl | 3-biphenyl |
| 1b-28 | Me | Me | 2-biphenyl | 2-biphenyl |
| 1b-29 | Me | Me | 2-naphthyl | 2-naphthyl |

-continued
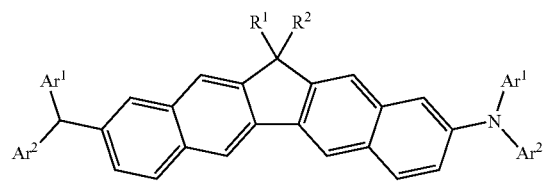
1-b
| Compound for example | R¹ | R² | Ar¹ | Ar² |
|---|---|---|---|---|
| 1b-30 | Me | Me | 1-methylnaphthyl | 1-methylnaphthyl |
| 1b-31 | Me | Me | Ph | 9,9-dimethylfluorenyl |
| 1b-32 | Me | Me | Ph | methylphenanthrenyl |
| 1b-33 | Me | Me | 9,9-dimethylfluorenyl | 9,9-dimethylfluorenyl |
| 1b-34 | Me | Me | methylphenanthrenyl | methylphenanthrenyl |
| 1b-35 | Me | Me | Ph | p-terphenyl-methyl |
| 1b-36 | Me | Me | Ph | m-terphenyl-methyl |
| 1b-37 | Me | Me | Ph | o-terphenyl-methyl |

-continued
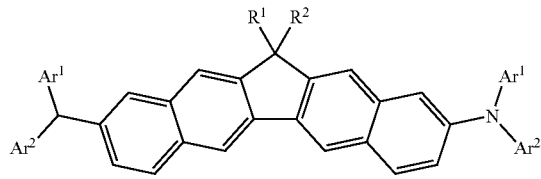
1-b
| Compound for example | R¹ | R² | Ar¹ | Ar² |
|---|---|---|---|---|
| 1b-38 | Me | Me | Ph | 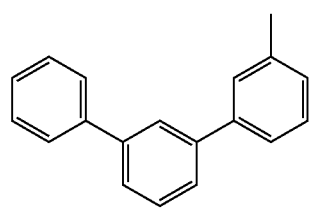 |
| 1b-39 | Me | Me | Ph | 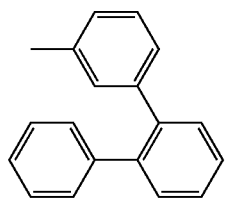 |
| 1b-40 | Me | Me | Ph | 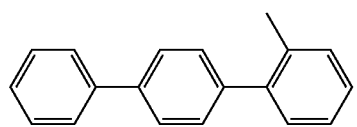 |
| 1b-41 | Me | Me | Ph | 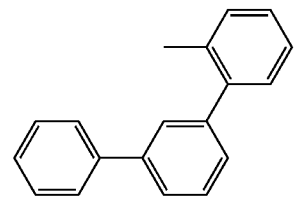 |
| 1b-42 | Me | Me | Ph | 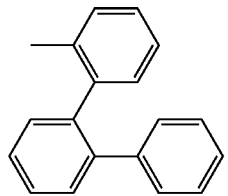 |
| 1b-43 | Me | Me | Ph |  |
| 1b-44 | Me | Me | Ph | 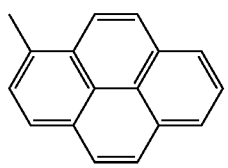 |

-continued
1-b
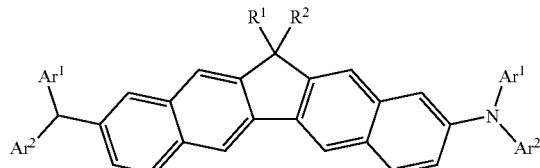
| Compound for example | R¹ | R² | Ar¹ | Ar² |
|---|---|---|---|---|
| 1b-45 | Me | Me | Ph | 4-(1-naphthyl)phenyl |
| 1b-46 | Me | Me | Ph | 4-(2-naphthyl)phenyl |
| 1b-47 | Me | Me | Ph | 4-phenyl-1-naphthyl |
| 1b-48 | Me | Me | Ph | 6-phenyl-2-naphthyl |
| 1b-49 | Me | Me | 4-(1-naphthyl)phenyl | 4-(1-naphthyl)phenyl |
| 1b-50 | Me | Me | 4-(2-naphthyl)phenyl | 4-(2-naphthyl)phenyl |
| 1b-51 | n-Hexyl | n-Hexyl | Ph | Ph |
| 1b-52 | n-Hexyl | n-Hexyl | 4-Me-C₆H₄ | 4-Me-C₆H₄ |
| 1b-53 | n-Hexyl | n-Hexyl | 4-iPr-C₆H₄ | 4-iPr-C₆H₄ |
| 1b-54 | n-Hexyl | n-Hexyl | 4-C(CH₃)₃-C₆H₄ | 4-C(CH₃)₃-C₆H₄ |

-continued 1-b

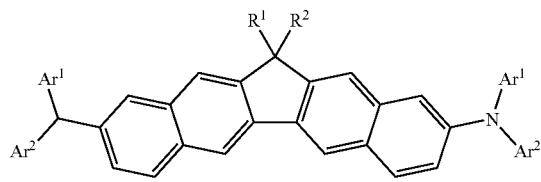

| Compound for example | R¹ | R² | Ar¹ | Ar² |
|---|---|---|---|---|
| 1b-55 | n-Hexyl | n-Hexyl | 2,3,5-trimethylphenyl (Me,Me,Me) | 2,3,5-trimethylphenyl (Me,Me,Me) |
| 1b-56 | n-Hexyl | n-Hexyl | 2-naphthyl | 2-naphthyl |
| 1b-57 | n-Hexyl | n-Hexyl | 1-naphthyl | 1-naphthyl |
| 1b-58 | n-Hexyl | n-Hexyl | 4-biphenyl | 4-biphenyl |
| 1b-59 | n-Octyl | n-Octyl | Ph | Ph |
| 1b-60 | n-Octyl | n-Octyl | 4-Me-phenyl | 4-Me-phenyl |
| 1b-61 | n-Octyl | n-Octyl | 4-isopropyl-phenyl | 4-isopropyl-phenyl |
| 1b-62 | n-Octyl | n-Octyl | 4-C(CH₃)₃-phenyl | 4-C(CH₃)₃-phenyl |
| 1b-63 | n-Octyl | n-Octyl | 2,3,5-trimethylphenyl (Me,Me,Me) | 2,3,5-trimethylphenyl (Me,Me,Me) |
| 1b-64 | n-Octyl | n-Octyl | 2-naphthyl | 2-naphthyl |
| 1b-65 | n-Octyl | n-Octyl | 1-naphthyl | 1-naphthyl |

-continued
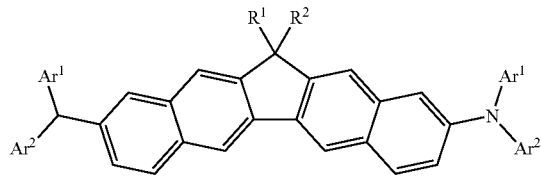
1-b
| Compound for example | R[1] | R[2] | Ar[1] | Ar[2] |
|---|---|---|---|---|
| 1b-66 | 2-ethylhexyl | 2-ethylhexyl | 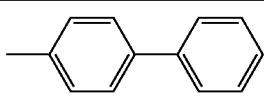 | 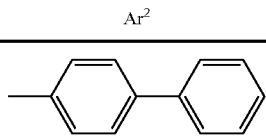 |
| 1b-67 | 2-ethylhexyl | 2-ethylhexyl | Ph | Ph |
| 1b-68 | 2-ethylhexyl | 2-ethylhexyl | 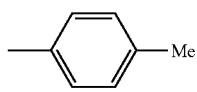 | 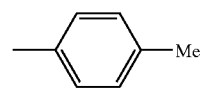 |
| 1b-69 | 2-ethylhexyl | 2-ethylhexyl | 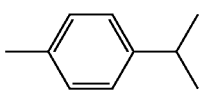 | 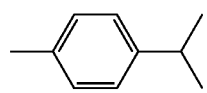 |
| 1b-70 | 2-ethylhexyl | 2-ethylhexyl | 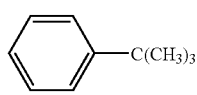 | 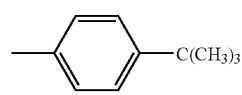 |
| 1b-71 | 2-ethylhexyl | 2-ethylhexyl | 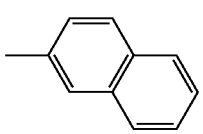 | 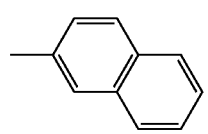 |
| 1b-72 | 2-ethylhexyl | 2-ethylhexyl | 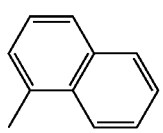 | 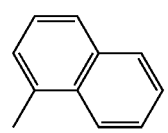 |
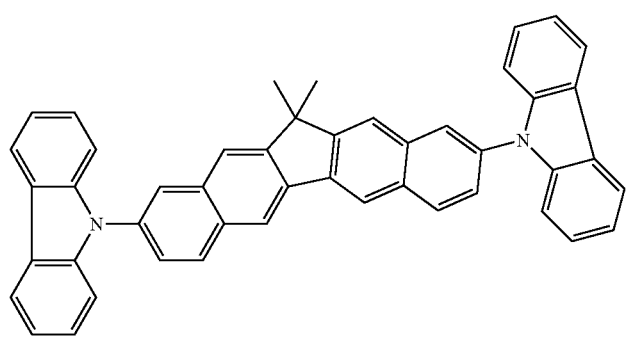
1b-73

-continued
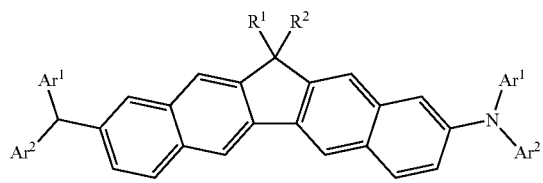
1-b
Compound for example | R¹ | R² | Ar¹ | Ar²
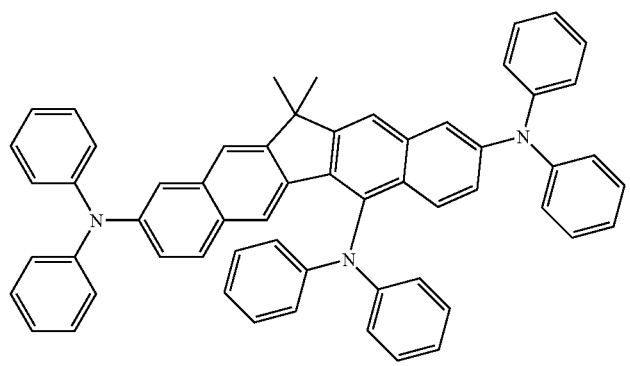
1b-74
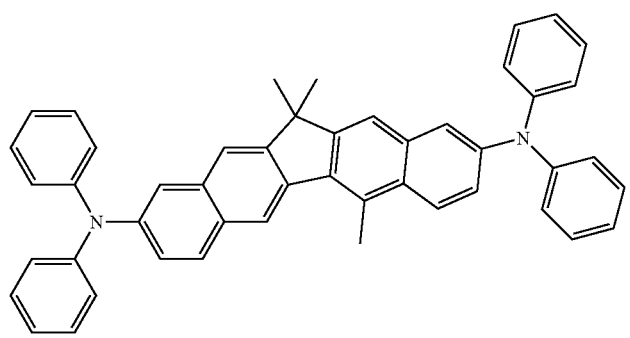
1b-75
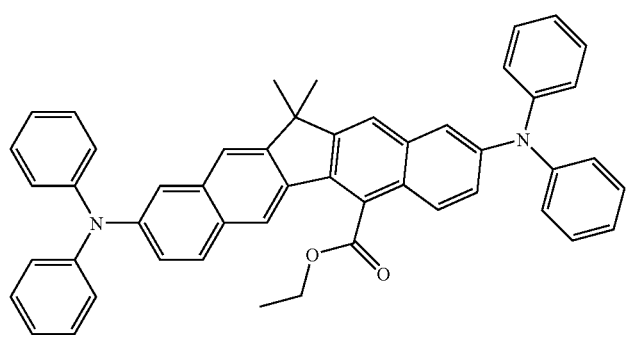
1b-76

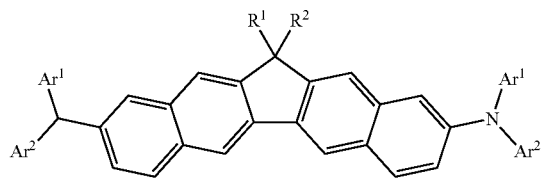
| Compound for example | R¹ | R² | Ar¹ | Ar² |
|---|---|---|---|---|
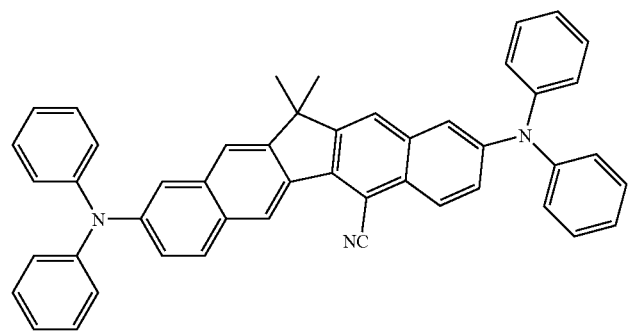
1b-77
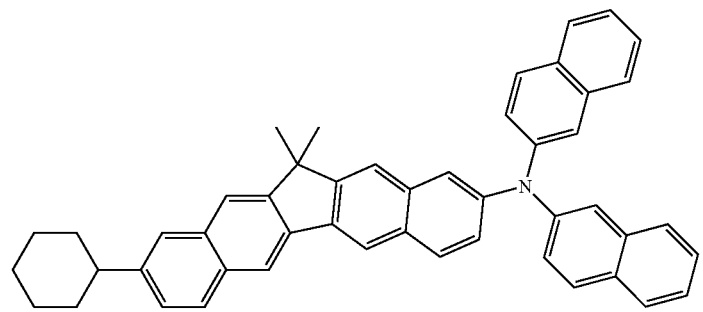
1b-78
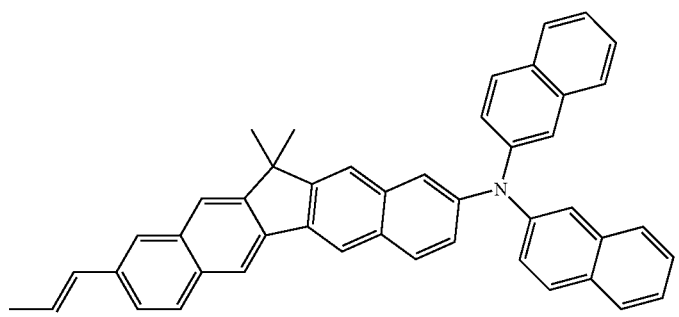
1b-79

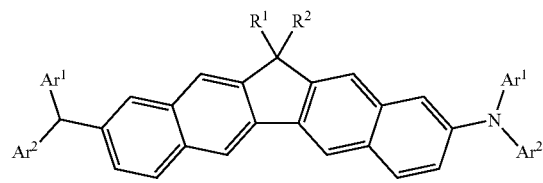
| Compound for example | R¹ | R² | Ar¹ | Ar² |
|---|---|---|---|---|
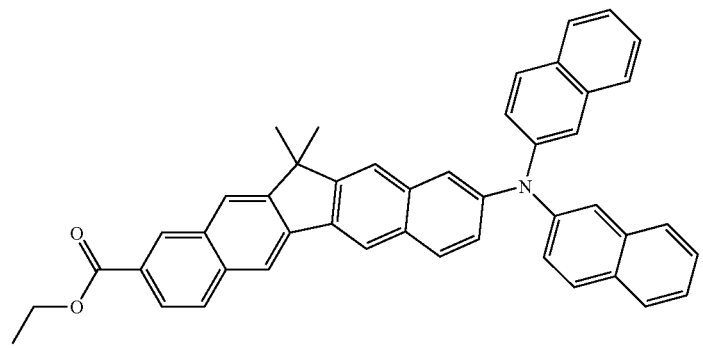
1b-80
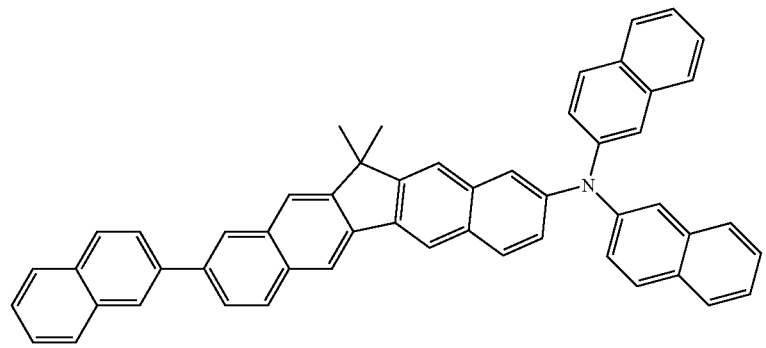
1b-81
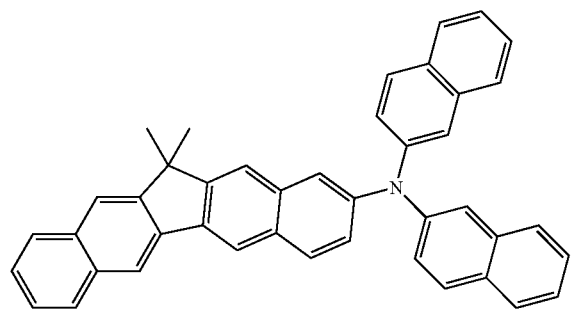
1b-82

-continued
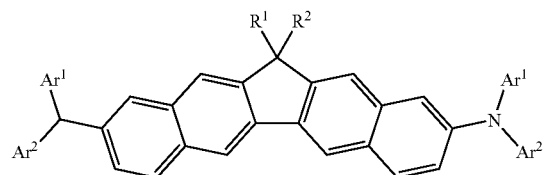
1-b
| Compound for example | R¹ | R² | Ar¹ | Ar² |
|---|---|---|---|---|
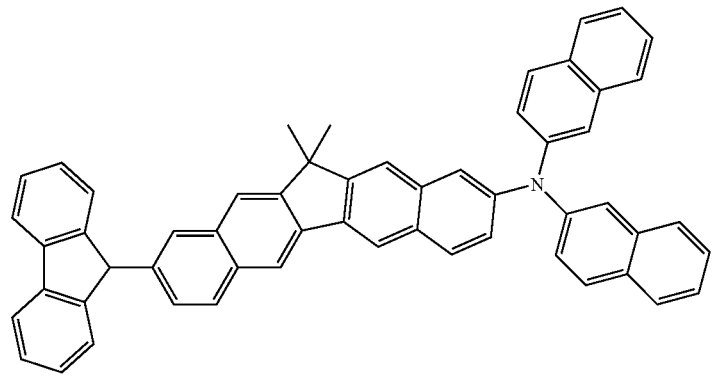
1b-83
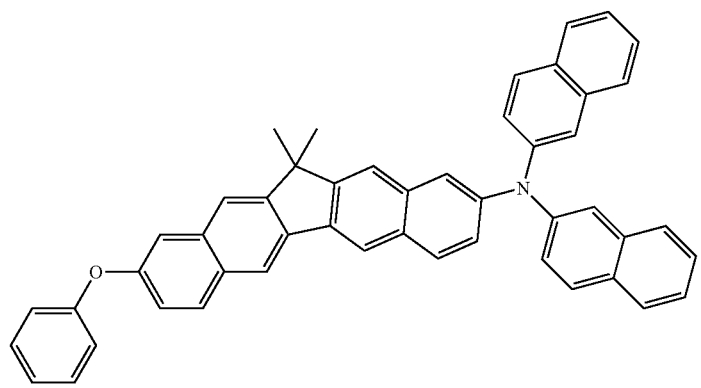
1b-84
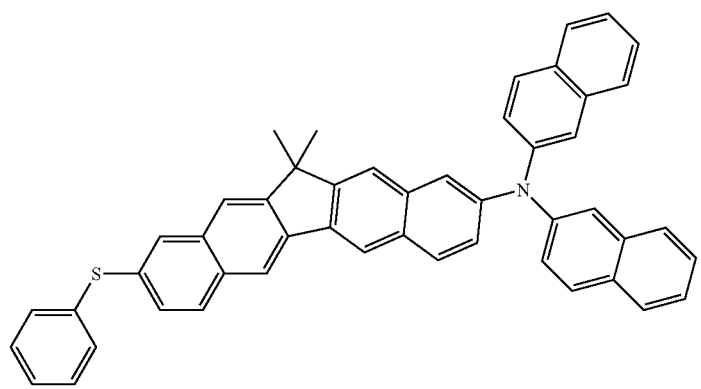
1b-85

-continued
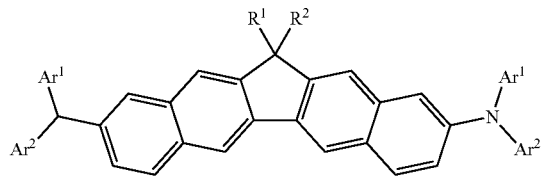
1-b
| Compound for example | R¹ | R² | Ar¹ | Ar² |
|---|---|---|---|---|
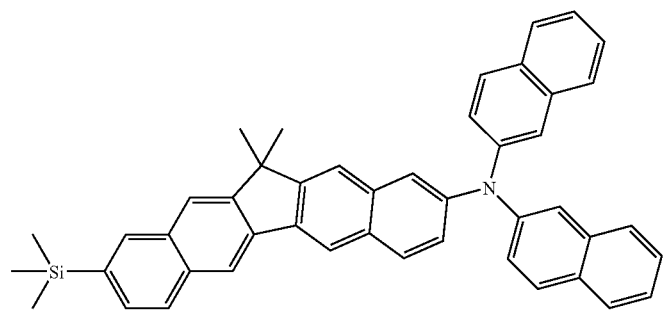
1b-86
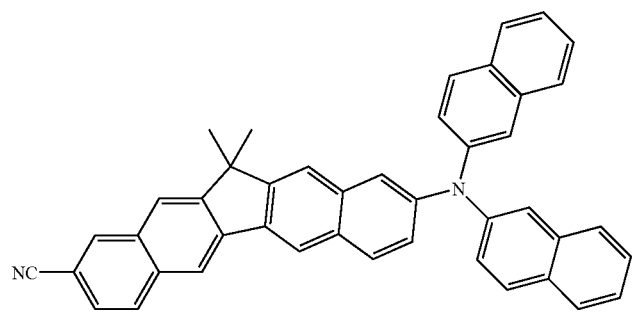
1b-87
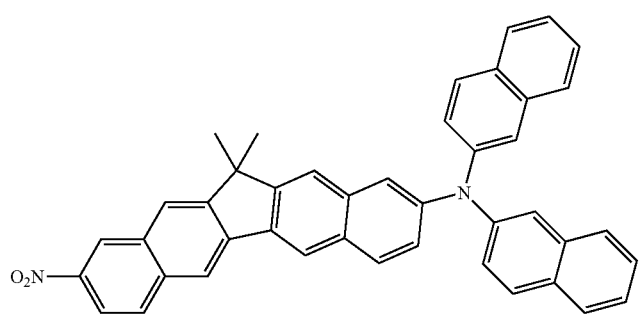
1b-88

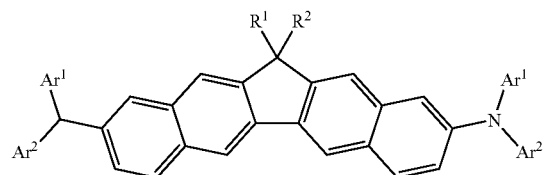
1-b
| Compound for example | R¹ | R² | Ar¹ | Ar² |
|---|---|---|---|---|
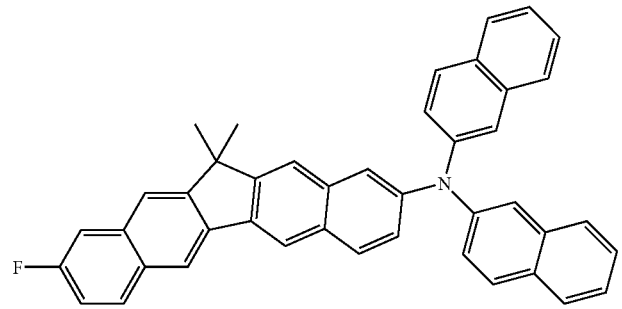
1b-89
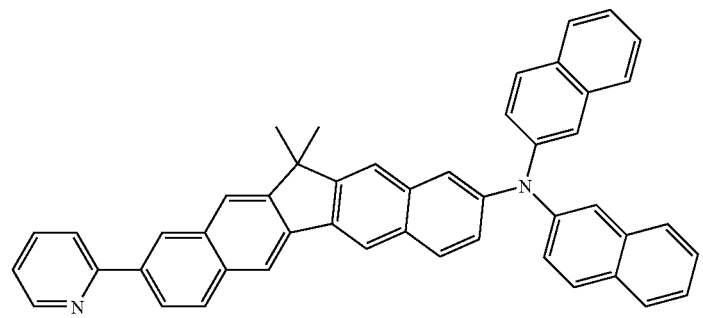
1b-90
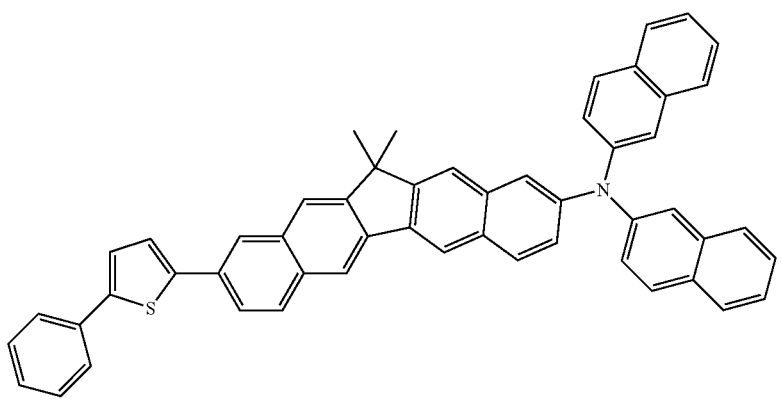
1b-91

-continued
1-b
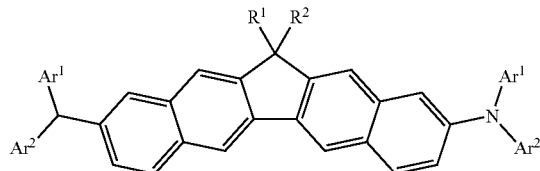
| Compound for example | R¹ | R² | Ar¹ | Ar² |
|---|---|---|---|---|
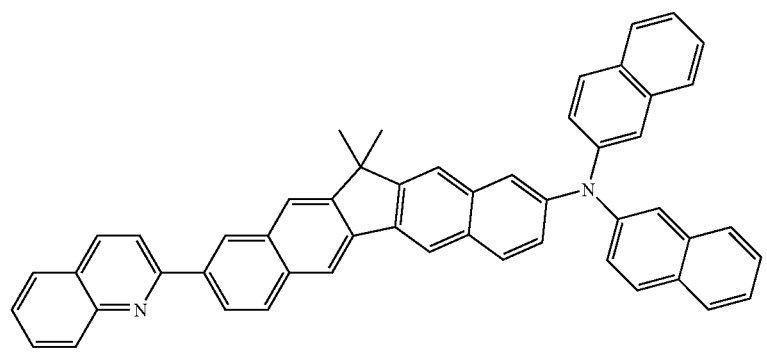
1b-92
1-c
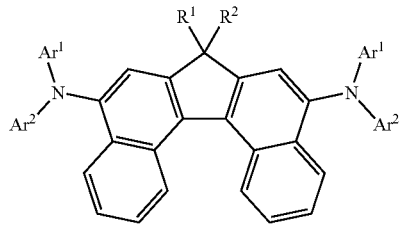
| Compound for example | R¹ | R² | Ar¹ | Ar² |
|---|---|---|---|---|
| 1c-1 | Me | Me | Ph | Ph |
| 1c-2 | Me | Me | Ph | 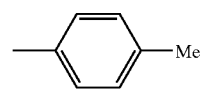 |
| 1c-3 | Me | Me | Ph | 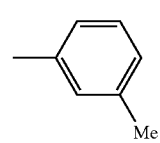 |
| 1c-4 | Me | Me | Ph | 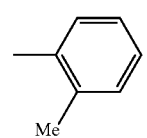 |
| 1c-5 | Me | Me | Ph | 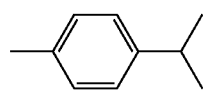 |

-continued
1-c
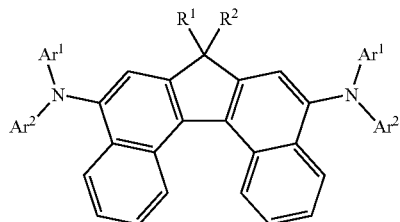
| Compound for example | R¹ | R² | Ar¹ | Ar² |
|---|---|---|---|---|
| 1c-6 | Me | Me | Ph | 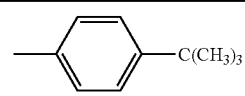 |
| 1c-7 | Me | Me | Ph | 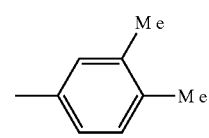 |
| 1c-8 | Me | Me | Ph | 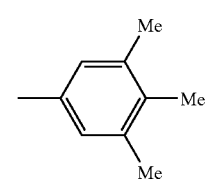 |
| 1c-9 | Me | Me | 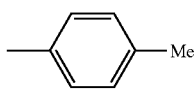 | 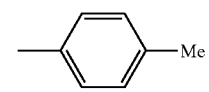 |
| 1c-10 | Me | Me | 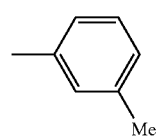 | 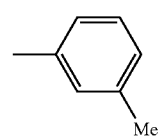 |
| 1c-11 | Me | Me | 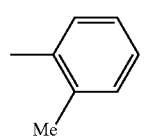 | 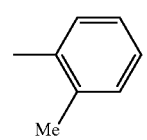 |
| 1c-12 | Me | Me | 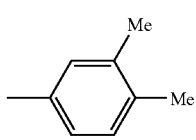 | 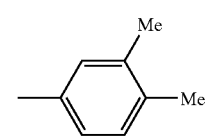 |
| 1c-13 | Me | Me | 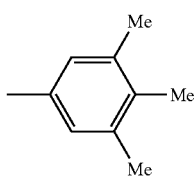 | 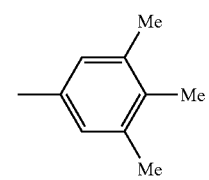 |
| 1c-14 | Me | Me | 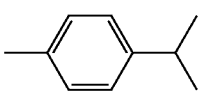 | 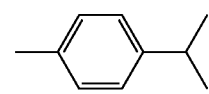 |

-continued
1-c
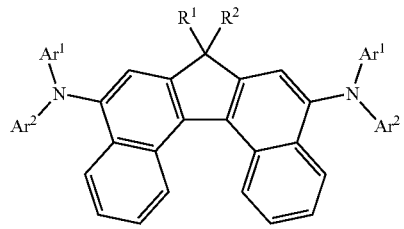
| Compound for example | R¹ | R² | Ar¹ | Ar² |
|---|---|---|---|---|
| 1c-15 | Me | Me | —⟨C6H4⟩—Me (4-Me-phenyl) | —⟨C6H4⟩—iPr (4-isopropyl-phenyl) |
| 1c-16 | Me | Me | Ph | 4-biphenyl |
| 1c-17 | Me | Me | Ph | 3-biphenyl |
| 1c-18 | Me | Me | Ph | 2-biphenyl |
| 1c-19 | Me | Me | Ph | 2-naphthyl |
| 1c-20 | Me | Me | Ph | 1-naphthyl |
| 1c-21 | Me | Me | 4-Me-phenyl | 4-biphenyl |
| 1c-22 | Me | Me | 4-Me-phenyl | 3-biphenyl |

-continued
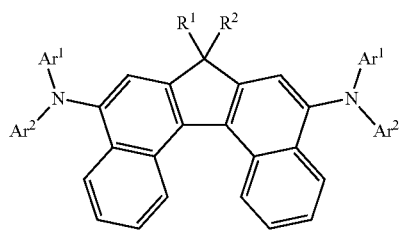
1-c
| Compound for example | R¹ | R² | Ar¹ | Ar² |
|---|---|---|---|---|
| 1c-23 | Me | Me | -C₆H₄-Me (para) | 2-biphenyl |
| 1c-24 | Me | Me | -C₆H₄-Me (para) | 2-naphthyl |
| 1c-25 | Me | Me | -C₆H₄-Me (para) | 1-naphthyl |
| 1c-26 | Me | Me | 4-biphenyl | 4-biphenyl |
| 1c-27 | Me | Me | 3-biphenyl | 3-biphenyl |
| 1c-28 | Me | Me | 2-biphenyl | 2-biphenyl |
| 1c-29 | Me | Me | 2-naphthyl | 2-naphthyl |
| 1c-30 | Me | Me | 1-naphthyl | 1-naphthyl |

-continued
1-c
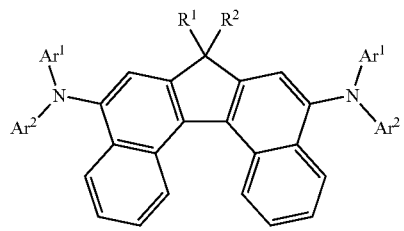
| Compound for example | R¹ | R² | Ar¹ | Ar² |
|---|---|---|---|---|
| 1c-31 | Me | Me | Ph | 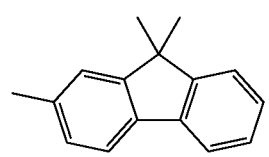 |
| 1c-32 | Me | Me | Ph | 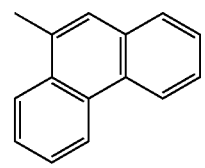 |
| 1c-33 | Me | Me | 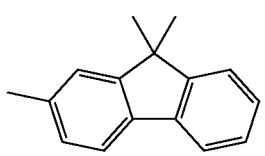 | 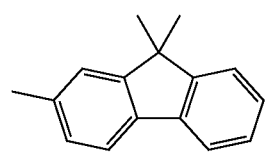 |
| 1c-34 | Me | Me | 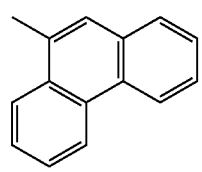 | 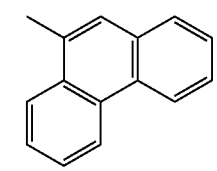 |
| 1c-35 | Me | Me | Ph | 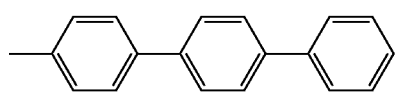 |
| 1c-36 | Me | Me | Ph | 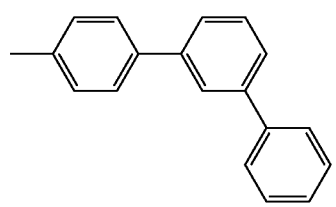 |
| 1c-37 | Me | Me | Ph | 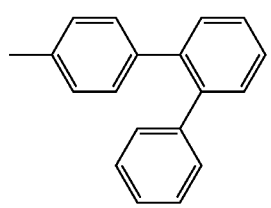 |

-continued
1-c
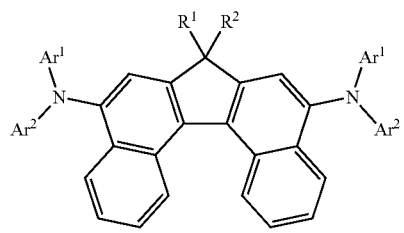
| Compound for example | R¹ | R² | Ar¹ | Ar² |
|---|---|---|---|---|
| 1c-38 | Me | Me | Ph | *m-terphenyl (3,3')* |
| 1c-39 | Me | Me | Ph | *terphenyl isomer* |
| 1c-40 | Me | Me | Ph | *terphenyl isomer* |
| 1c-41 | Me | Me | Ph | *terphenyl isomer* |
| 1c-42 | Me | Me | Ph | *o-terphenyl* |
| 1c-43 | Me | Me | Ph | *phenanthrenyl* |
| 1c-44 | Me | Me | Ph | *pyrenyl* |

-continued
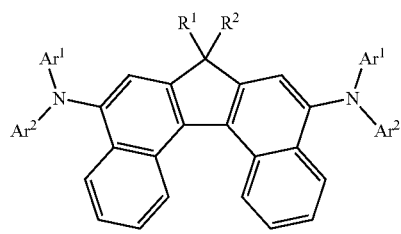
1-c
| Compound for example | R¹ | R² | Ar¹ | Ar² |
|---|---|---|---|---|
| 1c-45 | Me | Me | Ph | 4-(1-naphthyl)phenyl |
| 1c-46 | Me | Me | Ph | 4-(2-naphthyl)phenyl |
| 1c-47 | Me | Me | Ph | 4-phenyl-1-naphthyl |
| 1c-48 | Me | Me | Ph | 6-phenyl-2-naphthyl |
| 1c-49 | Me | Me | 4-(1-naphthyl)phenyl | 4-(1-naphthyl)phenyl |
| 1c-50 | Me | Me | 4-(2-naphthyl)phenyl | 4-(2-naphthyl)phenyl |
| 1c-51 | n-Hexyl | n-Hexyl | Ph | Ph |
| 1c-52 | n-Hexyl | n-Hexyl | 4-Me-C₆H₄ | 4-Me-C₆H₄ |
| 1c-53 | n-Hexyl | n-Hexyl | 4-iPr-C₆H₄ | 4-iPr-C₆H₄ |
| 1c-54 | n-Hexyl | n-Hexyl | 4-C(CH₃)₃-C₆H₄ | 4-C(CH₃)₃-C₆H₄ |

-continued 1-c

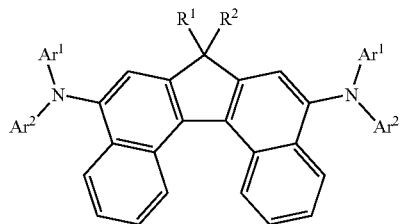

| Compound for example | R¹ | R² | Ar¹ | Ar² |
|---|---|---|---|---|
| 1c-55 | n-Hexyl | n-Hexyl | 2,4,6-trimethylphenyl | 2,4,6-trimethylphenyl |
| 1c-56 | n-Hexyl | n-Hexyl | 2-naphthyl | 2-naphthyl |
| 1c-57 | n-Hexyl | n-Hexyl | 1-naphthyl | 1-naphthyl |
| 1c-58 | n-Hexyl | n-Hexyl | 4-biphenyl | 4-biphenyl |
| 1c-59 | n-Octyl | n-Octyl | Ph | Ph |
| 1c-60 | n-Octyl | n-Octyl | 4-methylphenyl | 4-methylphenyl |
| 1c-61 | n-Octyl | n-Octyl | 4-isopropylphenyl | 4-isopropylphenyl |
| 1c-62 | n-Octyl | n-Octyl | 4-C(CH₃)₃-phenyl | 4-C(CH₃)₃-phenyl |
| 1c-63 | n-Octyl | n-Octyl | 2,4,6-trimethylphenyl | 2,4,6-trimethylphenyl |
| 1c-64 | n-Octyl | n-Octyl | 2-naphthyl | 2-naphthyl |

-continued 1-c

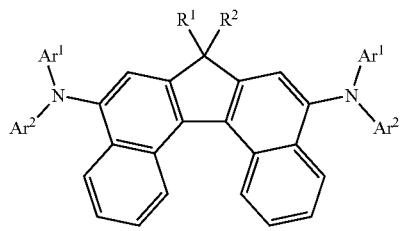

| Compound for example | R¹ | R² | Ar¹ | Ar² |
|---|---|---|---|---|
| 1c-65 | n-Octyl | n-Octyl | 1-methylnaphthyl | 1-methylnaphthyl |
| 1c-66 | 2-ethylhexyl | 2-ethylhexyl | 4-biphenyl | 4-biphenyl |
| 1c-67 | 2-ethylhexyl | 2-ethylhexyl | Ph | Ph |
| 1c-68 | 2-ethylhexyl | 2-ethylhexyl | 4-Me-C₆H₄ | 4-Me-C₆H₄ |
| 1c-69 | 2-ethylhexyl | 2-ethylhexyl | 4-iPr-C₆H₄ | 4-iPr-C₆H₄ |
| 1c-70 | 2-ethylhexyl | 2-ethylhexyl | 4-tBu-C₆H₄ | 4-tBu-C₆H₄ |
| 1c-71 | 2-ethylhexyl | 2-ethylhexyl | 2-naphthyl | 2-naphthyl |
| 1c-72 | 2-ethylhexyl | 2-ethylhexyl | 4-methylphenanthryl | 1-methylnaphthyl |

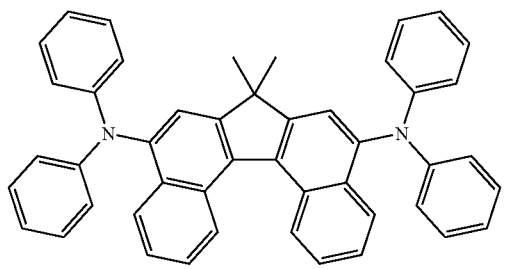

1c-73

-continued
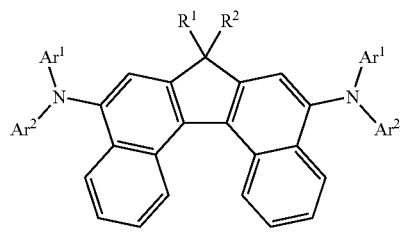
1-c
| Compound for example | R¹ | R² | Ar¹ | Ar² |
|---|---|---|---|---|
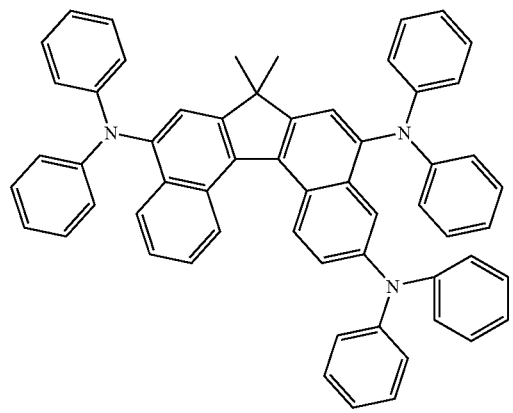
1c-74
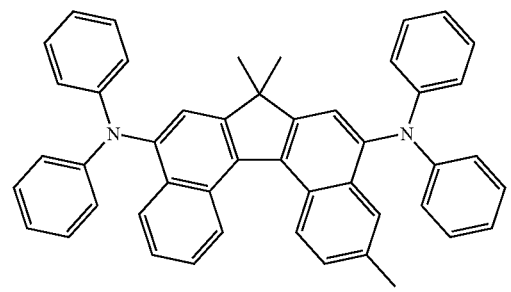
1c-75
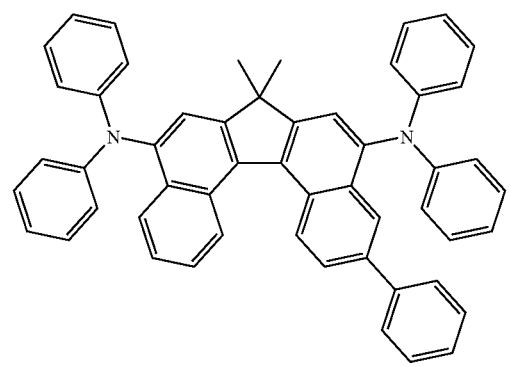
1c-76

-continued
1-c
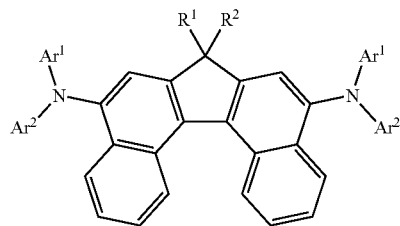
| Compound for example | R¹ | R² | Ar¹ | Ar² |
|---|---|---|---|---|
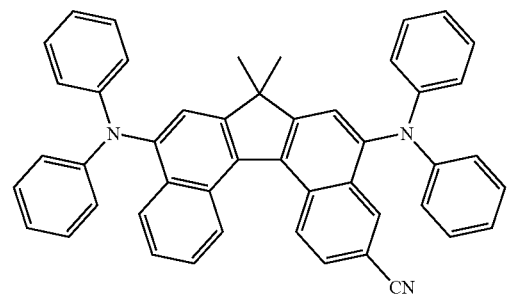
1c-77
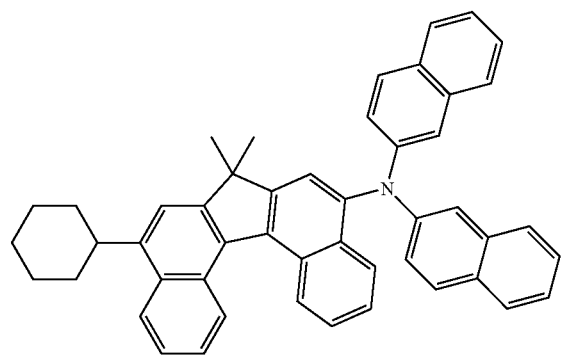
1c-78
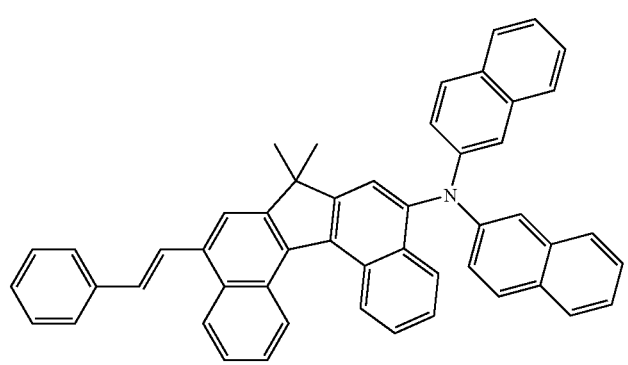
1c-79

-continued
1-c
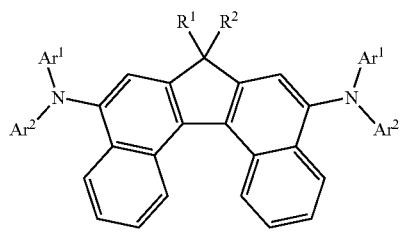
| Compound for example | R[1] | R[2] | Ar[1] | Ar[2] |
|---|---|---|---|---|
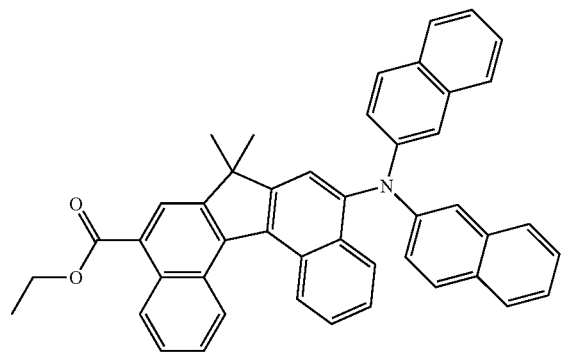
1c-80
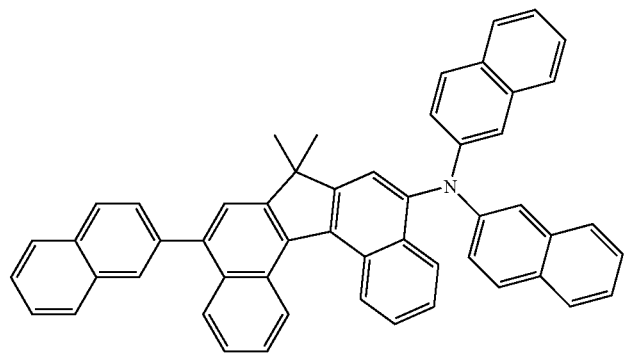
1c-81
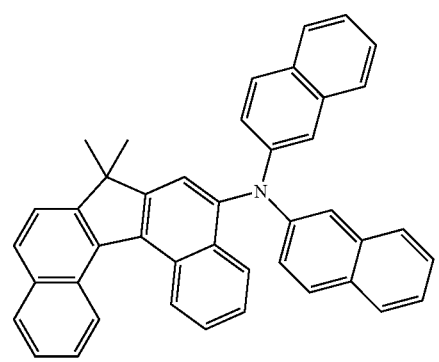
1c-82

1-c
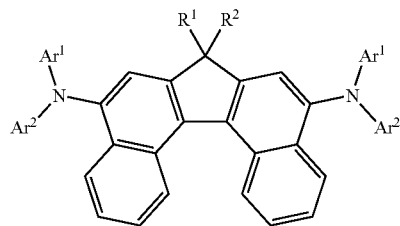
| Compound for example | R¹ | R² | Ar¹ | Ar² |
|---|---|---|---|---|
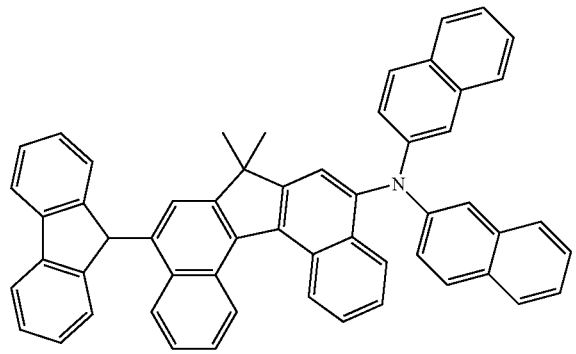
1c-83
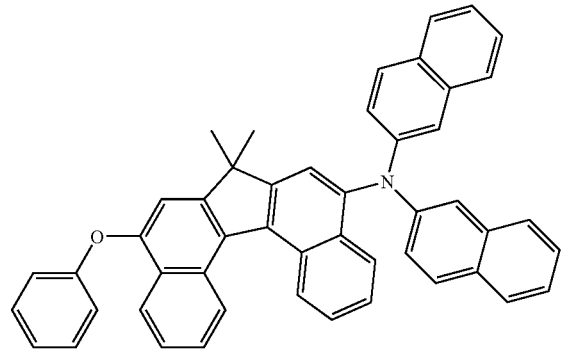
1c-84
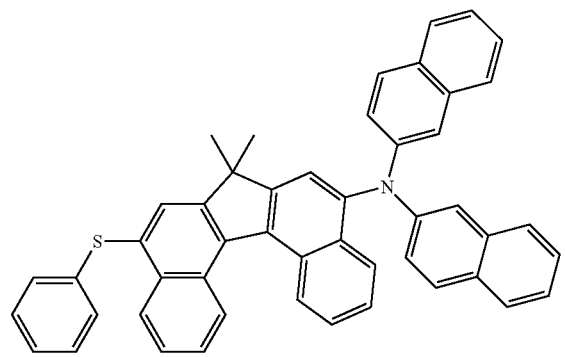
1c-85

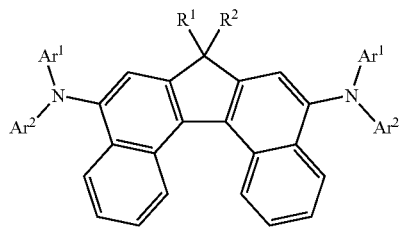
1-c
| Compound for example | R¹ | R² | Ar¹ | Ar² |
|---|---|---|---|---|
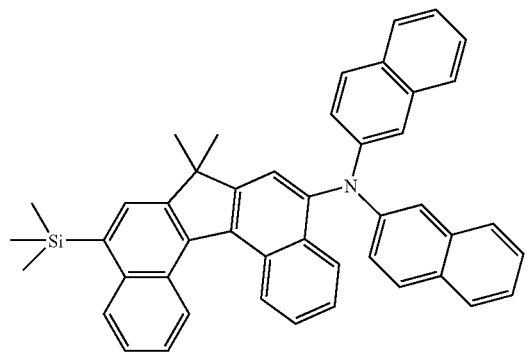
1c-86
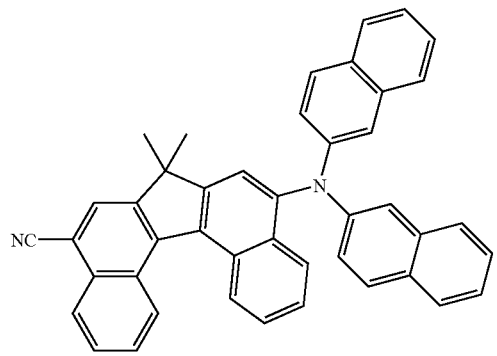
1c-87
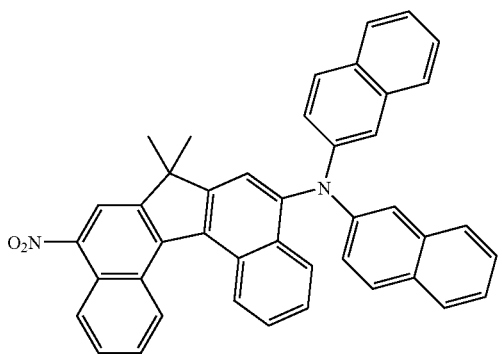
1c-88

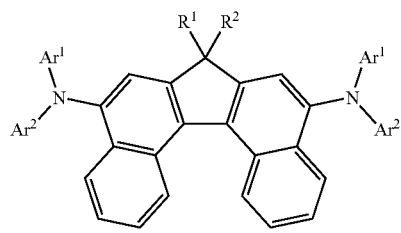
1-c
| Compound for example | R¹ | R² | Ar¹ | Ar² |
|---|---|---|---|---|
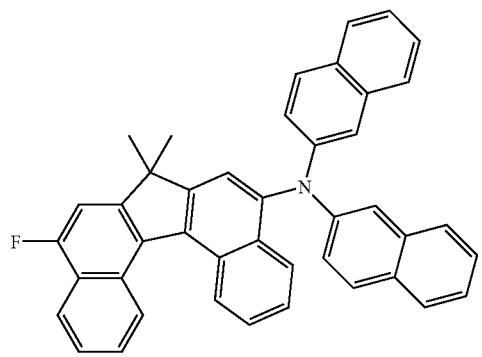
1c-89
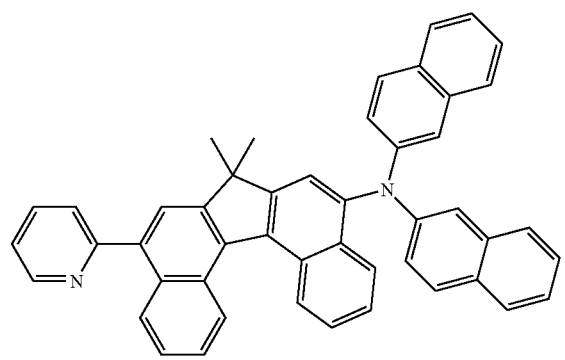
1c-90
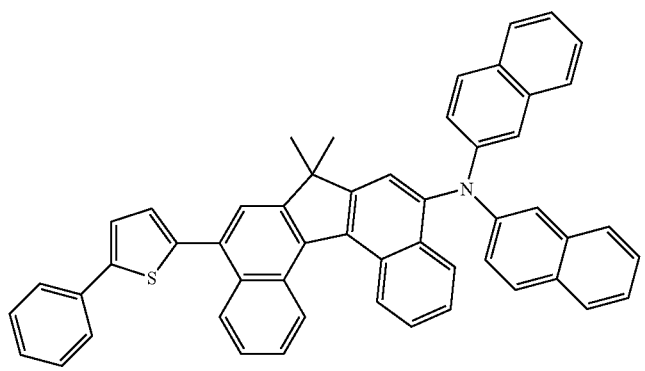
1c-91

1-c
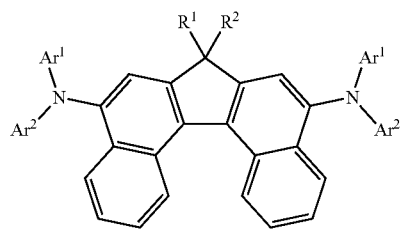
| Compound for example | R¹ | R² | Ar¹ | Ar² |
|---|---|---|---|---|
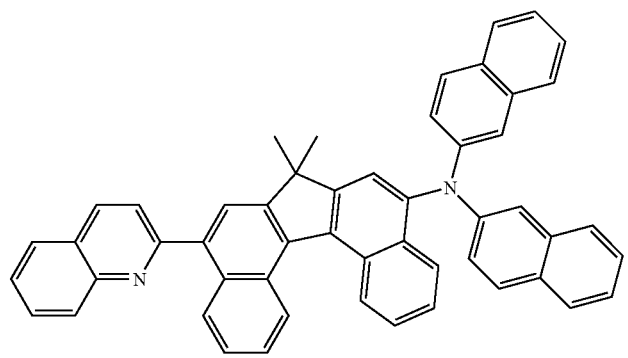
1c-92
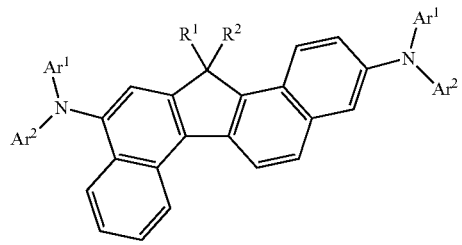
1-d
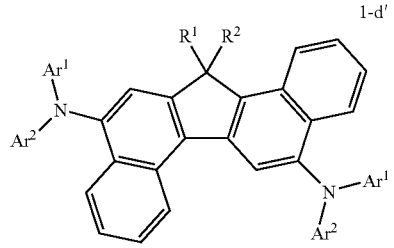
1-d'
| Compound for example | R¹ | R² | Ar¹ | Ar² |
|---|---|---|---|---|
| 1d-1 | Me | Me | Ph | Ph |
| 1d-2 | Me | Me | Ph | 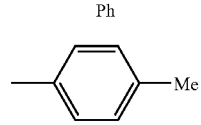 |
| 1d-3 | Me | Me | Ph | 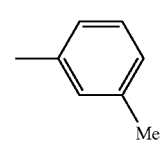 |
| 1d-4 | Me | Me | Ph | 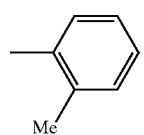 |

-continued
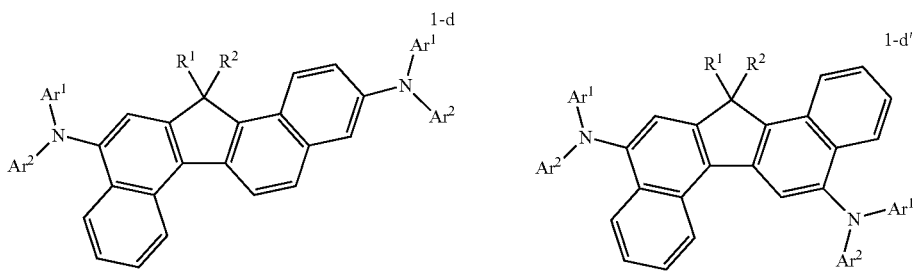
| Compound for example | R¹ | R² | Ar¹ | Ar² |
|---|---|---|---|---|
| 1d-5 | Me | Me | Ph | 4-isopropylphenyl |
| 1d-6 | Me | Me | Ph | 4-C(CH₃)₃-phenyl |
| 1d-7 | Me | Me | Ph | 2,4-Me₂-phenyl |
| 1d-8 | Me | Me | Ph | 2,3,4-Me₃-phenyl |
| 1d-9 | Me | Me | 4-Me-phenyl | 4-Me-phenyl |
| 1d-10 | Me | Me | 3-Me-phenyl | 3-Me-phenyl |
| 1d-11 | Me | Me | 2,3-Me₂-phenyl | 2,3-Me₂-phenyl |
| 1d-12 | Me | Me | 2,4-Me₂-phenyl | 2,4-Me₂-phenyl |
| 1d-13 | Me | Me | 2,3,4-Me₃-phenyl | 2,3,4-Me₃-phenyl |

-continued
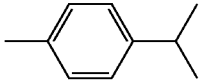
1-d
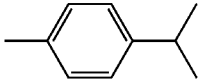
1-d'
| Compound for example | R¹ | R² | Ar¹ | Ar² |
|---|---|---|---|---|
| 1d-14 | Me | Me | 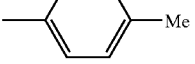 | 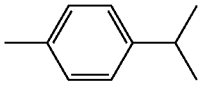 |
| 1d-15 | Me | Me | 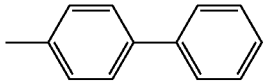 | 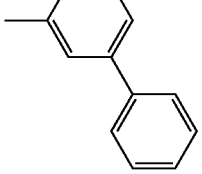 |
| 1d-16 | Me | Me | Ph | 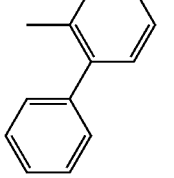 |
| 1d-17 | Me | Me | Ph | 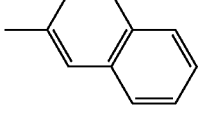 |
| 1d-18 | Me | Me | Ph | 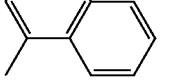 |
| 1d-19 | Me | Me | Ph | 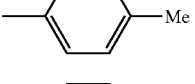 |
| 1d-20 | Me | Me | Ph | 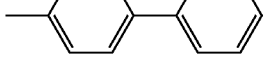 |
| 1d-21 | Me | Me | 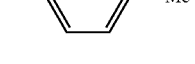 | 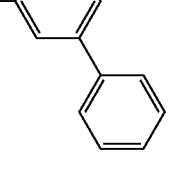 |
| 1d-22 | Me | Me | | |

-continued
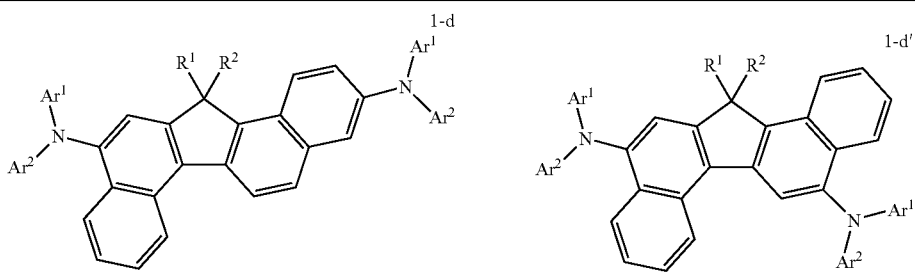
| Compound for example | R¹ | R² | Ar¹ | Ar² |
|---|---|---|---|---|
| 1d-23 | Me | Me | 4-MeC₆H₄ | 2-biphenyl |
| 1d-24 | Me | Me | 4-MeC₆H₄ | 2-naphthyl |
| 1d-25 | Me | Me | 4-MeC₆H₄ | 1-naphthyl |
| 1d-26 | Me | Me | 4-biphenyl | 4-biphenyl |
| 1d-27 | Me | Me | 3-biphenyl | 3-biphenyl |
| 1d-28 | Me | Me | 2-biphenyl | 2-biphenyl |
| 1d-29 | Me | Me | 2-naphthyl | 2-naphthyl |
| 1d-30 | Me | Me | 1-naphthyl | 1-naphthyl |

-continued
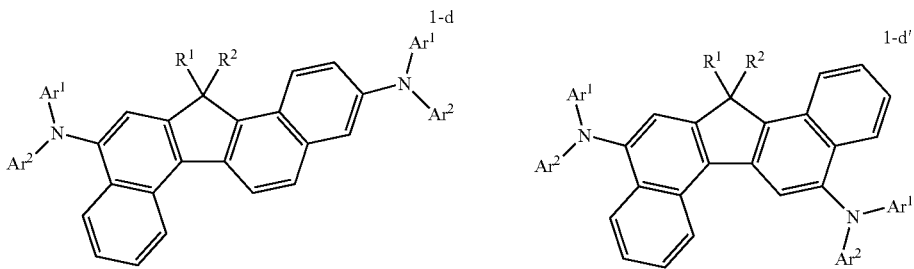
| Compound for example | R¹ | R² | Ar¹ | Ar² |
|---|---|---|---|---|
| 1d-31 | Me | Me | Ph | 9,9-dimethyl-2-fluorenyl |
| 1d-32 | Me | Me | Ph | phenanthrenyl |
| 1d-33 | Me | Me | 9,9-dimethyl-2-fluorenyl | 9,9-dimethyl-2-fluorenyl |
| 1d-34 | Me | Me | phenanthrenyl | phenanthrenyl |
| 1d-35 | Me | Me | Ph | p-terphenyl |
| 1d-36 | Me | Me | Ph | m,p-terphenyl |
| 1d-37 | Me | Me | Ph | o,p-terphenyl |

-continued
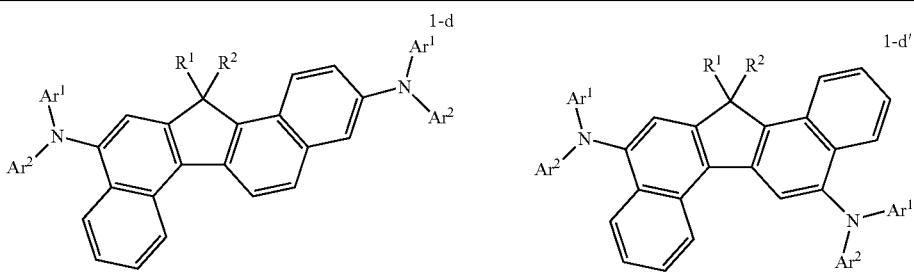
| Compound for example | R¹ | R² | Ar¹ | Ar² |
|---|---|---|---|---|
| 1d-38 | Me | Me | Ph | *m-terphenyl-3-yl* |
| 1d-39 | Me | Me | Ph | *o-terphenyl-3'-yl* |
| 1d-40 | Me | Me | Ph | *p-terphenyl-2-yl* |
| 1d-41 | Me | Me | Ph | *m-terphenyl-2'-yl* |
| 1d-42 | Me | Me | Ph | *biphenyl-2-yl substituted* |
| 1d-43 | Me | Me | Ph | phenanthren-yl |
| 1d-44 | Me | Me | Ph | pyrenyl |

-continued
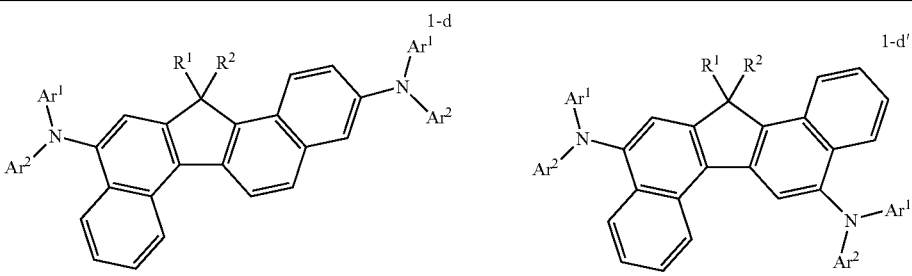
| Compound for example | R¹ | R² | Ar¹ | Ar² |
|---|---|---|---|---|
| 1d-45 | Me | Me | Ph | 4-(1-naphthyl)phenyl |
| 1d-46 | Me | Me | Ph | 4-(2-naphthyl)phenyl |
| 1d-47 | Me | Me | Ph | 4-phenyl-1-naphthyl |
| 1d-48 | Me | Me | Ph | 6-phenyl-2-naphthyl |
| 1d-49 | Me | Me | 4-(1-naphthyl)phenyl | 4-(1-naphthyl)phenyl |
| 1d-50 | Me | Me | 4-(2-naphthyl)phenyl | 4-(2-naphthyl)phenyl |
| 1d-51 | n-Hexyl | n-Hexyl | Ph | Ph |
| 1d-52 | n-Hexyl | n-Hexyl | 4-Me-C₆H₄ | 4-Me-C₆H₄ |
| 1d-53 | n-Hexyl | n-Hexyl | 4-iPr-C₆H₄ | 4-iPr-C₆H₄ |
| 1d-54 | n-Hetyl | n-Hexyl | 4-C(CH₃)₃-C₆H₄ | 4-C(CH₃)₃-C₆H₄ |

-continued

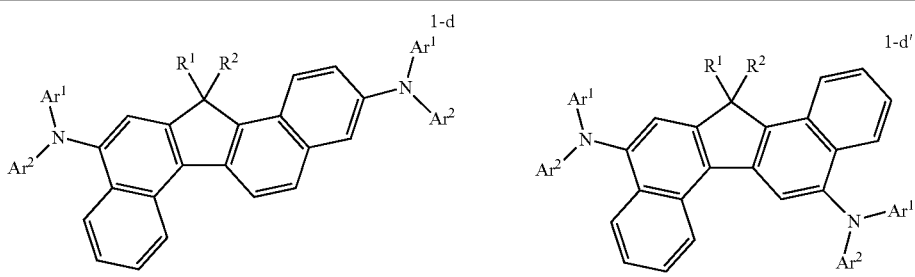

| Compound for example | R¹ | R² | Ar¹ | Ar² |
|---|---|---|---|---|
| 1d-55 | n-Hexyl | n-Hexyl | 2,3,5-trimethylphenyl | 2,3,5-trimethylphenyl |
| 1d-56 | n-Hexyl | n-Hexyl | 2-naphthyl | 2-naphthyl |
| 1d-57 | n-Hexyl | n-Hexyl | 1-methylnaphthyl | 1-methylnaphthyl |
| 1d-58 | n-Hexyl | n-Hexyl | 4-biphenyl | 4-biphenyl |
| 1d-59 | n-Octyl | n-Octyl | Ph | Ph |
| 1d-60 | n-Octyl | n-Octyl | 4-methylphenyl | 4-methylphenyl |
| 1d-61 | n-Octyl | n-Octyl | 4-isopropylphenyl | 4-isopropylphenyl |
| 1d-62 | n-Octyl | n-Octyl | 4-C(CH₃)₃-phenyl | 4-C(CH₃)₃-phenyl |
| 1d-63 | n-Octyl | n-Octyl | 2,3,5-trimethylphenyl | 2,3,5-trimethylphenyl |
| 1d-64 | n-Octyl | n-Octyl | 2-naphthyl | 2-naphthyl |

-continued

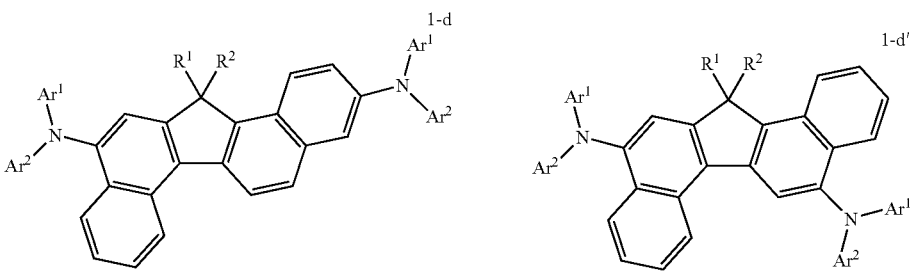

| Compound for example | R¹ | R² | Ar¹ | Ar² |
|---|---|---|---|---|
| 1d-65 | n-Octyl | n-Octyl | 1-naphthyl | 1-naphthyl |
| 1d-66 | 2-ethylhexyl | 2-ethylhexyl | 4-biphenyl | 4-biphenyl |
| 1d-67 | 2-ethylhexyl | 2-ethylhexyl | Ph | Ph |
| 1d-68 | 2-thylhexyl | 2-ethylhexyl | 4-tolyl | 4-tolyl |
| 1d-69 | 2-ethylhexyl | 2-ethylhexyl | 4-isopropylphenyl | 4-isopropylphenyl |
| 1d-70 | 2-ethylhexyl | 2-ethylhexyl | 4-tert-butylphenyl | 4-tert-butylphenyl |
| 1d-71 | 2-ethylhexyl | 2-ethylhexyl | 2-naphthyl | 2-naphthyl |
| 1d-72 | 2-ethylhexyl | 2-ethylhexyl | 1-naphthyl | 1-naphthyl |

*In the foregoing compounds given for the examples, the compounds in which the code d is turned to d' are comopunds given for the examples in Formula 1-d'.

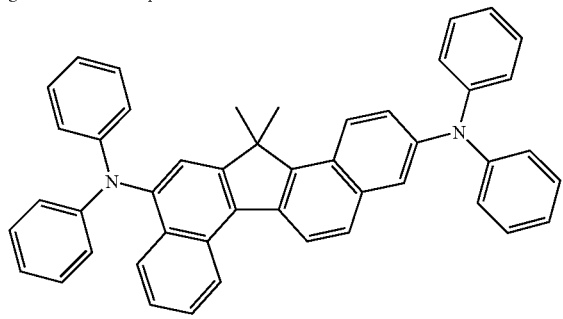

1d-73

-continued
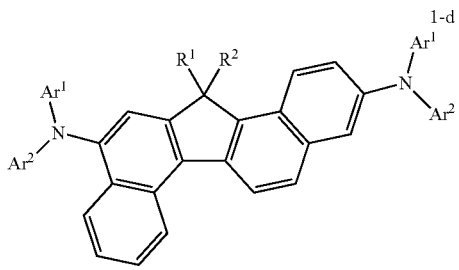
1-d
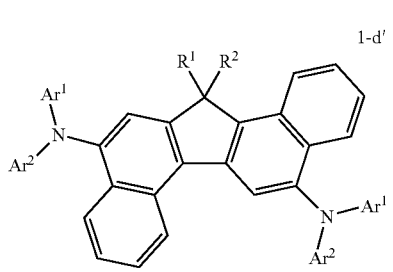
1-d'
| Compound for example | R¹ | R² | Ar¹ | Ar² |
|---|---|---|---|---|
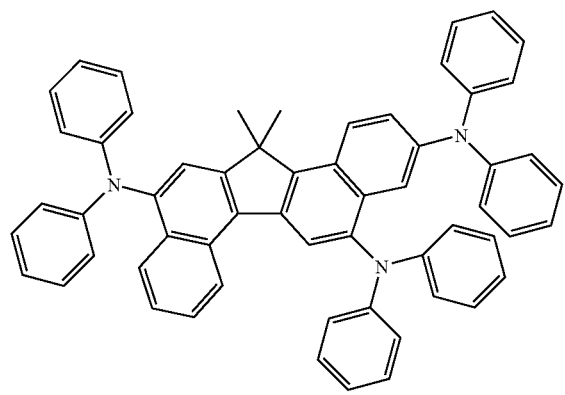
1d-74
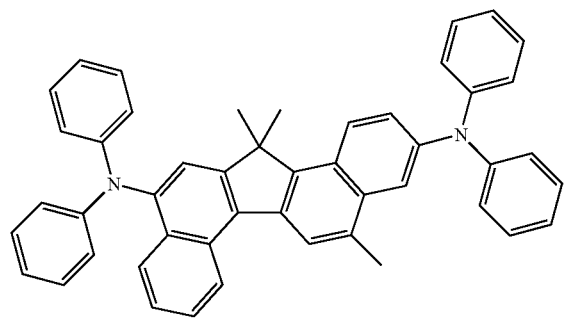
1d-75
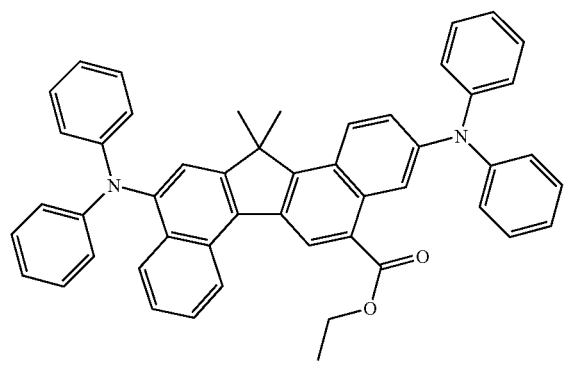
1d-76

-continued
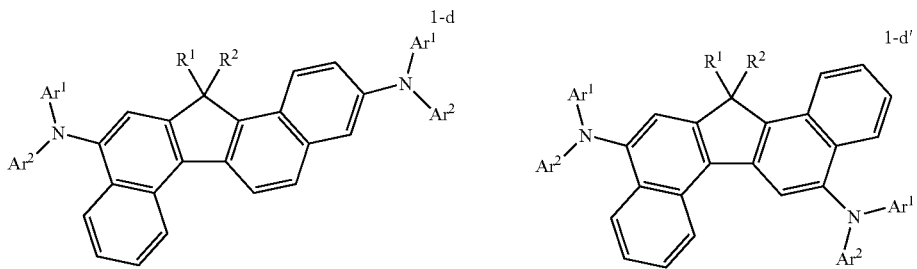
| Compound for example | R[1] | R[2] | Ar[1] | Ar[2] |
|---|---|---|---|---|
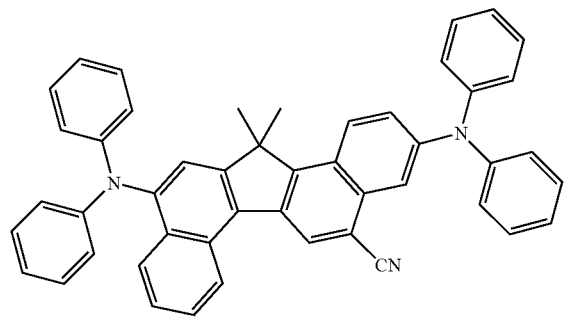
1d-77
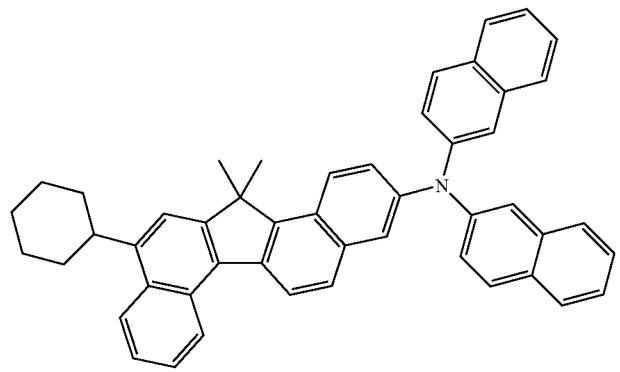
1d-78
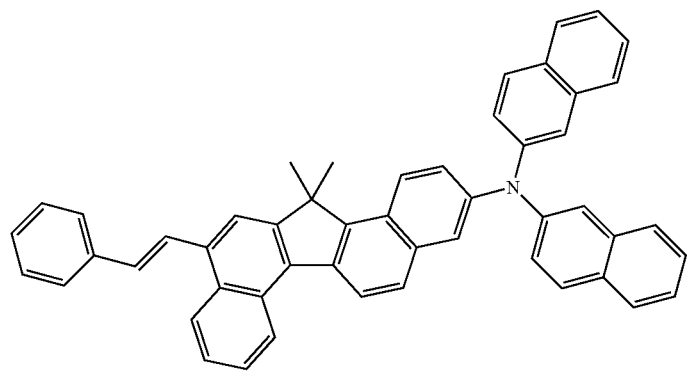
1d-79

-continued
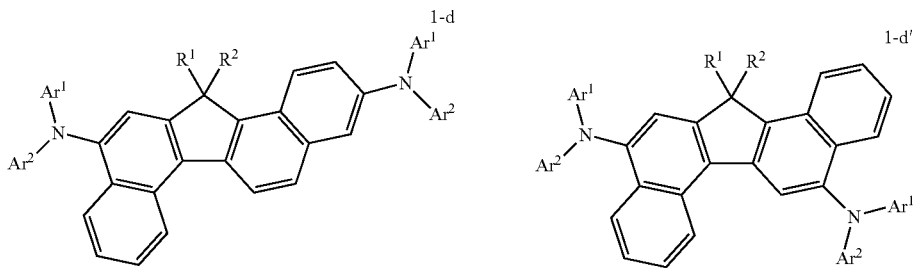
| Compound for example | R¹ | R² | Ar¹ | Ar² |
|---|---|---|---|---|
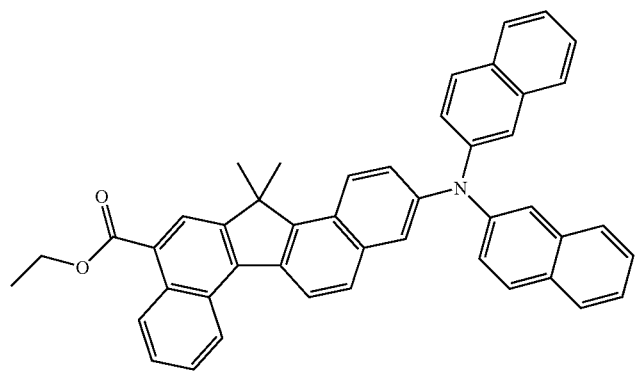
1d-80
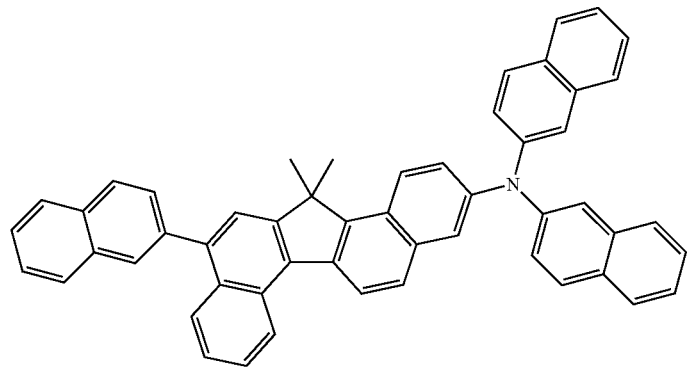
1d-81
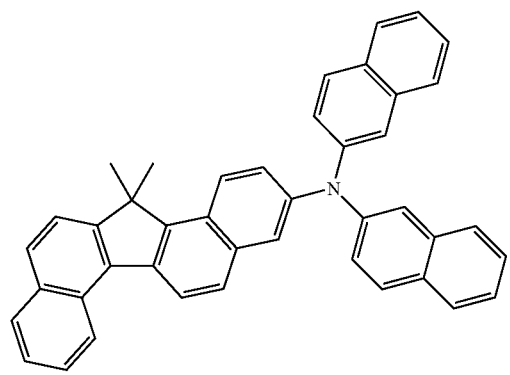
1d-82

-continued
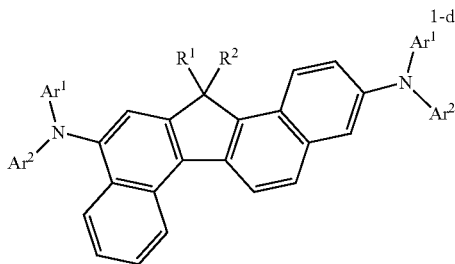
1-d
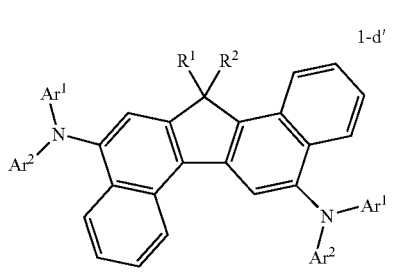
1-d'
| Compound for example | R¹ | R² | Ar¹ | Ar² |
|---|---|---|---|---|
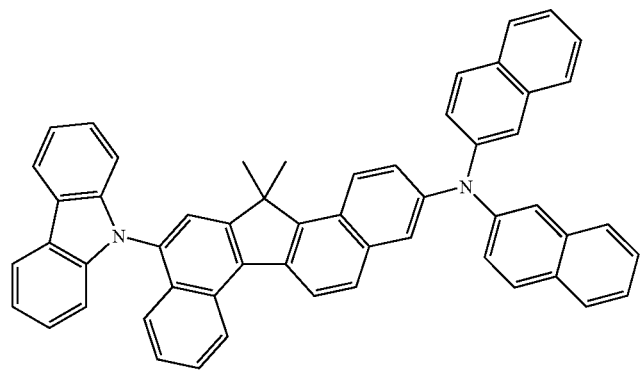
1d-83
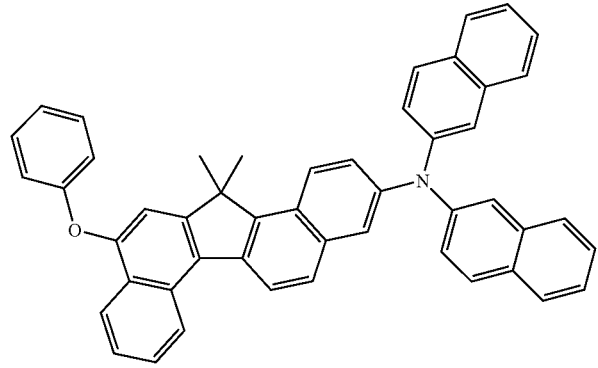
1d-84
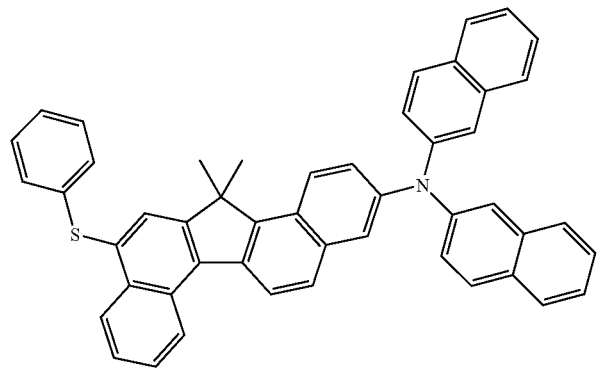
1d-85

-continued
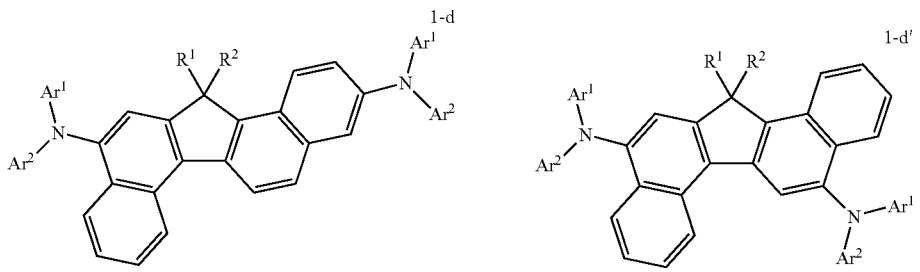
| Compound for example | R¹ | R² | Ar¹ | Ar² |
|---|---|---|---|---|
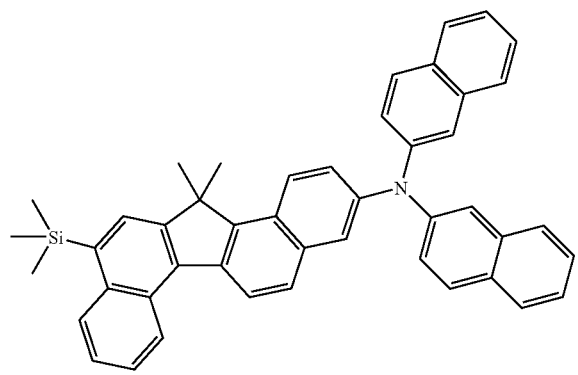
1d-86
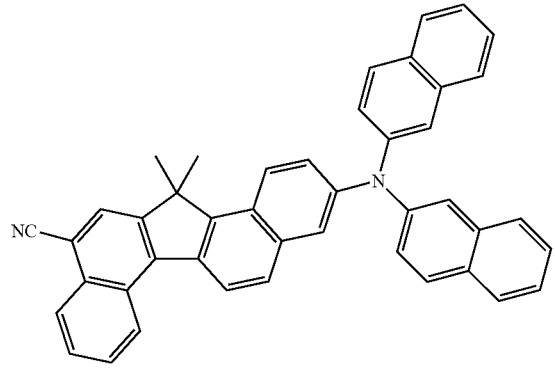
1d-87
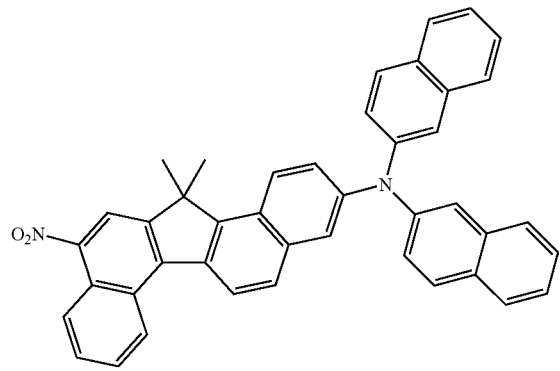
1d-88

-continued
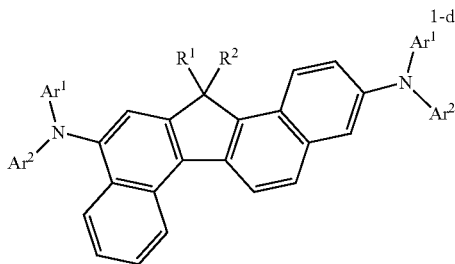
1-d
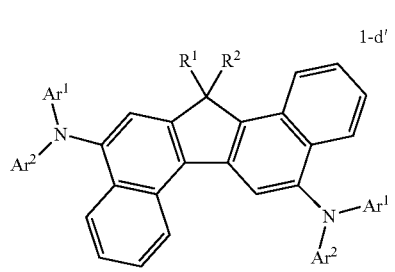
1-d'
| Compound for example | R¹ | R² | Ar¹ | Ar² |
|---|---|---|---|---|
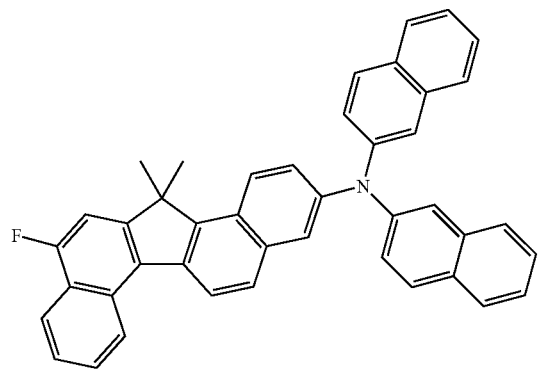
1d-89
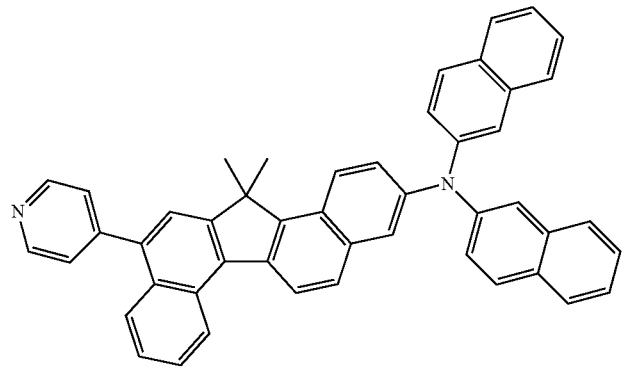
1d-90
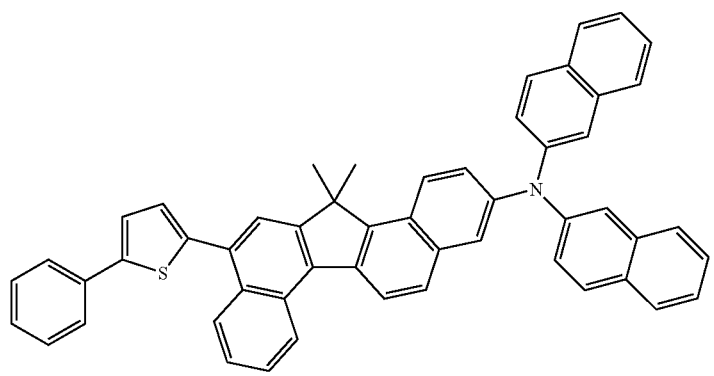
1d-91

-continued
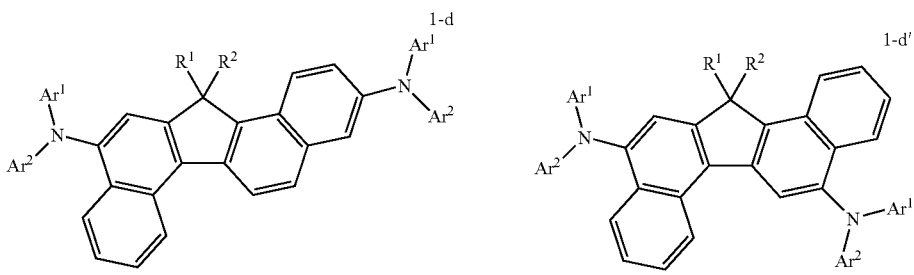
| Compound for example | R¹ | R² | Ar¹ | Ar² |
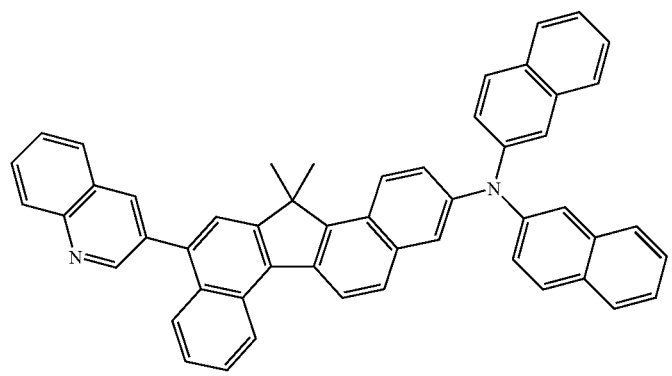
1d-92
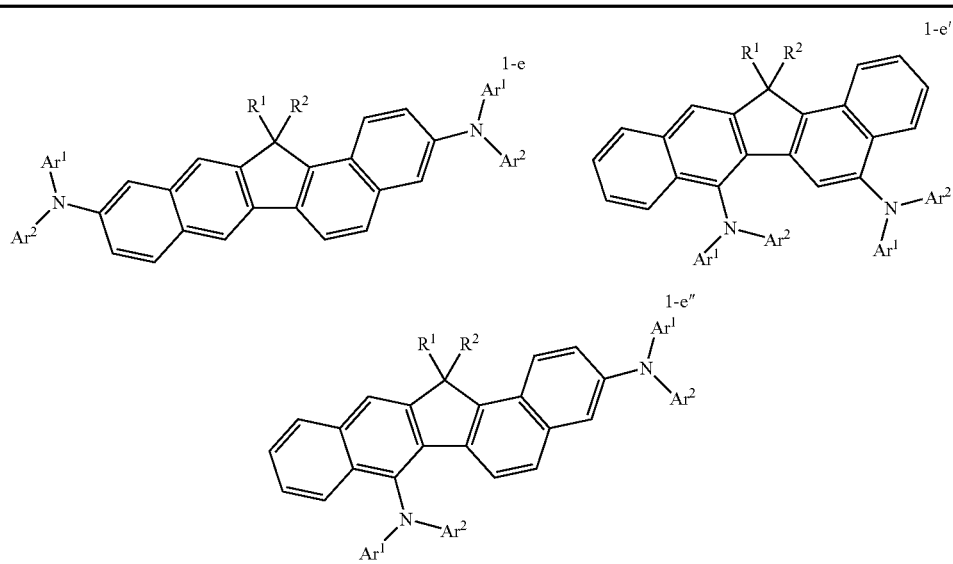
| Compound for example | R¹ | R² | Ar¹ | Ar² |
|---|---|---|---|---|
| 1e-1 | Me | Me | Ph | Ph |
| 1e-2 | Me | Me | Ph | 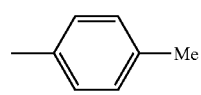 |

-continued
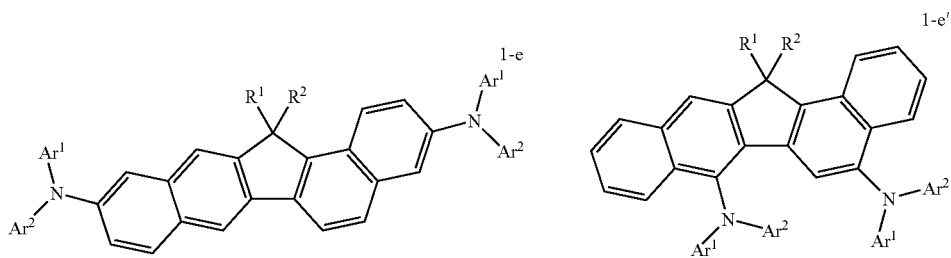
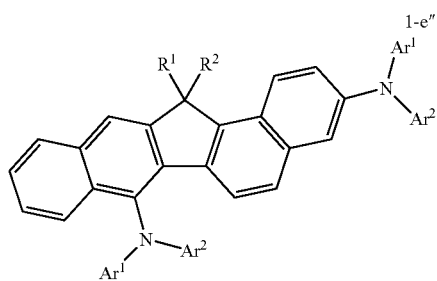
| Compound for example | R¹ | R² | Ar¹ | Ar² |
|---|---|---|---|---|
| 1e-3 | Me | Me | Ph | 3-MeC₆H₄ |
| 1e-4 | Me | Me | Ph | 2-MeC₆H₄ |
| 1e-5 | Me | Me | Ph | 4-iPrC₆H₄ |
| 1e-6 | Me | Me | Ph | 4-tBuC₆H₄ |
| 1e-7 | Me | Me | Ph | 2,4,5-Me₃C₆H₂ |
| 1e-8 | Me | Me | Ph | 2,3,5,6-Me₄C₆H (or 2,3,4,5-Me₄C₆H) |
| 1e-9 | Me | Me | 4-MeC₆H₄ | 4-MeC₆H₄ |

-continued
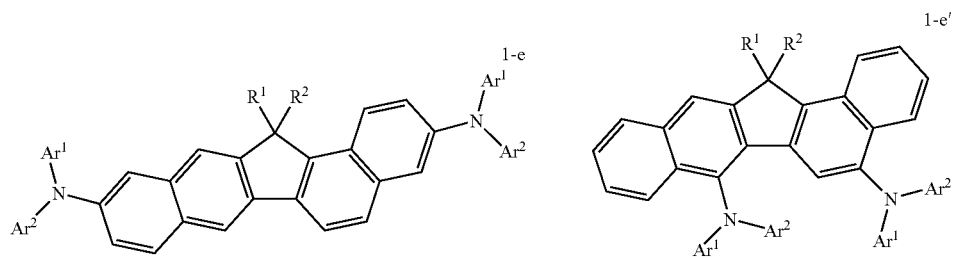
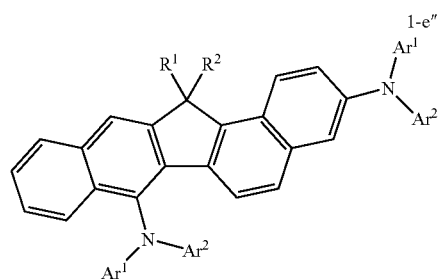
| Compound for example | R¹ | R² | Ar¹ | Ar² |
|---|---|---|---|---|
| 1e-10 | Me | Me | 3-MeC₆H₄ | 3-MeC₆H₄ |
| 1e-11 | Me | Me | 2-MeC₆H₄ | 2-MeC₆H₄ |
| 1e-12 | Me | Me | 2,4,5-trimethylphenyl | 2,4,5-trimethylphenyl |
| 1e-13 | Me | Me | 2,3,4,5-tetramethylphenyl | 2,3,4,5-tetramethylphenyl |
| 1e-14 | Me | Me | 4-iPrC₆H₄ | 4-iPrC₆H₄ |
| 1e-15 | Me | Me | 4-MeC₆H₄ | 4-iPrC₆H₄ |
| 1e-16 | Me | Me | Ph | 4-biphenylyl |

-continued
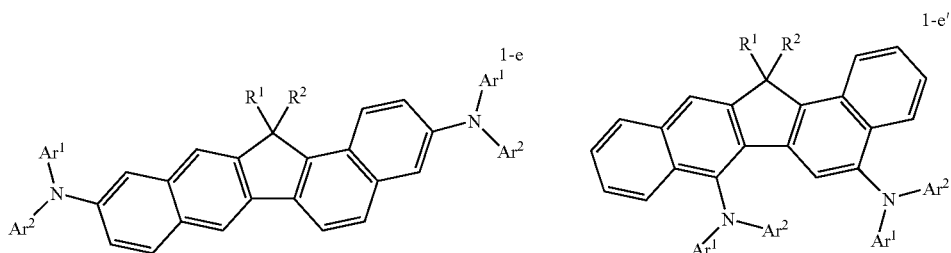
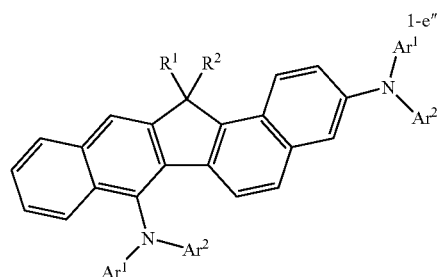
| Compound for example | R¹ | R² | Ar¹ | Ar² |
|---|---|---|---|---|
| 1e-17 | Me | Me | Ph | 3-biphenylyl |
| 1e-18 | Me | Me | Ph | 2-biphenylyl |
| 1e-19 | Me | Me | Ph | 2-naphthyl |
| 1e-20 | Me | Me | Ph | 1-naphthyl |
| 1e-21 | Me | Me | 4-methylphenyl | 4-biphenylyl |
| 1e-22 | Me | Me | 4-methylphenyl | 3-biphenylyl |

-continued
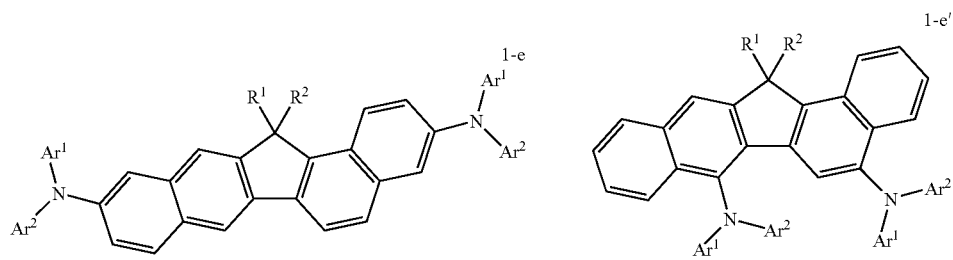
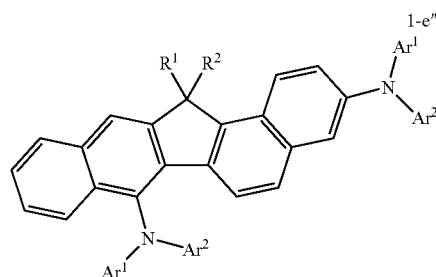
| Compound for example | R¹ | R² | Ar¹ | Ar² |
|---|---|---|---|---|
| 1e-23 | Me | Me | 4-methylphenyl | 2-biphenyl |
| 1e-24 | Me | Me | 4-methylphenyl | 2-naphthyl |
| 1e-25 | Me | Me | 4-methylphenyl | 1-naphthyl |
| 1e-26 | Me | Me | 4-biphenyl | 4-biphenyl |
| 1e-27 | Me | Me | 3-biphenyl | 3-biphenyl |
| 1e-28 | Me | Me | 2-biphenyl (methyl) | 2-biphenyl |

-continued
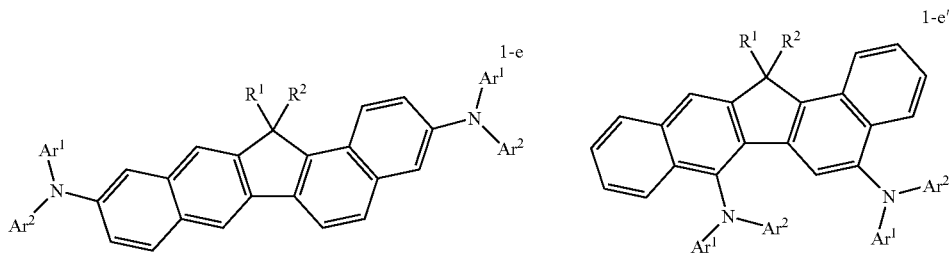
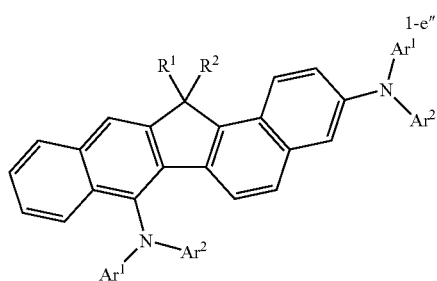
| Compound for example | R¹ | R² | Ar¹ | Ar² |
|---|---|---|---|---|
| 1e-29 | Me | Me | 2-naphthyl | 2-naphthyl |
| 1e-30 | Me | Me | 1-naphthyl | 1-naphthyl |
| 1e-31 | Me | Me | Ph | 9,9-dimethylfluorenyl |
| 1e-32 | Me | Me | Ph | phenanthrenyl |
| 1e-33 | Me | Me | 9,9-dimethylfluorenyl | 9,9-dimethylfluorenyl |
| 1e-34 | Me | Me | phenanthrenyl | phenanthrenyl |

-continued
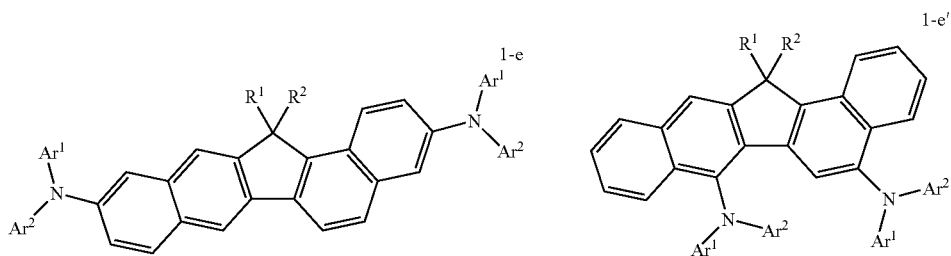
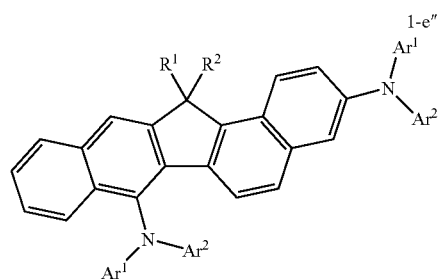
| Compound for example | R¹ | R² | Ar¹ | Ar² |
|---|---|---|---|---|
| 1e-35 | Me | Me | Ph | *p*-terphenyl-4-yl |
| 1e-36 | Me | Me | Ph | 4-(3-phenylphenyl)phenyl |
| 1e-37 | Me | Me | Ph | 4-(2-phenylphenyl)phenyl |
| 1e-38 | Me | Me | Ph | 3-(3-phenylphenyl)phenyl substituted |
| 1e-39 | Me | Me | Ph | 3-(2-phenylphenyl)phenyl |

-continued
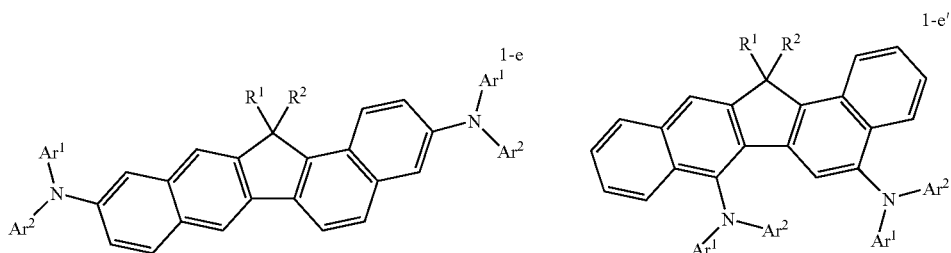
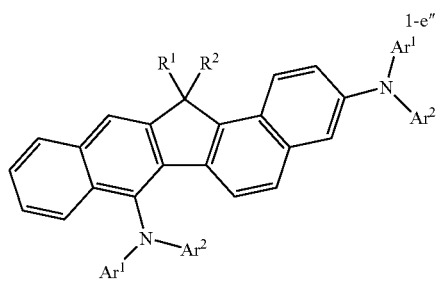
| Compound for example | R¹ | R² | Ar¹ | Ar² |
|---|---|---|---|---|
| 1e-40 | Me | Me | Ph | ![structure] |
| 1e-41 | Me | Me | Ph | ![structure] |
| 1e-42 | Me | Me | Ph | ![structure] |
| 1e-43 | Me | Me | Ph | ![structure] |
| 1e-44 | Me | Me | Ph | ![structure] |
| 1e-45 | Me | Me | Ph | ![structure] |

-continued
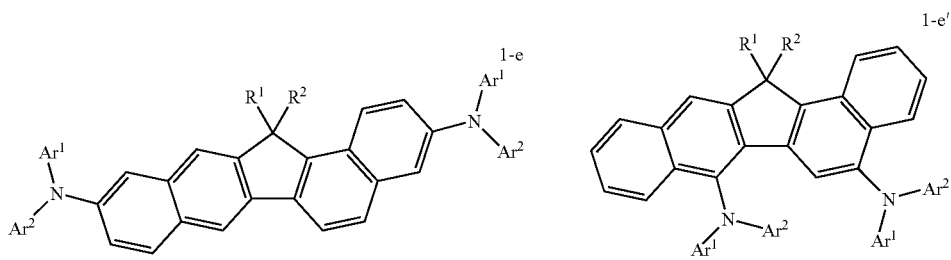
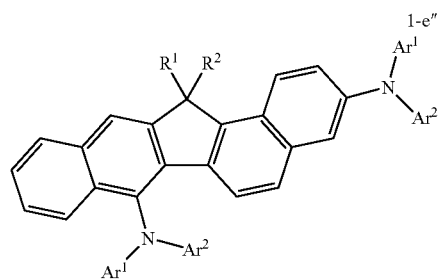
| Compound for example | R¹ | R² | Ar¹ | Ar² |
|---|---|---|---|---|
| 1e-46 | Me | Me | Ph | 4-(2-naphthyl)phenyl |
| 1e-47 | Me | Me | Ph | 4-phenyl-phenanthrenyl |
| 1e-48 | Me | Me | Ph | 6-phenyl-2-naphthyl |
| 1e-49 | Me | Me | 4-(1-naphthyl)phenyl | 4-(1-naphthyl)phenyl |
| 1e-50 | Me | Me | 4-(2-naphthyl)phenyl | 4-(2-naphthyl)phenyl |
| 1e-51 | n-Hexyl | n-Hexyl | Ph | Ph |
| 1e-52 | n-Hexyl | n-Hexyl | 4-methylphenyl | 4-methylphenyl |
| 1e-53 | n-Hexyl | n-Hexyl | 4-isopropylphenyl | 4-isopropylphenyl |

-continued

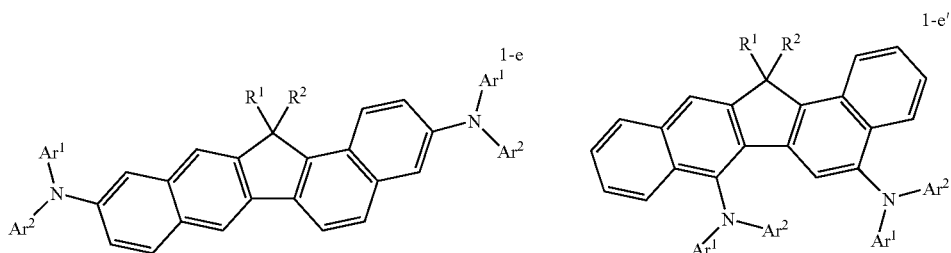

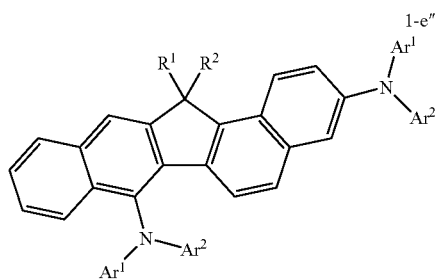

| Compound for example | R¹ | R² | Ar¹ | Ar² |
|---|---|---|---|---|
| 1e-54 | n-Hexyl | n-Hexyl | -C₆H₄-C(CH₃)₃ | -C₆H₄-C(CH₃)₃ |
| 1e-55 | n-Hexyl | n-Hexyl | 3,4,5-trimethylphenyl | 3,4,5-trimethylphenyl |
| 1e-56 | n-Hexyl | n-Hexyl | 2-naphthyl | 2-naphthyl |
| 1e-57 | n-Hexyl | n-Hexyl | 1-naphthyl | 1-naphthyl |
| 1e-58 | n-Hexyl | n-Hexyl | 4-biphenylyl | 4-biphenylyl |
| 1e-59 | n-Octyl | n-Octyl | Ph | Ph |
| 1e-60 | n-Octyl | n-Octyl | -C₆H₄-Me | -C₆H₄-Me |
| 1e-61 | n-Octyl | n-Octyl | -C₆H₄-iPr | -C₆H₄-iPr |
| 1e-62 | n-Octyl | n-Octyl | -C₆H₄-C(CH₃)₃ | -C₆H₄-C(CH₃)₃ |

-continued
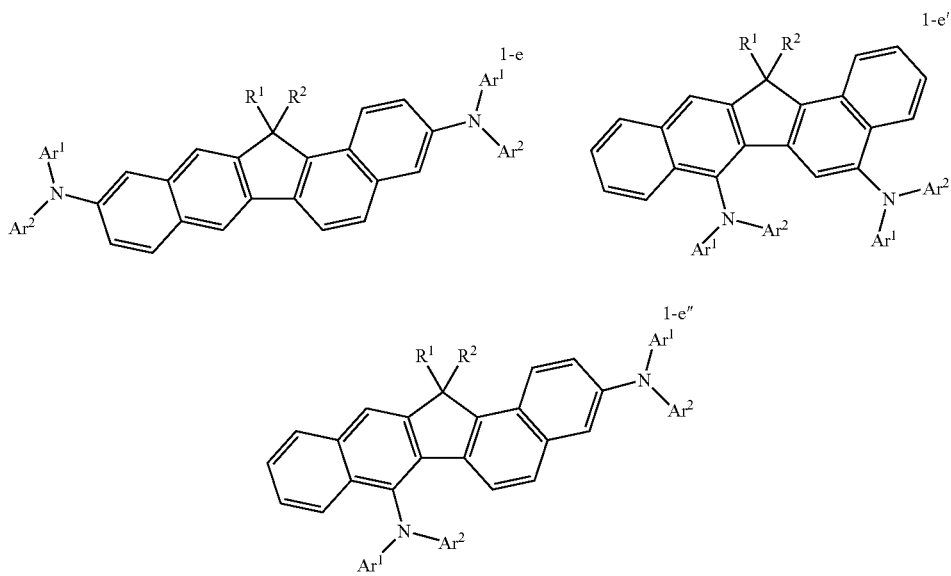
| Compound for example | R¹ | R² | Ar¹ | Ar² |
|---|---|---|---|---|
| 1e-63 | n-Octyl | n-Octyl | 2,3,5-trimethylphenyl | 2,3,5-trimethylphenyl |
| 1e-64 | n-Octyl | n-Octyl | 2-naphthyl | 2-naphthyl |
| 1e-65 | n-Octyl | n-Octyl | 1-naphthyl | 1-naphthyl |
| 1e-66 | 2-ethylhexyl | 2-ethylhexyl | 4-biphenyl | 4-biphenyl |
| 1e-67 | 2-ethylhexyl | 2-ethylhexyl | Ph | Ph |
| 1e-68 | 2-ethylhexyl | 2-ethylhexyl | 4-methylphenyl | 4-methylphenyl |
| 1e-69 | 2-ethylhexyl | 2-ethylhexyl | 4-isopropylphenyl | 4-isopropylphenyl |

-continued

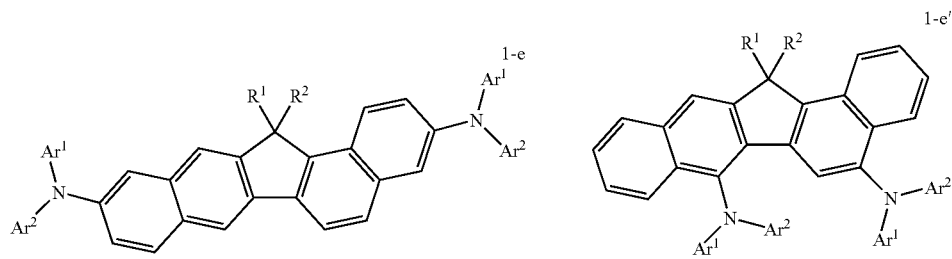

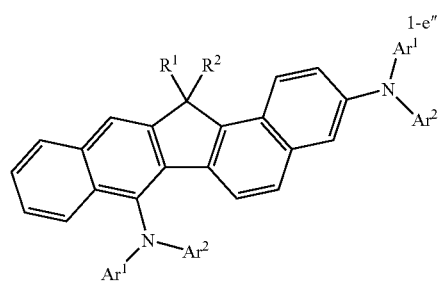

| Compound for example | R¹ | R² | Ar¹ | Ar² |
|---|---|---|---|---|
| 1e-70 | 2-ethylhexyl | 2-ethylhexyl | -C₆H₄-C(CH₃)₃ | -C₆H₄-C(CH₃)₃ |
| 1e-71 | 2-ethylhexyl | 2-ethylhexyl | 2-naphthyl | 2-naphthyl |
| 1e-72 | 2-ethylhexyl | 2-ethylhexyl | 1-naphthyl | 1-naphthyl |

*In the foregoing componds given for the examples, the compounds in which the code e is turned to e' are compounds given for the examples in Formula 1-e', and the compounds in which the code e is turned to e" are compounds given for the examples in Formula 1-e".

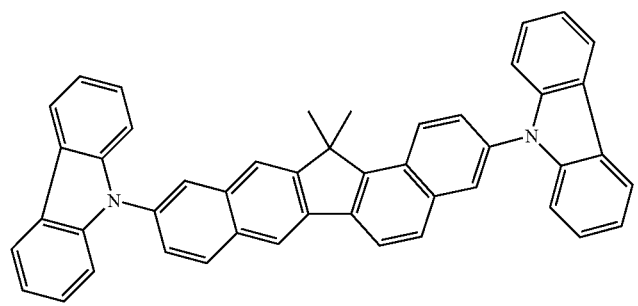

1e-73

-continued
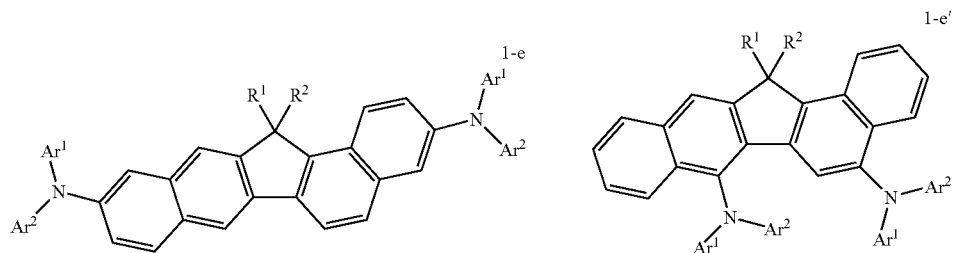
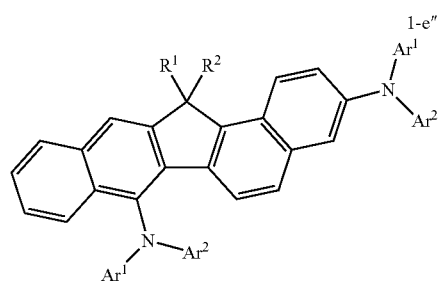
| Compound for example | R¹ | R² | Ar¹ | Ar² |
| --- | --- | --- | --- | --- |
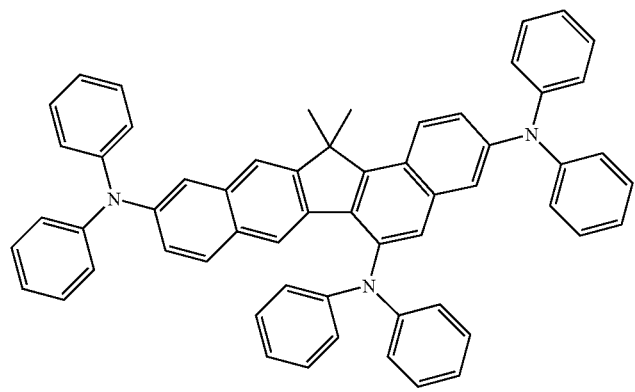
1e-74
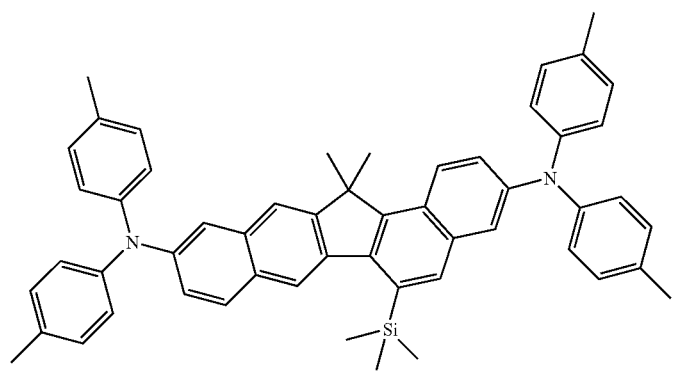
1e-75

-continued
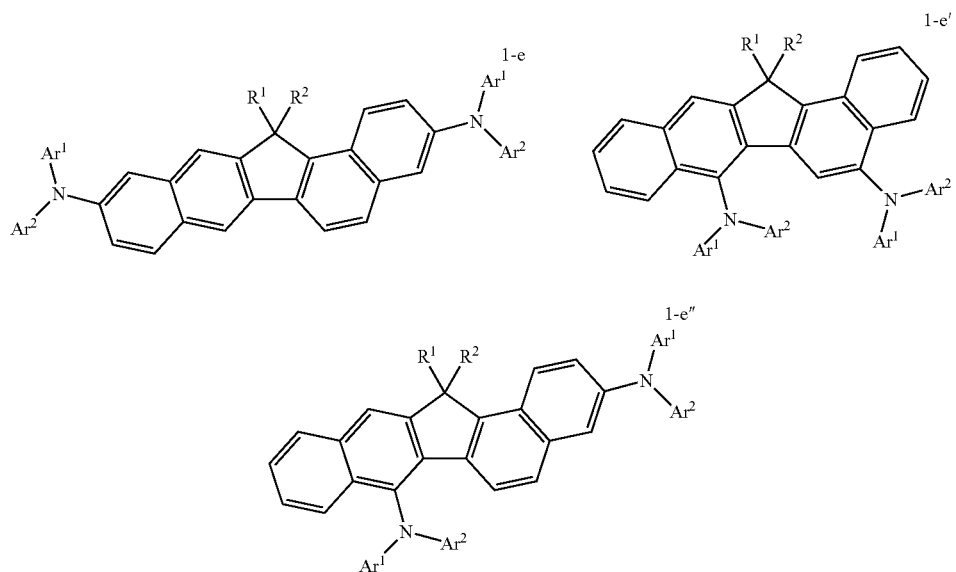
| Compound for example | R¹ | R² | Ar¹ | Ar² |
|---|---|---|---|---|
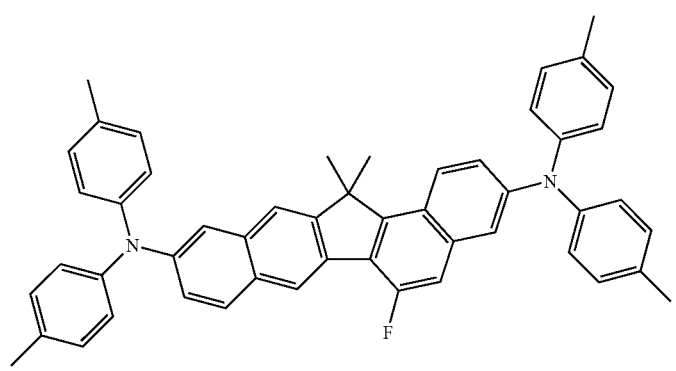
1e-76
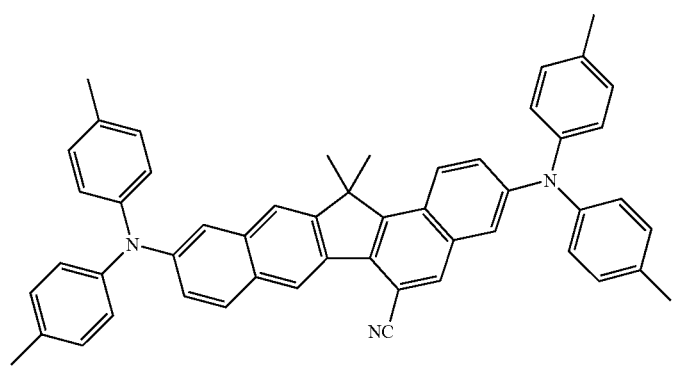
1e-77

-continued
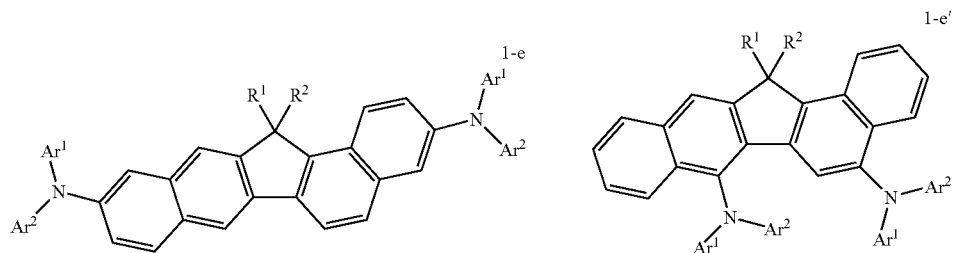
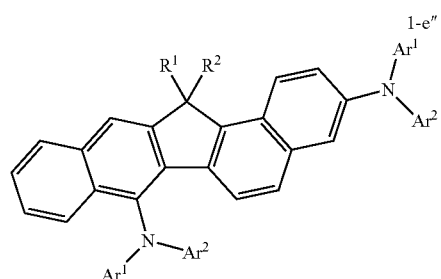
| Compound for example | R¹ | R² | Ar¹ | Ar² |
|---|---|---|---|---|
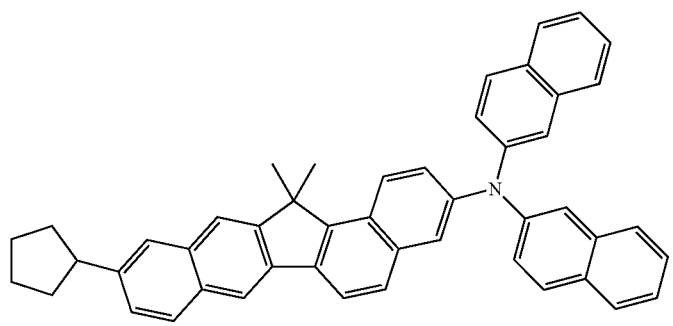
1e-78
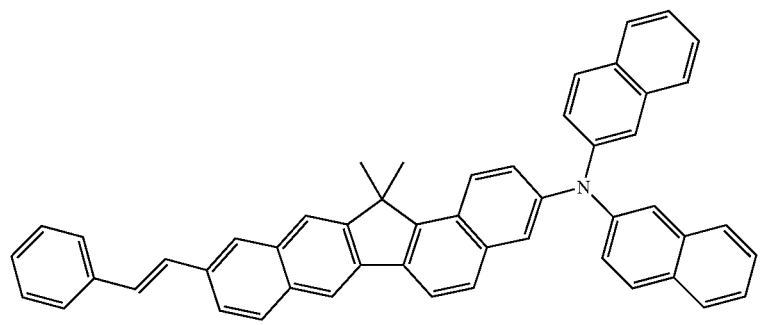
1e-79

-continued
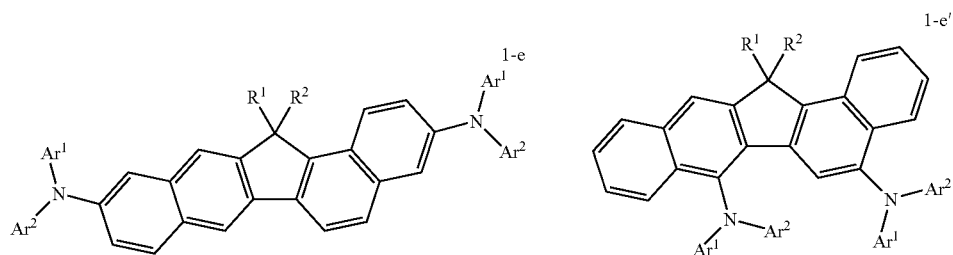
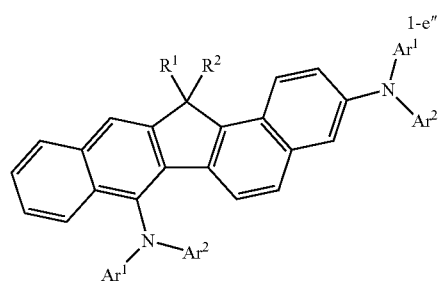
Compound for example | R¹ | R² | Ar¹ | Ar²
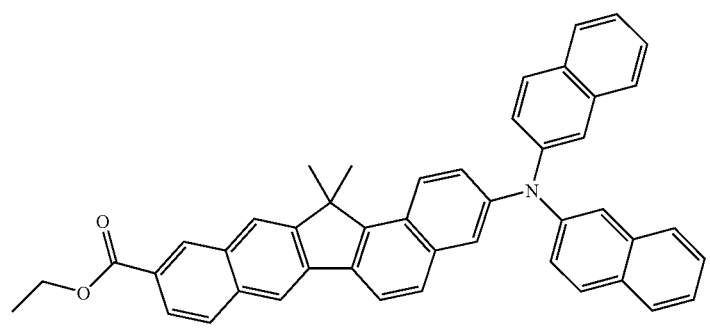
1e-80
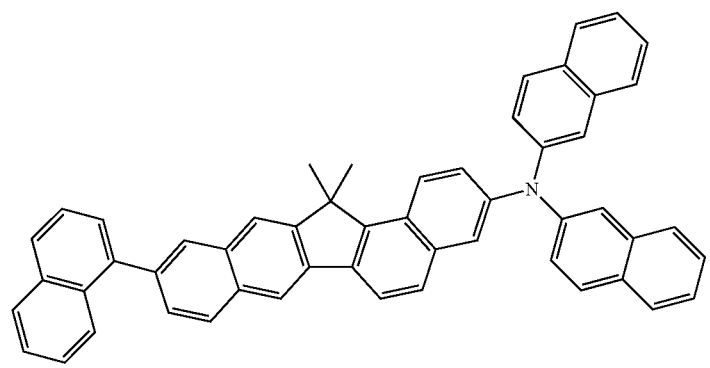
1e-81

-continued
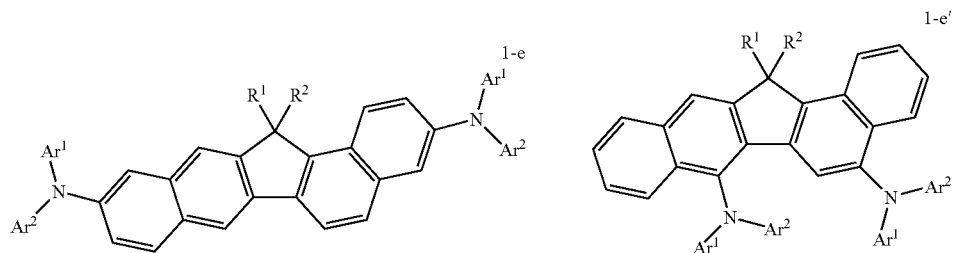
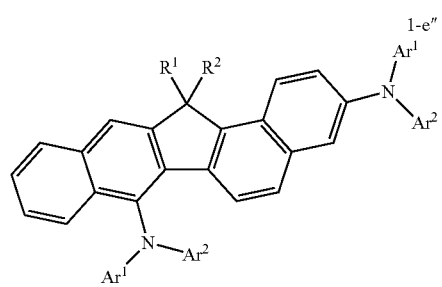
Compound for example    R¹    R²    Ar¹    Ar²
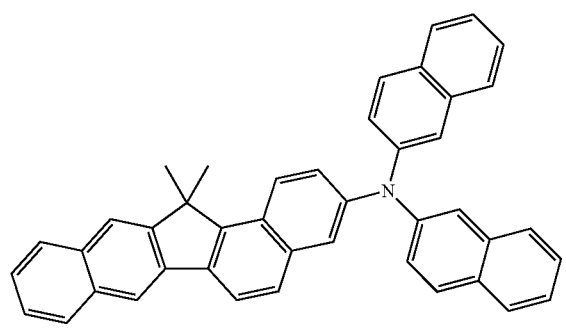
1e-82
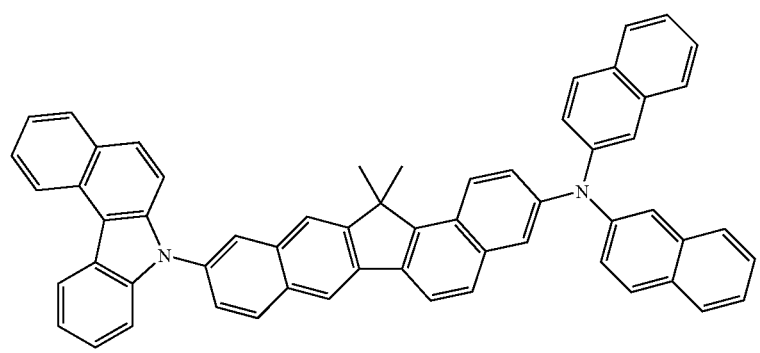
1e-83

-continued
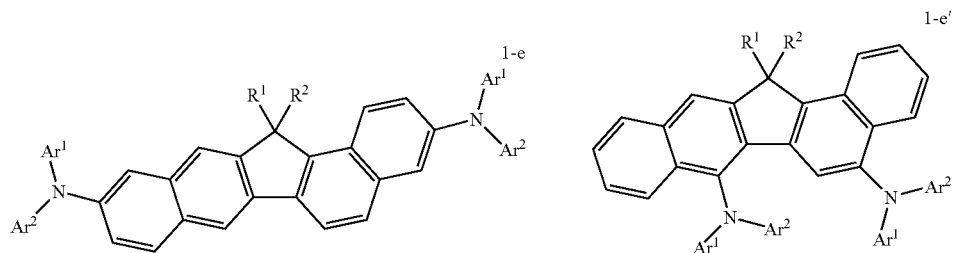
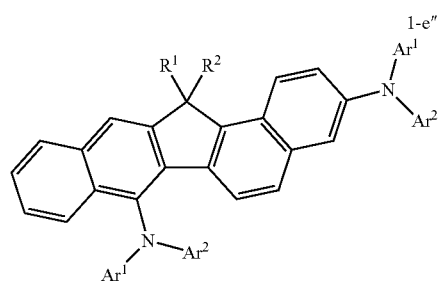
| Compound for example | R¹ | R² | Ar¹ | Ar² |
| --- | --- | --- | --- | --- |
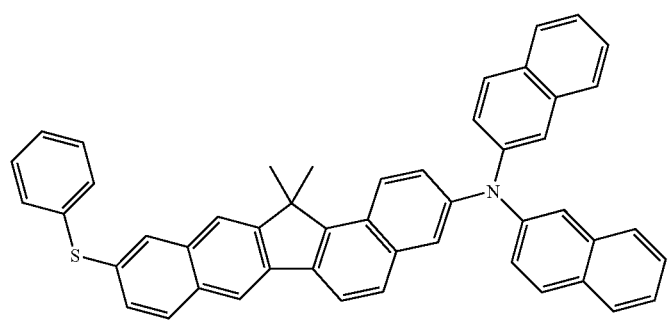
1e-84
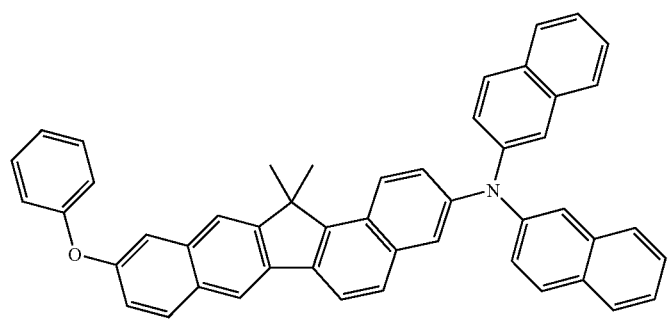
1e-85

-continued
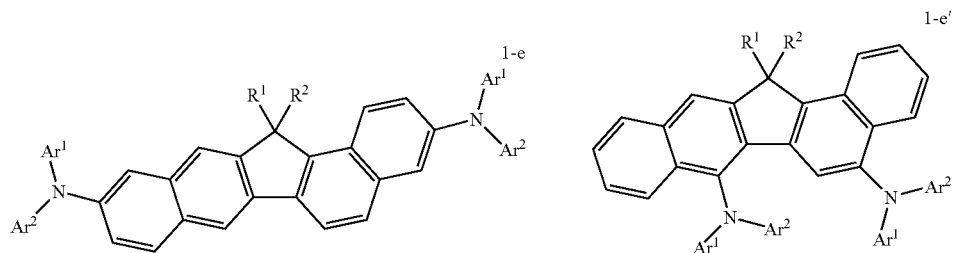
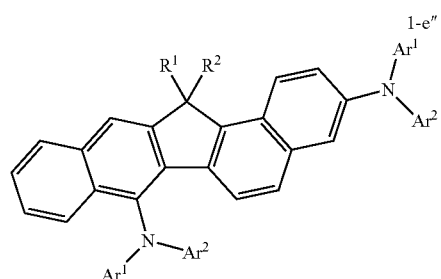
| Compound for example | R¹ | R² | Ar¹ | Ar² |
|---|---|---|---|---|
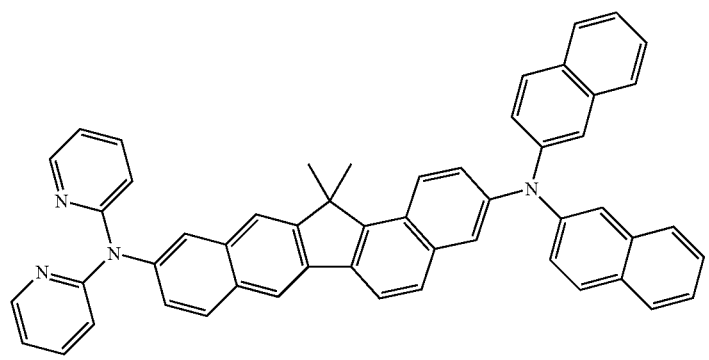
1e-86
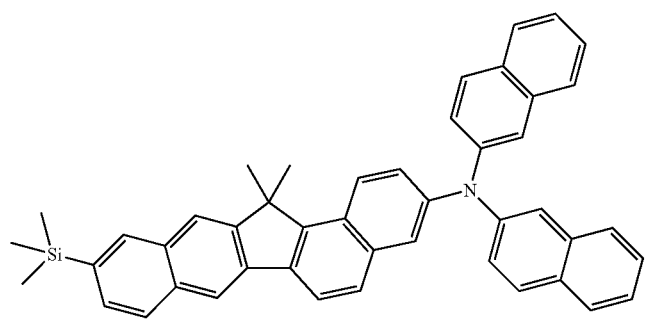
1e-87

-continued
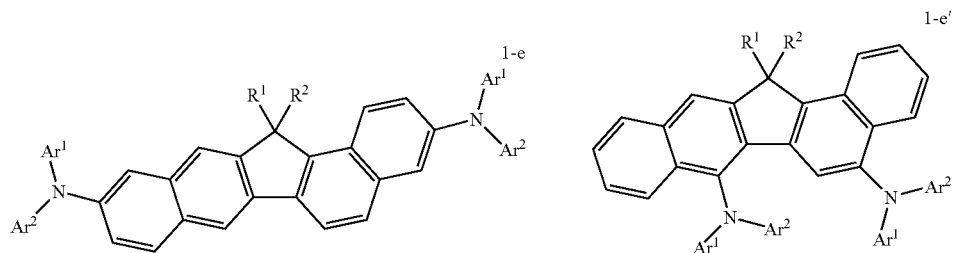
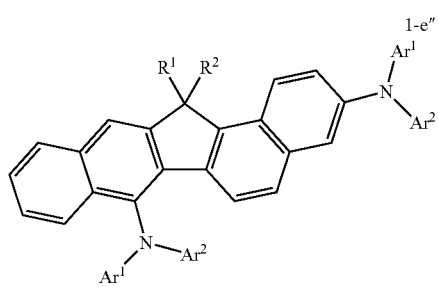
| Compound for example | R¹ | R² | Ar¹ | Ar² |
|---|---|---|---|---|
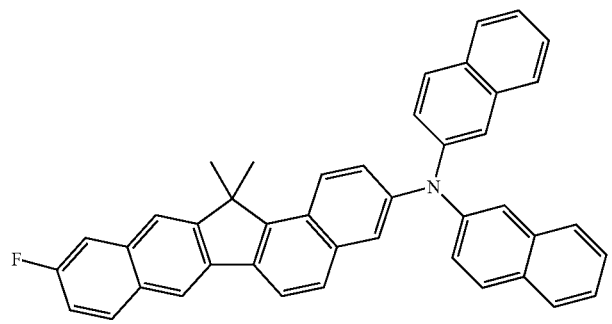
1e-88
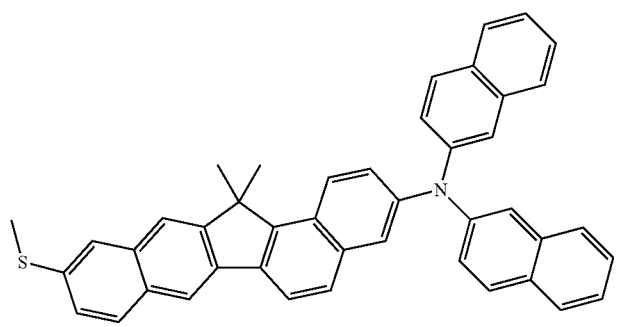
1e-89

-continued
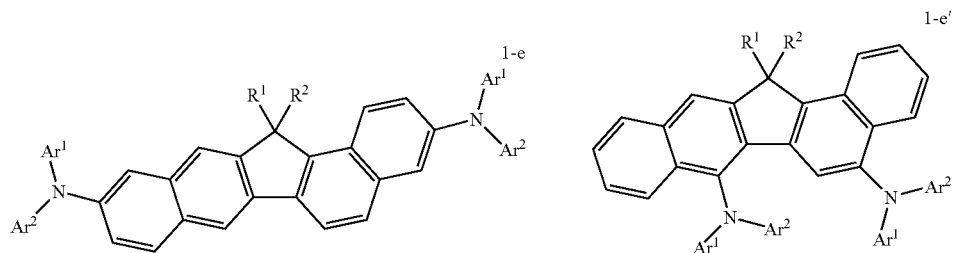
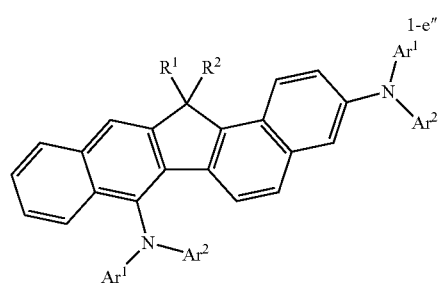
| Compound for example | R¹ | R² | Ar¹ | Ar² |
|---|---|---|---|---|
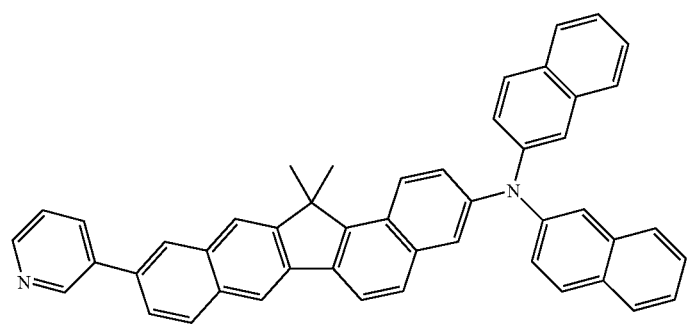
1e-90
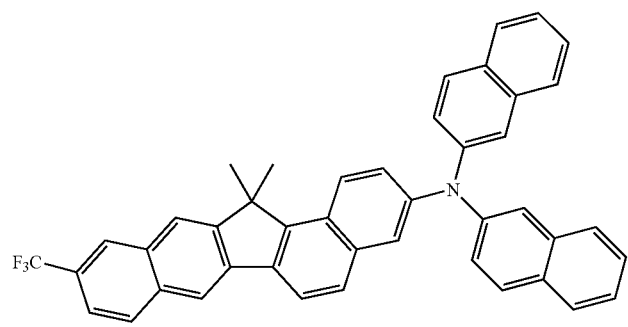
1e-91

-continued
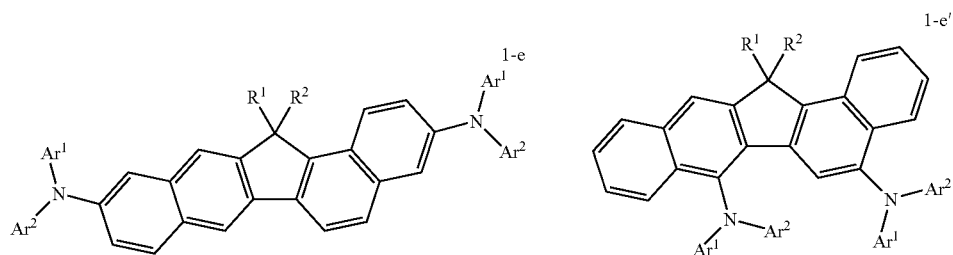
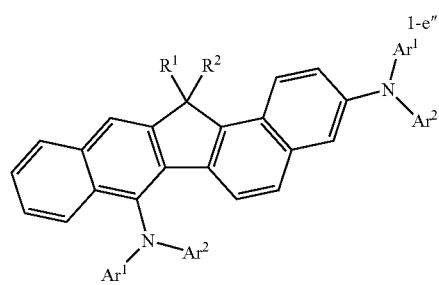
Compound for example | R¹ | R² | Ar¹ | Ar²
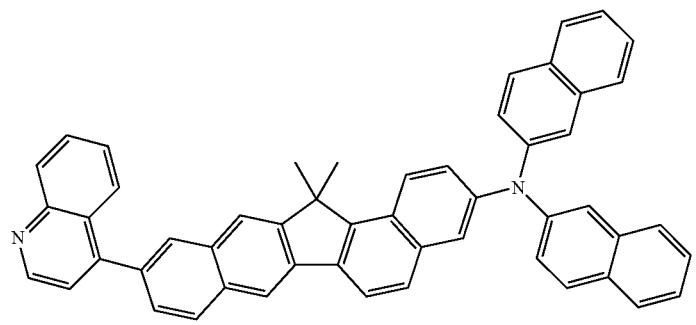
1e-92
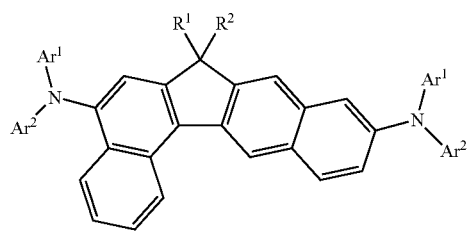
| Compound for example | R¹ | R² | Ar¹ | Ar² |
|---|---|---|---|---|
| 1f-1 | Me | Me | Ph | Ph |
| 1f-2 | Me | Me | Ph | —⟨⟩—Me |

-continued
1-f
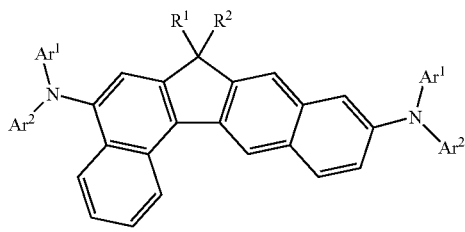
| Compound for example | R¹ | R² | Ar¹ | Ar² |
|---|---|---|---|---|
| 1f-3 | Me | Me | Ph | 3-MeC₆H₄ |
| 1f-4 | Me | Me | Ph | 2-MeC₆H₄ |
| 1f-5 | Me | Me | Ph | 4-iPrC₆H₄ |
| 1f-6 | Me | Me | Ph | 4-tBuC₆H₄ |
| 1f-7 | Me | Me | Ph | 2,4-Me₂C₆H₃ |
| 1f-8 | Me | Me | Ph | 2,3,5-Me₃C₆H₂ |
| 1f-9 | Me | Me | 4-MeC₆H₄ | 4-MeC₆H₄ |
| 1f-10 | Me | Me | 3-MeC₆H₄ | 3-MeC₆H₄ |
| 1f-11 | Me | Me | 2-MeC₆H₄ | 2-MeC₆H₄ |

-continued
1-f
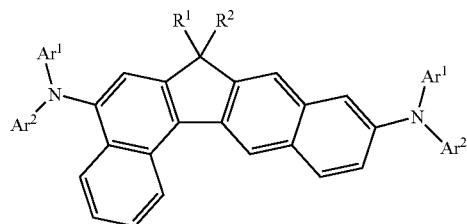
| Compound for example | R¹ | R² | Ar¹ | Ar² |
|---|---|---|---|---|
| 1f-12 | Me | Me | 2,5-dimethylphenyl (Me, Me) | 2,5-dimethylphenyl (Me, Me) |
| 1f-13 | Me | Me | 2,3,5-trimethylphenyl (Me, Me, Me) | 2,3,5-trimethylphenyl (Me, Me, Me) |
| 1f-14 | Me | Me | 4-isopropylphenyl | 4-isopropylphenyl |
| 1f-15 | Me | Me | 4-methylphenyl | 4-isopropylphenyl |
| 1f-16 | Me | Me | Ph | 4-biphenylyl |
| 1f-17 | Me | Me | Ph | 3-biphenylyl |
| 1f-18 | Me | Me | Ph | 2-biphenylyl |
| 1f-19 | Me | Me | Ph | 2-naphthyl |
| 1f-20 | Me | Me | Ph | 1-naphthyl |

-continued
1-f
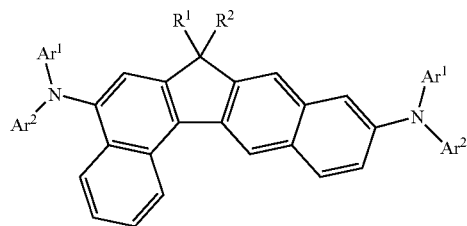
| Compound for example | R¹ | R² | Ar¹ | Ar² |
|---|---|---|---|---|
| 1f-21 | Me | Me | —C₆H₄—Me (para) | —C₆H₄—C₆H₅ (para) |
| 1f-22 | Me | Me | —C₆H₄—Me (para) | —C₆H₄—C₆H₅ (meta) |
| 1f-23 | Me | Me | —C₆H₄—Me (para) | —C₆H₄—C₆H₅ (ortho) |
| 1f-24 | Me | Me | —C₆H₄—Me (para) | 2-naphthyl |
| 1f-25 | Me | Me | —C₆H₄—Me (para) | 1-naphthyl |
| 1f-26 | Me | Me | —C₆H₄—C₆H₅ (para) | —C₆H₄—C₆H₅ (para) |
| 1f-27 | Me | Me | —C₆H₄—C₆H₅ (meta) | —C₆H₄—C₆H₅ (meta) |
| 1f-28 | Me | Me | —C₆H₄—C₆H₅ (ortho) | —C₆H₄—C₆H₅ (ortho) |

-continued
1-f
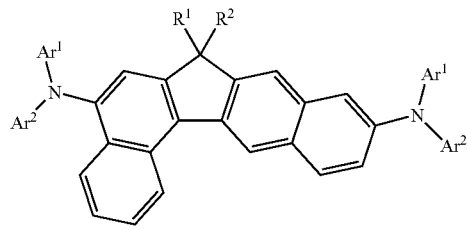
| Compound for example | R¹ | R² | Ar¹ | Ar² |
|---|---|---|---|---|
| 1f-29 | Me | Me | 2-naphthyl | 2-naphthyl |
| 1f-30 | Me | Me | 1-naphthyl | 1-naphthyl |
| 1f-31 | Me | Me | Ph | 2-(9,9-dimethylfluorenyl) |
| 1f-32 | Me | Me | Ph | 9-phenanthryl |
| 1f-33 | Me | Me | 2-(9,9-dimethylfluorenyl) | 2-(9,9-dimethylfluorenyl) |
| 1f-34 | Me | Me | 9-phenanthryl | 9-phenanthryl |
| 1f-35 | Me | Me | Ph | 4-(p-terphenyl) |
| 1f-36 | Me | Me | Ph | 4-(m-terphenyl) |

-continued
1-f
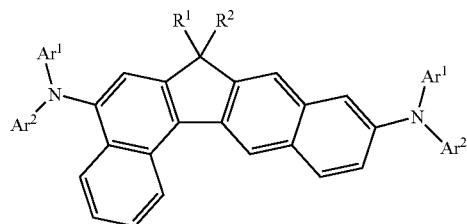
| Compound for example | R¹ | R² | Ar¹ | Ar² |
|---|---|---|---|---|
| 1f-37 | Me | Me | Ph | ![structure] |
| 1f-38 | Me | Me | Ph | ![structure] |
| 1f-39 | Me | Me | Ph | ![structure] |
| 1f-40 | Me | Me | Ph | ![structure] |
| 1f-41 | Me | Me | Ph | ![structure] |
| 1f-42 | Me | Me | Ph | ![structure] |
| 1f-43 | Me | Me | Ph | ![structure] |

-continued
1-f
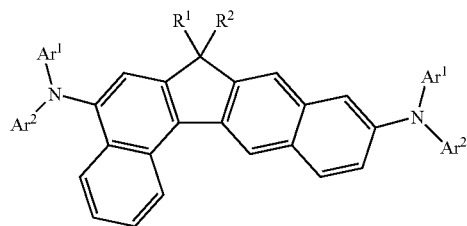
| Compound for example | R¹ | R² | Ar¹ | Ar² |
|---|---|---|---|---|
| 1f-44 | Me | Me | Ph | 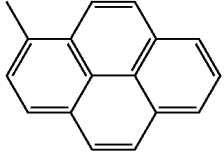 |
| 1f-45 | Me | Me | Ph | 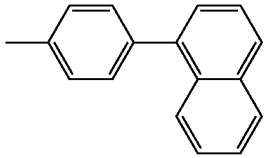 |
| 1f-46 | Me | Me | Ph | 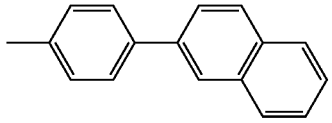 |
| 1f-47 | Me | Me | Ph | 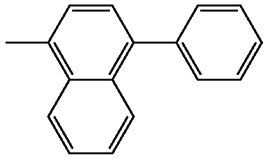 |
| 1f-48 | Me | Me | Ph | 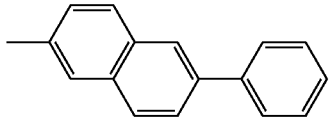 |
| 1f-49 | Me | Me | 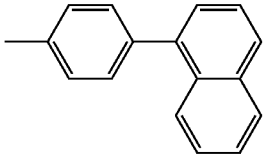 | 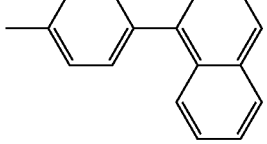 |
| 1f-50 | Me | Me | 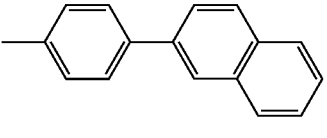 | 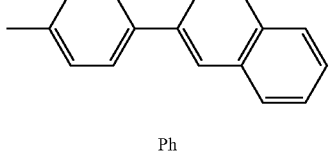 |
| 1f-51 | n-Hexyl | n-Hexyl | Ph | Ph |
| 1f-52 | n-Hexyl | n-Hexyl | 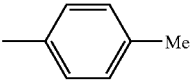 |  |

-continued 1-f

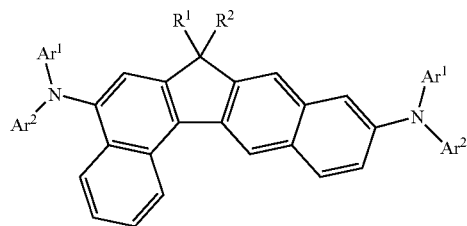

| Compound for example | R¹ | R² | Ar¹ | Ar² |
|---|---|---|---|---|
| 1f-53 | n-Hexyl | n-Hexyl | 4-isopropylphenyl | 4-isopropylphenyl |
| 1f-54 | n-Hexyl | n-Hexyl | 4-tert-butylphenyl (—C(CH₃)₃) | 4-tert-butylphenyl (—C(CH₃)₃) |
| 1f-55 | n-Hexyl | n-Hexyl | 2,3,5-trimethylphenyl | 2,3,5-trimethylphenyl |
| 1f-56 | n-Hexyl | n-Hexyl | 2-naphthyl | 2-naphthyl |
| 1f-57 | n-Hexyl | n-Hexyl | 1-naphthyl | 1-naphthyl |
| 1f-58 | n-Hexyl | n-Hexyl | 4-biphenyl | 4-biphenyl |
| 1f-59 | n-Octyl | n-Octyl | Ph | Ph |
| 1f-60 | n-Octyl | n-Octyl | 4-methylphenyl | 4-methylphenyl |
| 1f-61 | n-Octyl | n-Octyl | 4-isopropylphenyl | 4-isopropylphenyl |
| 1f-62 | n-Octyl | n-Octyl | 4-tert-butylphenyl (—C(CH₃)₃) | 4-isopropylphenyl (—CH(CH₃)₃) |
| 1f-63 | n-Octyl | n-Octyl | 2,3,5-trimethylphenyl | 2,3,5-trimethylphenyl |

-continued 1-f

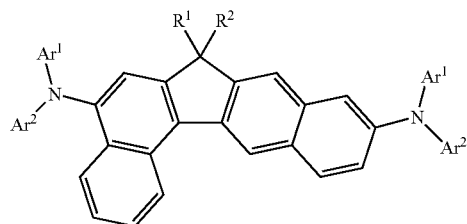

| Compound for example | R¹ | R² | Ar¹ | Ar² |
|---|---|---|---|---|
| 1f-64 | n-Octyl | n-Octyl | 2-methylnaphthyl | 2-methylnaphthyl |
| 1f-65 | n-Octyl | n-Octyl | 1-methylnaphthyl | 1-methylnaphthyl |
| 1f-66 | 2-ethylhexyl | 2-ethylhexyl | 4-methylbiphenyl | 4-methylbiphenyl |
| 1f-67 | 2-ethylhexyl | 2-ethylhexyl | Ph | Ph |
| 1f-68 | 2-ethylhexyl | 2-ethylhexyl | p-tolyl-Me | p-tolyl-Me |
| 1f-69 | 2-ethylhexyl | 2-ethylhexyl | p-isopropylphenyl | p-isopropylphenyl |
| 1f-70 | 2-ethylhexyl | 2-ethylhexyl | p-tert-butylphenyl -C(CH₃)₃ | p-tert-butylphenyl -C(CH₃)₃ |
| 1f-71 | 2-ethylhexyl | 2-ethylhexyl | 2-naphthyl | 2-naphthyl |

-continued
1-f
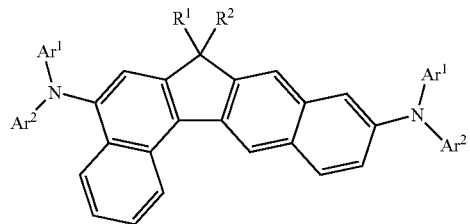
| Compound for example | R¹ | R² | Ar¹ | Ar² |
|---|---|---|---|---|
| 1f-72 | 2-ethylhexyl | 2-ethylhexyl | 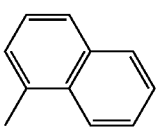 | 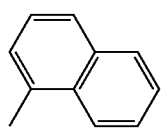 |
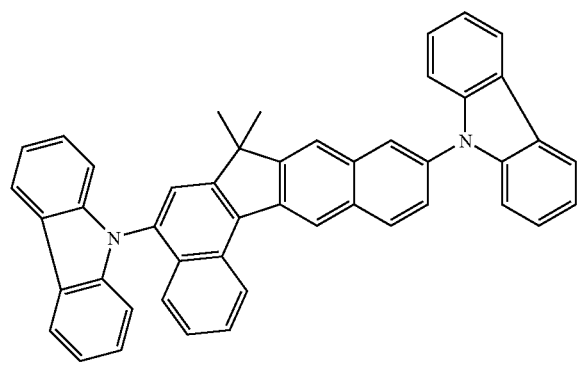
1f-73
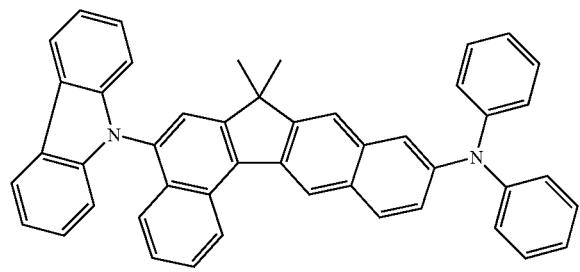
1f-74
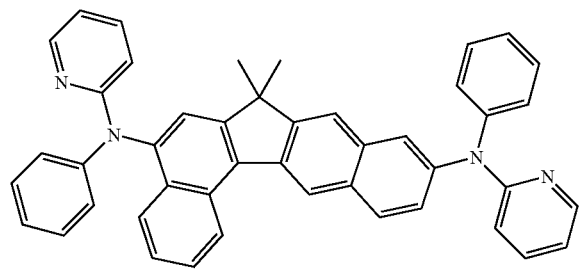
1f-75

1-f
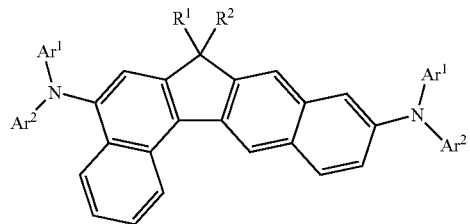
| Compound for example | R¹ | R² | Ar¹ | Ar² |
|---|---|---|---|---|
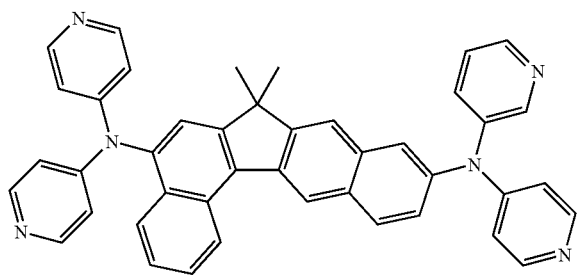
1f-76
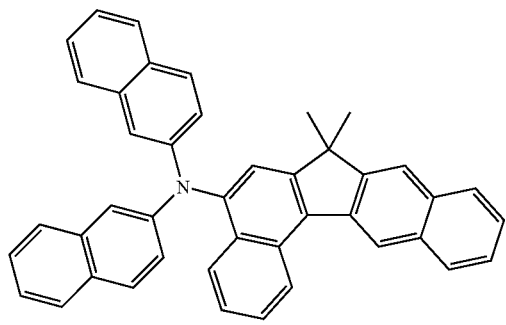
1f-77
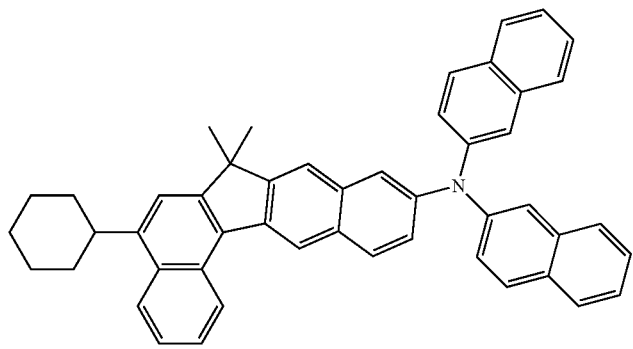
1f-78

-continued
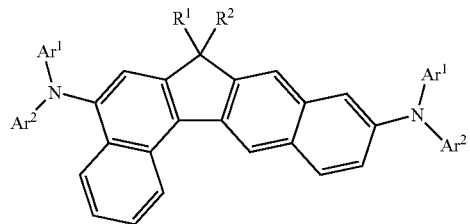
1-f
| Compound for example | R¹ | R² | Ar¹ | Ar² |
|---|---|---|---|---|
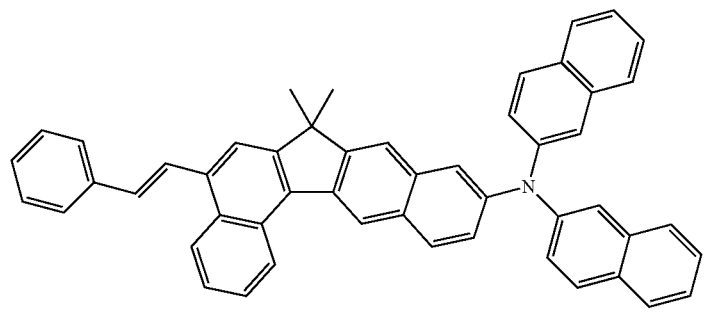
1f-79
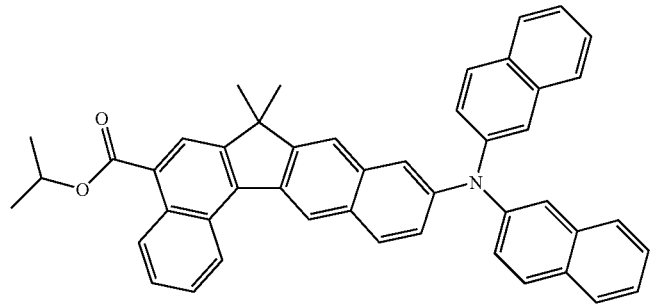
1f-80
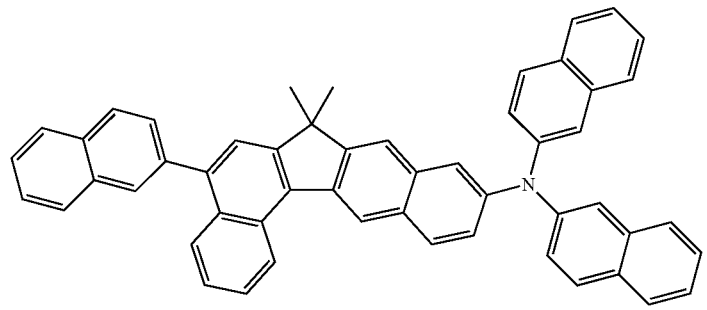
1f-81

-continued
1-f
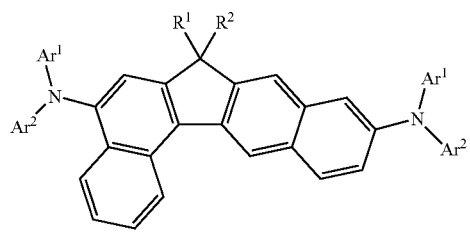
| Compound for example | R¹ | R² | Ar¹ | Ar² |
|---|---|---|---|---|
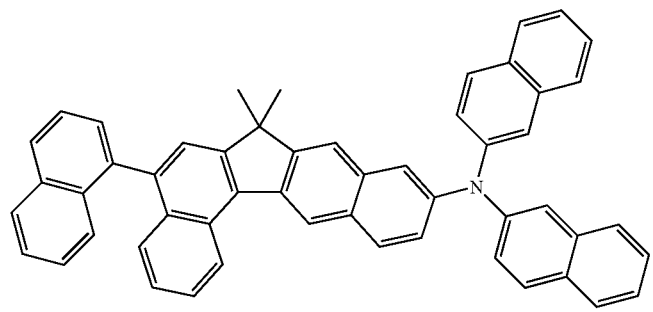
1f-82
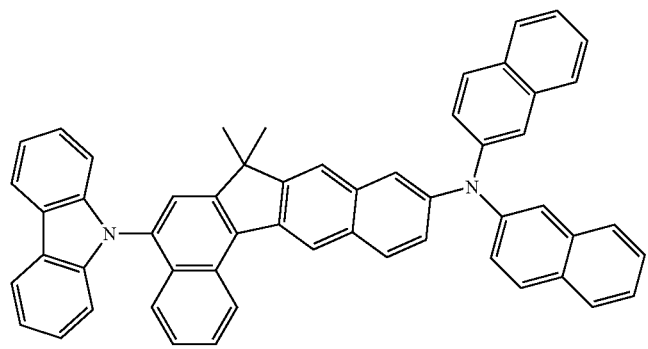
1f-83
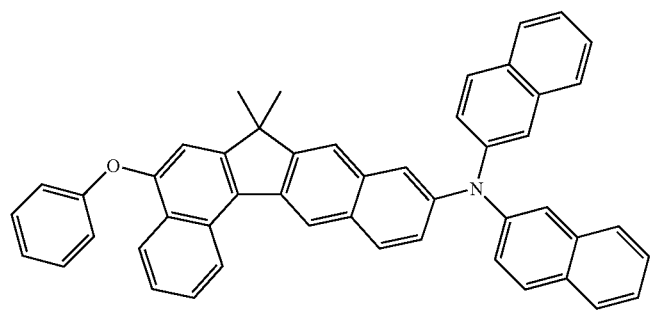
1f-84

-continued
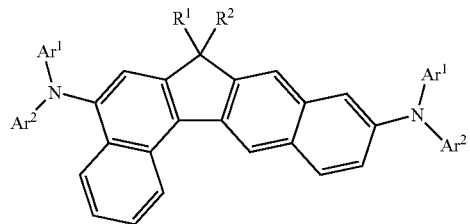
1-f
| Compound for example | R¹ | R² | Ar¹ | Ar² |
|---|---|---|---|---|
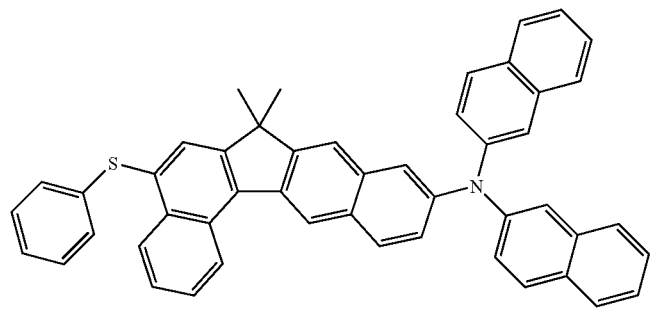
1f-85
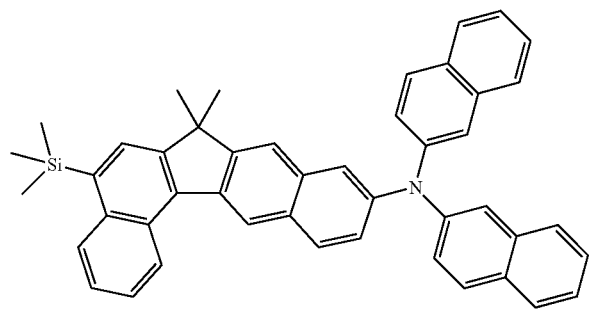
1f-86
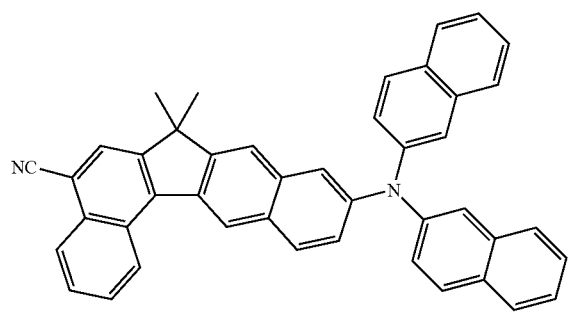
1f-87

-continued
1-f
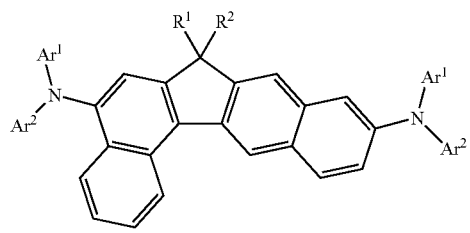
| Compound for example | R¹ | R² | Ar¹ | Ar² |
|---|---|---|---|---|
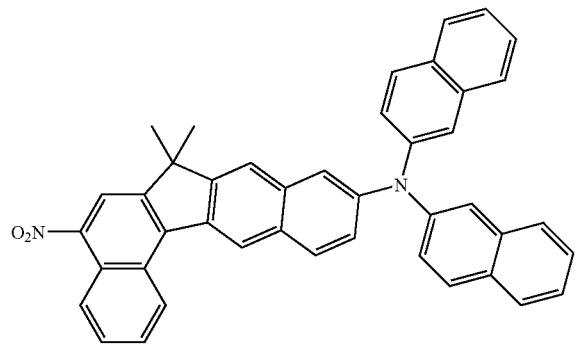
1f-88
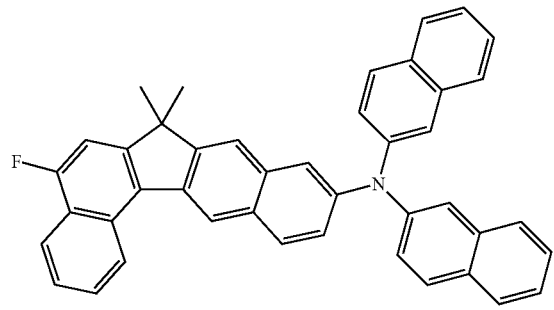
1f-89
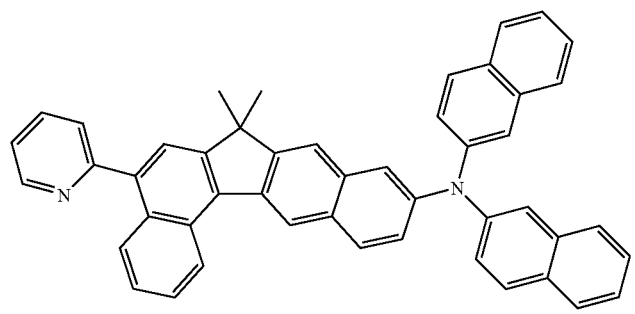
1f-90

-continued

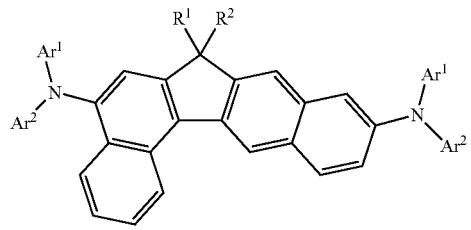

1-f

| Compound for example | R¹ | R² | Ar¹ | Ar² |
| --- | --- | --- | --- | --- |

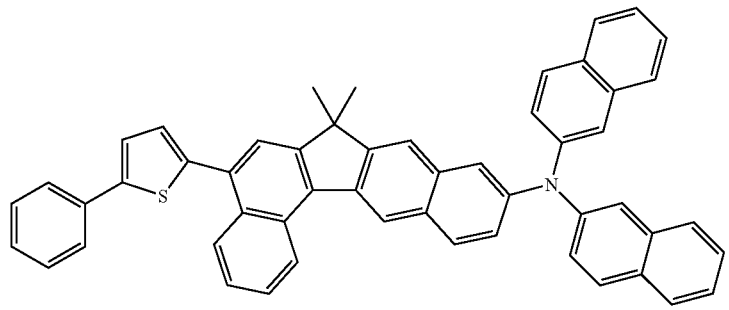

1f-91

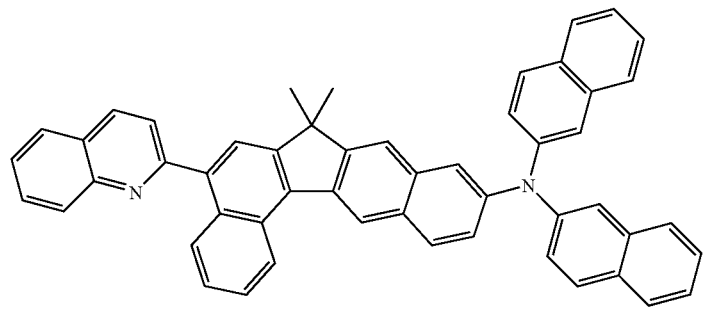

1f-92

Dibenzofluorene precursors suited to use in the present invention can be synthesized by any of processes described in the following documents 1 to 3.

Document 1: Ronald G. Harvey et al., Journal of Organic Chemistry, Vol. 56, 1210 (1991)

Document 2: Carlos Saá et al., Journal of Organic Chemistry, Vol. 69, 3842 (2004)

Document 3: Mark L. McLaughlin et al., Journal of Organic Chemistry, Vol. 59, 6484 (1994)

The dibenzofluorene precursor thus obtained is dialkylated and brominated, for example, by a process described in Yasuhiko Shirota et al., Journal of American Chemical Society, Vol. 122, 11021 (2000) and subsequently subjected to a process such as Buchwald-Hartwig cross coupling reaction, whereby the aminodibenzofluorene derivative of the present invention can be produced.

The aminodibenzofluorene derivative of the present invention is preferably used as a material for an organic EL device, and it is more preferably used particularly as a doping material.

In the organic EL device of the present invention in which an organic compound layer comprising a single layer or plural layers including at least a light emitting layer is interposed between a pair of electrodes, at least one layer in the above organic compound layer contains at least one kind of the aminodibenzofluorene derivatives of the present invention.

In the organic EL device of the present invention, the light emitting layer described above preferably contains at least one kind of the aminodibenzofluorene derivatives described above, and the aminodibenzofluorene derivative of the present invention is contained in the light emitting layer in a proportion of preferably 0.01 to 20% by weight, more preferably 0.5 to 20% by weight.

When the aminodibenzofluorene derivatives of the present invention is used as the light emitting material for the organic EL device, the light emitting layer described above preferably contains at least one kind of the aminodibenzofluorene derivatives described above and at least one selected from compounds represented by the following Formulas (2a) to (2d), and at least one selected from the compounds represented by the following Formulas (2a) to (2d) is preferably a host material.

Formulas (2a) to (2d) shall be explained below.

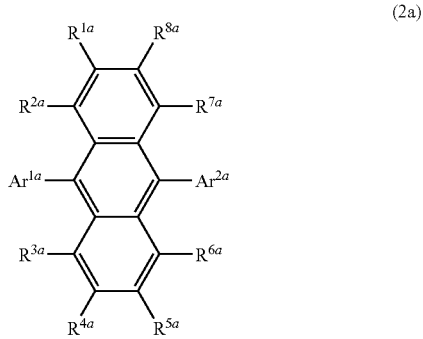

(2a)

(in Formula (2a), $Ar^{1a}$ and $Ar^{2a}$ each are independently a group derived from a substituted or non-substituted aromatic ring having 6 to 20 ring carbon atoms; the aromatic ring described above may be substituted with at least one substituent; the substituent described above is selected from a substituted or non-substituted aryl group having 6 to 50 carbon atoms forming the aromatic ring, a substituted or non-substituted alkyl group having 1 to 50 carbon atoms, a substituted or non-substituted cycloalkyl group having 3 to 50 carbon atoms, a substituted or non-substituted alkoxyl group having 1 to 50 carbon atoms, a substituted or non-substituted aralkyl group having 6 to 50 carbon atoms, a substituted or non-substituted aryloxy group having 5 to 50 atoms forming a ring, a substituted or non-substituted arylthio group having 5 to 50 atoms forming a ring, a substituted or non-substituted alkoxycarbonyl group having 1 to 50 carbon atoms, a substituted or non-substituted silyl group, a carboxyl group, a halogen atom, a cyano group, a nitro group and a hydroxyl group; when the aromatic ring described above is substituted with two or more substituents, the substituents described above may be the same or different, and the substituents which are adjacent to each other may be combined with each other to form a saturated or unsaturated cyclic structure;

$R^{1a}$ to $R^{8a}$ each are selected independently from a hydrogen atom, a substituted or non-substituted aryl group having 6 to 50 carbon atoms forming the aromatic ring, a substituted or non-substituted heteroaryl group having 5 to 50 atoms forming a ring, a substituted or non-substituted alkyl group having 1 to 50 carbon atoms, a substituted or non-substituted cycloalkyl group having 3 to 50 carbon atoms, a substituted or non-substituted alkoxyl group having 1 to 50 carbon atoms, a substituted or non-substituted aralkyl group having 6 to 50 carbon atoms, a substituted or non-substituted aryloxy group having 5 to 50 atoms forming a ring, a substituted or non-substituted arylthio group having 5 to 50 atoms forming a ring, a substituted or non-substituted alkoxycarbonyl group having 1 to 50 carbon atoms, a substituted or non-substituted silyl group, a carboxyl group, a halogen atom, a cyano group, a nitro group and a hydroxyl group).

The group derived from the substituted or non-substituted aromatic ring having 6 to 20 ring carbon atoms represented by $Ar^{1a}$ and $Ar^{2a}$ in Formula (2a) includes phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl and the like. It is preferably a group derived from a substituted or non-substituted aromatic ring having 10 to 14 ring carbon atoms, and it is particularly 1-naphthyl, 2-naphthyl or 9-phenanthryl.

The substituted or non-substituted aryl group having 6 to 50 carbon atoms forming the aromatic ring which is the substituent of the aromatic ring described above includes phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl and the like. It is preferably a substituted or non-substituted aryl group having 6 to 18 carbon atoms forming the aromatic ring, and it is particularly phenyl, 1-naphthyl, 2-naphthyl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, o-tolyl, m-tolyl, p-tolyl or p-t-butylphenyl.

The substituted or non-substituted aryl group having 6 to 50 carbon atoms forming the aromatic ring represented by $R^{1a}$ to $R^{8a}$ in Formula (2a) includes phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl and the like.

The substituted or non-substituted heteroaryl group having 5 to 50 atoms forming a ring represented by $R^{1a}$ to $R^{8a}$ in Formula (2a) includes 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9- phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like.

The substituted or non-substituted alkyl group having 1 to 50 carbon atoms which is represented by $R^{1a}$ to $R^{8a}$ in Formula (2a) and which is the substituent of the aromatic ring described above includes methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl and the like.

The substituted or non-substituted cycloalkyl group having 3 to 50 carbon atoms which is represented by $R^{1a}$ to $R^{8a}$ in Formula (2a) and which is the substituent of the aromatic ring described above include cyclopropyl, cyclobutyl, cyclopentyl, cyclohexyl, 4-methylcyclohexyl, 1-adamantyl, 2-adamantyl, 1-norbornyl, 2-norbornyl and the like.

The substituted or non-substituted alkoxyl group having 1 to 50 carbon atoms which is represented by $R^{1a}$ to $R^{8a}$ in Formula (2a) and which is the substituent of the aromatic ring described above is a group represented by —OY, and Y includes the same examples as given in the substituted or non-substituted alkyl group having 1 to 50 carbon atoms which is represented by $R^1$ to $R^8$ described above and which is the substituent of the aromatic ring described above.

The substituted or non-substituted aralkyl group having 6 to 50 carbon atoms which is represented by $R^{1a}$ to $R^{8a}$ in Formula (2a) and which is the substituent of the aromatic ring described above includes benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, 1-chloro-2-phenylisopropyl and the like.

The substituted or non-substituted aryloxy group and arylthio group each having 5 to 50 atoms forming a ring which are represented by $R^{1a}$ to $R^{8a}$ in Formula (2a) and which are the substituents of the aromatic ring described above are represented by —OY' and SY" respectively, and Y' and Y" include the same examples as given in the substituted or non-substituted aryl group having 6 to 50 carbon atoms forming the aromatic ring which is represented by $R^{1a}$ to $R^{8a}$ described above and which is the substituent of the aromatic ring described above.

The substituted or non-substituted alkoxycarbonyl group having 1 to 50 carbon atoms which is represented by $R^{1a}$ to $R^{8a}$ in Formula (2a) and which is the substituent of the aromatic ring described above is a group represented by —COOZ, and Z includes the same examples as given in the substituted or non-substituted alkyl group having 1 to 50 carbon atoms which is represented by $R^{1a}$ to $R^{8a}$ described above and which is the substituent of the aromatic ring described above.

The silyl group which is represented by $R^{1a}$ to $R^{8a}$ in Formula (2a) and which is the substituent of the aromatic ring described above includes trimethylsilyl, triethylsilyl, t-butyldimethylsilyl, vinyldimethylsilyl, propyldimethylsilyl, triphenylsilyl and the like.

The halogen atom which is represented by $R^{1a}$ to $R^{8a}$ in Formula (2a) and which is the substituent of the aromatic ring described above includes fluorine, chlorine, bromine and iodine.

Substituents in the groups which are represented by $R^{1a}$ to $R^{8a}$ described above and which are the substituents of the aromatic ring described above include a halogen atom, a hydroxyl group, a nitro group, a cyano group, an alkyl group, an aryl group, a cycloalkyl group, an alkoxyl group, an aromatic heteroaryl group, an aralkyl group, an aryloxy group, an arylthio group, an alkoxycarbonyl group, a carboxyl group and the like.

Further, the cyclic structure which may be formed includes cycloalkanes having 4 to 12 carbon atoms such as cyclobutane, cyclopentane, cyclohexane, adamantane, norbornane and the like, cycloalkenes having 4 to 12 carbon atoms such as cyclobutene, cyclopentene, cyclohexene, cycloheptene, cyclooctene and the like, cycloalkadienes having 6 to 12 carbon atoms such as cyclohexadiene, cycloheptadiene, cyclooctadiene and the like and aromatic rings having 6 to 50 carbon atoms such as benzene, naphthalene, phenanthrene, anthracene, pyrene chrysene, acenaphthylene and the like. Substituents therefor include the same groups as the examples described above.

The anthracene derivative represented by Formula (2a) described above is preferably a compound having a structure represented by the following Formula (2a'):

(2a')

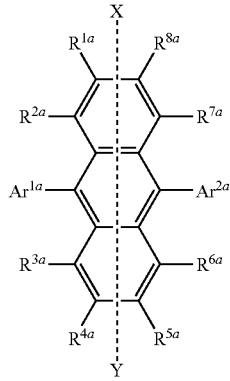

(in Formula (2a'), $Ar^{1a}$, $Ar^{2a}$, $R^{1a}$ to $R^{8a}$ each are independently the same as in Formula (2a), and the same specific examples are given;

provided that included is no case where in Formula (2a'), groups staying in a symmetric form to an X-Y axis shown on the anthracene are bonded to a 9-position and a 10-position of the anthracene in the center).

The specific examples of the anthracene derivative represented by Formula (2a) used for the organic EL device of the present invention include publicly known various derivatives such as compounds having two anthracene skeletons in a molecule which are shown in [0043] to [0063] of Japanese Patent Application Laid-Open No. 356033/2004 and compounds having one anthracene skeleton which are shown at pages 27 to 28 of International Publication NO. 2005/061656. The representative specific examples thereof are shown below.

2a-1

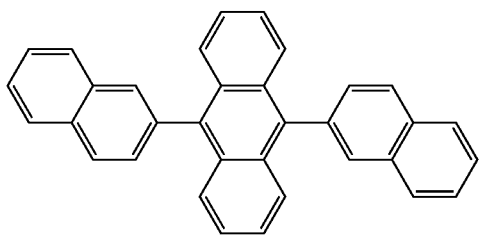

2a-2

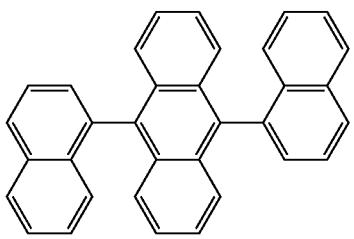

2a-3

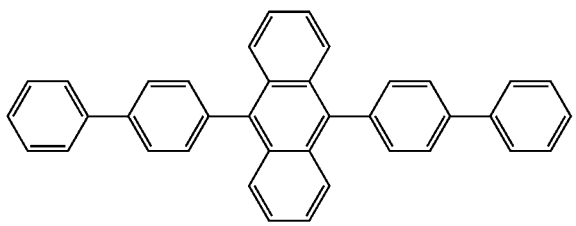

2a-4

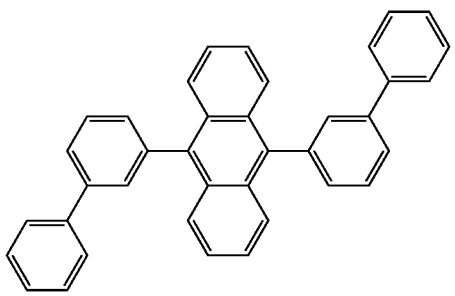

2a-5

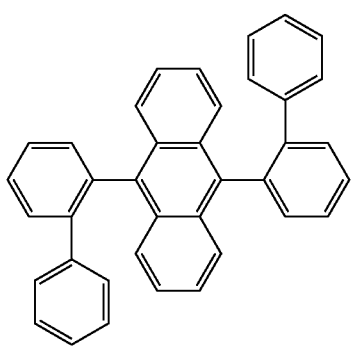

2a-6

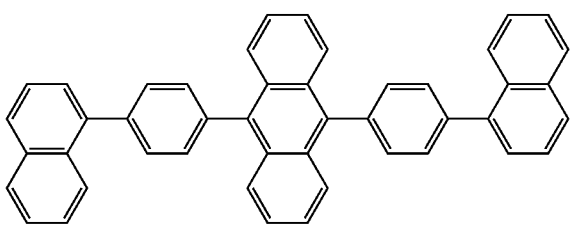

2a-7

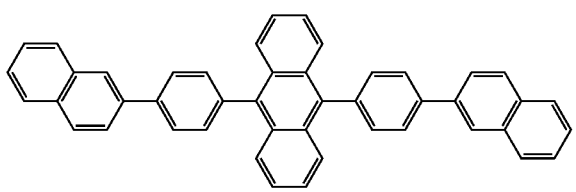

2a-8

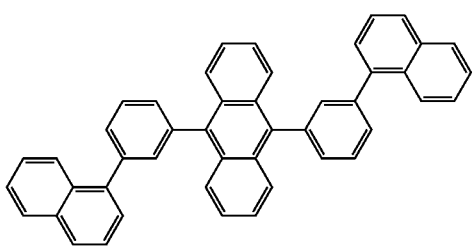

-continued
2a-9
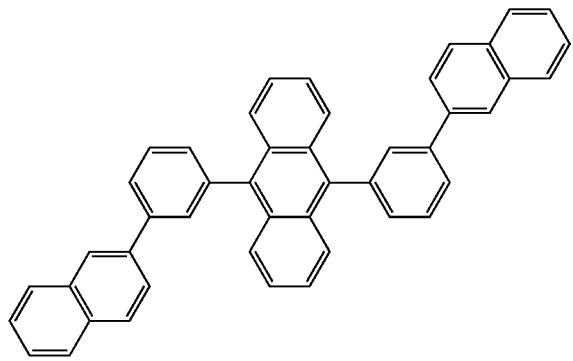
2a-10
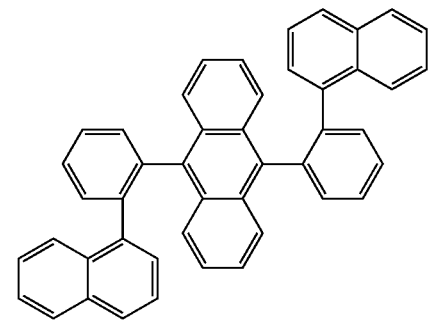
2a-11
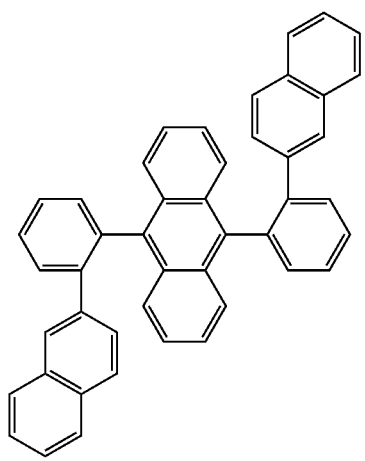
2a-12
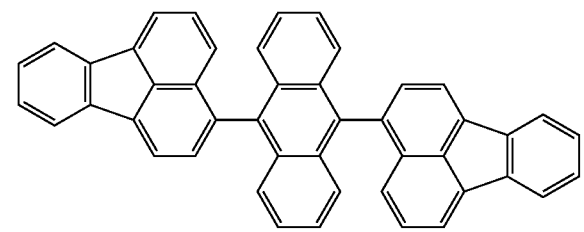
2a-13
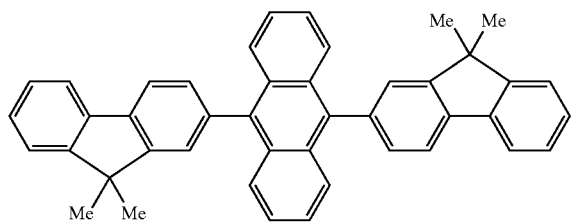
2a-14
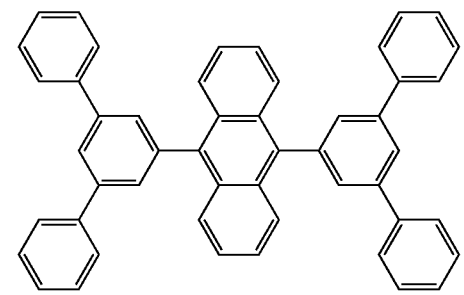
2a-15
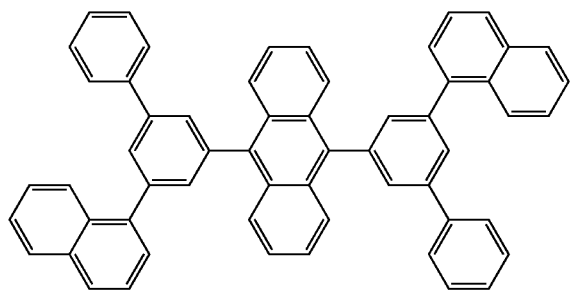
2a-16
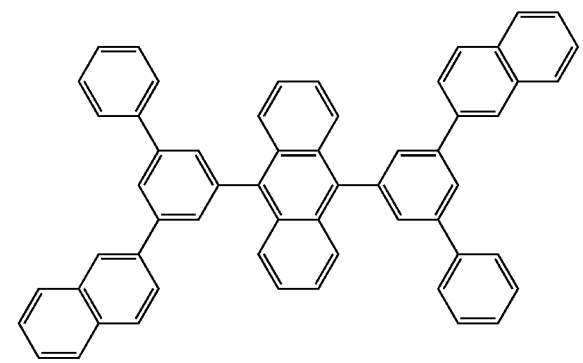

-continued
2a-17
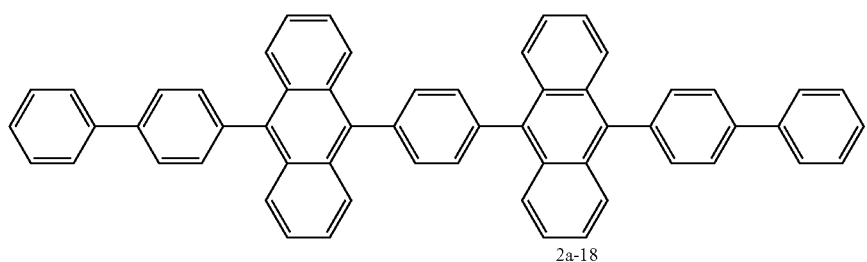
2a-18
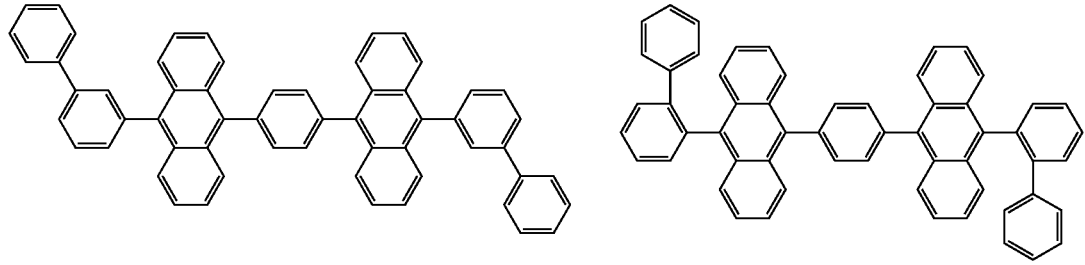
2a-19
2a-20
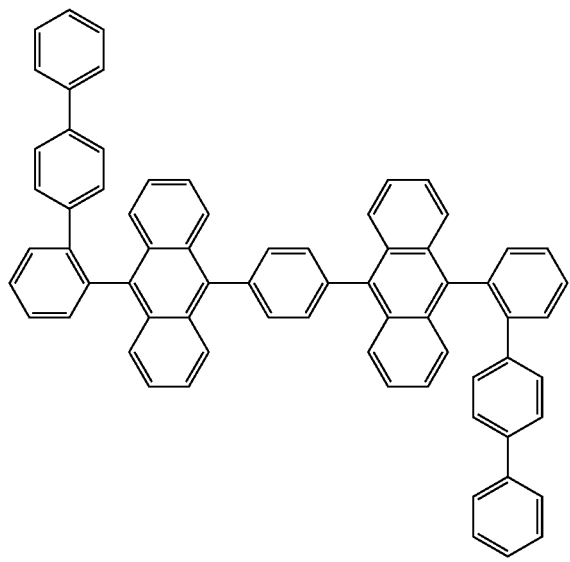
2a-21
2a-22
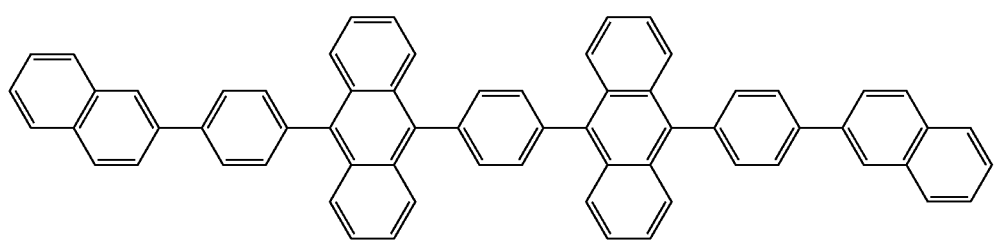

-continued
2a-23
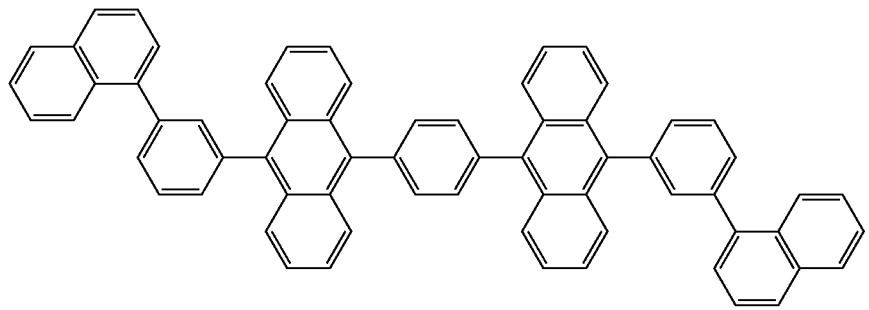
2a-24
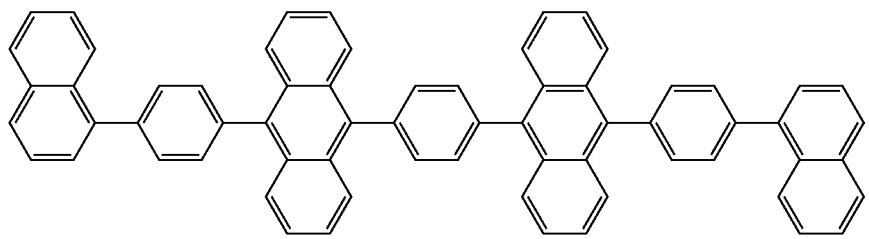
2a-25
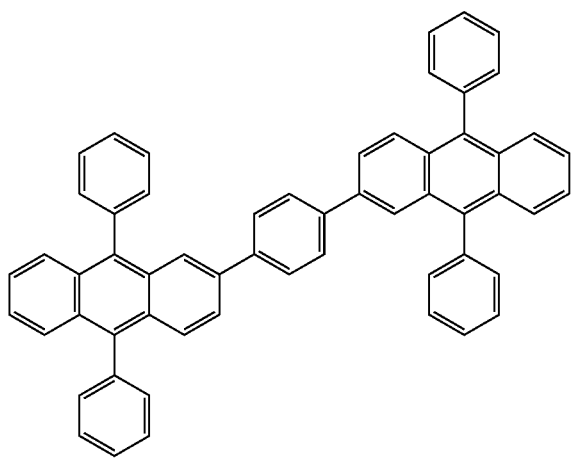
2a-26
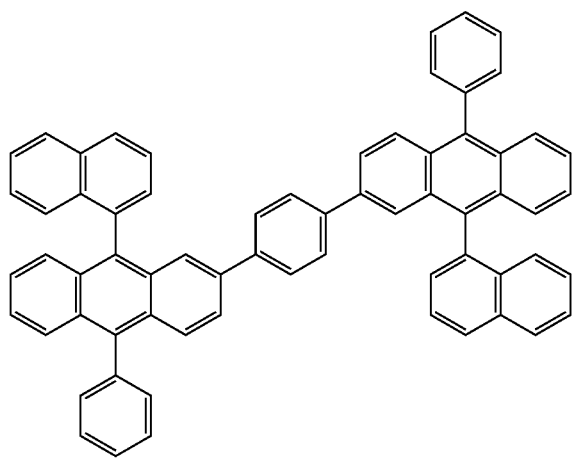
2a-27
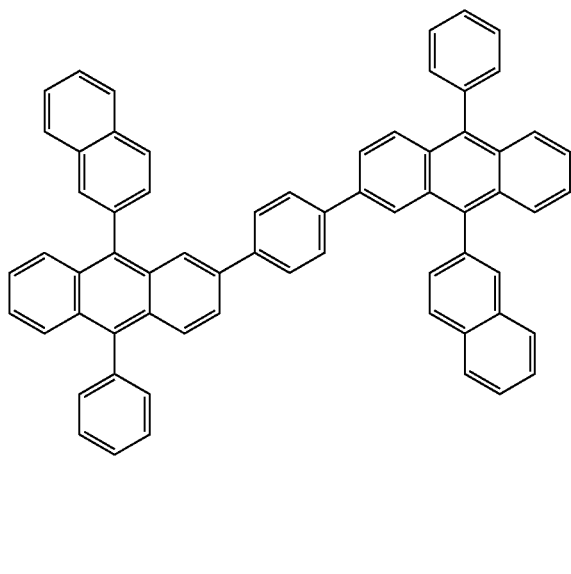
2a-28
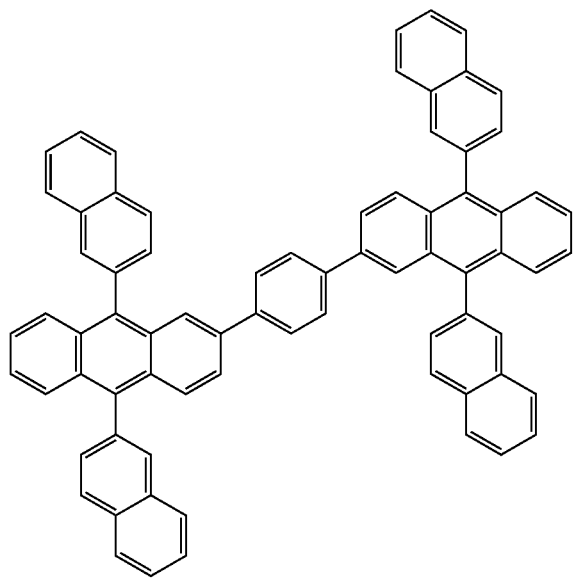

-continued
2a-29
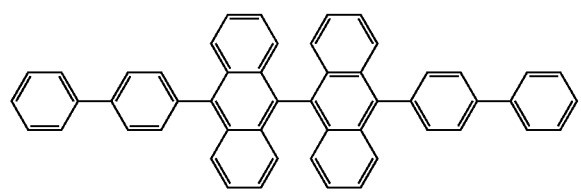
2a-30
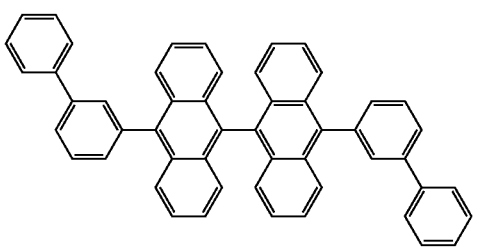
2a-31
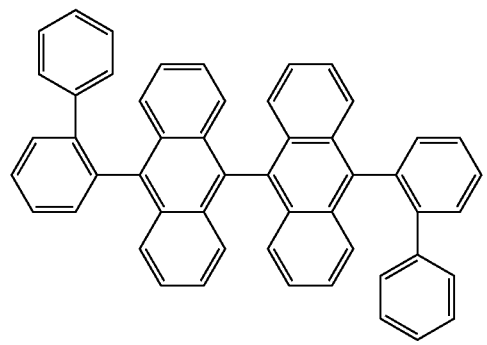
2a-32
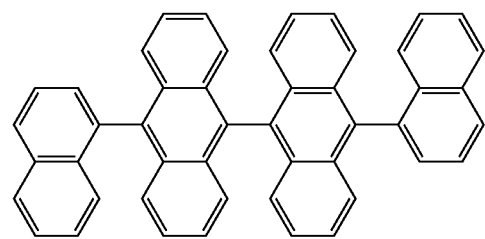
2a-33
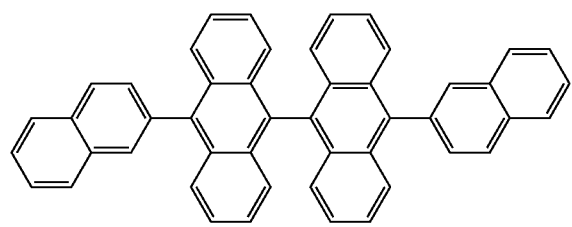
2a-34
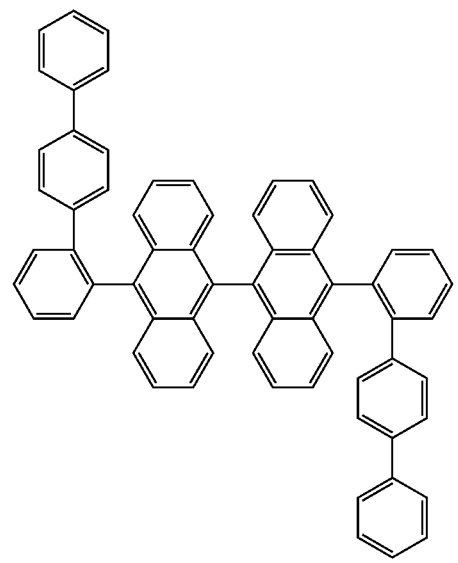
2a-35
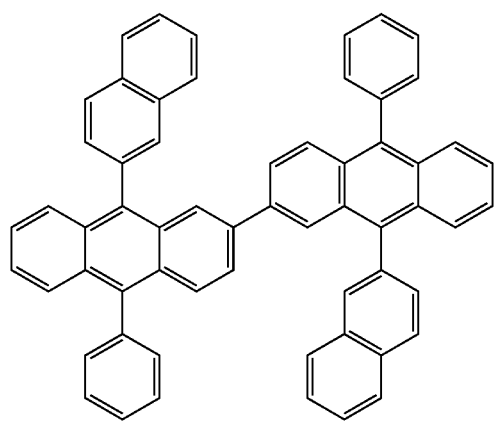
2a-36
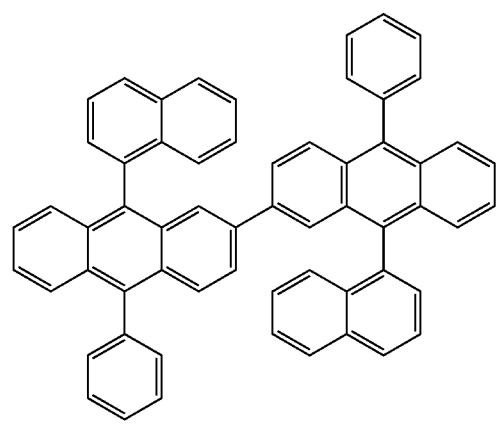

-continued
2a-37
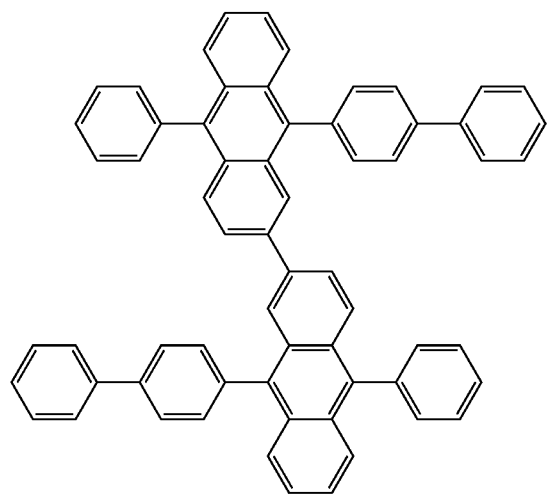
2a-38
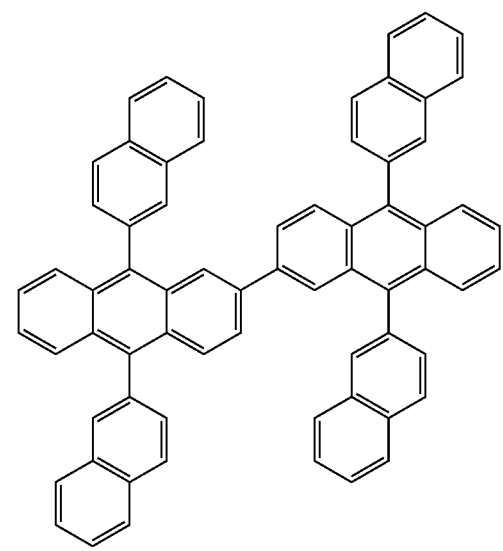
2a-39
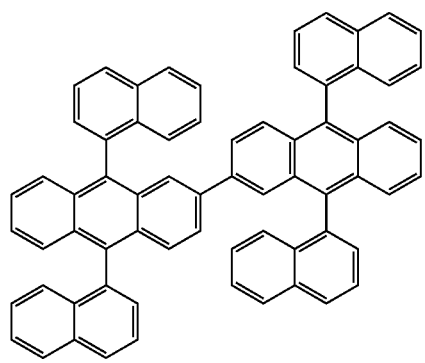
2a-40
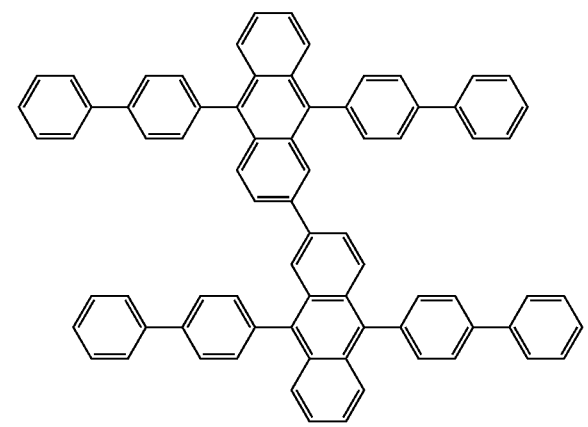
2a-41
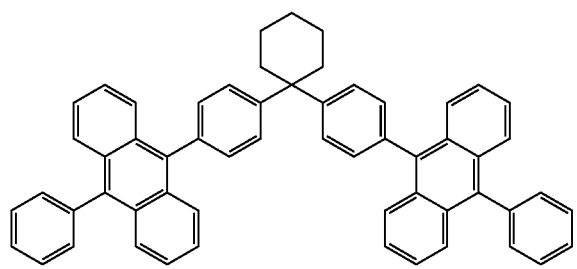
2a-42
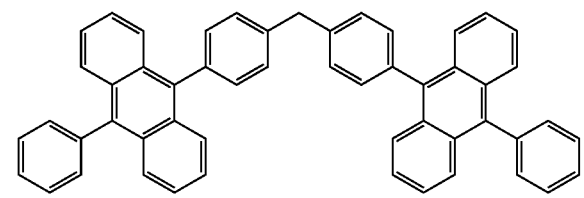
2a-43
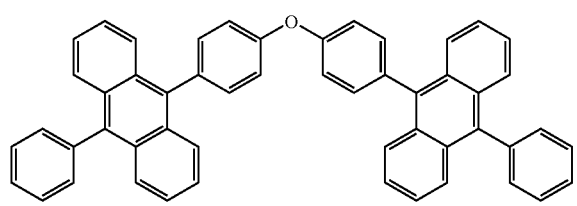
2a-44
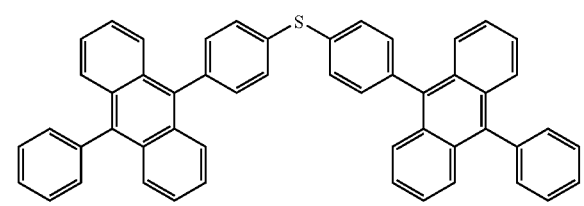

-continued
2a-45
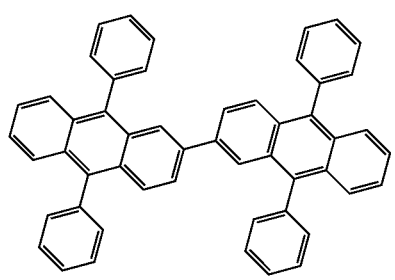
2a-46
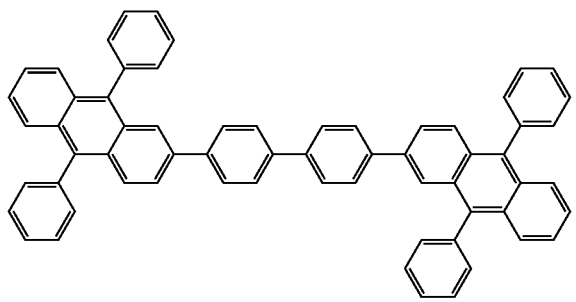
2a-47
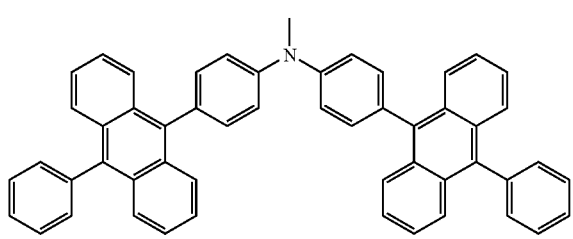
2a-48
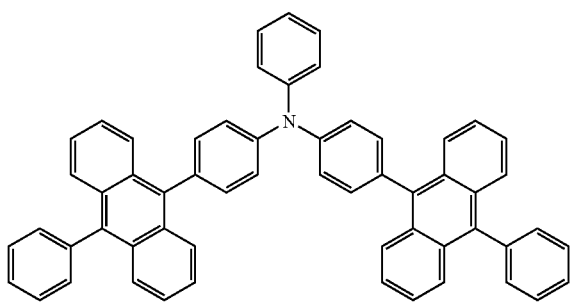
2a-49
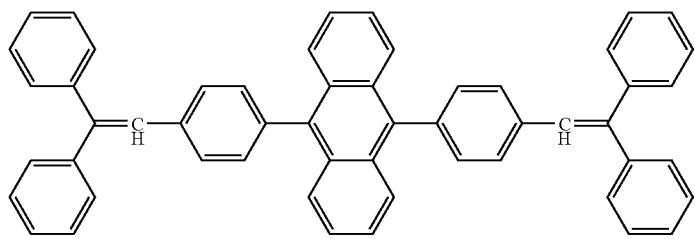
2a-50
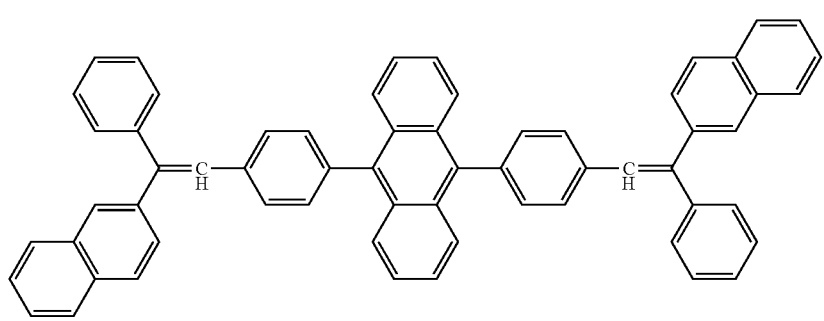

-continued
2a-51
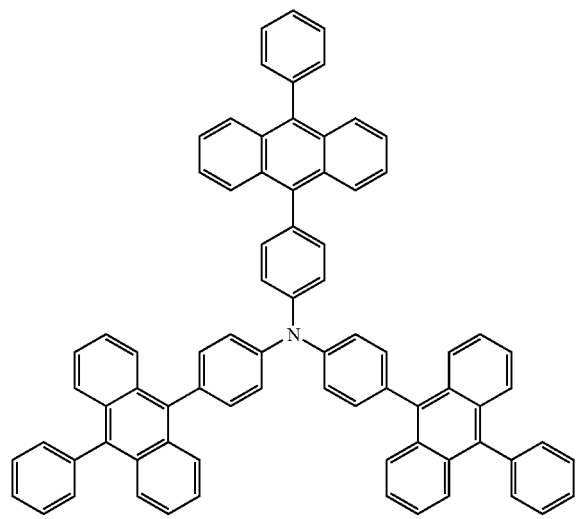
2a'-52
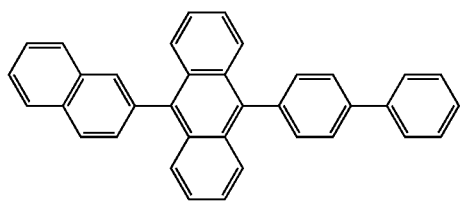
2a'-53
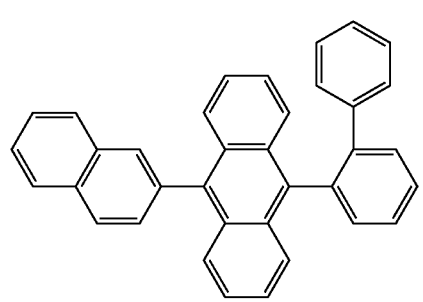
2a'-54
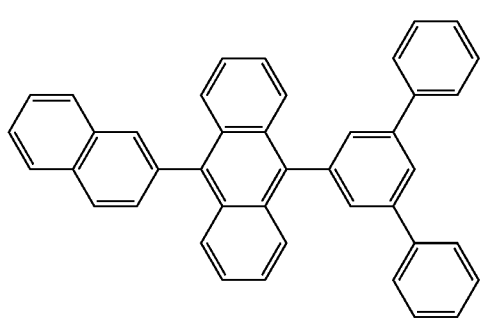
2a'-55
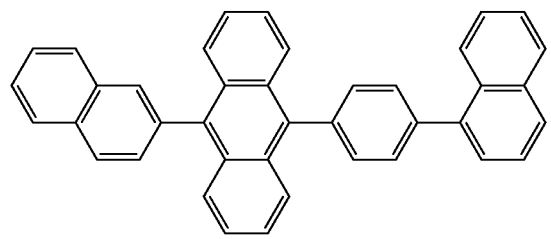
2a'-56
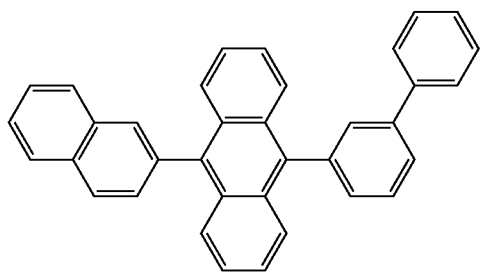
2a'-57
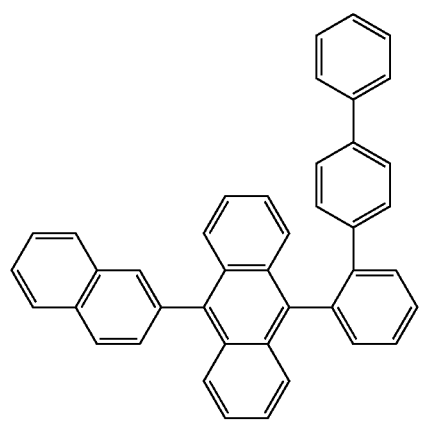
2a'-58
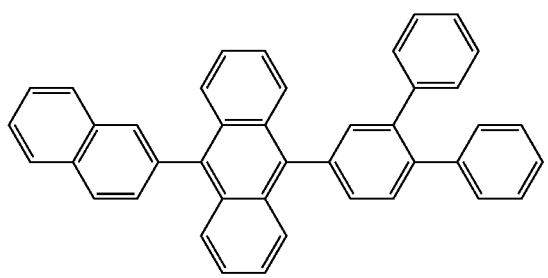

-continued
2a'-59
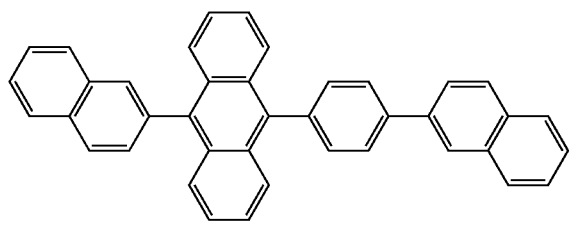
2a'-60
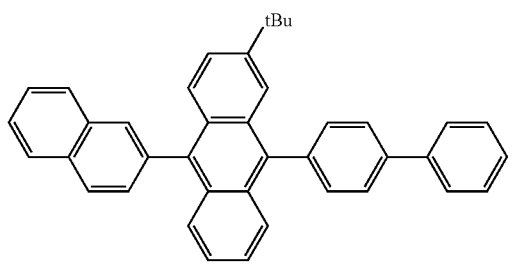
2a'-61
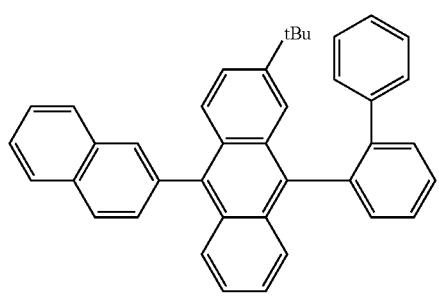
2a'-62
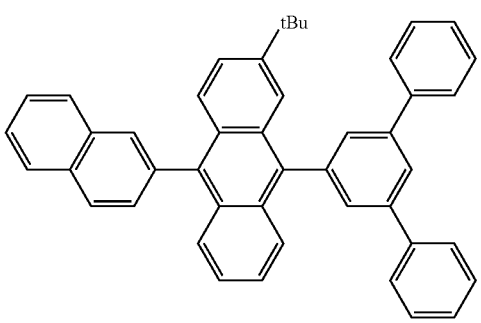
2a'-63
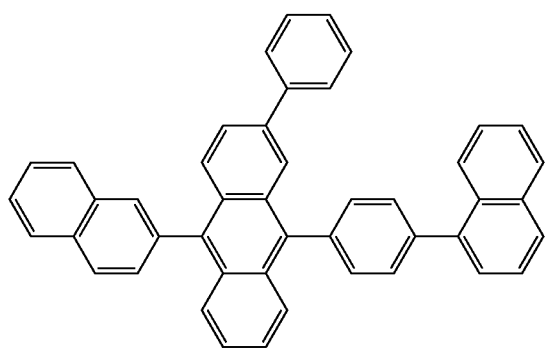
2a'-64
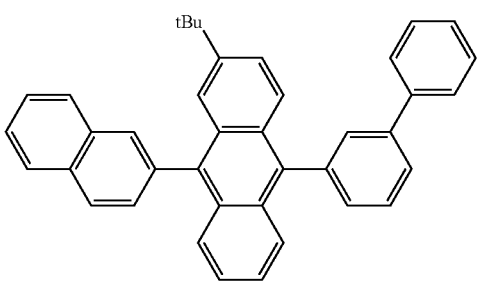
2a'-65
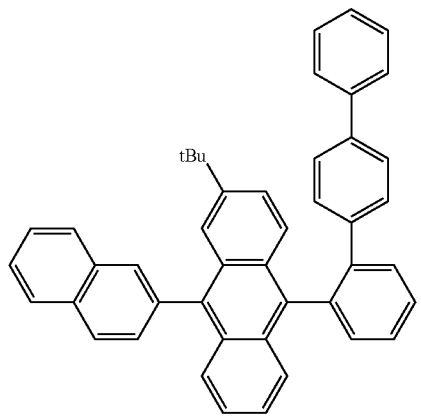
2a'-66
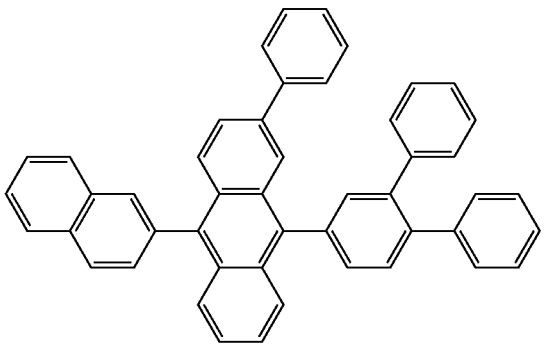

-continued
2a'-67
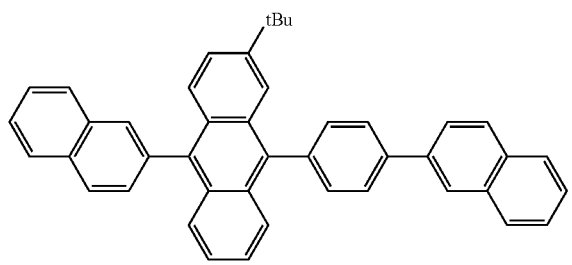
2a'-68
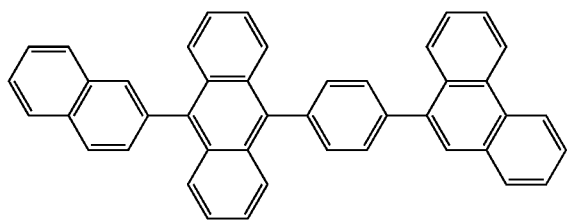
2a'-69
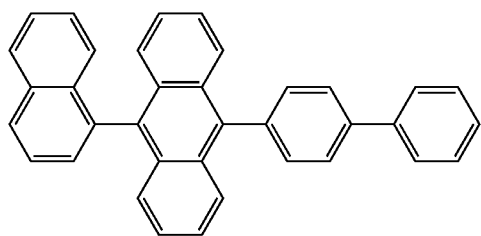
2a'-70
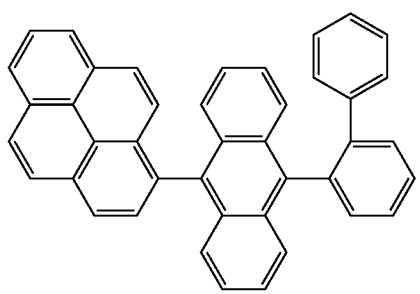
2a'-71
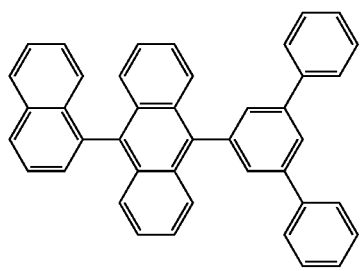
2a'-72
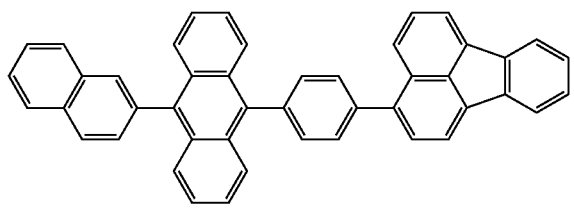
2a'-73
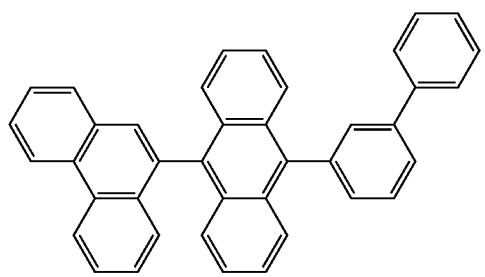
2a'-74
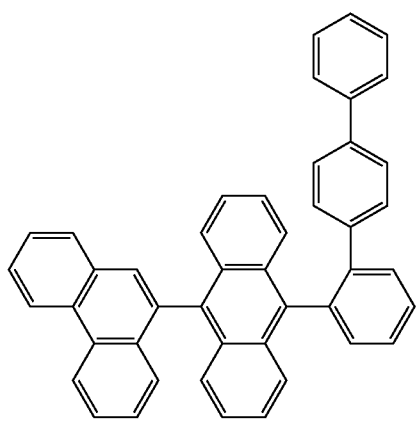

-continued
2a′-75
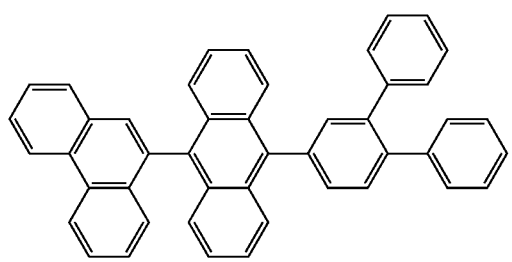
2a′-76
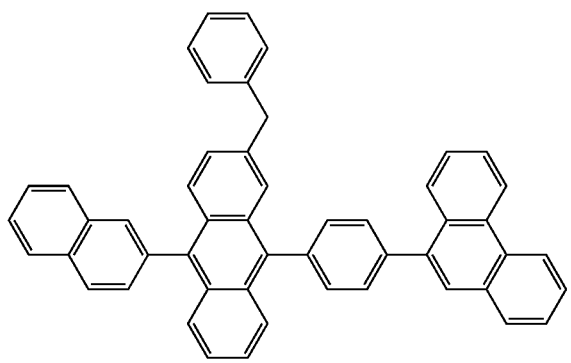
2a′-77
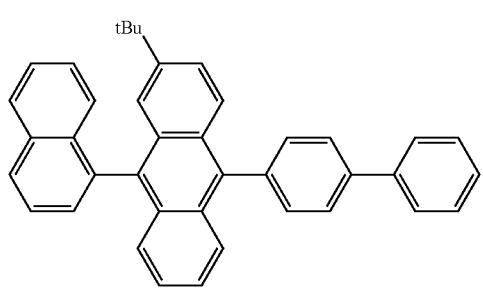
2a′-78
2a′-79
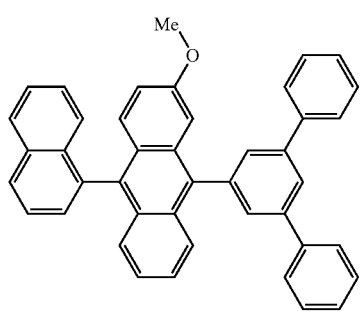
2a′-80
2a′-81
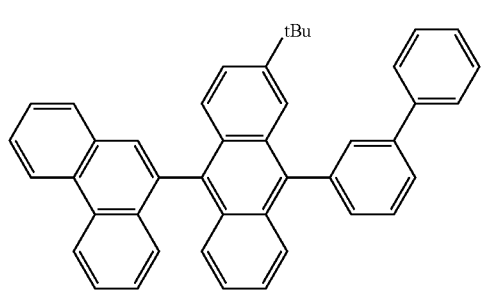
2a′-82
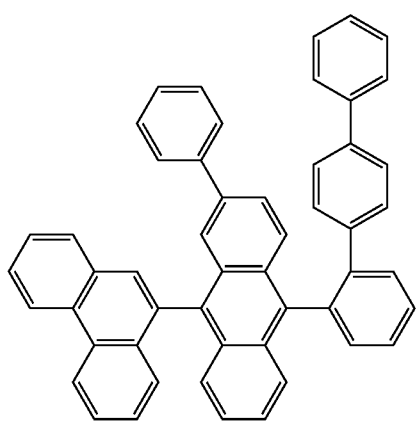

-continued
2a'-83
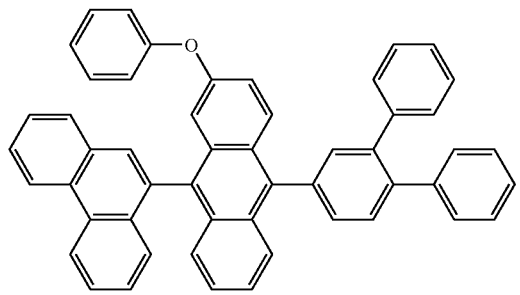
2a'-84
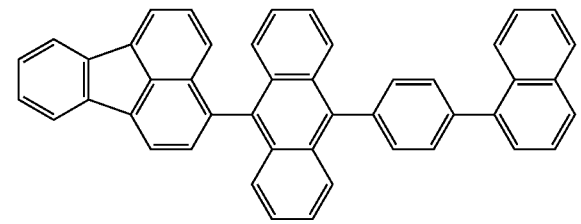
2a'-85
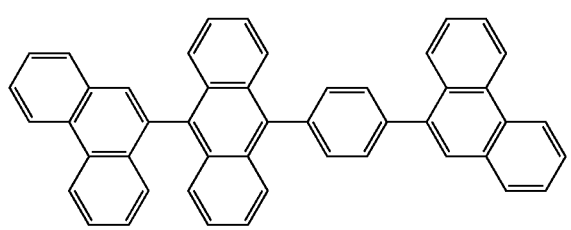
2a'-86
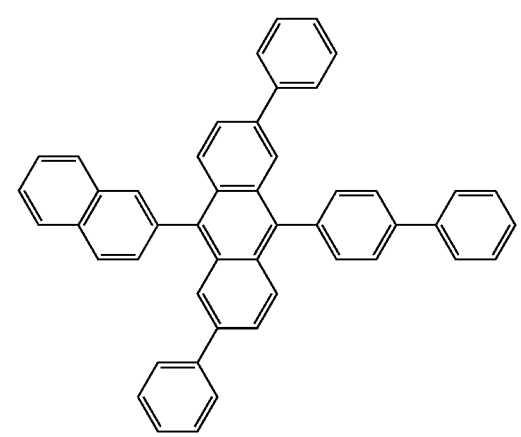
2a'-87
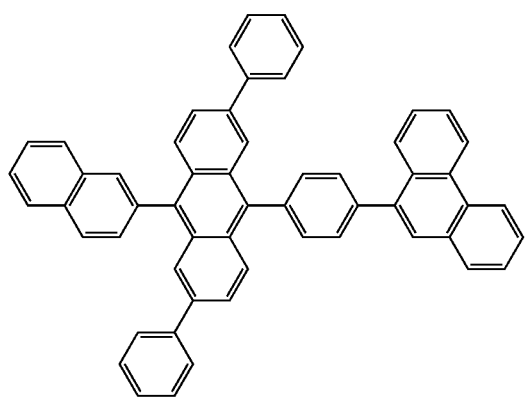
2a'-88
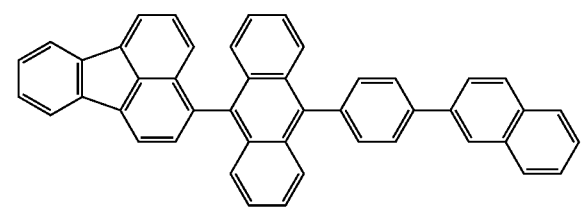
2a'-89
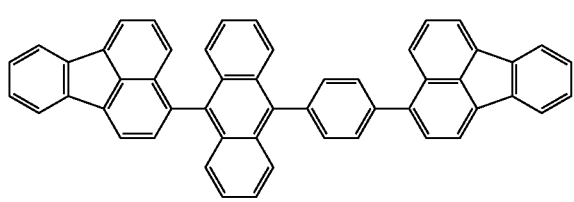
2a'-90
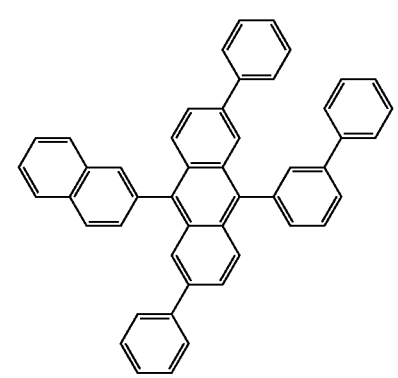

-continued
2a'-91
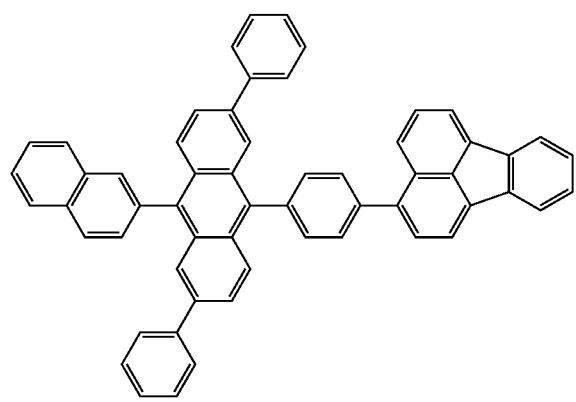
2a'-92
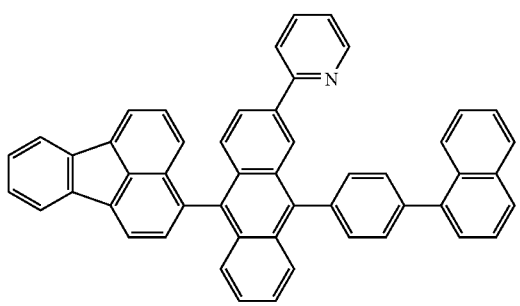
2a'-93
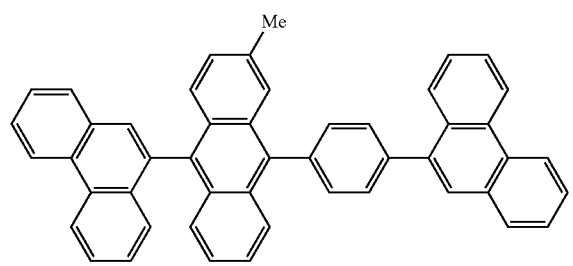
2a'-94
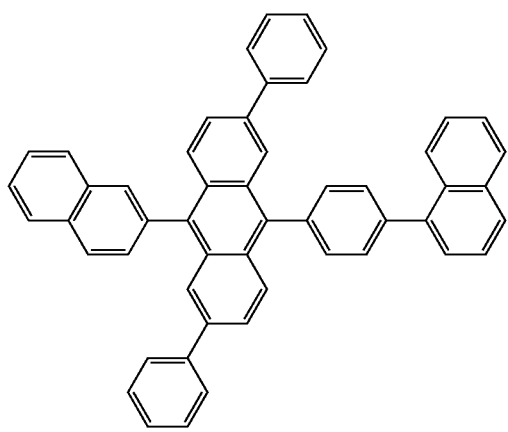
2a'-95
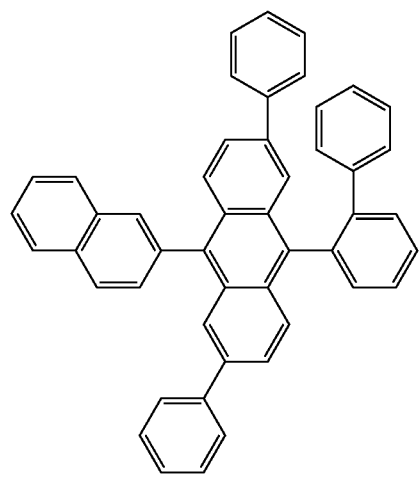
2a'-96
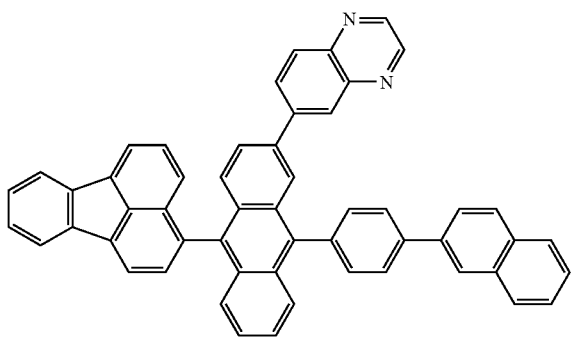

-continued
2a'-97
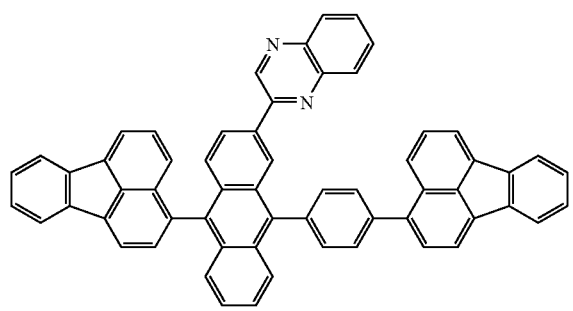
2a'-98
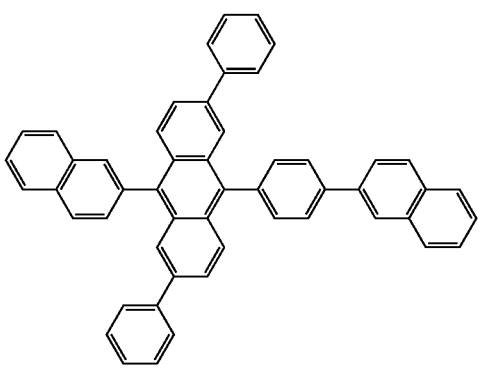
2a'-99
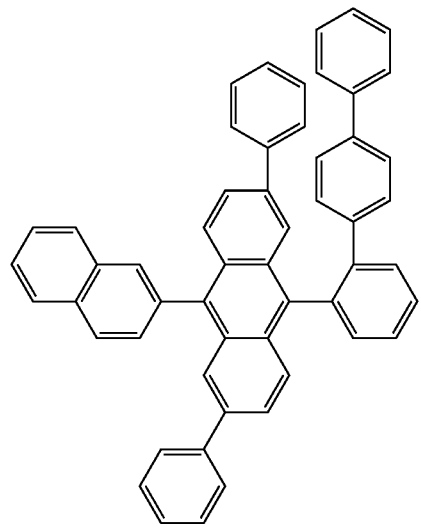
2a'-100
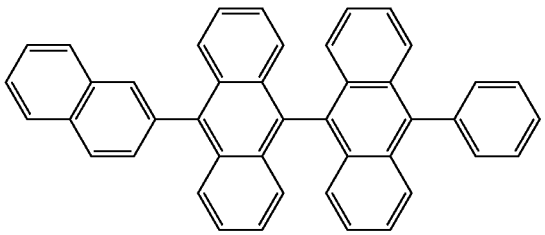
2a'-101
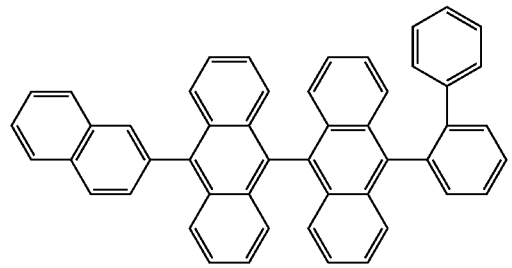
2a'-102
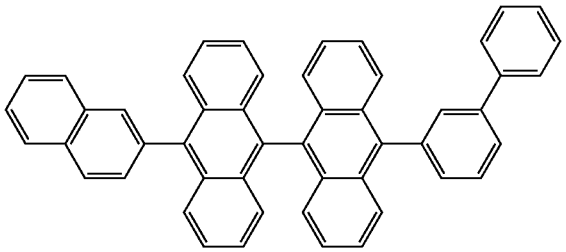
2a'-103
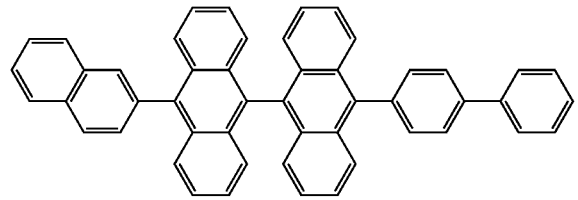
2a'-104
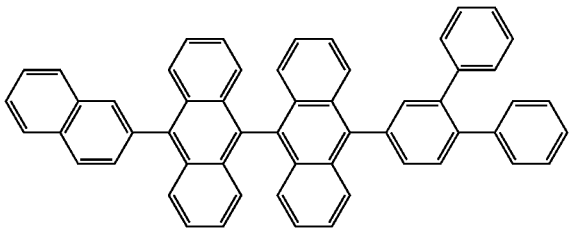

-continued
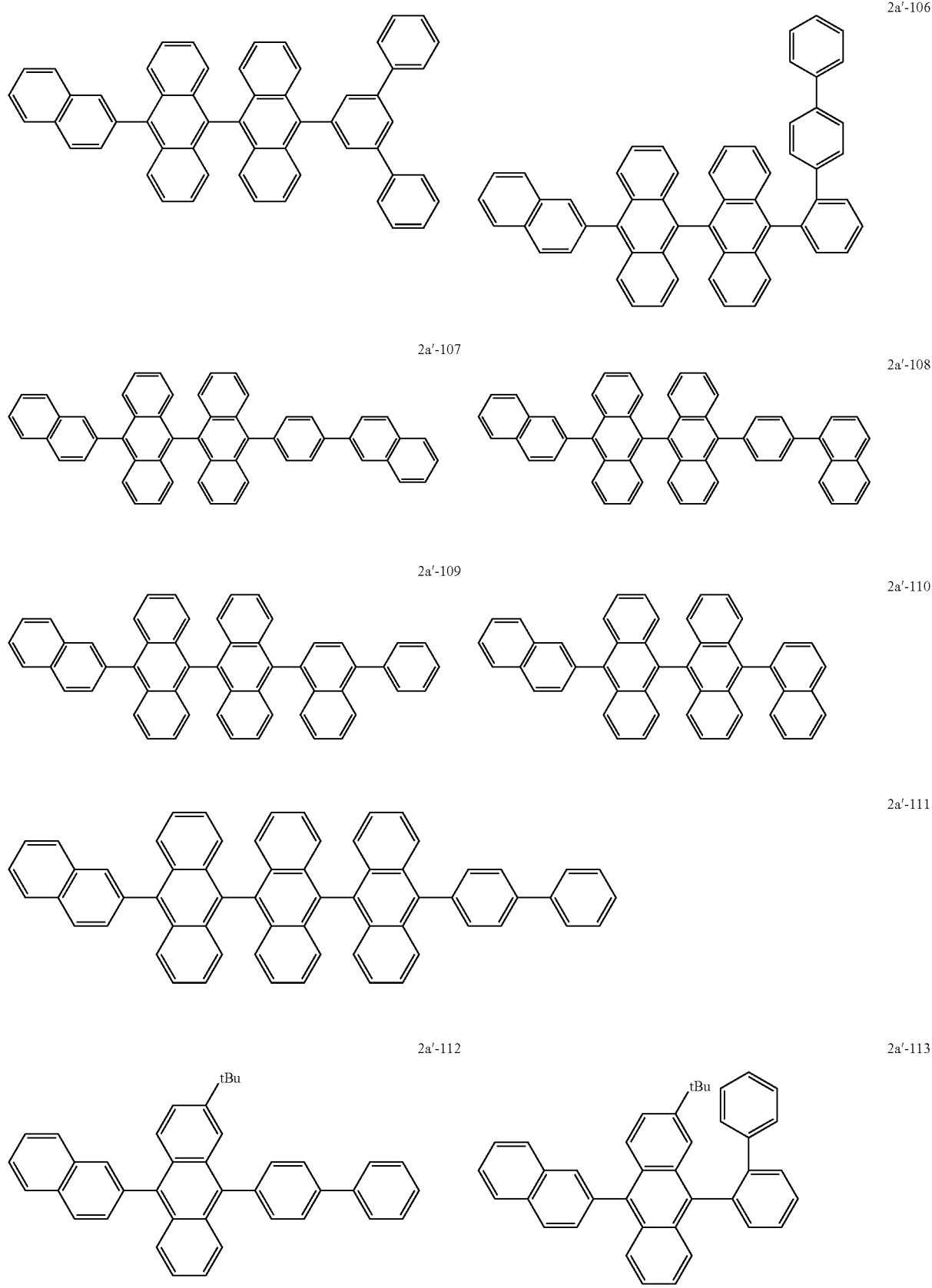

-continued
2a'-114
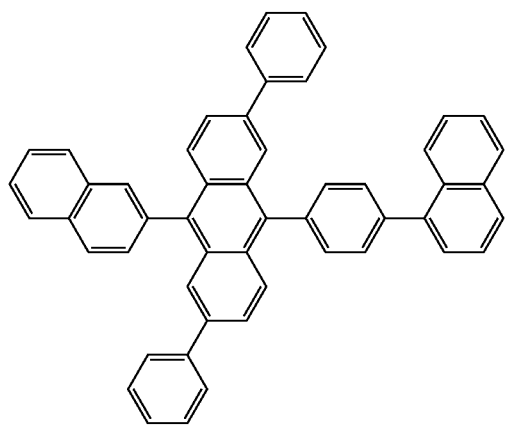
2a'-115
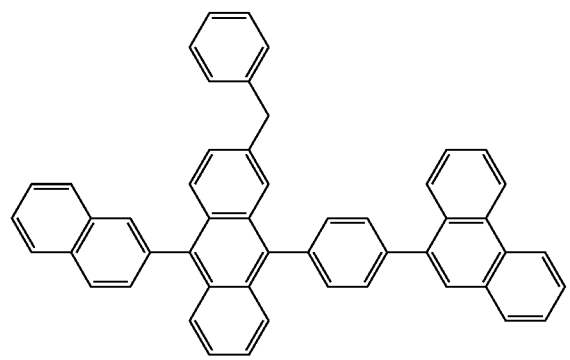
2a'-116
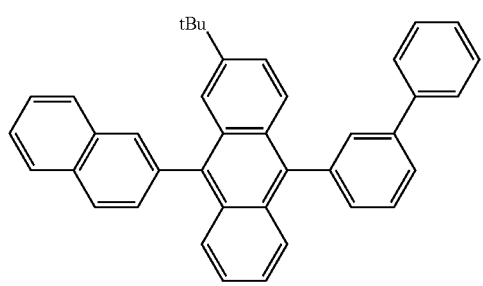
2a'-117
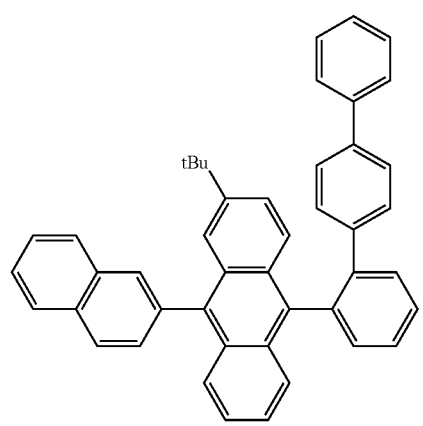
2a'-118
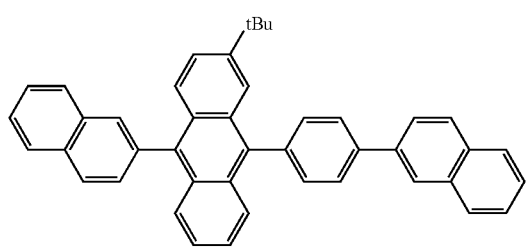
2a'-119
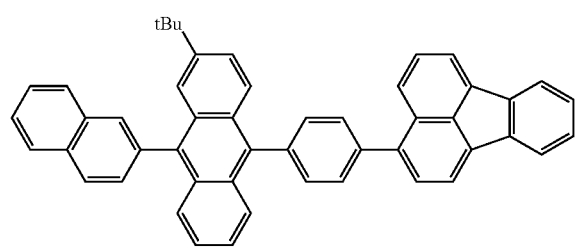
2a'-120
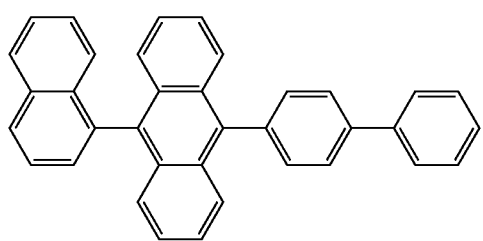
2a'-121
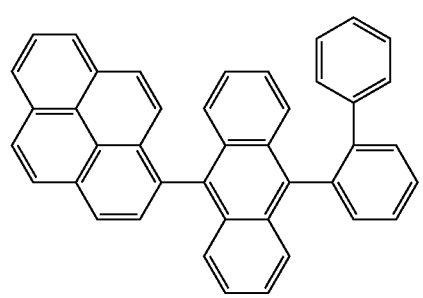

-continued
2a'-122
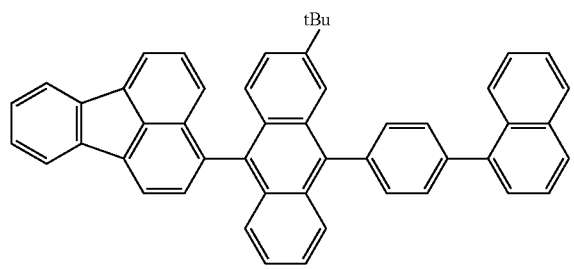
2a'-123
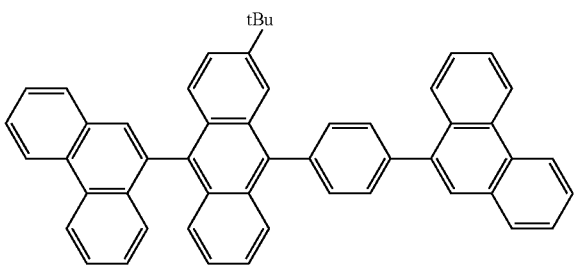
2a'-124
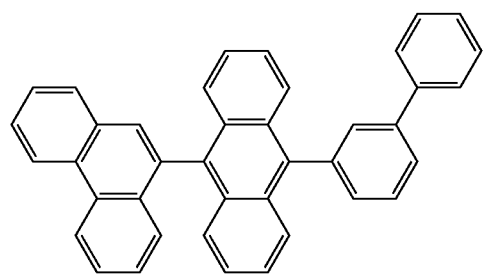
2a'-125
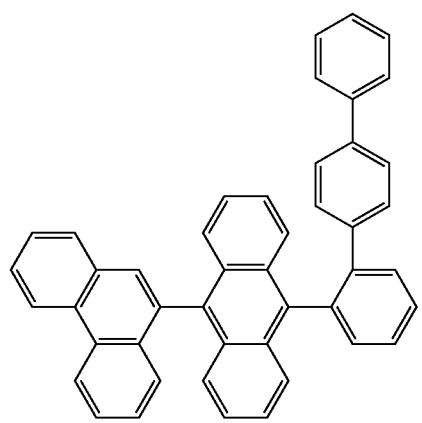
2a'-126
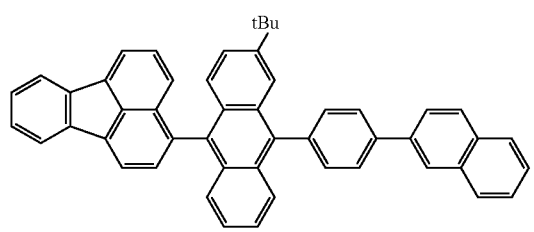
2a'-127
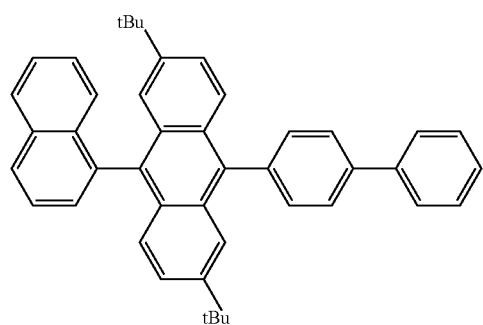
2a'-128
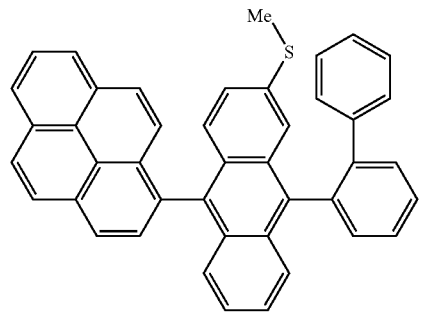
2a'-129
2a'-130
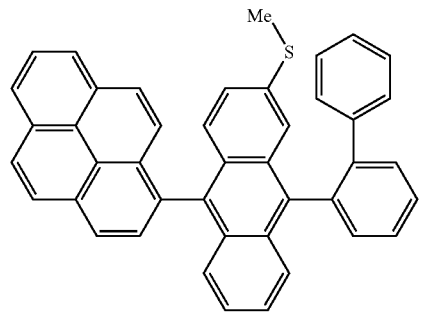
2a'-131
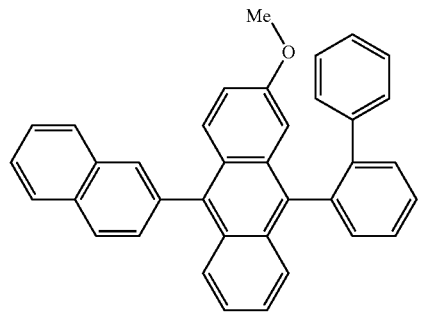

-continued
2a'-132
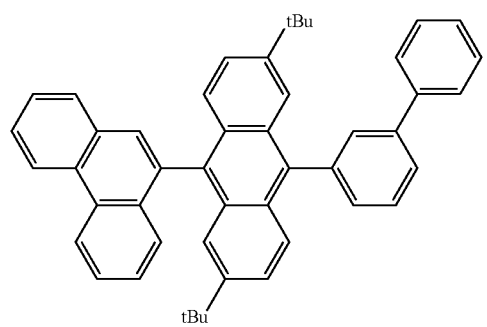
2a'-133
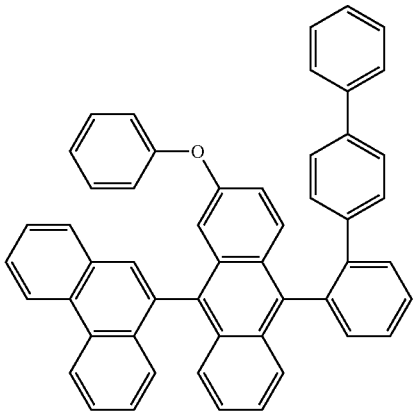
2a'-134
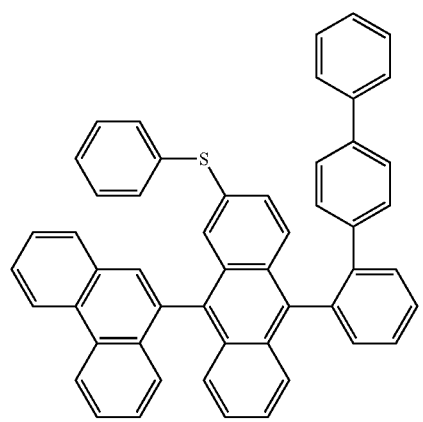
2a'-135
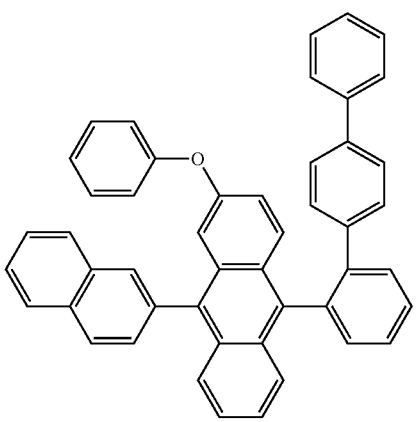
2a'-136
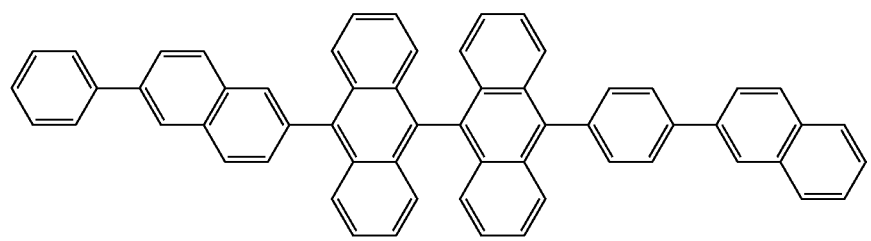
2a'-137
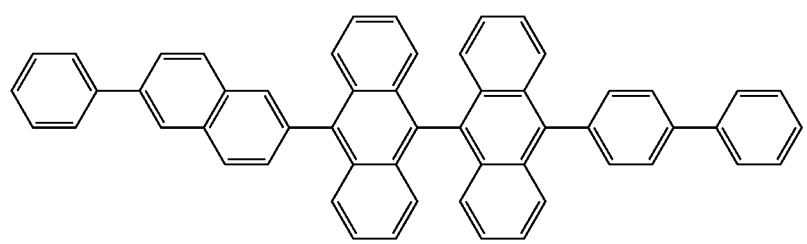
2a'-138
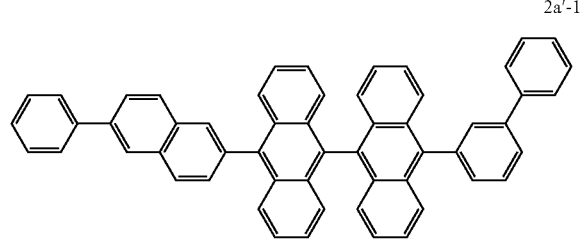
2a'-139
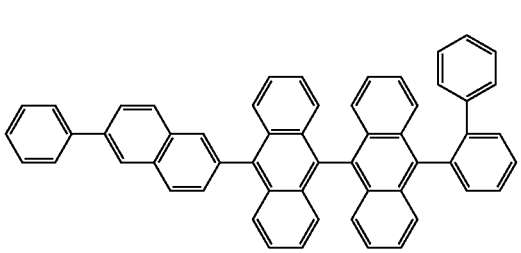

-continued

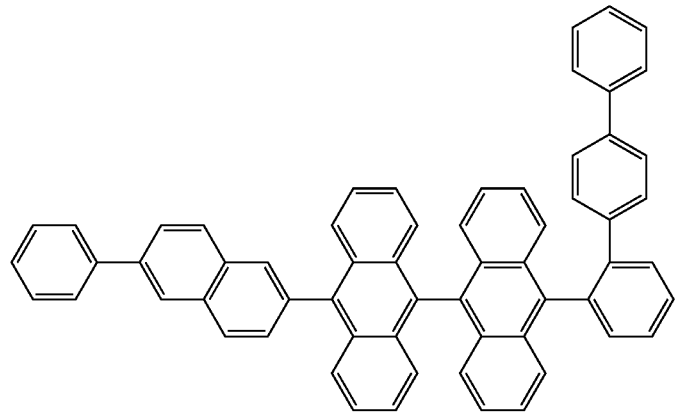
2a'-140

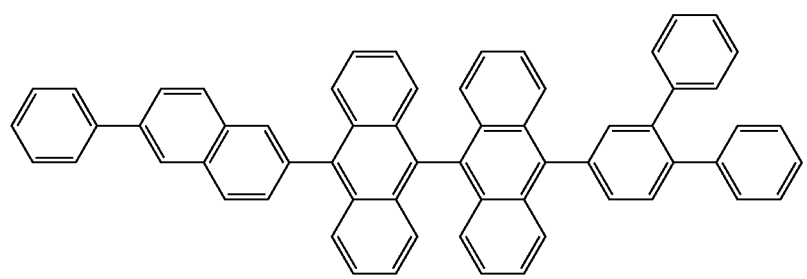
2a'-141

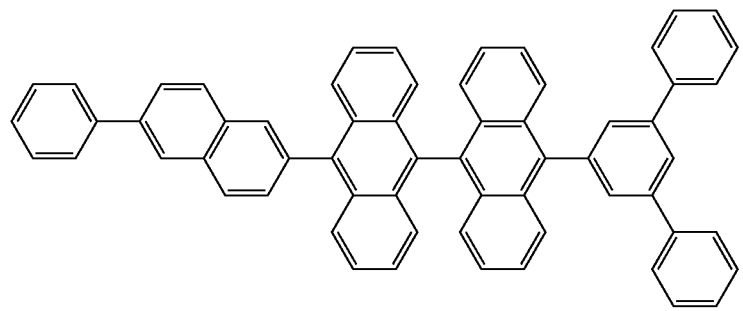
2a'-142

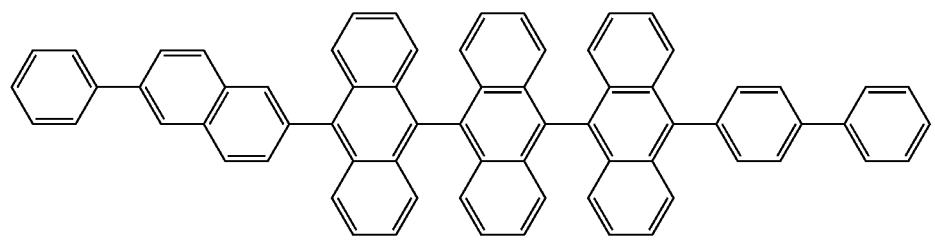
2a'-143

Formula (2b)

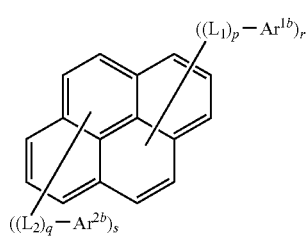
(2b)

(in Formula (2b), $Ar^{1b}$ and $Ar^{2b}$ each are independently a substituted or non-substituted aryl group having 6 to 50 carbon atoms forming the aromatic ring;

$L_1$ and $L_2$ each are selected independently from a substituted or non-substituted phenylene group, a substituted or non-substituted naphthalenylene group, a substituted or non-substituted fluorenylene group and a substituted or non-substituted dibenzosilolylene group;

p and q are an integer of 0 to 2, and r and s are an integer of 1 to 4;

$L_1$ or $Ar^{1b}$ is bonded to any of 1- to 5-positions of pyrene, and $L_2$ or $Ar^{2b}$ is bonded to any of 6- to 10-positions of pyrene).

The substituted or non-substituted aryl group having 6 to 50 carbon atoms forming the aromatic ring represented by $Ar^{1b}$ and $Ar^{2b}$ in Formula (2b) includes phenyl, 1-naphthyl, 2-naphthyl, 1-anthryl, 2-anthryl, 9-anthryl, 9-(10-phenyl)anthryl, 9-(10-naphthyl-1-yl)anthryl, 9-(10-naphthyl-2-yl)anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, 3-methyl-2-naphthyl, 4-methyl-1-naphthyl, 4-methyl-1-anthryl and the like. It is preferably an aromatic cyclic group having 6 to 16 ring carbon atoms, and it is particularly phenyl, 1-naphthyl, 2-naphthyl, 9-(10-phenyl)anthryl, 9-(10-naphthyl-1-yl)anthryl, 9-(10-naphthyl-2-yl)anthryl, 9-phenanthryl, 1-pyrenyl, 2-pyrenyl, 4-pyrenyl, 2-biphenylyl, 3-biphenylyl, 4-biphenylyl, o-tolyl, m-tolyl, p-tolyl and p-t-butylphenyl.

The aryl group described above may be further substituted with a substituent, and the substituent includes an alkyl group (methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl, cyclopropyl, cyclobutyl, cyclopentyl, cyclohexyl, 4-methylcyclohexyl, 1-adamantyl, 2-adamantyl, 1-norbornyl, 2-norbornyl and the like), an alkoxyl group having 1 to 6 carbon atoms (ethoxy, methoxy, i-propoxy, n-propoxy, s-butoxy, t-butoxy, pentoxy, hexyloxy, cyclopentoxy, cyclohexyloxy and the like), an aryl group having 5 to 40 carbon atoms forming the aromatic ring, an amino group substituted with an aryl group having 5 to 40 carbon atoms forming the aromatic ring, an ester group having an aryl group having 5 to 40 carbon atoms forming the aromatic ring, an ester group having an alkyl group having 1 to 6 carbon atoms, a cyano group, a nitro group, a halogen atom and the like.

$L_1$ and $L_2$ in Formula (2b) are selected preferably from a substituted or non-substituted phenylene group and a substituted or non-substituted fluorenylene group.

The substituents therefor include the same groups as given in the aromatic group described above.

The term p in Formula (2b) is preferably an integer of 0 to 1. The term r in Formula (2b) is preferably an integer of 1 to 2. The term q in Formula (2b) is preferably an integer of 0 to 1. The term s in Formula (2b) is preferably an integer of 0 to 2.

The specific examples of the pyrene derivative represented by Formula (2b) used for the organic EL device of the present invention include asymmetric pyrene derivatives shown in [0020] to [0023] of International Publication NO. 2005/115950. In addition thereto, symmetric pyrene derivatives can also be used as a material for the organic EL device of the present invention. The representative specific examples thereof are shown below.

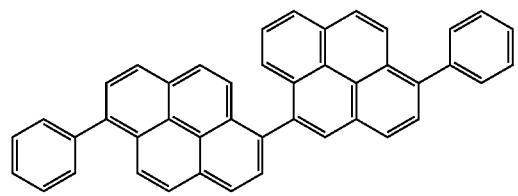

2b-1

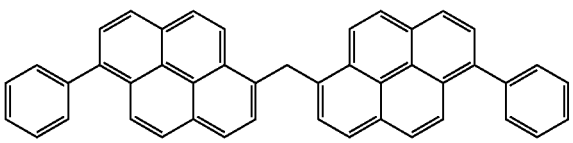

2b-2

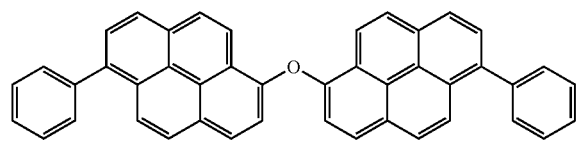

2b-3

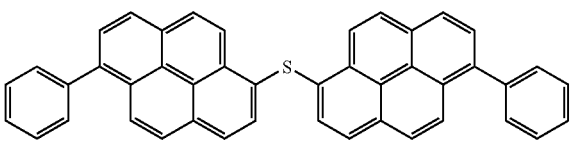

2b-4

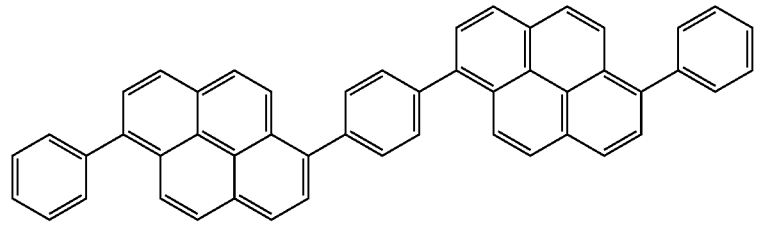

2b-5

-continued
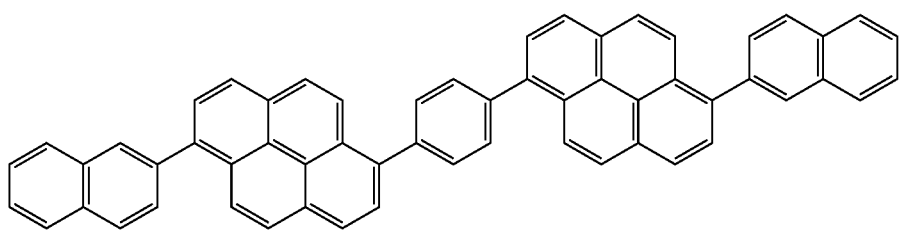
2b-6
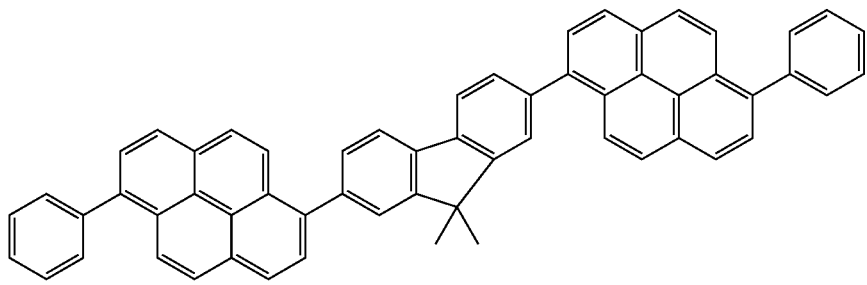
2b-7
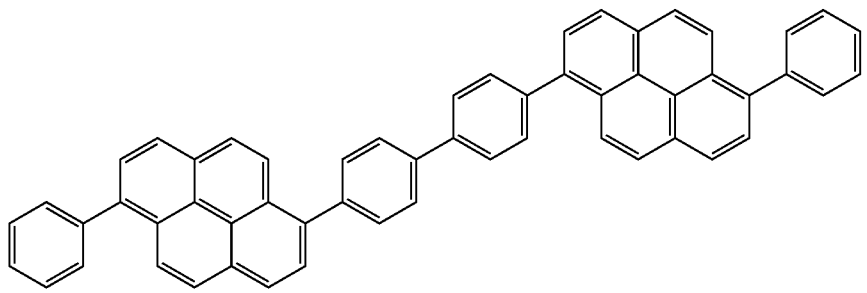
2b-8
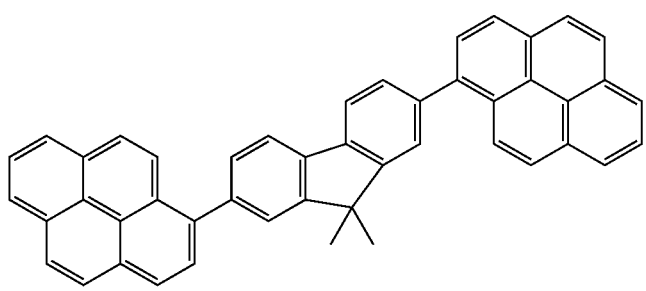
2b-9
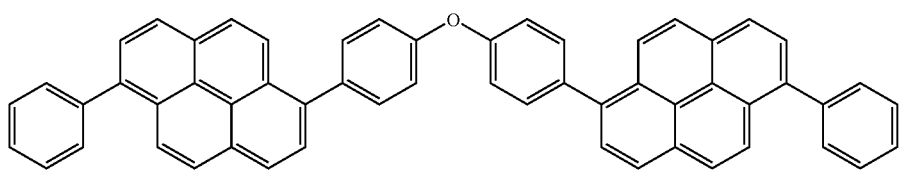
2b-10
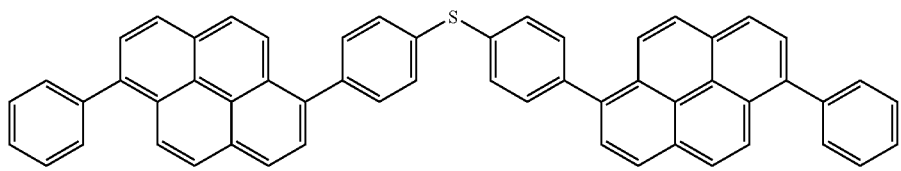
2b-11

-continued
2b-12
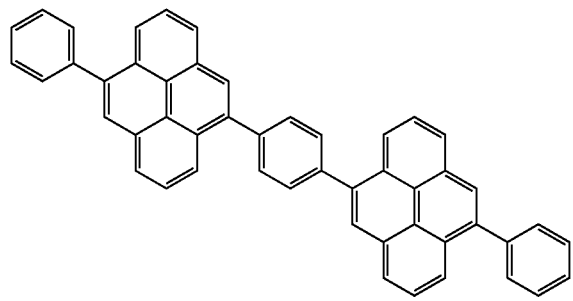
2b-13
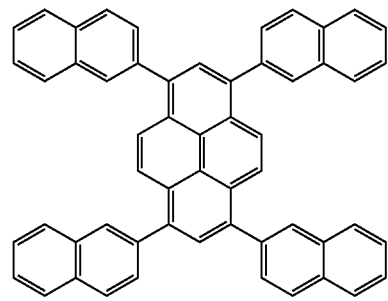
2b-14
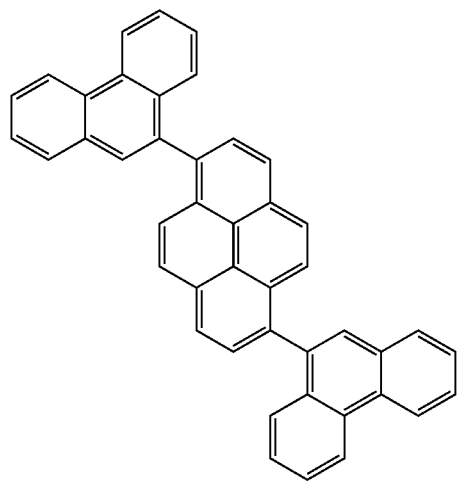
2b-15
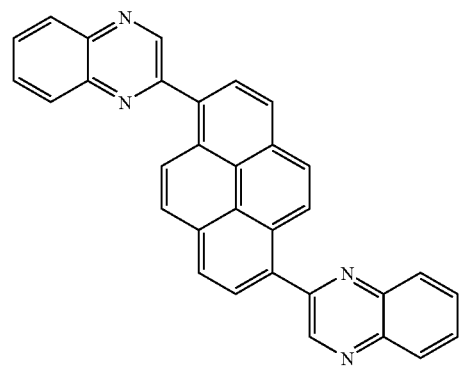
2b-16
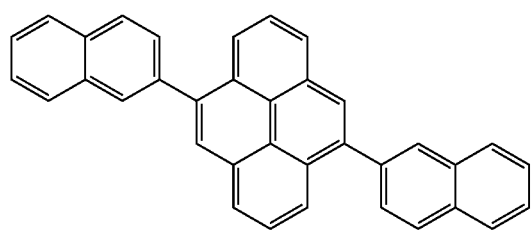
2b-17
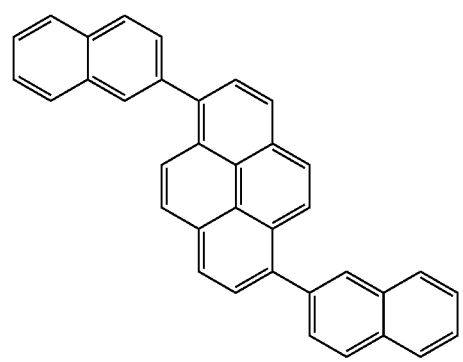
2b-18
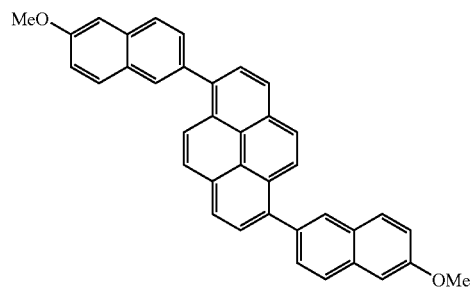
2b-19
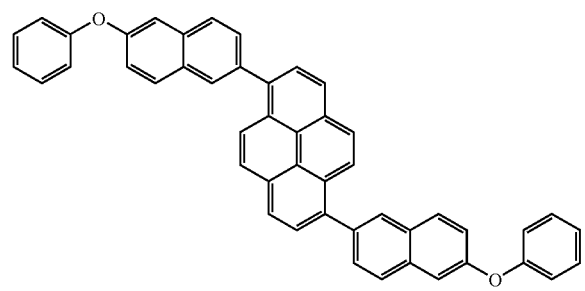

-continued
2b-20
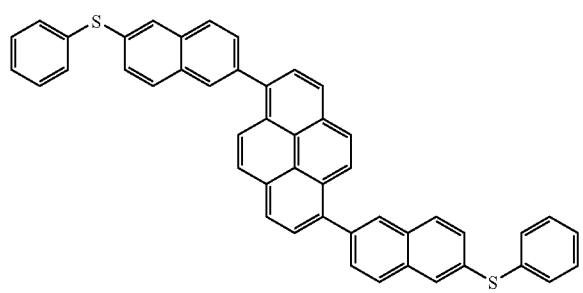
2b-21
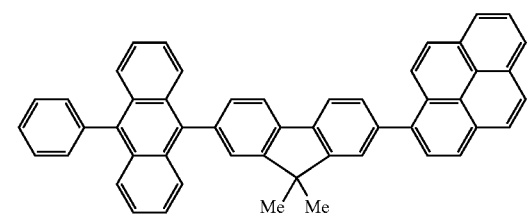
2b-22 2b-23
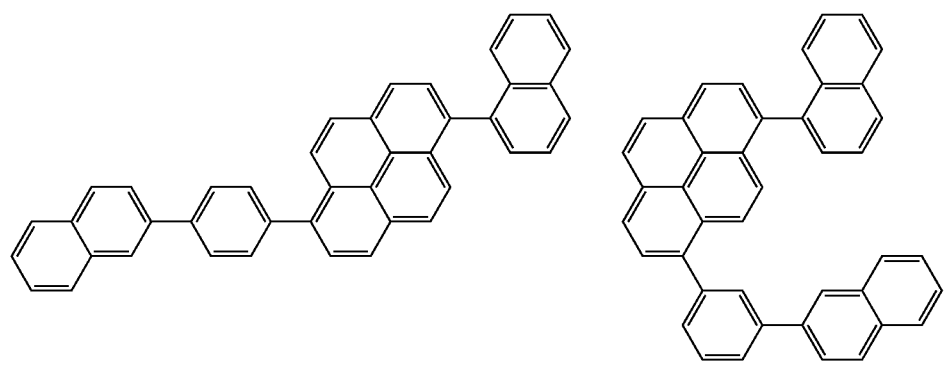
2b-24 2b-25
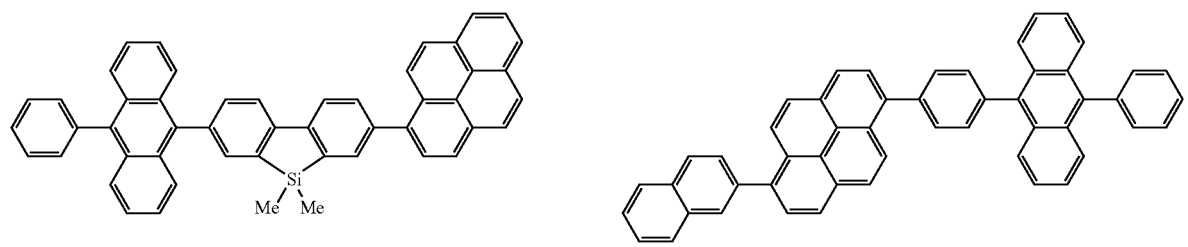
2b-26 2b-27
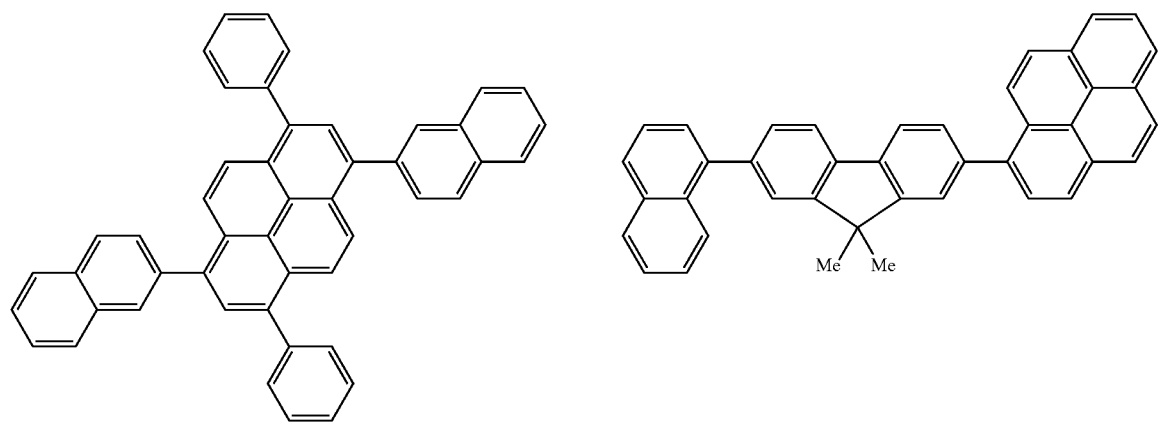

-continued
2b-28
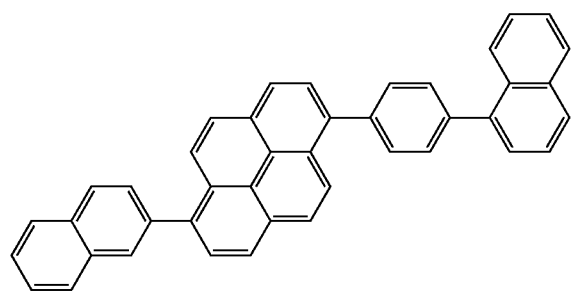
2b-29
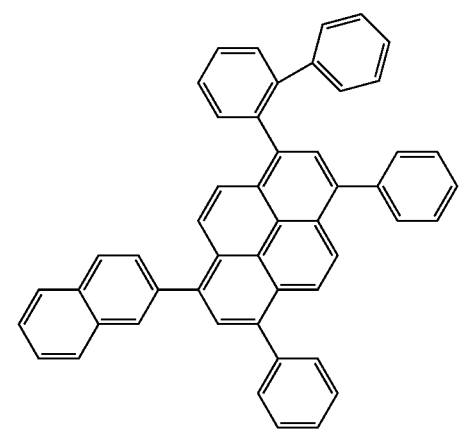
2b-30
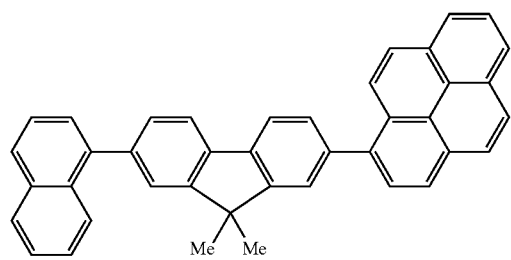
2b-31
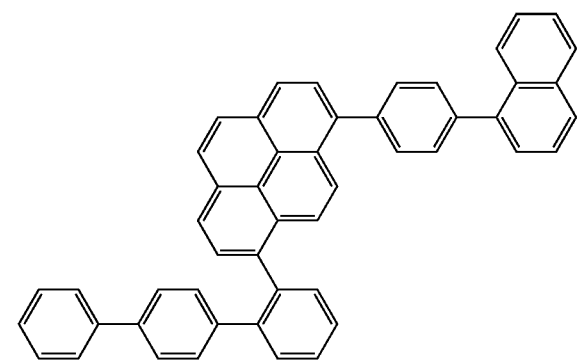
2b-32
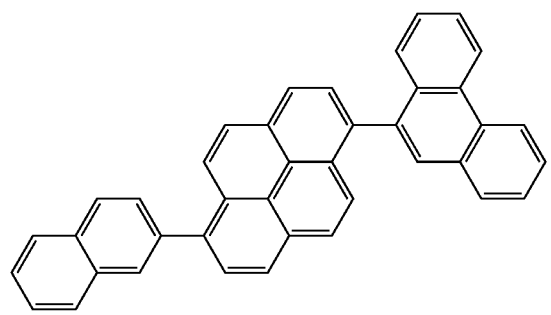
2b-33
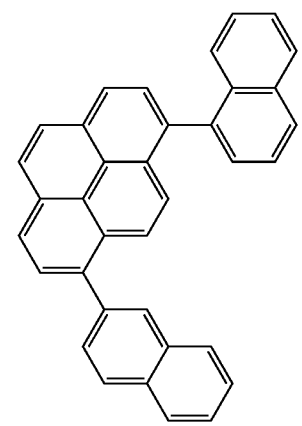
2b-34
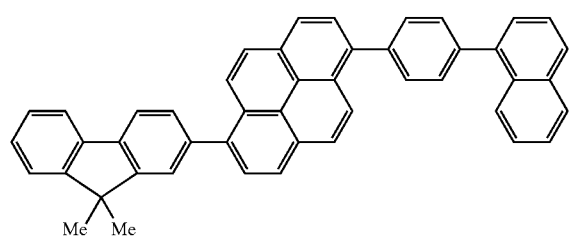
2b-35
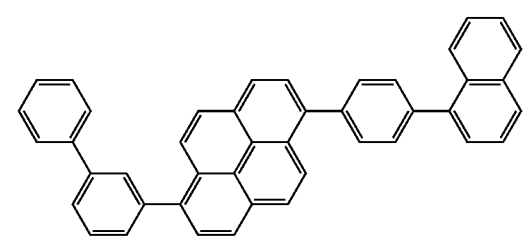

-continued

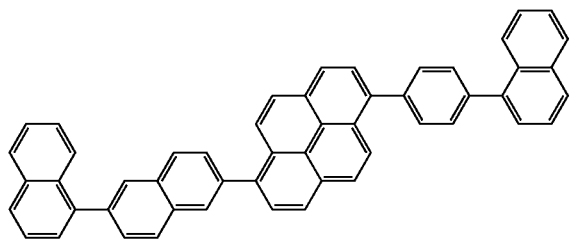
2b-36

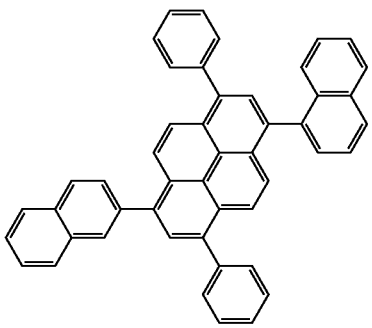
2b-37

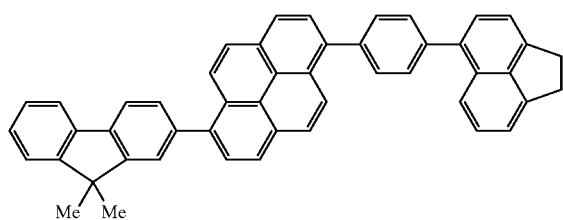
2b-38

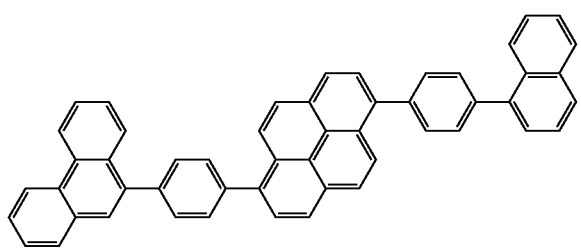
2b-39

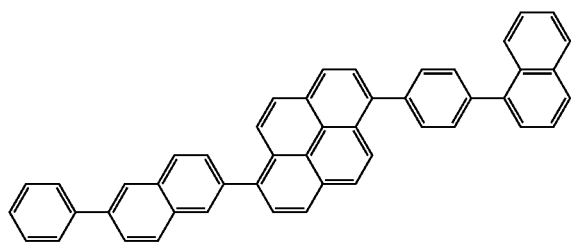
2b-40

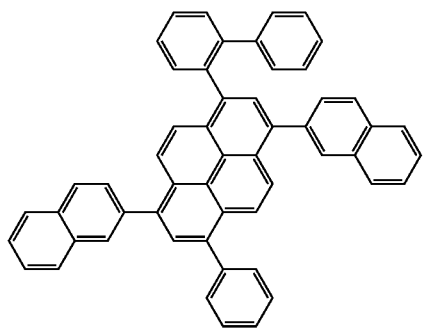
2b-41

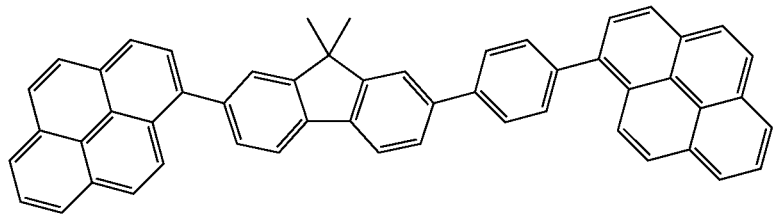
2b-42

Formula (2c)

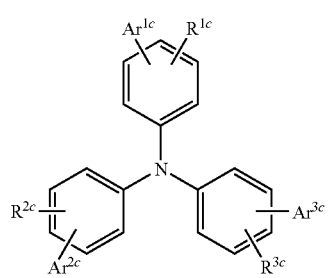

(2c)

(in Formula (2c), $Ar^{1c}$, $Ar^{2c}$ and $Ar^{3c}$ each are selected independently from a group having an anthracene structure, a group having a phenanthrene structure, a group having a pyrene structure, a group having a fluorene structure and a group having a perylene structure; and $R^{1c}$, $R^{2c}$ and $R^{3c}$ each represent independently a hydrogen atom or a substituent).

$Ar^{1c}$, $Ar^{2c}$ and $Ar^{3c}$ in Formula (2c) are selected preferably from substituted or non-substituted anthrylphenyl, anthryl, phenanthrenyl, perylenyl and pyrenyl, and they are selected more preferably from alkyl-substituted or non-substituted anthrylphenyl, phenanthryl and pyrenyl. They are selected particularly preferably from pyrenyl and phenanthryl.

$R^{1c}$, $R^{2c}$ and $R^{3c}$ in Formula (2c) include an alkyl group (it has preferably 1 to 30 carbon atoms, more preferably 1 to 20 carbon atoms and particularly preferably 1 to 10 carbon atoms and includes, for example, methyl, ethyl, isopropyl, t-butyl, n-octyl, n-decyl, n-hexadecyl, cyclopropyl, cyclopentyl, cyclohexyl and the like), an alkenyl group (it has preferably 2 to 30 carbon atoms, more preferably 2 to 20 carbon atoms and particularly preferably 2 to 10 carbon atoms and includes, for example, vinyl, allyl, 2-butenyl, 3-pentenyl and the like), an alkynyl group (it has preferably 2 to 30 carbon atoms, more preferably 2 to 20 carbon atoms and particularly preferably 2 to 10 carbon atoms and includes, for example, propargyl, 3-pentynyl and the like), an aryl group (it has preferably 6 to 30 carbon atoms, more preferably 6 to 20 carbon atoms and particularly preferably 6 to 12 carbon atoms and includes, for example, phenyl, p-methylphenyl, naphthyl, anthranyl and the like), an amino group (it has preferably 0 to 30 carbon atoms, more preferably 0 to 20 carbon atoms and particularly preferably 0 to 10 carbon atoms and includes, for example, amino, methylamino, dimethylamino, diethylamino, dibenzylamino, diphenylamino, ditolylamino and the like), an alkoxyl group (it has preferably 1 to 30 carbon atoms, more preferably 1 to 20 carbon atoms and particularly preferably 1 to 10 carbon atoms and includes, for example, methoxy, ethoxy, butoxy, 2-ethylhexyloxy and the like), an aryloxy group (it has preferably 6 to 30 carbon atoms, more preferably 6 to 20 carbon atoms and particularly preferably 6 to 12 carbon atoms and includes, for example, phenyloxy, 1-naphthyloxy, 2-naphthyloxy and the like), a heteroaryloxy group (it has preferably 1 to 30 carbon atoms, more preferably 1 to 20 carbon atoms and particularly preferably 1 to 12 carbon atoms and includes, for example, pyridyloxy, pyrazyloxy, pyrimidyloxy, quinolyloxy and the like), an acyl group (it has preferably 1 to 30 carbon atoms, more preferably 1 to 20 carbon atoms and particularly preferably 1 to 12 carbon atoms and includes, for example, acetyl, benzoyl, formyl, pivaloyl and the like), an alkoxycarbonyl group (it has preferably 2 to 30 carbon atoms, more preferably 2 to 20 carbon atoms and particularly preferably 2 to 12 carbon atoms and includes, for example, methoxycarbonyl, ethoxycarbonyl and the like), an aryloxycarbonyl group (it has preferably 7 to 30 carbon atoms, more preferably 7 to 20 carbon atoms and particularly preferably 7 to 12 carbon atoms and includes, for example, phenyloxycarbonyl and the like), an acyloxy group (it has preferably 2 to 30 carbon atoms, more preferably 2 to 20 carbon atoms and particularly preferably 2 to 10 carbon atoms and includes, for example, acetoxy, benzoyloxy and the like), an acylamino group (it has preferably 2 to 30 carbon atoms, more preferably 2 to 20 carbon atoms and particularly preferably 2 to 10 carbon atoms and includes, for example, acetylamino, benzoylamino and the like), an alkoxycarbonylamino group (it has preferably 2 to 30 carbon atoms, more preferably 2 to 20 carbon atoms and particularly preferably 2 to 12 carbon atoms and includes, for example, methoxycarbonylamino and the like), an aryloxycarbonylamino group (it has preferably 7 to 30 carbon atoms, more preferably 7 to 20 carbon atoms and particularly preferably 7 to 12 carbon atoms and includes, for example, phenyloxycarbonylamino and the like), a sulfonylamino group (it has preferably 1 to 30 carbon atoms, more preferably 1 to 20 carbon atoms and particularly preferably 1 to 12 carbon atoms and includes, for example, methanesulfonylamino, benzenesulfonylamino and the like), a sulfamoyl group (it has preferably 0 to 30 carbon atoms, more preferably 0 to 20 carbon atoms and particularly preferably 0 to 12 carbon atoms and includes, for example, sulfamoyl, methylsulfamoyl, dimethylsulfamoyl, phenylsulfamoyl and the like), a carbamoyl group (it has preferably 1 to 30 carbon atoms, more preferably 1 to 20 carbon atoms and particularly preferably 1 to 12 carbon atoms and includes, for example, carbamoyl, methylcarbamoyl, diethylcarbamoyl, phenylcarbamoyl and the like), an alkylthio group (it has preferably 1 to 30 carbon atoms, more preferably 1 to 20 carbon atoms and particularly preferably 1 to 12 carbon atoms and includes, for example, methylthio, ethylthio and the like), an arylthio group (it has preferably 6 to 30 carbon atoms, more preferably 6 to 20 carbon atoms and particularly preferably 6 to 12 carbon atoms and includes, for example, phenylthio and the like), a heteroarylthio group (it has preferably 1 to 30 carbon atoms, more preferably 1 to 20 carbon atoms and particularly preferably 1 to 12 carbon atoms and includes, for example, pyridylthio, 2-benzimidazolylthio, 2-benzoxazolylthio, 2-benzothiazolylthio and the like), a sulfonyl group (it has preferably 1 to 30 carbon atoms, more preferably 1 to 20 carbon atoms and particularly preferably 1 to 12 carbon atoms and includes, for example, mesyl, tosyl and the like), a sulfinyl group (it has preferably 1 to 30 carbon atoms, more preferably 1 to 20 carbon atoms and particularly preferably 1 to 12 carbon atoms and includes, for example, methanesulfinyl, benznesulfinyl and the like), a ureido group (it has preferably 1 to 30 carbon atoms, more preferably 1 to 20 carbon atoms and particularly preferably 1 to 12 carbon atoms and includes, for example, ureido, methylureido, phenylureido and the like), a phosphoric amide group (it has preferably 1 to 30 carbon atoms, more preferably 1 to 20 carbon atoms and particularly preferably 1 to 12 carbon atoms and includes, for example, diethylphosphoric amide, phenylphosphoric amide and the like), a hydroxy group, a mercapto group, a halogen atom (including, for example, a fluorine atom, a chlorine atom, a bromine atom and an iodine atom), a cyano group, a sulfo group, a carboxyl group, a nitro group, a hydroxamic acid group, a sulfino group, a hydrazine group, an imino group, a heterocyclic group (it has preferably 1 to 30 carbon atoms, more preferably 1 to 12 carbon atoms, and a hetero atom includes, for example, a nitrogen atom, an oxygen atom and a sulfur atom; to be specific, it includes, for example, imidazolyl, pyridyl, quinolyl, furyl, thienyl, piperidyl, morpholino, benzoxazolyl, benzimidazolyl, benzothiazolyl and the like), a silyl group (it has preferably 3 to 40 carbon atoms, more preferably 3 to 30 carbon atoms and particularly preferably 3 to 24 carbon atoms and includes, for example, trimethylsilyl, triphenylsilyl and the like) and the like. The above substituents may be further substituted.

The substituents $R^{1c}$, $R^{2c}$ and $R^3$, in Formula (2c) are selected from an alkyl group and an aryl group.

Publicly known various amine derivatives such as amine derivatives shown in [0079] to [0083] of Japanese Patent Application Laid-Open No. 324678/2002 can be given as the specific examples of the amine derivative represented by Formula (2c) used for the organic EL device of the present invention. The representative specific examples thereof are shown below.

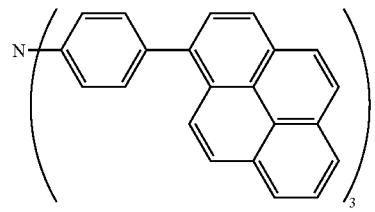

2c-1

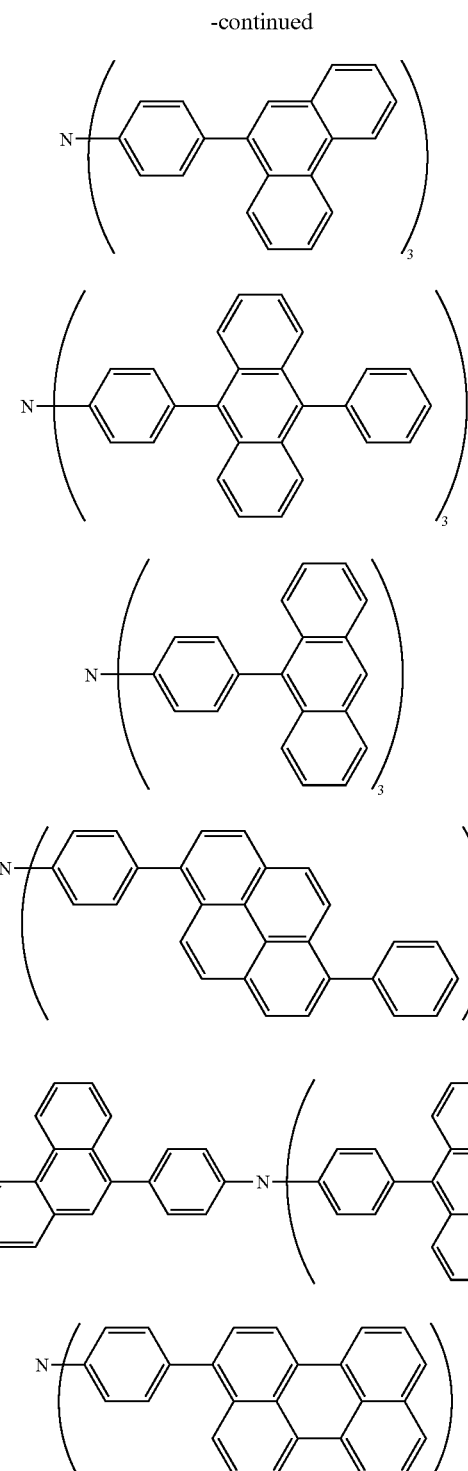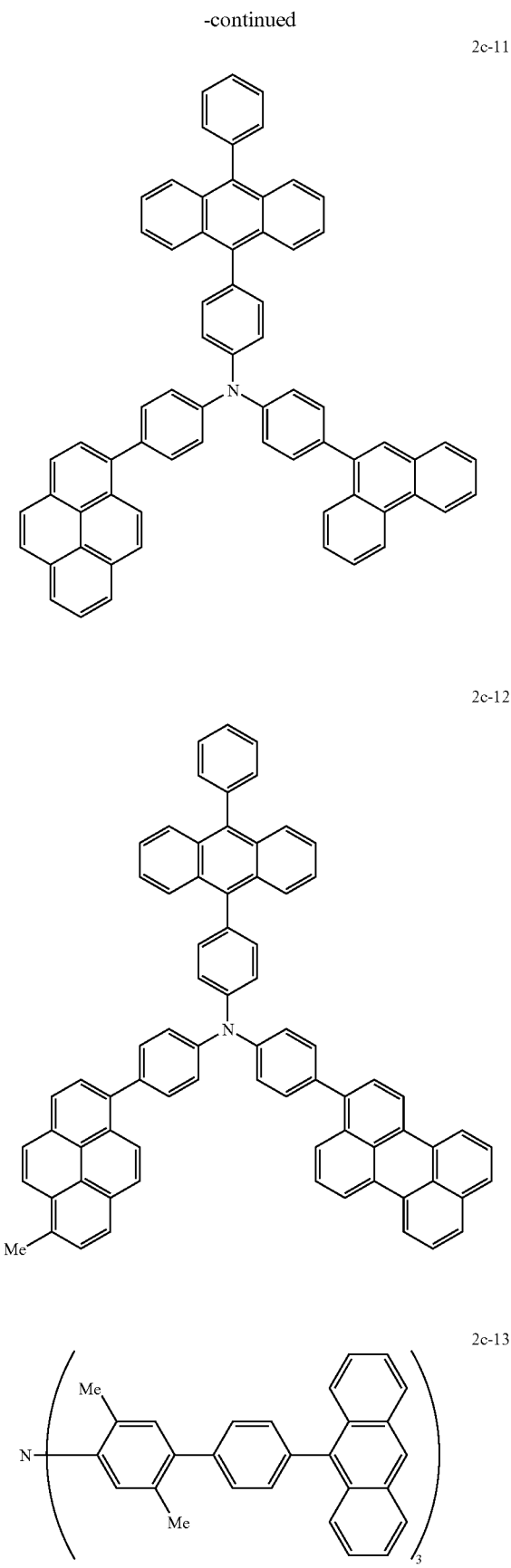

-continued

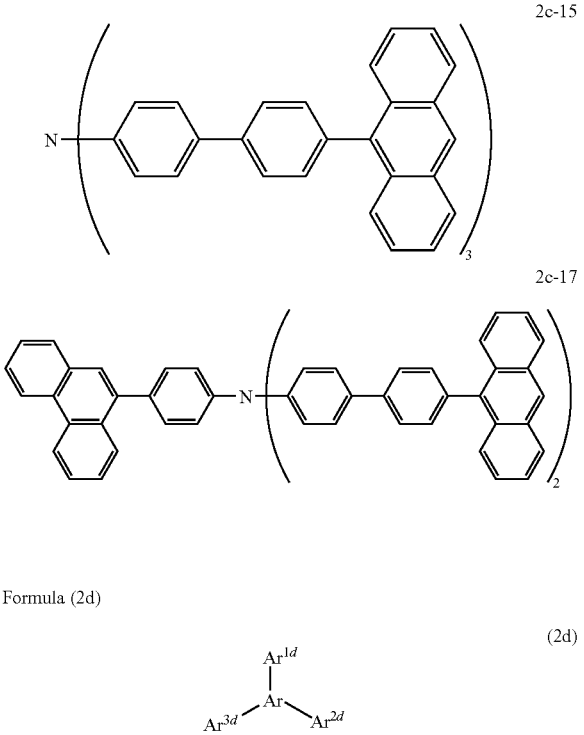

Formula (2d)

$$\underset{Ar^{3d}}{\overset{Ar^{1d}}{\underset{|}{Ar}}}Ar^{2d}$$ (2d)

(in Formula (2d), $Ar^{1d}$, $Ar^{2d}$ and $Ar^{3d}$ each represent independently a substituted or non-substituted aryl group having 6 to 50 carbon atoms forming the aromatic ring; the aryl group described above may be substituted with at least one substituent;

at least one of $Ar^{1d}$, $Ar^{2d}$, $Ar^{3d}$ and the substituents present on the above aryl groups has a fused ring aryl structure having 10 to 20 carbon atoms forming the aromatic ring or a fused ring heteroaryl structure having 6 to 20 atoms forming a ring; and Ar represents a trivalent group derived from an aromatic ring or an aromatic heterocycle).

The aryl group having 6 to 50 carbon atoms forming the aromatic ring represented by $Ar^{1d}$, $Ar^{2d}$ and $Ar^{3d}$ in Formula (2d) has preferably 6 to 30 carbon atoms forming the aromatic ring, more preferably 6 to 20 carbon atoms forming the aromatic ring and further preferably 6 to 16 carbon atoms forming the aromatic ring. The aryl group includes phenyl, naphthyl, anthryl, phenanthrenyl, pyrenyl, perylenyl, fluorenyl, biphenylyl, terphenylyl, rubrenyl, chrysenyl, triphenylenyl, benzoanthryl, benzophenanthrenyl, diphenylylanthryl and the like. The above aryl groups may further have substituents.

The substituents present on the aryl groups include, for example, an alkyl group (it has preferably 1 to 30 carbon atoms, more preferably 1 to 20 carbon atoms and particularly preferably 1 to 10 carbon atoms and includes, for example, methyl, ethyl, isopropyl, t-butyl, n-octyl, n-decyl, n-hexadecyl, cyclopropyl, cyclopentyl, cyclohexyl and the like), an alkenyl group (it has preferably 2 to 30 carbon atoms, more preferably 2 to 20 carbon atoms and particularly preferably 2 to 10 carbon atoms and includes, for example, vinyl, allyl, 2-butenyl, 3-pentenyl and the like), an alkynyl group (it has preferably 2 to 30 carbon atoms, more preferably 2 to 20 carbon atoms and particularly preferably 2 to 10 carbon atoms and includes, for example, propargyl, 3-pentynyl and the like), an aryl group (it has preferably 6 to 30 carbon atoms, more preferably 6 to 20 carbon atoms and particularly preferably 6 to 12 carbon atoms and includes, for example, phenyl, p-methylphenyl, naphthyl, anthranyl and the like), an amino group (it has preferably 0 to 30 carbon atoms, more preferably 0 to 20 carbon atoms and particularly preferably 0 to 10 carbon atoms and includes, for example, amino, methylamino, dimethylamino, diethylamino, dibenzylamino, diphenylamino, ditolylamino and the like), an alkoxyl group (it has preferably 1 to 30 carbon atoms, more preferably 1 to 20 carbon atoms and particularly preferably 1 to 10 carbon atoms and includes, for example, methoxy, ethoxy, butoxy, 2-ethylhexyloxy and the like), an aryloxy group (it has preferably 6 to 30 carbon atoms, more preferably 6 to 20 carbon atoms and particularly preferably 6 to 12 carbon atoms and includes, for example, phenyloxy, 1-naphthyloxy, 2-naphthyloxy and the like), a heteroaryloxy group (it has preferably 1 to 30 carbon atoms, more preferably 1 to 20 carbon atoms and particularly preferably 1 to 12 carbon atoms and includes, for example, pyridyloxy, pyrazyloxy, pyrimidyloxy, quinolyloxy and the like), an acyl group (it has preferably 1 to 30 carbon atoms, more preferably 1 to 20 carbon atoms and particularly preferably 1 to 12 carbon atoms and includes, for example, acetyl, benzoyl, formyl, pivaloyl and the like), an alkoxycarbonyl group (it has preferably 2 to 30 carbon atoms, more preferably 2 to 20 carbon atoms and particularly preferably 2 to 12 carbon atoms and includes, for example, methoxycarbonyl, ethoxycarbonyl and the like), an aryloxycarbonyl group (it has preferably 7 to 30 carbon atoms, more preferably 7 to 20 carbon atoms and particularly preferably 7 to 12 carbon atoms and includes, for example, phenyloxycarbonyl and the like), an acyloxy group (it has preferably 2 to 30 carbon atoms, more preferably 2 to 20 carbon atoms and particularly preferably 2 to 10 carbon atoms and includes, for example, acetoxy, benzoyloxy and the like), an acylamino group (it has preferably 2 to 30 carbon atoms, more preferably 2 to 20 carbon atoms and particularly preferably 2 to 10 carbon atoms and includes, for example, acetylamino, benzoylamino and the like), an alkoxycarbonylamino group (it has preferably 2 to 30 carbon atoms, more preferably 2 to 20 carbon atoms and particularly preferably 2 to 12 carbon atoms and includes, for example, methoxycarbonylamino and the like), an aryloxycarbonylamino group (it has preferably 7 to 30 carbon atoms, more preferably 7 to 20 carbon atoms and particularly preferably 7 to 12 carbon atoms and includes, for example, phenyloxycarbonylamino and the like), a sulfonylamino group (it has preferably 1 to 30 carbon atoms, more preferably 1 to 20 carbon atoms and particularly preferably 1 to 12 carbon atoms and includes, for example, methanesulfonylamino, benzenesulfonylamino and the like), a sulfamoyl group (it has preferably 0 to 30 carbon atoms, more preferably 0 to 20 carbon atoms and particularly preferably 0 to 12 carbon atoms and includes, for example, sulfamoyl, methylsulfamoyl, dimethylsulfamoyl, phenylsulfamoyl and the like), a carbamoyl group (it has preferably 1 to 30 carbon atoms, more preferably 1 to 20 carbon atoms and particularly preferably 1 to 12 carbon atoms and includes, for example, carbamoyl, methylcarbamoyl, diethylcarbamoyl, phenylcarbamoyl and the like), an alkylthio group (it has preferably 1 to 30 carbon atoms, more preferably 1 to 20 carbon atoms and particularly preferably 1 to 12 carbon atoms and includes, for example, methylthio, ethylthio and the like), an arylthio group (it has preferably 6 to 30 carbon atoms, more preferably 6 to 20 carbon atoms and particularly preferably 6 to 12 carbon atoms and includes, for example, phenylthio and the like), a heteroarylthio group (it has preferably 1 to 30 carbon atoms, more preferably 1 to 20 carbon atoms and particularly preferably 1 to 12 carbon atoms and includes, for example, pyridylthio, 2-benzimidazolylthio, 2-benzoxazolylthio, 2-benzothiazolylthio and the like), a sulfonyl group (it has preferably 1 to 30 carbon atoms, more preferably 1 to 20 carbon atoms and particularly preferably 1 to 12 carbon atoms and includes, for example, mesyl, tosyl and the like), a sulfinyl group (it has preferably 1 to 30 carbon atoms, more preferably 1 to 20 carbon atoms and particularly preferably 1 to 12 carbon atoms and includes, for example, methanesulfinyl, benznesulfinyl and the like), a ureido group (it has preferably 1 to 30 carbon atoms, more preferably 1 to 20 carbon atoms and particularly preferably 1 to 12 carbon atoms and includes, for example, ureido, methylureido, phenylureido and the like), a phosphoric amide group (it has preferably 1 to 30 carbon atoms, more preferably 1 to 20 carbon atoms and particularly preferably 1 to 12 carbon atoms and includes, for example, diethylphosphoric amide, phenylphosphoric amide and the like), a hydroxy group, a mercapto group, a halogen atom (including, for example, a fluorine atom, a chlorine atom, a bromine atom and an iodine atom), a cyano group, a sulfo group, a carboxyl group, a nitro group, a hydroxamic acid group, a sulfino group, a hydrazino group, an imino group, a heterocyclic group (it has preferably 1 to 30 carbon atoms, more preferably 1 to 12 carbon atoms, and a hetero atom includes, for example, a nitrogen atom, an oxygen atom and a sulfur atom; to be specific, it includes, for example, imidazolyl, pyridyl, quinolyl, furyl, thienyl, piperidyl, morpholino, benzoxazolyl, benzimidazolyl, benzothiazolyl, carbazolyl, azepinyl and the like), a silyl group (it has preferably 3 to 40 carbon atoms, more preferably 3 to 30 carbon atoms and particularly preferably 3 to 24 carbon atoms and includes, for example, trimethylsilyl, triphenylsilyl and the like) and the like. The above substituents may be further substituted.

The fused ring aryl structure having 10 to 20 carbon atoms forming the aromatic ring present on at least one of $Ar^{1d}$, $Ar^{2d}$ and $Ar^{3d}$ in Formula (2d) and the substituent present on the above aryl groups includes a naphthalene structure, an anthracene structure, a phenanthrene structure, a pyrene structure, a perylene structure and the like, and it is preferably a naphthalene structure, an anthracene structure, a pyrene structure and a phenanthrene structure, more preferably a phenanthrene structure and an aryl structure comprising 4 or more rings and particularly preferably a pyrene structure.

The fused ring heteroaryl structure having 6 to 20 atoms forming a ring present on at least one of $Ar^{1d}$, $Ar^{2d}$ and $Ar^{3d}$ in Formula (2d) and the substituent present on the above aryl groups includes a quinoline structure, a quinoxaline structure, a quinazoline structure, an acridine structure, a phenanthridine structure, a phthalazine structure, a phenanthroline structure and the like, and it is preferably a quinoline structure, a quinoxaline structure, a quinazoline structure, a phthalazine structure and a phenanthroline structure.

The trivalent group derived from an aromatic ring represented by Ar in Formula (2d) has preferably 6 to 30 carbon atoms, more preferably 6 to 20 carbon atoms and further preferably 6 to 16 carbon atoms. To be specific, it includes trivalent groups derived from benzene, naphthalene, anthracene, phenanthrene, pyrene and triphenylene.

The trivalent group derived from an aromatic heterocycle represented by Ar in Formula (2d) contains preferably an atom selected from a nitrogen atom, a sulfur atom and an oxygen atom as a hetero atom, and it contains more preferably a nitrogen atom. It has preferably 2 to 30 carbon atoms, more preferably 3 to 20 carbon atoms and further preferably 3 to 16 carbon atoms. To be specific, it includes trivalent groups derived from pyridine, pyrazine, thiopyran, quinoline, quinoxaline and triazine. The trivalent groups derived from the above aromatic rings and aromatic heterocycles may have substituents. The substituents include groups shown by the substituents on the aryl groups represented by the substituents $Ar^{1d}$, $Ar^{2d}$ and $Ar^{3d}$. Ar is preferably a trivalent group derived from benzenetriyl, naphthalenetriyl, anthracenetriyl, pyrenetriyl or triphenylene, more preferably benzenetriyl and further preferably non-substituted ($Ar^{1d}$, $Ar^{2d}$ and $Ar^{3d}$ are substituted) benzenetriyl or alkyl-substituted benzenetriyl.

Publicly known various benzene derivatives such as benzene derivatives shown in [0079] to [0083] of Japanese Patent Application Laid-Open No. 324678/2002 can be given as the specific examples of the benzene derivative represented by Formula (2d) used for the organic EL device of the present invention. The representative specific examples thereof are shown below.

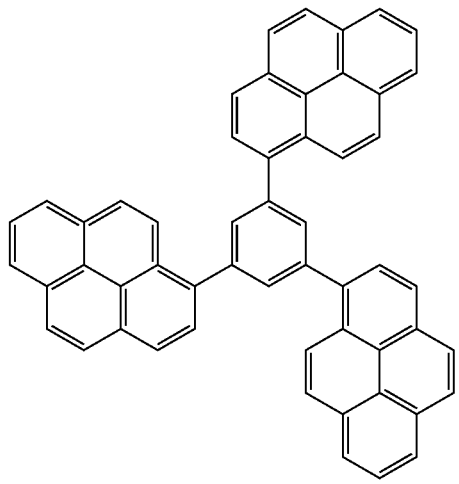

2d-1

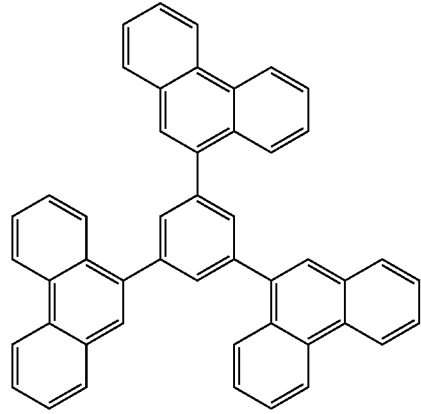

2d-2

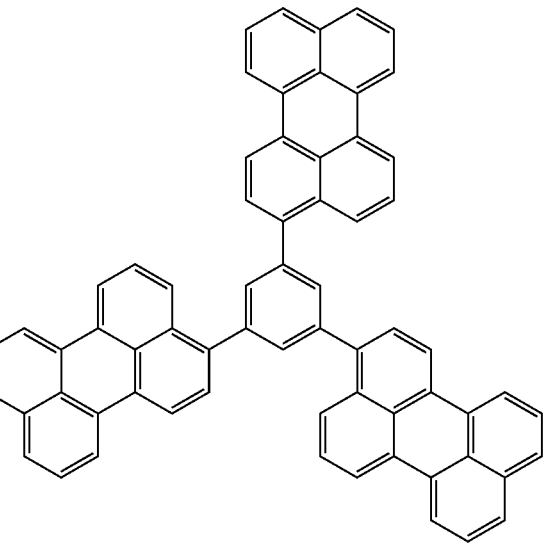

2d-3

-continued
2d-4
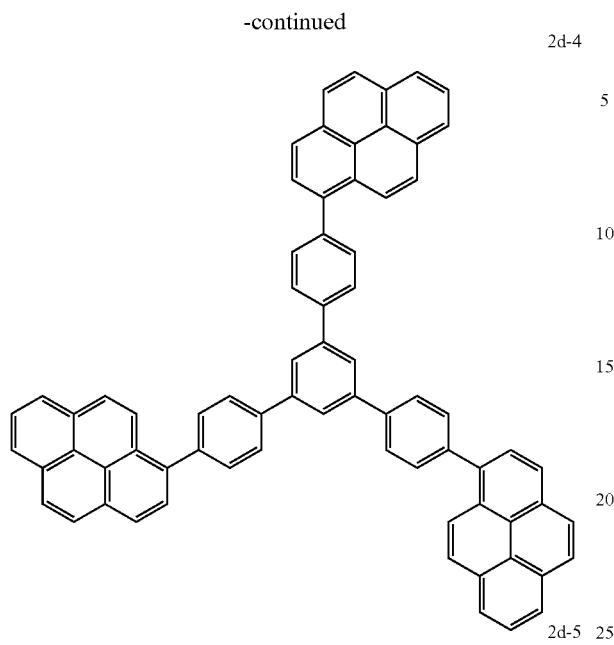
2d-5
2d-7
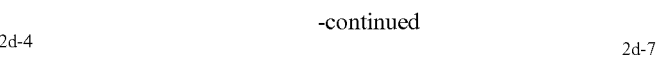
-continued
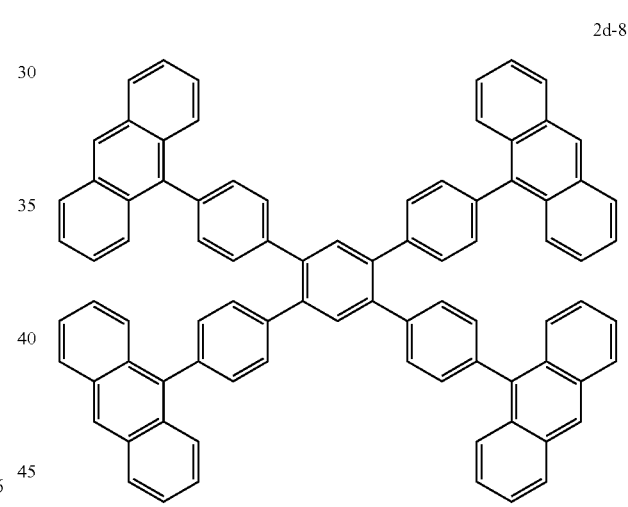
2d-8
2d-6
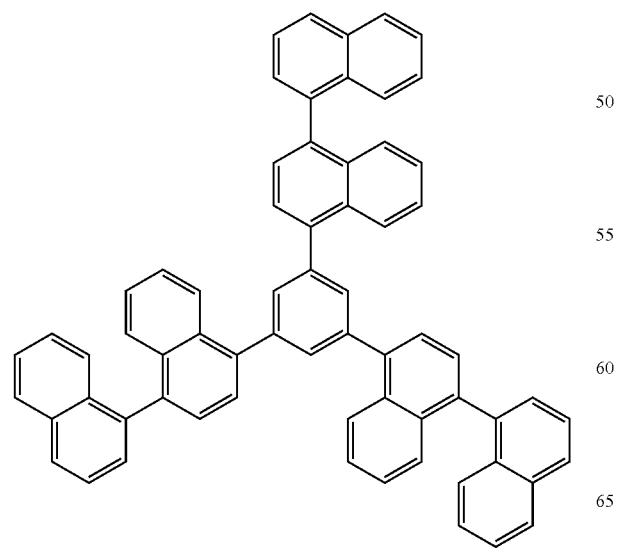
2d-9
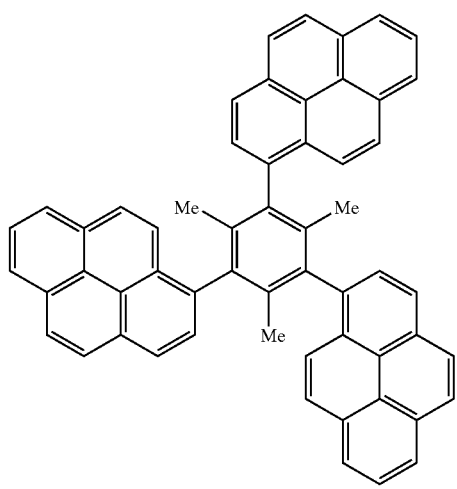

-continued
2d-10
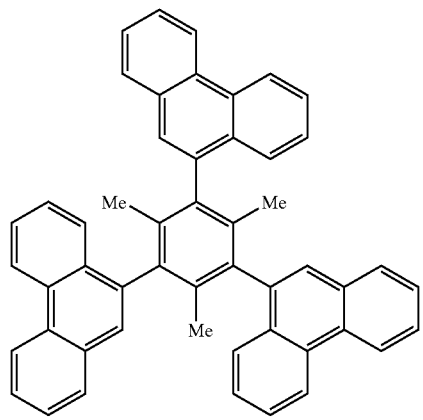
2d-11
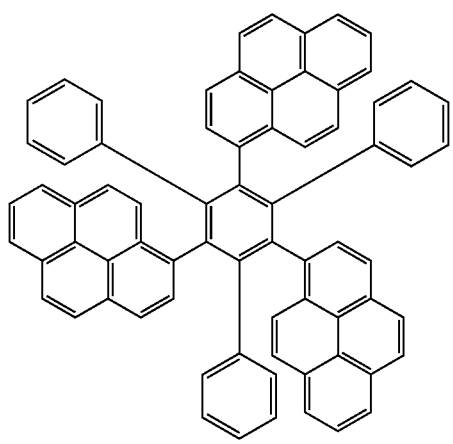
2d-12
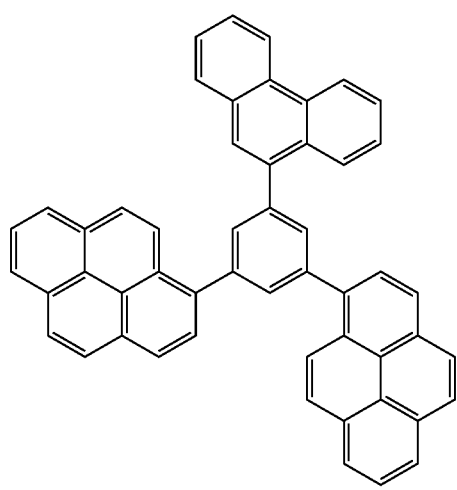
-continued
2d-13
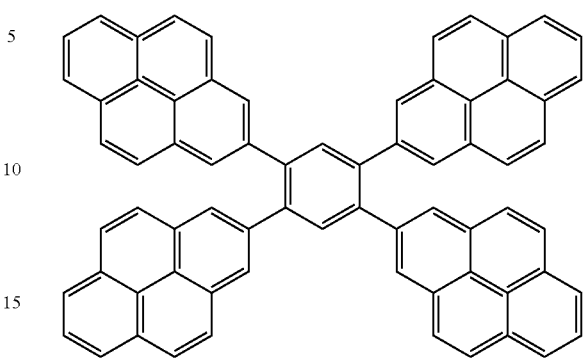
2d-14
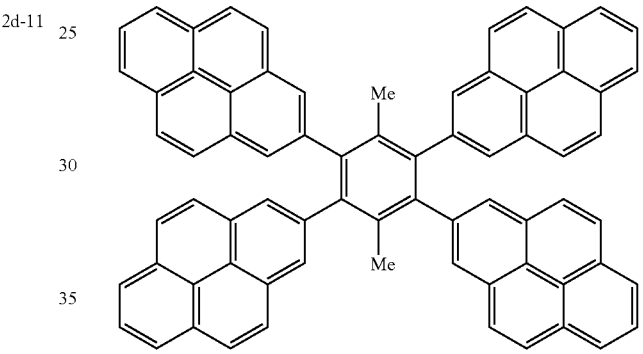
2d-15
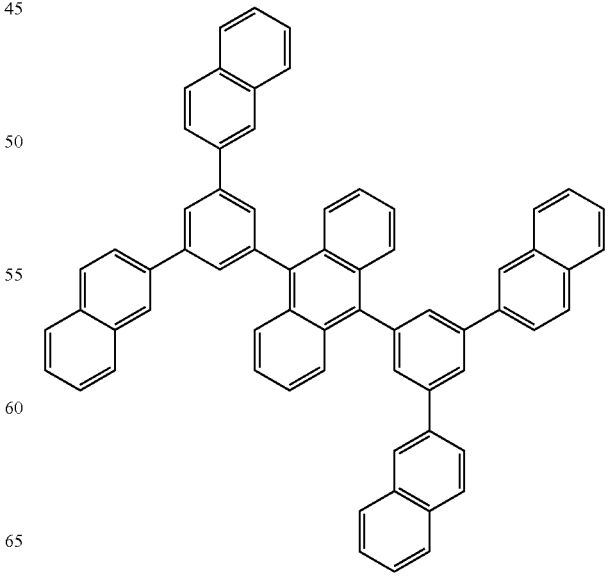

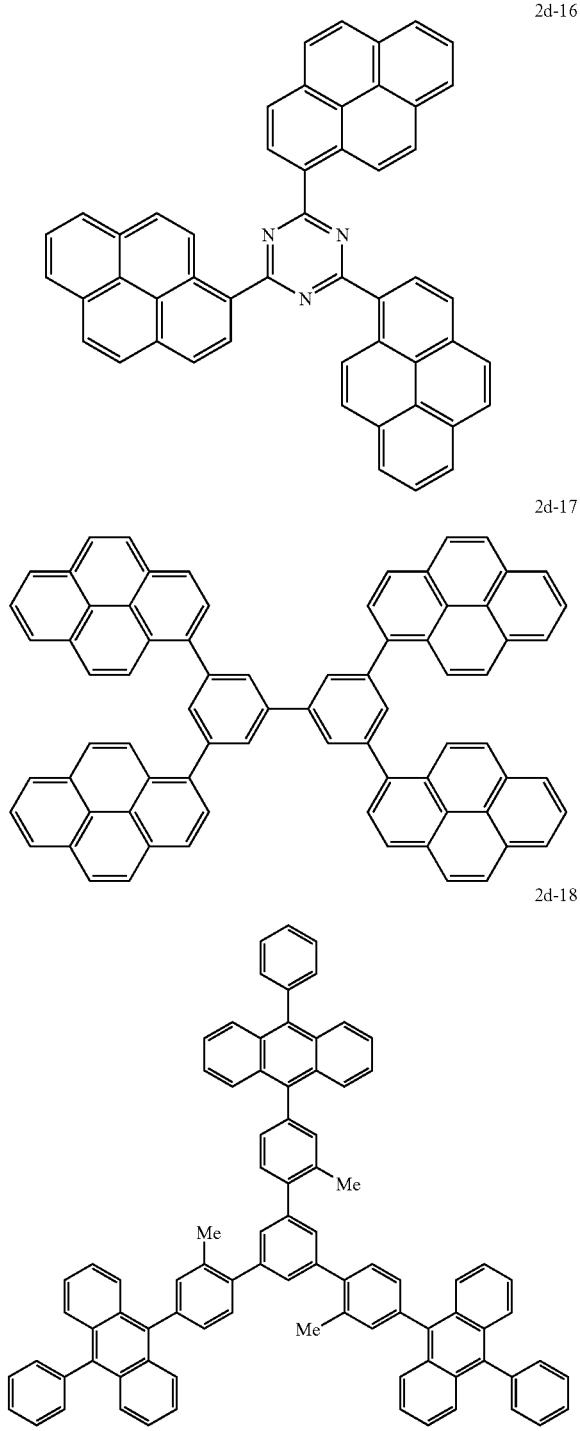

In the organic EL device of the present invention, dry film forming methods such as vacuum vapor deposition, a molecular beam evaporation method (MBE method), sputtering, plasma and ion plating and coating methods such as spin coating, dipping, casting, bar coating, roll coating, flow coating and ink jet each using a solution prepared by dissolving the compound in a solvent can be applied to the formation of the respective organic layers such as the light emitting layer and the like.

In particular, when the organic EL device is produced by using the aminodibenzofluorene derivative of the present invention, the organic compound layer and the light emitting layer can be formed not only by vapor deposition but also by a wet method.

The film thicknesses of the respective layers in the organic compound layer shall not specifically be restricted but have to be set to suitable film thicknesses. In general, if the film thicknesses are too small, pinholes and the like are produced, and when an electric field is applied, no satisfactory light emitting luminance is likely to be obtained. On the other hand, if they are too large, high voltage has to be applied in order to obtain a constant light output, and the efficiency is deteriorated. Accordingly, they fall usually in a range of suitably 5 nm to 10 μm, preferably 10 nm to 0.2 μm.

In the case of a wet film forming method, capable of being used is a luminescent organic solution containing the aminodibenzofluorene derivative of the present invention or a light emitting organic solution containing at least one of the aminodibenzofluorene derivatives of the present invention and at least one selected from the compounds represented by Formulas (2a) to (2d) described above.

In the above case, the materials forming the respective layers are dissolved or dispersed in suitable solvents to prepare the light emitting organic solutions, and the thin films are formed therefrom. The solvents may be any ones. The solvents include, for example, halogen base hydrocarbon solvents such as dichloromethane, dichloroethane, chloroform, carbon tetrachloride, tetrachloroethane, trichloroethane, chlorobenzene, dichlorobenzene, chlorotoluene, trifluorotoluene and the like, ether base solvents such as dibutyl ether, tetrahydrofuran, tetrahydropyran, dioxane, anisole, dimethoxyethane and the like, alcohol base solvents such as methanol, ethanol, propanol, isopropanol, butanol, pentanol, hexanol, cyclohexanol, methyl cellosolve, ethyl cellosolve, ethylene glycol and the like, ketone base solvents such as acetone, methyl ethyl ketone, diethyl ketone, 2-hexanone, methyl isobutyl ketone, 2-heptanone, 4-heptanone, diisobutyl ketone, acetonylacetone, isophorone, cyclohexanone, methylhexanone, acetophenone and the like, hydrocarbon base solvents such as benzene, toluene, xylene, ethylbenzene, hexane, cyclohexane, octane, decane, tetralin and the like, ester base solvents such as ethyl acetate, butyl acetate, amyl acetate and the like, chain carbonic ester base solvents such as dimethyl carbonate, diethyl carbonate and the like and cyclic carbonic ester base solvents such as ethylene carbonate, propylene carbonate and the like. Among them, the hydrocarbon base solvents and the ether base solvents such as toluene, dioxane and the like are preferred. The above solvents may be used alone or in a mixture of two or more kinds thereof. Solvents which can be used shall not be restricted to them.

In any organic compound layers, suitable resins and additives may be used in order to improve a film forming property and prevent pinholes from being formed on the films. The resins which can be used include insulating resins such as polystyrene, polycarbonate, polyallylate, polyester, polyamide, polyurethane, polysulfone, polymethyl methacrylate, polymethyl acrylate, cellulose and the like and copolymers thereof, photoconductive resins such as poly-N-vinylcarbazole, polysilane and the like and conductive resins such as polyaniline, polythiophene, polypyrrole and the like. The additives include antioxidants, UV absorbers, plasticizers and the like.

For the purpose of enhancing a stability of the organic EL device obtained according to the present invention toward temperature, humidity, atmosphere and the like, a protective layer can be provided on the surface of the device or the whole part of the device can be protected by silicone oil, resins and the like.

In the organic EL device of the present invention, a layer selected from a chalcogenide layer, a halogenated metal layer and a metal oxide layer is preferably provided on a surface of at least one of a pair of the electrodes.

Structure of the Organic EL Device:

The device structure of the organic EL device of the present invention shall be explained below.

(1) Structure of the Organic EL Device

The representative device structure of the organic EL device of the present invention includes structures such as:
(1) Anode/light emitting layer/cathode
(2) Anode/hole injecting layer/light emitting layer/cathode
(3) Anode/light emitting layer/electron injecting layer/cathode
(4) Anode/hole injecting layer/light emitting layer/electron injecting layer/cathode
(5) Anode/organic semiconductor layer/light emitting layer/cathode
(6) Anode/organic semiconductor layer/electron barrier layer/light emitting layer/cathode
(7) Anode/organic semiconductor layer/light emitting layer/adhesion improving layer/cathode
(8) Anode/hole injecting layer/hole transporting layer/light emitting layer/electron injecting layer/cathode
(9) anode/insulating layer/light emitting layer/insulating layer/cathode,
(10) anode/inorganic semiconductor layer/insulating layer/light emitting layer/insulating layer/cathode
(11) anode/organic semiconductor layer/insulating layer/light emitting layer/insulating layer/cathode,
(12) anode/insulating layer/hole injecting layer/hole transporting layer/light emitting layer/insulating layer/cathode and
(13) anode/insulating layer/hole injecting layer/hole transporting layer/light emitting layer/electron injecting layer/cathode Among them, usually the structure of (8) is preferably used.

The compound of the present invention may be used in any organic layers described above and is preferably contained in the light emitting zone or the hole transporting zone among the above structural elements.

(2) Light Transmitting Substrate

The organic EL device of the present invention is prepared on a light transmitting substrate. The light transmitting substrate referred to in this case is a substrate for supporting the organic EL device, and it is preferably a flat substrate in which light in a visible region of 400 to 700 nm has a transmittance of 50% or more.

To be specific, it includes a glass plate, a polymer plate and the like. In particular, the glass plate includes soda lime glass, barium-strontium-containing glass, lead glass, aluminosilicate glass, borosilicate glass, barium borosilicate glass, quartz and the like. The polymer plate includes polycarbonate, acryl, polyethylene terephthalate, polyether sulfide, polysulfone and the like.

(3) Anode

An anode in the organic EL device of the present invention assumes a role of injecting a hole into the hole transporting layer or the light emitting layer, and it is effective to provide the anode with a work function of 4.5 eV or more. The specific examples of a material for the anode used in the present invention include indium oxide tin alloy (ITO), tin oxide (NESA), gold, silver, platinum, copper and the like. A material having a small work function is preferred as the anode for the purpose of injecting an electron into the electron transporting layer or the light emitting layer.

The anode can be prepared by forming a thin film from the above electrode substances by a method such as a vapor deposition method, a sputtering method and the like.

When light emitted from the light emitting layer is taken out from the anode, a transmittance of light in the anode based on light emitted is preferably larger than 10%. A sheet resistance of the anode is preferably several hundred $\Omega/\square$ or less. A film thickness of the anode is selected, though depending on the material, in a range of usually 10 nm to 1 µm, preferably 10 to 200 nm.

(4) Light Emitting Layer

The light emitting layer in the organic EL device has the following functions in combination.

(1) Injecting function: a function in which a hole can be injected from an anode or a hole injecting layer in applying an electric field and in which an electron can be injected from a cathode or an electron injecting layer.

(2) Transporting function: a function in which a charge (electron and hole) injected is transferred by virtue of a force of an electric field.

(3) Light emitting function: a function in which a field for recombination of an electron and a hole is provided and in which this is connected to light emission. Provided that a difference may be present between an easiness in injection of a hole and an easiness in injection of an electron and that a difference may be present in a transporting ability shown by the mobilities of a hole and an electron, and any one of the charges is preferably transferred.

A publicly known method such as, for example, a vapor deposition method, a spin coating method, an LB method, a dipping method, a spin coating method, a casting method, a bar coating method, a roll coating method and the like can be applied as a method for forming the above light emitting layer. In particular, the light emitting layer is preferably a molecular deposit film.

In this regard, the molecular deposit film means a thin film formed by depositing a material compound staying in a gas phase state and a film formed by solidifying a material compound staying in a solution state or a liquid phase state, and the above molecular deposit film can usually be distinguished from a thin film (molecular accumulation film) formed by an LB method by a difference in an aggregation structure and a higher order structure and a functional difference originating in it.

Further, as disclosed in Japanese Patent Application Laid-Open No. 51781/1982, the light emitting layer can be formed as well by dissolving a binding agent such as a resin and the material compound in a solvent to prepare a solution and then coating the solution by a spin coating method and the like to form a thin film.

In the present invention, other publicly known light emitting materials excluding the light emitting material comprising the compound containing the dibenzofluorene derivative of the present invention and the fused ring-containing compound may be added, if necessary, to the light emitting layer as long as the object of the present invention is not damaged. Further, a light emitting layer containing a different publicly known light emitting material may be laminated on the light emitting layer containing the light emitting material of the present invention.

The host material or the doping material other than the compounds represented by Formulas (2a) to (2d) described above which can be used for the light emitting layer together with the aminodibenzofluorene derivative of the present invention includes, for example, fused polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethynyl)anthracene, 1,4-bis(9'-ethynylanthracenyl)benzene and the like and derivatives thereof, organic metal complexes such as tris(8-quinolinolate)aluminum, bis-(2-methyl-8-quinolinolate)-4-(phenylphenolinate)aluminum and the like, triarylamine derivatives, styrylamine derivatives, stilbene derivatives, coumarin derivatives, pyran derivatives, oxazoline derivatives, benzothiazole derivatives, benzoxazole derivatives, benzimidazole derivatives, pyrazine derivatives, cinnamic acid ester derivatives, diketopyrrolopyrrole derivatives, acridone derivatives, quinacridone derivatives and the like, but it shall not be restricted to the above compounds.

Further, a film thickness of the light emitting layer is preferably 5 to 50 nm, more preferably 7 to 50 nm and most preferably 10 to 50 nm. If it is 5 nm or more, it is easy to form the light emitting layer and control the chromaticity. On the other hand, if it is 50 nm or less, the operating voltage does not go up.

(5) Hole Injecting and Transporting Layer (Hole Transporting Zone)

The hole injecting and transporting layer is a layer for assisting injection of a hole into the light emitting layer to transport it to the light emitting region, and it has a large hole mobility and shows usually as small ionization energy as 5.6 eV or less. A material which transports a hole to the light emitting layer by a lower electric field strength is preferred for the above hole injecting and transporting layer, and more preferred is a material in which a mobility of a hole is at least $10^{-4}$ cm$^2$/V·second in applying an electric field of, for example, $10^4$ to $10^6$ V/cm.

When the compound containing the aminodibenzofluorene derivative of the present invention is used in the hole transporting zone, the hole injecting and transporting layers may be formed from the compound containing the aminodibenzofluorene derivative of the present invention alone or it may be used in a mixture with other materials.

The materials for forming the hole injecting and transporting layer in a mixture with the compound containing the aminodibenzofluorene derivative of the present invention shall not specifically be restricted as long as they have the preferred properties described above, and capable of being used are optional materials selected from materials which have so far conventionally been used as charge transporting materials for holes in photoconductive materials and publicly known materials which are used for a hole injecting and transporting layer in an organic EL device.

The specific examples thereof include triazole derivatives (refer to U.S. Pat. No. 3,112,197 and the like), oxadiazole derivatives (refer to U.S. Pat. No. 3,189,447 and the like), imidazole derivatives (refer to Japanese Patent Publication No. 16096/1962 and the like), polyarylalkane derivatives (refer to U.S. Pat. No. 3,615,402, U.S. Pat. No. 3,820,989 and U.S. Pat. No. 3,542,544, Japanese Patent Publication No. 555/1970 and ditto No. 10983/1976 and Japanese Patent Application Laid-Open No. 93224/1976, No. 17105/1980, ditto No. 4148/1981, ditto No. 108667/1980, ditto No. 156953/1980 and ditto No. 36656/1981 and the like), pyrazoline derivatives and pyrazolone derivatives (refer to U.S. Pat. No. 3,180,729 and U.S. Pat. No. 4,278,746 and Japanese Patent Application Laid-Open No. 88064/1980, ditto No. 88065/1980, ditto No. 105537/1974, ditto No. 51086/1980, ditto No. 80051/1981, ditto No. 88141/1981, ditto No. 45545/1982, ditto No. 112637/1979 and ditto No. 74546/1980 and the like), phenylenediamine derivatives (refer to U.S. Pat. No. 3,615,404, Japanese Patent Publication No. 10105/1976, ditto No. 3712/1971, ditto No. 25336/1972 and ditto 119925/1979 and the like), arylamine derivatives (refer to U.S. Pat. No. 3,567,450, U.S. Pat. No. 3,240,597, U.S. Pat. No. 3,658,520, U.S. Pat. No. 4,232,103, U.S. Pat. No. 4,175,961 and U.S. Pat. No. 4,012,376, Japanese Patent Publication No. 35702/1974 and ditto No. 27577/1964, Japanese Patent Application Laid-Open No. 144250/1980, ditto No. 119132/1981 and ditto No. 22437/1981 and German Patent No. 1,110,518 and the like), amino-substituted chalcone derivatives (refer to U.S. Pat. No. 3,526,501 and the like), oxazole derivatives (disclosed in U.S. Pat. No. 3,257,203 and the like), styrylanthracene derivatives (refer to Japanese Patent Application Laid-Open No. 46234/1981 and the like), fluorenone derivatives (refer to Japanese Patent Application Laid-Open No. 110837/1979 and the like), hydrazone derivatives (refer to U.S. Pat. No. 3,717,462, Japanese Patent Application Laid-Open No. 59143/1979, ditto No. 52063/1980, ditto No. 52064/1980, ditto No. 46760/1980, ditto No. 11350/1982 and ditto No. 148749/1982, Japanese Patent Application Laid-Open No. 311591/1990 and the like), stilbene derivatives (refer to Japanese Patent Application Laid-Open No. 210363/1986, ditto No. 228451/1986, ditto No. 14642/1986, ditto No. 72255/1986, ditto No. 47646/1987, ditto No. 36674/1987, ditto No. 10652/1987, ditto No. 30255/1987, ditto No. 93455/1985, ditto No. 94462/1985, ditto No. 174749/1985 and ditto No. 175052/1985 and the like), silazane derivatives (U.S. Pat. No. 4,950,950), polysilane base (Japanese Patent Application Laid-Open No. 204996/1990), aniline base copolymers (Japanese Patent Application Laid-Open No. 282263/1990), conductive high molecular oligomers (particularly, thiophene oligomers) and the like.

The compounds described above can be used as the material for the hole injecting and transporting layer, and preferably used are porphyrin compounds (disclosed in Japanese Patent Application Laid-Open No. 295695/1988 and the like) and aromatic tertiary amine compounds and styrylamine compounds (refer to U.S. Pat. No. 4,127,412 and Japanese Patent Application Laid-Open No. 27033/1978, ditto No. 58445/1979, ditto No. 79450/1980, ditto No. 144250/1980, ditto No. 119132/1981, ditto No. 295558/1986, ditto No. 98353/1986 and ditto No. 295695/1988 and the like), and the aromatic tertiary amine compounds are particularly preferably used.

Further, capable of being given are compounds having two fused aromatic rings in a molecule described in U.S. Pat. No. 5,061,569, for example, 4,4'-bis(N-(1-naphthyl)-N-phenylamino)biphenyl (hereinafter abbreviated as NPD) and 4,4',4''-tris(N-(3-methylphenyl)-N-phenylamino)triphenylamine (hereinafter abbreviated as MTDATA) in which three triphenylamine units are connected in the form of a star burst type disclosed in Japanese Patent Application Laid-Open No. 308688/1992.

Further, inorganic compounds such as p type Si, p type SiC and the like can also be used as the material for the hole injecting layer in addition to the aromatic dimethylidene base compounds described above shown as the material for the light emitting layer.

The hole injecting layer can be formed by making a thin film from the compound described above by a publicly known method such as, for example, a vacuum vapor deposition method, a spin coating method, a casting method, an LB method and the like. A film thickness of the hole injecting and transporting layer shall not specifically be restricted, and it is usually 5 nm to 5 µm.

(6) Electron Injecting Layer

The electron injecting layer is a layer for assisting injection of an electron into the light emitting layer, and it has a large electron mobility. Also, the adhesion improving layer is a layer comprising particularly a material having a good adhesive property with the cathode in the above electron injecting layer. Materials used for the electron injecting layer are suitably metal complexes of 8-hydroxyquinoline or derivatives thereof and oxadiazole derivatives.

The specific examples of the metal complexes of 8-hydroxyquinoline or the derivatives thereof include metal chelate oxynoid compounds containing chelates of oxine (in general, 8-quinolinol or 8-hydroxyquinoline).

For example, Alq described in the item of the light emitting material can be used as the electron injecting layer.

On the other hand, the oxadiazole derivative includes an electron transfer compound represented by the following formula:

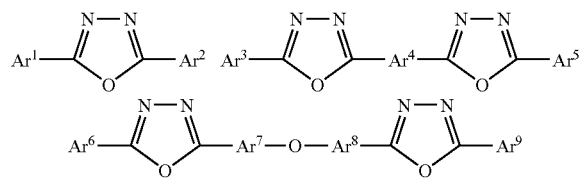

(wherein $Ar^1$, $Ar^2$, $Ar^3$, $Ar^5$, $Ar^6$ and $Ar^9$ represent a substituted or non-substituted aryl group, and they may be the same as or different from each other; $Ar^4$, $Ar^7$ and $Ar^8$ represent a substituted or non-substituted arylene group, and they may be the same as or different from each other).

In this regard, the aryl group includes phenyl, biphenyl, anthranyl, perylenyl and pyrenyl. The arylene group includes phenylene, naphthylene, biphenylene, anthranylene, perylenylene and pyrenylene. The substituent is preferably an alkyl group having 1 to 10 carbon atoms, an alkoxyl group having 1 to 10 carbon atoms or a cyano group.

The following compounds can be given as the specific examples of the oxadiazole derivative.

The preferred mode of the organic EL device of the present invention includes a device containing a reducing dopant in the region which transports an electron or an interfacial region between the cathode and the organic layer. In this case, the reducing dopant is defined by a substance which can reduce an electron transporting compound. Accordingly, various compounds can be used as long as they have a certain reducing property, and capable of being suitably used is at least one substance selected from the group consisting of, for example, alkali metals, alkali earth metals, rare earth metals, oxides of alkali metals, halides of alkali metals, oxides of alkali earth metals, halides of alkali earth metals, oxides of rare earth metals or halides of rare earth metals, organic complexes of alkali metals, organic complexes of alkali earth metals and organic complexes of rare earth metals.

To be more specific, the preferred reducing dopant includes at least one alkali metal selected from the group consisting of Li (work function: 2.9 eV), Na (work function: 2.36 eV), K (work function: 2.28 eV), Rb (work function: 2.16 eV) and Cs (work function: 1.95 eV) and at least one alkali earth metal selected from the group consisting of Ca (work function: 2.9 eV), Sr (work function: 2.0 to 2.5 eV) and Ba (work function: 2.52 eV), and the compounds having a work function of 2.9 eV or less are particularly preferred. Among them, the more preferred reducing dopant is at least one alkali metal selected from the group consisting of K, Rb and Cs, and it is more preferably Rb or Cs. It is most preferably Cs. The above alkali metals have a particularly high reducing ability, and addition of a relatively small amount thereof to the electron injecting zone makes it possible to raise a light emitting luminance in the organic EL device and extend a lifetime thereof. The combination of two or more kinds of the above alkali metals is preferred as the reducing dopant having a work function of 2.9 eV or less, and particularly preferred is the combination containing Cs, for example, the combination of Cs with Na, Cs with K, Cs with Rb or Cs with Na and K. Containing Cs in combination makes it possible to efficiently exhibit the reducing ability, and addition thereof to the electron injecting zone makes it possible to enhance a light emitting luminance in the organic EL device and extend a lifetime thereof.

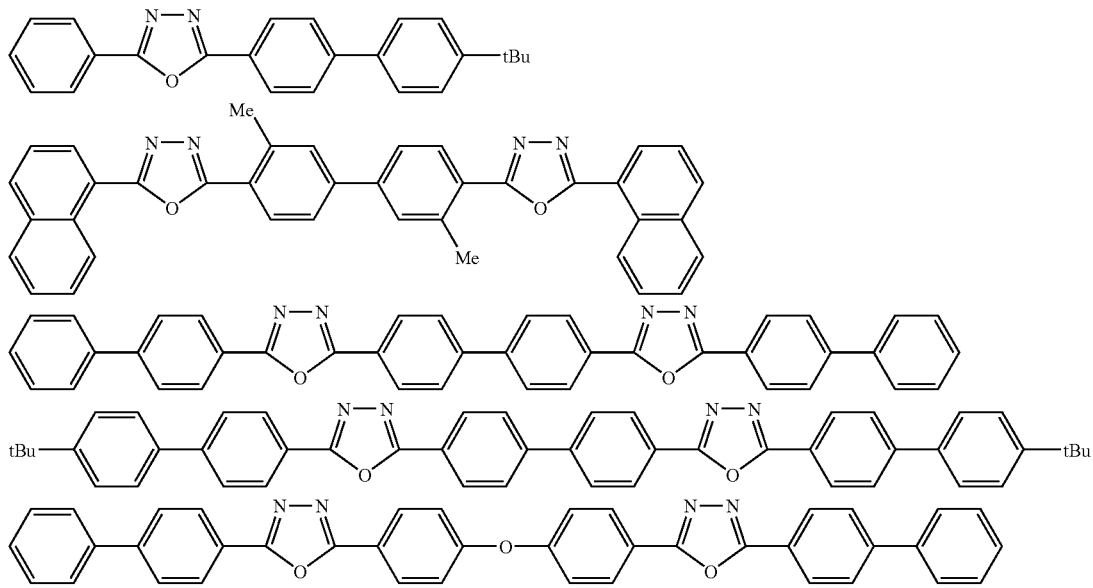

In the present invention, an electron injecting layer constituted from an insulator and a semiconductor may further be provided between the cathode and the organic layer. In this case, an electric current can effectively be prevented from leaking to enhance the electron injecting property. Preferably used as the above insulator is at least one metal compound selected from the group consisting of alkali metal chalcogenides, alkali earth metal chalcogenides, halides of alkali metals and halides of alkali earth metals. If the electron injecting layer is constituted from the above alkali metal chalcogenides and the like, it is preferred from the viewpoint that the electron injecting property can further be enhanced. To be specific, the preferred alkali metal chalcogenides include, for example, $Li_2O$, $K_2O$, $Na_2S$, $Na_2Se$ and $Na_2O$, and the preferred alkali earth metal chalcogenides include, for example, CaO, BaO, SrO, BeO, BaS and CaSe. Also, the preferred halides of alkali metals include, for example, LiF, NaF, KF, LiCl, KCl and NaCl. Further, the preferred halides of alkali earth metals include, for example, fluorides such as $CaF_2$, $BaF_2$, $SrF_2$, $MgF_2$ and $BeF_2$ and halides other than the fluorides.

The semiconductor constituting the electron transporting layer includes a single kind of oxides, nitrides or nitride oxides containing at least one element of Ba, Ca, Sr, Yb, Al, Ga, In, Li, Na, Cd, Mg, Si, Ta, Sb and Zn or combinations of two or more kinds thereof. The inorganic compound constituting the electron transporting layer is preferably a microcrystalline or amorphous insulating thin film. If the electron transporting layer is constituted from the above insulating thin film, the more homogeneous thin film is formed, and therefore picture element defects such as dark spots can be reduced. The above inorganic compound includes the alkali metal chalcogenides, the alkali earth metal chalcogenides, the halides of alkali metals and the halides of alkali earth metals each described above.

(7) Cathode

Cathodes prepared by using metals, alloys, electroconductive compounds and mixtures thereof each having a small work function (4 eV or less) for electrode materials are used as the cathode in order to inject electrons into the electron injecting and transporting layer or the light emitting layer. The specific examples of the above electrode materials include sodium, sodium.potassium alloys, magnesium, lithium, magnesium.silver alloys, aluminum/aluminum oxide, aluminum.lithium alloys, indium, rare earth metals and the like.

The above cathode can be prepared by forming a thin film from the above electrode materials by a method such as vapor deposition, sputtering and the like.

In this respect, when light emitted from the light emitting layer is taken out from the cathode, a transmittance of the cathode based on light emitted is preferably larger than 10%.

A sheet resistance of the cathode is preferably several hundred Ω/square or less, and a film thickness thereof is usually 10 nm to 1 μm, preferably 50 to 200 nm.

(8) Insulating Layer

The organic EL device is liable to cause picture element defects by leak and short since an electric field is applied to a ultrathin film. In order to prevent the above matter, an insulating thin film layer is preferably interposed between a pair of the electrodes.

A material used for the insulating layer includes, for example, aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide and the like, and mixtures and laminates thereof may be used as well.

(9) Production Process for Organic EL Device

According to the materials and the forming methods which have been shown above as the examples, the anode, the light emitting layer, if necessary, the hole injecting layer and, if necessary, the electron injecting layer are formed, and further the cathode is formed, whereby the organic EL device can be prepared. Also, the organic EL device can be prepared as well in an order of from the cathode to the anode which is reverse to the order described above.

A preparation example of an organic EL device having a structure in which an anode/a hole injecting layer/a light emitting layer/an electron injecting layer/a cathode are provided in order on a light transmitting substrate shall be described below.

First, a thin film comprising an anode material is formed on a suitable light transmitting substrate by a method such as vapor deposition, sputtering and the like so that a film thickness falling in a range of 1 μm or less, preferably 10 to 200 nm is obtained, whereby an anode is prepared. Next, a hole injecting layer is provided on the above anode. The hole injecting layer can be formed, as described above, by a method such as a vacuum vapor deposition method, a spin coating method, a casting method, an LB method, an ink jet method and the like. When forming the hole injecting layer by the vacuum vapor deposition method, the depositing conditions thereof are varied according to the compounds used (materials for the hole injecting layer), the crystal structure of the targeted hole injecting layer and the recombination structure thereof, and in general, they are suitably selected preferably in the ranges of a depositing source temperature of 50 to 450° C., a vacuum degree of $10^{-7}$ to $10^{-3}$ Torr, a depositing speed of 0.01 to 50 nm/second, a substrate temperature of −50 to 300° C. and a film thickness of 5 nm to 5 μm.

Next, a light emitting layer can be formed on the hole injecting layer by forming a thin film from the desired organic light emitting material by a method such as a vacuum vapor deposition method, sputtering, a spin coating method, a casting method and the like. When forming the light emitting layer by the vacuum vapor deposition method, the depositing conditions thereof are varied according to the compounds used, and in general, they can be selected from the same condition ranges as in the hole injecting layer.

Next, an electron injecting layer is provided on the above light emitting layer. It can be formed in the same manner as in the hole injecting layer and the light emitting layer. The depositing conditions thereof can be selected from the same condition ranges as in the hole injecting layer and the light emitting layer.

When using the vacuum vapor deposition method, the compound of the present invention can be codeposited together with the other materials, though varied depending on that it is added to any layer in the light emitting zone and the hole transporting zone. When using the spin coating method, it can be added as well in a mixture with the other materials.

Lastly, a cathode is laminated, whereby an organic EL device can be obtained.

The cathode is constituted from metal, and therefore the vapor deposition method and the sputtering method can be used. However, the vacuum vapor deposition method is preferred in order to protect the organic substance layer of the base from being damaged in making the film.

The film thicknesses of the respective organic layers in the organic EL device of the present invention shall not specifically be restricted, and in general, if the film thicknesses are too small, defects such as pinholes and the like are liable to be caused. On the other hand, if they are too large, high voltage has to be applied, and the efficiency is deteriorated, so that they fall usually in a range of preferably several nm to 1 μm.

When applying a DC voltage to the organic EL device, light emission can be observed by applying a voltage of 5 to 40 V setting a polarity of the anode to plus and that of the cathode to minus. An electric current does not flow by applying a voltage at a reverse polarity, and light emission is not caused at all. Further, when applying an AC voltage, uniform light emission can be observed only when the anode has a plus polarity and the cathode has a minus polarity. A waveform of an alternating current applied may be optional.

Application of the Organic EL Device

The organic EL device of the present invention can be used as a device for various equipments.

The organic EL device of the present invention can be applied to products to which a high luminance and a high current efficiency are required even at a low voltage. The application examples thereof include, display units, displays, lighting instruments, printer light sources, backlights for liquid crystal display equipments and the like, and the organic EL device of the present invention can be applied as well to the fields such as indicators, advertising displays, interiors and the like. The display units include flat panel displays which save energy and have a high visibility. In respect to the printer light sources, the organic EL device of the present invention can be used as a light source for laser beam printers. Further, using the device of the present invention makes it possible to reduce a volume of the equipments to a large extent. In respect to the lighting instruments and the backlights, the energy saving effect can be expected by using the organic EL device of the present invention.

EXAMPLES

The present invention shall be explained below in details with reference to examples, but the present invention shall not be restricted to the examples shown below as long as they do not exceed the scope of the present invention.

Synthetic Example 1

Synthesis of 13,13-dimethyl-$N^3,N^3,N^{10},N^{10}$-tetra (naphthalene-2-yl)-13H-dibenzo[a,i]fluorene-3,10-diamine (1a-29)

(1) Synthesis of 1-(bromomethyl)naphthalene

A mixture of 52.35 g (368.1 mmol) of 1-methylnaphthalene, 68.79 g (368.5 mmol) of N-bromosuccinimide (NBS), 0.45 g (1.86 mmol) of benzoyl peroxide (BPO) and 250 ml of carbon tetrachloride was stirred for 6 hours while heating and refluxing. The deposit was removed by filtration, and the filtrate was concentrated to obtain 84.64 g (purity: 90.4%, yield: 94%) of an oily crude product of 1-(bromomethyl) naphthalene.

(2) Synthesis of 1-(naphthalene-1-ylmethyl)-3,4-dihydronaphthalene-2(1H)-one

Added to a mixed solution of 30.53 g (124.08 mmol, purity: 90.4%) of 1-(bromomethyl)naphthalene and 180 ml of dehydrated dioxane was 30.27 g (151.89 mmol) of 1-(3,4-dihydronaphthalene-2-yl)pyrrolidine, and the mixture was stirred for 5 hours while heating and refluxing. After cooled down to room temperature, 100 ml of a 5% hydrochloric acid aqueous solution was dropwise added to the reaction mixture and stirred, and the mixture was extracted twice with dichloromethane. The organic phase was dried on anhydrous sodium sulfate and filtered, and then the solvent was removed by distillation. A crude product obtained was refined by column chromatograph (silica gel: hexane/ethyl acetate=10/1) to obtain 20.47 g (purity: 51.8%) of 1-(naphthalene-1-ylmethyl)-3,4-dihydronaphthalene-2(1H)-one.

(3) Synthesis of 13H-5,6-dihydrodibenzo[a,i]fluorene

A mixed solution of 20.47 g (71.48 mmol) of 1-(naphthalene-1-ylmethyl)-3,4-dihydronaphthalene-2(1H)-one, 42.89 ml of methanesulfonic acid and 386 ml of chloroform was stirred at room temperature for 6 hours. Water was added to the reaction mixture to dilute it, and after separating the solution, the organic phase was washed with a potassium carbonate aqueous solution. The organic phase was dried on anhydrous sodium sulfate and filtered, and then the solvent was removed by distillation to obtain 15.88 g (yield: 82.8%) of 13H-5,6-dihydrodibenzo[a,i]fluorene.

(4) Synthesis of 13H-dibenzo[a,i]fluorene

Added to a mixed solution of 15.88 g (59.2 mmol) of 13H-5,6-dihydrodibenzo[a,i]fluorene and 150 ml of triethylene glycol dimethyl ether was 3.0 g of 10% palladium carbon (10% Pd—C), and the mixture was stirred at 230° C. for 7 hours. Further, 2.0 g of 10% Pd—C was added four times every 12 hours, and the mixture was stirred at 230° C. for 133 hours in total. The insoluble matters were removed by filtering through celite and washed with chloroform. Chloroform was removed from the filtrate by distillation under reduced pressure, and methanol and water were added to the resulting residue to precipitate a solid matter, whereby 6.23 g (39.5%) of 13H-dibenzo[a,i]fluorene was obtained.

(5) Synthesis of 13,13-dimethyl-13H-dibenzo[a,i]fluorene

Methyl iodide 9.88 g (69.6 mmol) was dropwise added to a mixed solution of 6.18 g (23.2 mmol) of 13H-dibenzo[a,i] fluorene, 11.72 g (104.4 mmol) of potassium t-butoxide and 100 ml of dimethylsulfoxide at 20° C. in 20 minutes, and the solution was stirred for 10 hours. After left standing overnight, 9.88 g (69.6 mmol) of methyl iodide was further dropwise added and stirred for 5 hours. Water was dropwise added to the reaction mixture, and the solution was extracted with dichloromethane. After separating the solution, the organic phase was concentrated and refined by flash chromatograph (silica gel: hexane/dichloromethane=5/1) to obtain 4.01 g (yield: 58.7%) of 13,13-dimethyl-13H-dibenzo[a,i]fluorene.

(6) Synthesis of 3,10-dibromo-13,13-dimethyl-13H-dibenzo[a,i]fluorene

A piece (very small amount) of iodine was added to a mixed solution of 4.01 g (13.62 mmol) of 13,13-dimethyl-13H-dibenzo[a,i]fluorene and chloroform at room temperature, and 1.47 ml (28.6 mmol) of bromine was dropwise added thereto and stirred at room temperature for 6 hours. After left standing overnight, a sodium hydrogensulfite aqueous solution was added to the reaction mixture, and the solution was extracted with dichloromethane. After separating the solution, the organic phase was concentrated and refined by flash chromatograph (silica gel: hexane/dichloromethane=10/1) to obtain 4.55 g (yield: 74%) of 3,10-dibromo-13,13-dimethyl-13H-dibenzo[a,i]fluorene.

$^1$H-NMR of the compound thus obtained was measured, and the result thereof is shown below.

$^1$H-NMR (CDCl$_3$) δ: 8.21 (2H, d, J=9.3 Hz), 8.15 (2H, d, J=2.0 Hz), 8.02 (2H, d, J=8.3 Hz), 7.85 (2H, d, J=8.3 Hz), 7.69 (2H, dd, J=9.3, 2.0 Hz), 1.94 (6H, s)

(7) Synthesis of 13,13-dimethyl-$N^3,N^3,N^{10},N^{10}$-tetra(naphthalene-2-yl)-13H-dibenzo[a,i]fluorene-3,10-diamine (1a-29))

A tri-t-butylphosphine/toluene solution 0.14 ml (62 mass %, 0.42 mmol) was added to a suspension of 2.00 g (4.42 mmol) of 3,10-dibromo-13,13-dimethyl-13H-dibenzo[a,1]fluorene, 3.57 g (13.26 mmol) of dinaphthalene-2-ylamine, 0.06 g (0.26 mmol) of palladium acetate, 1.27 g (13.26 mmol) of sodium t-butoxide and 50 ml of toluene under argon atmosphere to react them for 10 hours under refluxing by heating. Methanol was added to the reaction mixture, and a solid matter deposited was obtained by filtering and washed with methanol. The solid matter thus obtained was recrystallized from dichloromethane and methanol and washed with dichloromethane and methanol to obtain 1.39 g (yield: 37.9%) of the targeted compound (1a-29).

FDMS (field desorption mass spectrum), a UV ray absorption spectrum (○ in FIG. 1) in a toluene solution and a fluorescence emission spectrum (● in FIG. 1) of the compound thus obtained were measured, and the results thereof are shown below (refer to FIG. 1).

FDMS, calculated for $C_{63}H_{44}N_2$=828, found m/z=828 ($M^+$)

UV (PhMe); λmax, 379 (ε4.65), FL (PhMe, λex=379 nm); λmax, 437 nm (half value width: 36 nm)

Synthetic Example 2

Synthesis of 13,13-dimethyl-$N^3,N^3,N^{10},N^{10}$-tetrakis(3,4,5-triphenyl)-13H-dibenzo[a,i]fluorene-3,10-diamine (1a-55)

A tri-t-butylphosphine/toluene solution 0.15 ml (62% by weight, 0.46 mmol) was added to a suspension of 2.16 g (4.78 mmol) of 3,10-dibromo-13,13-dimethyl-13H-dibenzo[a,1]fluorene, 3.63 g (14.34 mmol) of bis(3,4,5-triphenyl)amine, 0.06 g (0.26 mmol) of palladium acetate, 1.38 g (14.34 mmol) of sodium t-butoxide and 50 ml of dehydrated toluene under argon atmosphere to react them for 10 hours under refluxing by heating. Methanol was added to the reaction mixture, and a solid matter deposited was obtained by filtering and washed with methanol. The solid matter thus obtained was dissolved in toluene and refined by column chromatograph (silica gel: toluene) to obtain about 3 g of a yellow powder. This powder was recrystallized from ethyl acetate and ethanol and washed with ethanol to obtain 1.35 g (yield: 35.4%) of 13,13-dimethyl-$N^3,N^3,N^{10},N^{10}$-tetrakis(3,4,5-triphenyl)-13H-dibenzo[a,i]fluorene-3,10-diamine (1a-55).

FDMS, a UV ray absorption spectrum (○ in FIG. 2) in a toluene solution and a fluorescence emission spectrum (● in FIG. 2) of the compound thus obtained were measured, and the results thereof are shown below (refer to FIG. 2).

FDMS, calculated for $C_{59}H_{60}N_2$=796, found m/z=796 (M+)

UV (PhMe); λmax, 418 (ε4.43), FL (PhMe, λex=377 nm); λmax, 441 nm (half value width: 44 nm)

Synthetic Example 3

Synthesis of 13,13-dimethyl-$N^3,N^3,N^{11},N^{11}$-tetra(naphthalene-2-yl)-13H-dibenzo[a,i]fluorene-3,11-diamine (1d-29)

(1) Synthesis of 1-(naphthalene-2-ylmethyl)-3,4-dihydronaphthalene-2(1H)-one

A mixed solution of 0.53 g (92.87 mmol) of 2-(bromomethyl)naphthalene, 20.36 g (102.16 mmol) of 1-(3,4-dihydronaphthalene-2-yl)pyrrolidine and 120 ml of dehydrated dioxane was stirred for 4 hours while heating and refluxing. After cooled down to room temperature, 100 ml of a 5% hydrochloric acid aqueous solution was dropwise added to the reaction mixture, and the mixture was extracted twice with dichloromethane. The organic phase was dried on anhydrous sodium sulfate and filtered, and then the solvent was removed by distillation. A crude product obtained was refined by column chromatograph (silica gel: hexane/ethyl acetate=10/1) to obtain 16.05 g (yield: 60.5%) of 1-(naphthalene-2-ylmethyl)-3,4-dihydronaphthalene-2(1H)-one.

(2) Synthesis of 13H-5,6-dihydrodibenzo[a,g]fluorene

A mixed solution of 16.05 (56.05 mmol) of 1-(naphthalene-2-ylmethyl)-3,4-dihydronaphthalene-2(1H)-one, 33.6 ml of methanesulfonic acid and 303 ml f chloroform was stirred for 6 hours at room temperature. Water was added to the reaction mixture to dilute it, and after separating the solution, the organic phase was washed with a potassium carbonate aqueous solution. The organic phase was dried on anhydrous sodium sulfate and filtered, and then the solvent was removed by distillation to obtain 10.63 g (yield: 70.7%) of 13H-5,6-dihydrodibenzo[a,g]fluorene.

(3) Synthesis of 13H-dibenzo[a,g]fluorene

Added to a mixed solution of 10.63 g (39.61 mmol) of 13H-5,6-dihydrodibenzo[a,g]fluorene and 150 ml of triethylene glycol dimethyl ether was 2.0 g of 10% Pd—C, and the mixture was stirred at 230° C. for 7 hours. Further, 1.0 g of 10% Pd—C was added, and the mixture was stirred at 230° C. for 14 hours. The insoluble matters were removed by filtering through celite and washed with chloroform. Chloroform was removed from the filtrate by distillation under reduced pressure, and methanol and water were added to the resulting residue to precipitate a solid matter. The solid matter obtained by filtration and washed with methanol to obtain 8.41 g (79.7%) of 13H-dibenzo[a,g]fluorene.

(4) Synthesis of 13,13-dimethyl-13H-dibenzo[a,g]fluorene

Methyl iodide 13.45 g (94.74 mmol) was dropwise added to a mixed solution of 8.41 g (31.58 mmol) of 13H-dibenzo[a,g]fluorene, 15.95 g (142.11 mmol) of potassium t-butoxide and 100 ml of dimethylsulfoxide at 20° C. in 20 minutes, and the solution was stirred for 8 hours. After left standing overnight, 13.45 g (94.74 mmol) of methyl iodide was further dropwise added and stirred for 11 hours. Water was dropwise added to the reaction mixture, and the solution was extracted twice with dichloromethane. After separating the solution, the organic phase was concentrated and refined by flash chromatograph (silica gel: hexane/dichloromethane=5/1) to obtain 4.66 g (yield: 50.1%) of 13,13-dimethyl-13H-dibenzo[a,g]fluorene.

(5) Synthesis of 3,11-dibromo-13,13-dimethyl-13H-dibenzo[a,g]fluorene

A piece (very small amount) of iodine was added to a mixed solution of 4.65 g (15.80 mmol) of 13,13-dimethyl-13H-dibenzo[a,g]fluorene and chloroform, and 1.70 ml (33.17 mmol) of bromine was dropwise added thereto and stirred at room temperature for 9 hours. After left standing overnight, a sodium hydrogensulfite aqueous solution was added to the reaction mixture, and the solution was extracted with dichloromethane at room temperature. After separating the solution, the organic phase was concentrated and refined by flash chromatograph (silica gel: hexane/dichloromethane=10/1) to obtain 6.71 g (yield: 93.9%) of a mixture of 3,11-dibromo-13,13-dimethyl-13H-dibenzo[a,g]fluorene and 5,11-dibromo-13,13-dimethyl-13H-dibenzo[a,g]fluorene.

(6) Synthesis of 13,13-dimethyl-$N^3,N^3,N^{11},N^{11}$-tetra (naphthalene-2-yl)-13H-dibenzo[a,i]fluorene-3,11-diamine (1d-29)

A tri-t-butylphosphine/toluene solution 0.22 ml (62% by weight, 0.67 mmol) was added to a suspension of 3.20 g (7.08 mmol) of a mixture of 3,11-dibromo-13,13-dimethyl-13H-dibenzo[a,g]fluorene and 5,11-dibromo-13,13-dimethyl-13H-dibenzo[a,g]fluorene, 5.71 g (21.23 mmol) of dinaphthalene-2-ylamine, 0.10 g (0.42 mmol) of palladium acetate, 2.04 g (21.23 mmol) of sodium t-butoxide and 50 ml of toluene under argon atmosphere to react them for 10 hours under refluxing by heating. Methanol was added to the reaction mixture, and a solid matter deposited was obtained by filtration and washed with methanol. The solid matter thus obtained was recrystallized from dichloromethane and methanol and washed with methanol and dichloromethane to obtain 0.69 g (yield: 37.9%) of a mixture of 13,13-dimethyl-$N^3,N^3,N^{11},N^{11}$-tetra(naphthalene-2-yl)-13H-dibenzo[a,g]fluorene-3,11-diamine (1d-29) and 13,13-dimethyl-$N^5,N^5,N^{11},N^{11}$-tetra(naphthalene-2-yl)-13H-dibenzo[a,g]fluorene-3,11-diamine (1d'-29).

Figure 3:
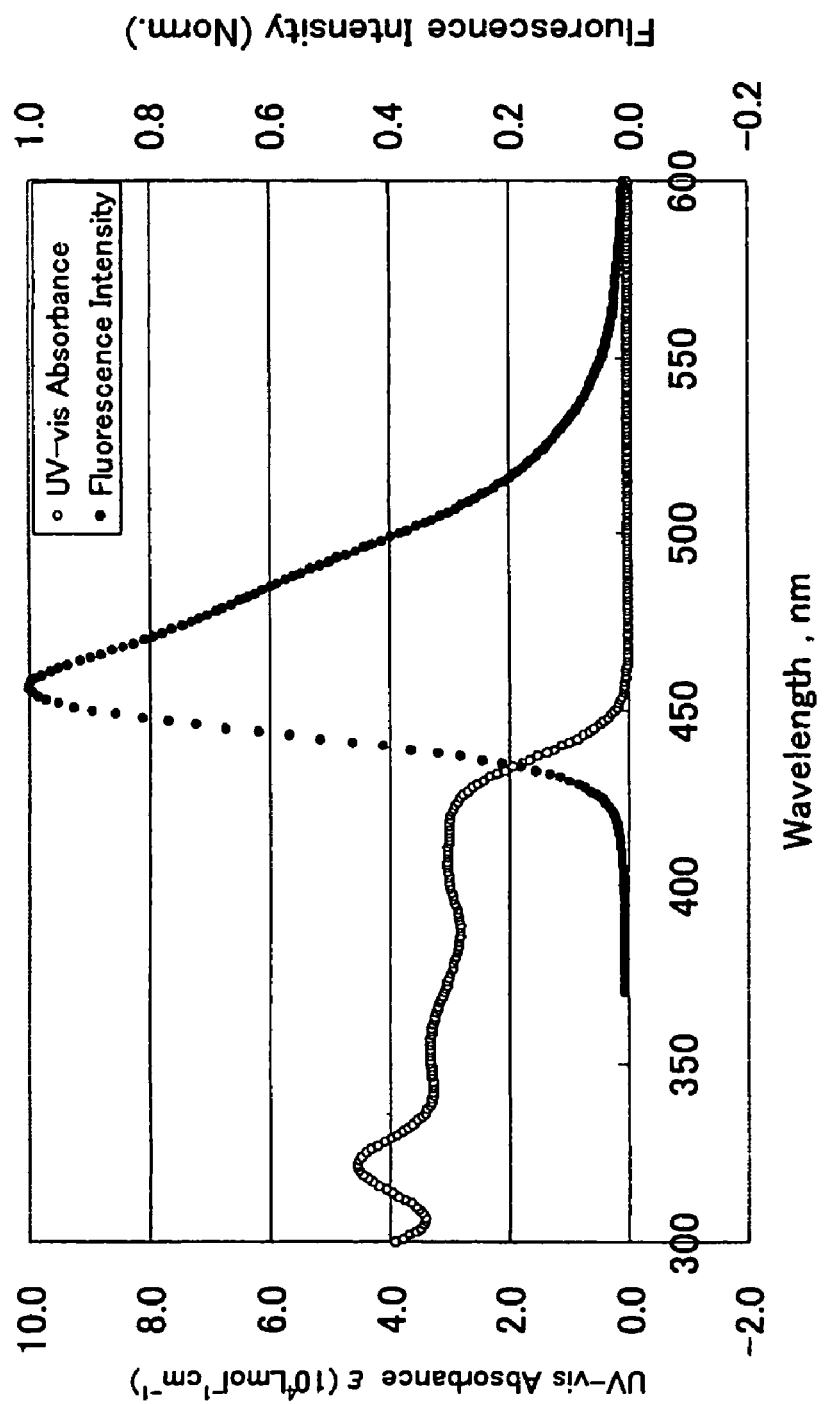
FIG. 3 is a diagram showing results obtained by measuring a UV ray absorbance and a fluorescence intensity of a mixture of a compound (1d-29) and a compound (1d'-29) produced in Synthetic Example 1.
Figure 4:
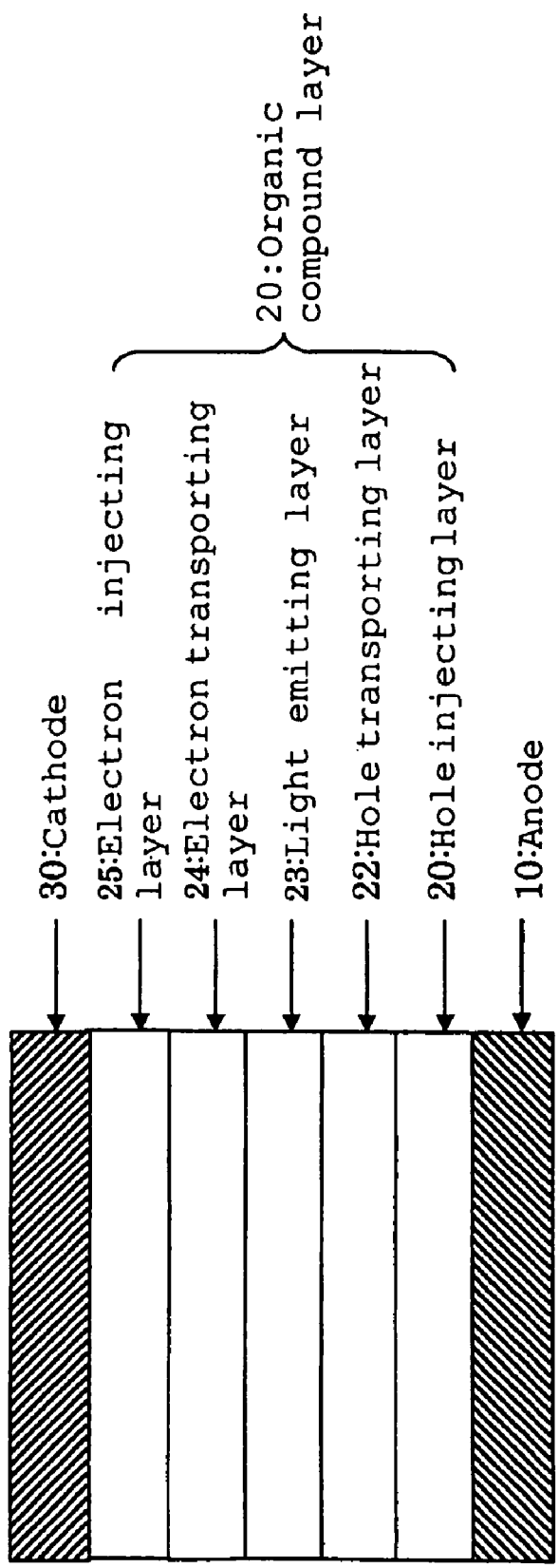
FIG. 4 is a cross-sectional drawing showing one embodiment of the organic EL device of the present invention.

LC-MS (liquid chromatograph mass spectrum), a UV ray absorption spectrum (○ in FIG. 3) in a toluene solution and a fluorescence emission spectrum (● in FIG. 3) of the compound thus obtained were measured, and the results thereof are shown below (refer to FIG. 3).

LC-MS (APCI$^+$), calculated for $C_{63}H_{44}N_2$=828, found m/z=828 (M$^+$)

UV (PhMe); λmax, 406 (ε4.48), FL (PhMe, λex=283 nm); λmax, 457 nm (half value width: 50 nm)

Example 1

(1) Production of Organic EL Device

A transparent electrode having a film thickness of 120 nm comprising indium tin oxide was provided on a glass substrate of 25 mm×75 mm×1.1 mm thickness. The above glass substrate was subjected to supersonic wave washing in isopropyl alcohol and then washed by irradiating with a UV ray and ozone.

Then, the glass substrate equipped with the transparent electrode was loaded on a substrate holder in a vapor deposition bath of a vacuum vapor deposition apparatus, and a vacuum degree in the vacuum bath was reduced to a pressure of 1×10$^{-3}$ Pa.

First, a layer of N',N'''-bis[4-(diphenylamino)phenyl]-N', N'''-diphenylbiphenyl-4,4'-diamine was formed on a face of a side at which the transparent electrode was formed at a vapor deposition speed of 2 nm/second in a film thickness of 60 nm so that it covered the transparent electrode described above. The above film functions as a hole injecting layer.

Next, a layer of N,N,N',N'-tetra(4-biphenylyl)benzidine was formed on the above hole injecting layer at a vapor deposition speed of 2 nm/second in a film thickness of 20 nm. The above film functions as a hole transporting layer.

The compound (2a'-55) (a light emitting material 1) described above and the compound (1a-29) (a light emitting material 2) described above which was obtained in Synthetic Example 1 were deposited at the same time on the hole transporting layer at the vapor deposition speeds of 2 nm/second and 0.2 nm/second respectively in a film thickness of 40 nm so that a weight ratio of (2a'-55):(1a-29) was controlled to 40:2. The above film functions as a light emitting layer.

Tris(8-hydroxyquinolinolate)aluminum was deposited thereon at a vapor deposition speed of 2 nm/second in a film thickness of 20 nm to form an electron transporting layer.

Further, lithium fluoride was deposited thereon at a vapor deposition speed of 0.1 nm/second in a film thickness of 1 nm to form an electron injecting layer.

Figure 2:
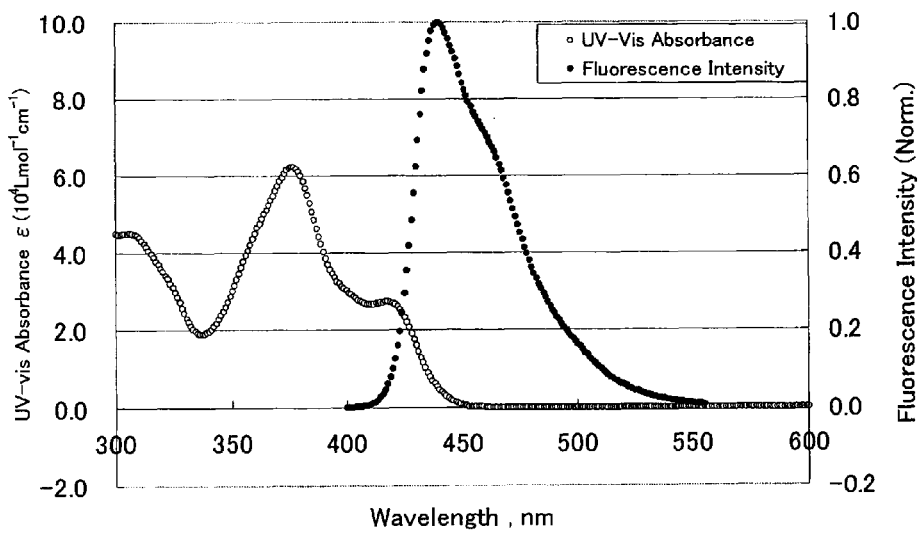
FIG. 2 is a diagram showing results obtained by measuring a UV ray absorbance and a fluorescence intensity of a compound (1a-55) produced in Synthetic Example 1.

Lastly, aluminum was deposited thereon at a vapor deposition speed of 2 nm/second in a film thickness of 200 nm to form a cathode layer, whereby an organic EL device was produced (refer to FIG. 2).

(2) Evaluation of Organic EL Device

Next, the device obtained above was subjected to a current carrying test to find that a light emitting luminance was 310 cd/m$^2$ at a voltage of 6.3 V, and a light emitting peak wavelength (EL λmax) was measured to confirm that a light emitting color was blue. Further, constant current operation was carried out at an initial light emitting luminance controlled to 100 cd/m$^2$ to confirm that a half lifetime was hours or longer and fell in a sufficiently practical area. The results obtained are shown in Table 1.

Examples 2 to 3

Organic EL devices were prepared in the same manner as in Example 1, except that the compound (1a-55) obtained in Synthetic Example 2 was used in Example 2 and that a mixture of the compound (1d-29) and the compound (1d'-29) obtained in Synthetic Example 3 was used in Example 3 each in place of the compound (1a-29) used in Example 1.

The organic EL devices were evaluated in the same manner as in Example 1 to observe blue light emission in all examples as shown in Table 1 and find that a light emitting luminance was 320 to 330 cd/m$^2$ and that a half lifetime was 10,000 hours or longer.

Examples 4 to 5

Organic EL devices were prepared in the same manner as in Example 1, except that the compound (2a'-59) was used in Example 4 and that the compound (2b-42) was used in Example 5 each in place of the comII examples as shown in Table 1 and find that a light emitting luminance was 300 to 320 cd/m$^2$ and that a half lifetime was 10,000 hours or longer.

Examples 6 to 7

Organic EL devices were prepared in the same manner as in Example 1, except that the compound (2c-1) was used in Example 6 and that the compound (2d-1) was used in Example 7 each in place of the compound (2a'-55) used in Example 1.

The organic EL devices were evaluated in the same manner as in Example 1 to observe blue light emission in all examples as shown in Table 1 and find that a light emitting luminance was 200 to 250 cd/m$^2$ and that a half lifetime was 6,000 hours or longer.

Comparative Examples 1 to 3

Organic EL devices were prepared in the same manner as in Example 1, except that used respectively in place of the compound (1a-29) used in Example 1 were the following compound (A) in Comparative Example 1, the following compound (B) in Comparative Example 2 and the following compound (C) in Comparative Example 3.

The organic EL devices were evaluated in the same manner as in Example 1 to observe blue light emission in all examples as shown in Table 1, but these were emission originating in the compound (2a'-55). The light emitting luminance was 100 to 125 cd/m$^2$, and the half lifetime was as short as 3,000 hours or less.

TABLE 1
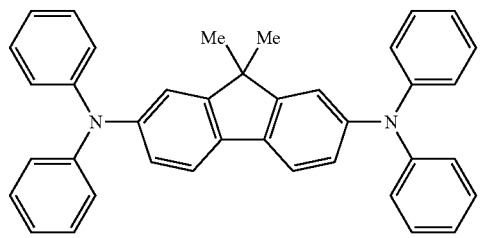
Compound (A)
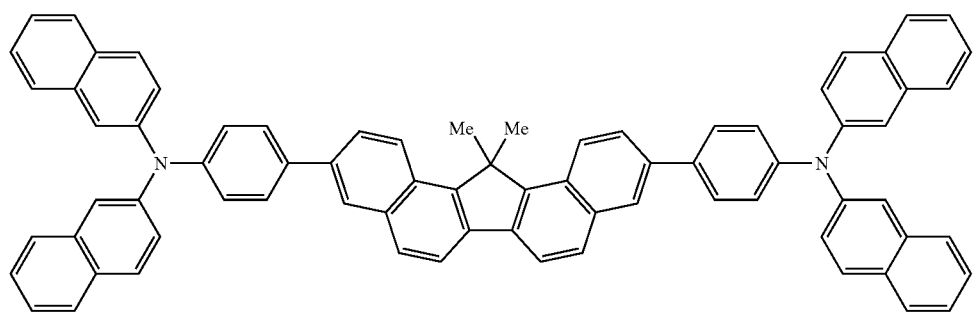
Compound (B)
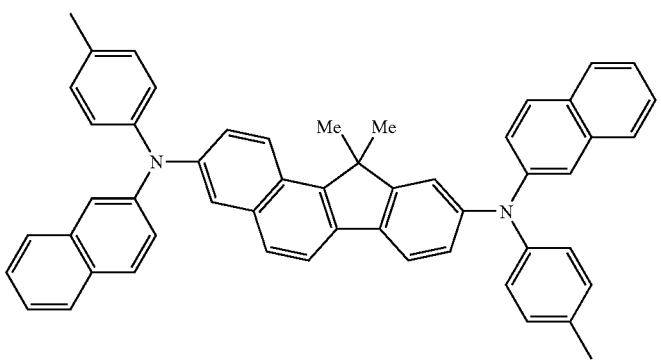
Compound (C)
|  | Example | | | | |
|---|---|---|---|---|---|
|  | 1 | 2 | 3 | 4 | 5 |
| Light emitting material 1 | 2a'-55 | 2a'-55 | 2a'-55 | 2a'-59 | 2b-42 |
| Light emitting material 2 | 1a-29 | 1a-55 | 1d-29 1d'-29 | 1a-29 | 1a-29 |
| Operating voltage (V) | 6.3 | 6.3 | 6.3 | 6.3 | 6.3 |
| EL λmax | 447 | 449 | 449 | 447 | 448 |
| Light emitting luminance (cd/m$^2$) | 310 | 320 | 330 | 320 | 300 |
| Half lifetime (hours) | >10,000 | >10,000 | >10,000 | >10,000 | >10,000 |
|  | Example | | Comparative Example | | |
|---|---|---|---|---|---|
|  | 6 | 7 | 1 | 2 | 3 |
| Light emitting material 1 | 2c-1 | 2d-1 | 2a'-55 | 2a'-55 | 2a'-55 |
| Light emitting material 2 | 1a-29 | 1a-29 | Compound A | Compound B | Compound C |
| Operating voltage (V) | 6.3 | 6.3 | 6.3 | 6.3 | 6.3 |

TABLE 1-continued

| | | | | | |
|---|---|---|---|---|---|
| EL λmax | 447 | 447 | 450 | 450 | 445 |
| Light emitting luminance (cd/m²) | 200 | 250 | 100 | 105 | 125 |
| Half lifetime (hours) | 6,000 | 7,000 | 2,000 | 2,200 | 3,000 |

Example 8

A glass substrate (manufactured by Geomatech Co., Ltd.) of 25 mm×75 mm×1.1 mm thickness equipped with an ITO transparent electrode was subjected to supersonic wave washing in isopropyl alcohol for 5 minutes and then to UV ozone washing for 30 minutes.

A hole injecting and transporting layer having a laminate structure was formed on the above substrate. First, a film was formed from polyethylenedioxythiophene-polystyrenesulfonic acid (PEDOT-PSS) in a film thickness of 100 nm by a spin coating method. Then, a film was formed from a toluene solution (0.6% by weight) of a polymer 1 (molecular weight (Mw): 145000) shown below in a film thickness of 20 nm by the spin coating method and dried at 170° C. for 30 minutes.

Next, a light emitting layer was formed from a toluene solution containing 1% by weight of the compound (2a'-55) described above and the compound (1a-29) ((2a'-55):(1a-29)=20:2 (weight ratio)) described above which was obtained in Synthetic Example 1 as the light emitting materials by the spin coating method. The above light emitting layer had a film thickness of 50 nm.

A tris(8-quinolinol)aluminum film (hereinafter abbreviated as "the Alq film") having a film thickness of 10 nm was formed on the above light emitting layer. The above Alq film functions as an electron transporting layer.

Then, Li (Li source: manufactured by Saesgetter Co., Ltd.) which was a reducing dopant and Alq were subjected to binary vapor deposition to form an Alq:Li film as an electron injecting layer (cathode). Metal Al was deposited on the above Alq:Li film to form a metal cathode, whereby an organic EL device was formed.

The above device emitted a blue light, and the light emitting face was even. In this case, the current efficiency was 2.5 cd/A.

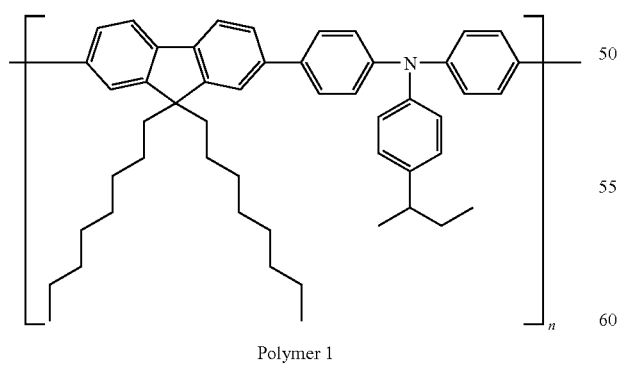

Polymer 1

Example 9

An organic EL device was prepared in the same manner as in Example 8, except that the compound (1a-55) described above which was obtained in Synthetic Example 2 was used in place of the compound (1a-29) used in Example 8.

The above device emitted a blue light, and the light emitting face was even. In this case, the current efficiency was 2.6 cd/A.

INDUSTRIAL APPLICABILITY

A practical organic EL device which has a low operating voltage, a long lifetime and a high current efficiency and which provides blue light emission having an excellent color purity is obtained by using the aminodibenzofluorene derivative of the present invention as a material for the organic EL device. Further, a light emitting organic solution containing the aminodibenzofluorene derivative of the present invention is suited for forming an organic compound layer in an organic EL device by a wet method.

The organic EL device of the present invention is highly practical and useful as a light source for a flat light emitting body of wall-mounted TV, a backlight of displays and the like. It can also be used as an organic EL device, an hole injecting and transporting material and an electron transporting material for electrophotographic photoreceptors and organic semiconductors

What is claimed is:
1. An aminodibenzofluorene derivative:
of the formula 1a-29:

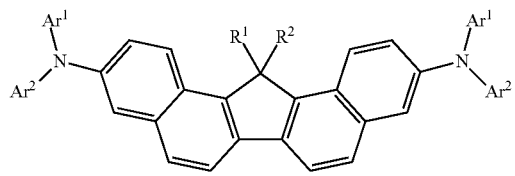

where $R^1$ and $R^2$ are Me and $Ar^1$ and $Ar^2$ are:

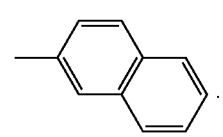

2. An aminodibenzofluorene derivative represented by any of the following Formulae (1-a), (1-b), (1-d), (1-e) and (1-f):

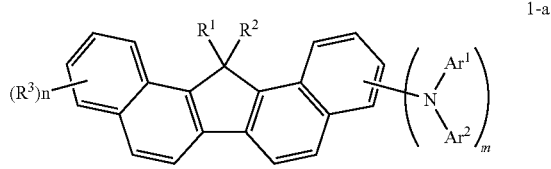

-continued

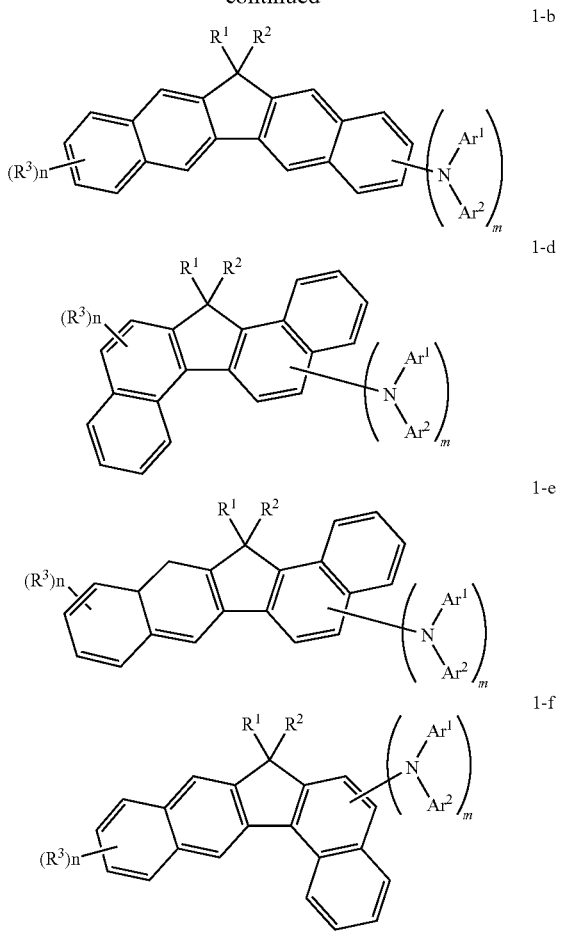

wherein $R^1$ to $R^2$ each represent independently a hydrogen atom, a substituted or non-substituted alkyl group having 1 to 50 carbon atoms, a substituted or non-substituted aralkyl group having 1 to 50 carbon atoms, a substituted or non-substituted cycloalkyl group having 5 to 50 carbon atoms, a substituted or non-substituted aryl group having 5 to 50 carbon atoms forming the aromatic ring or a substituted or non-substituted heteroaryl group having 5 to 50 atoms forming a ring;

$R^3$ represents a substituted or non-substituted alkyl group having 1 to 50 carbon atoms, a substituted or non-substituted aralkyl group having 1 to 50 carbon atoms, a substituted or non-substituted cycloalkyl group having 5 to 50 carbon atoms, a substituted or non-substituted alkoxyl group having 1 to 50 carbon atoms, a substituted or non-substituted alkoxycarbonyl group having 1 to 50 carbon atoms, a substituted or non-substituted aryl group having 5 to 50 carbon atoms forming the aromatic ring, a substituted or non-substituted aryloxy group having 5 to 50 atoms forming a ring, a substituted or non-substituted arylthio group having 5 to 50 atoms forming a ring, a substituted or non-substituted heteroaryl group having 5 to 50 atoms forming a ring, a substituted or non-substituted silyl group having 1 to 20 carbon atoms, a halogen atom, a cyano group or a nitro group;

$Ar^1$ to $Ar^2$ each represent independently a substituted or non-substituted aryl group having 5 to 50 carbon atoms forming the aromatic ring or a substituted or non-substituted heteroaryl group having 5 to 50 atoms forming a ring;

m is an integer of 1 to 4, and n is an integer of 0 to 8;

when $R^1$, $R^2$, $R^3$, $Ar^1$ and $Ar^2$ are not a hydrogen atom, a halogen atom, a cyano group and a nitro group, the groups which are adjacent to each other may be combined with each other to form saturated or unsaturated cyclic structures, and these cyclic structures may be substituted.

3. An organic electroluminescence device comprising the aminodibenzofluorene derivative as described in claim 1 or 2.

4. An organic electroluminescence device in which an organic compound layer comprising a single layer or plural layers and including at least a light emitting layer is interposed between a pair of electrodes, wherein at least one layer in the organic compound layer comprises at least one of the aminodibenzofluorene derivatives as described in claim 1 or 2.

5. The organic electroluminescence device as described in claim 4, wherein the light emitting layer comprises at least one kind of the aminodibenzofluorene derivatives.

6. The organic electroluminescence device as described in claim 5, wherein the light emitting layer further comprises at least one selected from compounds represented by the following Formulae (2a) to (2d):

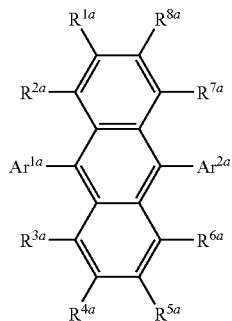

(2a)

in Formula (2a), $Ar^{1a}$ and $Ar^{2a}$ each are independently a group derived from a substituted or non-substituted aromatic ring having 6 to 20 ring carbon atoms; the aromatic ring described above may be substituted with at least one substituent; the substituent described above is selected from a substituted or non-substituted aryl group having 6 to 50 carbon atoms forming the aromatic ring, a substituted or non-substituted alkyl group having 1 to 50 carbon atoms, a substituted or non-substituted cycloalkyl group having 3 to 50 carbon atoms, a substituted or non-substituted alkoxyl group having 1 to 50 carbon atoms, a substituted or non-substituted aralkyl group having 6 to 50 carbon atoms, a substituted or non-substituted aryloxy group having 5 to 50 atoms forming a ring, a substituted or non-substituted arylthio group having 5 to 50 atoms forming a ring, a substituted or non-substituted alkoxycarbonyl group having 1 to 50 carbon atoms, a substituted or non-substituted silyl group, a carboxyl group, a halogen atom, a cyano group, a nitro group and a hydroxyl group; when the aromatic ring described above is substituted with two or more substituents, the substituents described above may be the same or different, and the substituents which are adjacent may be combined with each other to form a saturated or unsaturated cyclic structure;

$R^{1a}$ to $R^{8a}$ each are selected independently from a hydrogen atom, a substituted or non-substituted aryl group having 6 to 50 carbon atoms forming the aromatic ring, a substituted or non-substituted heteroaryl group having 5 to 50 atoms forming a ring, a substituted or non-substituted alkyl group having 1 to 50 carbon atoms, a substituted or non-substituted cycloalkyl group having 3 to 50 carbon atoms, a substituted or non-substituted alkoxyl group having 1 to 50 carbon atoms, a substituted or non-substituted aralkyl group having 6 to 50 carbon atoms, a substituted or non-substituted aryloxy group having 5 to 50 atoms forming a ring, a substituted or non-substituted arylthio group having 5 to 50 atoms forming a ring, a substituted or non-substituted alkoxycarbonyl group having 1 to 50 carbon atoms, a substituted or non-substituted silyl group, a carboxyl group, a halogen atom, a cyano group, a nitro group and a hydroxyl group;

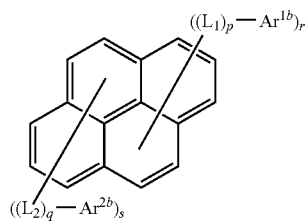

(2b)

in Formula (2b), $Ar^{1b}$ and $Ar^{2b}$ each are independently a substituted or non-substituted aryl group having 6 to 50 carbon atoms forming the aromatic ring;

$L_1$ and $L_2$ each are selected independently from a substituted or non-substituted phenylene group, a substituted or non-substituted naphthalenylene group, a substituted or non-substituted fluorenylene group and a substituted or non-substituted dibenzosilolylene group;

p and q are an integer of 0 to 2, and r and s are an integer of 1 to 4;

$L_1$ or $Ar^{1b}$ is boded to any of 1- to 5-positions of pyrene, and $L_2$ or $Ar^{2b}$ is boded to any of 6- to 10-positions of pyrene);

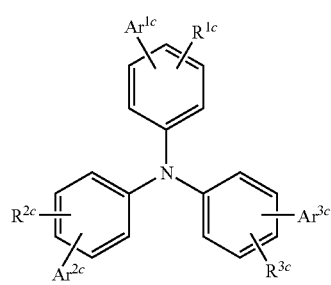

(2c)

(n Formula (2c), $Ar^{1c}$, $Ar^{2c}$ and $Ar^{3c}$ each are selected independently from a group having an anthracene structure, a group having a phenanthrene structure, a group having a pyrene structure, a group having a fluorene structure and a group having a perylene structure; and $R^{1c}$, $R^{2c}$ and $R^{3c}$ each represent independently a hydrogen atom or a substituent;

(2d)

in Formula (2d), $Ar^{1d}$, $Ar^{2d}$ and $Ar^{3d}$ each represent independently a substituted or non-substituted aryl group having 6 to 50 carbon atoms forming the aromatic ring; the aryl group described above may be substituted with at least one substituent;

at least one of $Ar^{1d}$, $Ar^{2d}$, $Ar^{3d}$ and the substituents present in these aryl groups has a fused ring aryl structure having 10 to 20 carbon atoms forming the aromatic ring or a fused ring heteroaryl structure having 6 to 20 atoms forming a ring; and Ar represents a trivalent group derived from an aromatic ring or an aromatic heterocycle).

7. The organic electroluminescence device as described in claim 4, wherein 0.01 to 20% by weight of the aminodibenzofluorene is contained in the light emitting layer.

8. The organic electroluminescence device as described in claim 4, wherein a layer selected from a chalcogenide layer, a halogenated metal layer and a metal oxide layer is further provided on at least one surface of the pair of the electrodes.

9. A light emitting organic solution comprising the aminodibenzofluorene derivative as described in claim 1 or 2.

10. The light emitting organic solution as described in claim 9, further comprising at least one selected from the compounds represented by Formulas (2a) to (2d):

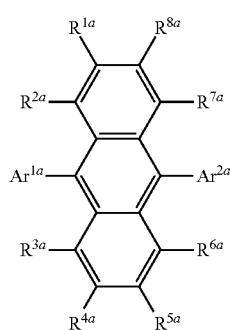

(2a)

in Formula (2a), $Ar^{1a}$ and $Ar^{2a}$ each are independently a group derived from a substituted or non-substituted aromatic ring having 6 to 20 ring carbon atoms; the aromatic ring described above may be substituted with at least one substituent; the substituent described above is selected from a substituted or non-substituted aryl group having 6 to 50 carbon atoms forming the aromatic ring, a substituted or non-substituted alkyl group having 1 to 50 carbon atoms, a substituted or non-substituted cycloalkyl group having 3 to 50 carbon atoms, a substituted or non-substituted alkoxyl group having 1 to 50 carbon atoms, a substituted or non-substituted aralkyl group having 6 to 50 carbon atoms, a substituted or non-substituted aryloxy group having 5 to 50 atoms forming a ring, a substituted or non-substituted arylthio group having 5 to 50 atoms forming a ring, a substituted or non-substituted alkoxycarbonyl group having 1 to 50 carbon atoms, a substituted or non-substituted silyl group, a carboxyl group, a halogen atom, a cyano group, a nitro group and a hydroxyl group; when the aromatic ring described above is substituted with two or more substituents, the substituents described above may be the same or different, and the substituents which are adjacent may be combined with each other to form a saturated or unsaturated cyclic structure;

$R^{1a}$ to $R^{8a}$ each are selected independently from a hydrogen atom, a substituted or non-substituted aryl group having 6 to 50 carbon atoms forming the aromatic ring, a substituted or non-substituted heteroaryl group having 5 to 50 atoms forming a ring, a substituted or non-substituted alkyl group having 1 to 50 carbon atoms, a substituted or non-substituted cycloalkyl group having 3 to 50 carbon atoms, a substituted or non-substituted alkoxyl group having 1 to 50 carbon atoms, a substituted or non-substituted aralkyl group having 6 to 50 carbon atoms, a substituted or non-substituted aryloxy group having 5 to 50 atoms forming a ring, a substituted or non-substituted arylthio group having 5 to 50 atoms forming a ring, a substituted or non-substituted alkoxycarbonyl group having 1 to 50 carbon atoms, a substituted or non-substituted silyl group, a carboxyl group, a halogen atom, a cyano group, a nitro group and a hydroxyl group;

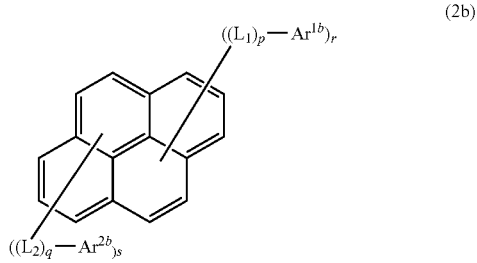

(2b)

in Formula (2b), $Ar^{1b}$ and $Ar^{2b}$ each are independently a substituted or non-substituted aryl group having 6 to 50 carbon atoms forming the aromatic ring;

$L_1$ and $L_2$ each are selected independently from a substituted or non-substituted phenylene group, a substituted or non-substituted naphthalenylene group, a substituted or non-substituted fluorenylene group and a substituted or non-substituted dibenzosilolylene group;

p and q are an integer of 0 to 2, and r and s are an integer of 1 to 4;

$L_1$ or $Ar^{1b}$ is boded to any of 1- to 5-positions of pyrene, and $L_2$ or $Ar^{2b}$ is boded to any of 6- to 10-positions of pyrene;

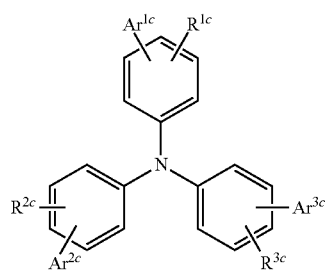

(2c)

in Formula (2c), $Ar^{1c}$, $Ar^{2c}$ and $Ar^{3c}$ each are selected independently from a group having an anthracene structure, a group having a phenanthrene structure, a group having a pyrene structure, a group having a fluorene structure and a group having a perylene structure; and $R^{1c}$, $R^{2c}$ and $R^{1c}$ each represent independently a hydrogen atom or a substituent;

(2d)

in Formula (2d), $Ar^{1d}$, $Ar^{2d}$ and $Ar^{3d}$ each represent independently a substituted or non-substituted aryl group having 6 to 50 carbon atoms forming the aromatic ring; the aryl group described above may be substituted with at least one substituent;

at least one of $Ar^{1d}$, $Ar^{2d}$, $Ar^{3d}$ and the substituents present in these aryl groups has a fused ring aryl structure having 10 to 20 carbon atoms forming the aromatic ring or a fused ring heteroaryl structure having 6 to 20 atoms forming a ring; and Ar represents a trivalent group derived from an aromatic ring or an aromatic heterocycle.

11. An aminodibenzofluorene derivative as described in claim 2, represented by Formula (1-a).

12. An aminodibenzofluorene derivative as described in claim 2, represented by Formula (1-b).

13. An aminodibenzofluorene derivative as described in claim 2, represented by Formula (1-d).

14. An aminodibenzofluorene derivative as described in claim 2, represented by Formula (1-e).

15. An aminodibenzofluorene derivative as described in claim 2, represented by Formula (1-f).

16. The organic electroluminescence device as described in claim 5, wherein the light emitting layer comprises an aminodibenzofluorene derivative of the formula 1a-29:

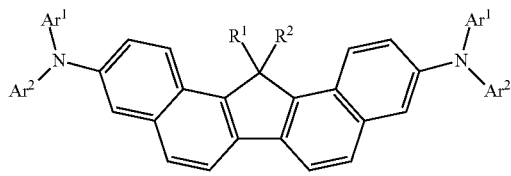

where $R^1$ and $R^2$ are Me and $Ar^1$ and $Ar^2$ are:

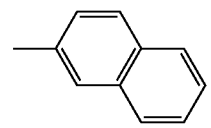

and further comprises a compound represented by the following formula 2a'-55:

2a'-55

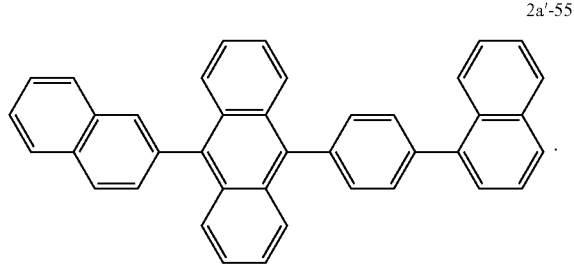

* * * * *